United States Patent
Vander Horn et al.

(10) Patent No.: US 12,152,256 B2
(45) Date of Patent: Nov. 26, 2024

(54) NUCLEOTIDE TRANSIENT BINDING FOR SEQUENCING METHODS

(71) Applicant: LIFE TECHNOLOGIES CORPORATION, Carlsbad, CA (US)

(72) Inventors: Peter Vander Horn, Encinitas, CA (US); Cheng-Yao Chen, Eugene, OR (US); Guobin Luo, Oceanside, CA (US); Michael Previte, Carlsbad, CA (US); Jamshid Temirov, Germantown, TN (US); Theo Nikiforov, Carlsbad, CA (US); Zhaohui Zhou, San Ramon, CA (US); Hongye Sun, Belmont, CA (US); Yufang Wang, San Carlos, CA (US); Stefanie Yukiko Nishimura, Mountain View, CA (US); Hongyi Wang, Pearland, TX (US); Marian Peris, Dublin, CA (US); Barnett Rosenblum, San Jose, CA (US); Michael Phelan, Millbrae, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 245 days.

(21) Appl. No.: 17/932,844

(22) Filed: Sep. 16, 2022

(65) Prior Publication Data
US 2023/0193223 A1    Jun. 22, 2023

Related U.S. Application Data

(60) Continuation of application No. 16/825,788, filed on Mar. 20, 2020, now Pat. No. 11,447,756, which is a
(Continued)

(51) Int. Cl.
*C12Q 1/68* (2018.01)
*C12N 9/12* (2006.01)
(Continued)

(52) U.S. Cl.
CPC .............. *C12N 9/1252* (2013.01); *C12Q 1/68* (2013.01); *C12Q 1/6804* (2013.01);
(Continued)

(58) Field of Classification Search
None
See application file for complete search history.

(56) References Cited

U.S. PATENT DOCUMENTS

| 5,001,050 A | 3/1991 | Blanco et al. |
| 5,198,543 A | 3/1993 | Blanco et al. |

(Continued)

FOREIGN PATENT DOCUMENTS

| WO | WO-9105060 A2 | 4/1991 |
| WO | WO-9106678 A1 | 5/1991 |

(Continued)

OTHER PUBLICATIONS

Arndt et al. (Insight into the Catalytic Mechanism of DNA Polymerase beta: Structures of Intermediate Complexes, Biochemistry, May 8, 2001;40(18), 5368-75).
(Continued)

*Primary Examiner* — Aaron A Priest

(57) ABSTRACT

Provided herein are compositions and systems for use in polymerase-dependent, nucleotide transient-binding methods. The methods are useful for deducing the sequence of a template nucleic acid molecule and single nucleotide polymorphism (SNP) analyses. The methods rely on the fact that the polymerase transient-binding time for a complementary nucleotide is longer compared to that of a non-complementary nucleotide. The labeled nucleotides transiently-binds the polymerase in a template-dependent manner, but does not incorporate. The methods are conducted under any reaction condition that permits transient binding of a
(Continued)

```
MKHMPRKMYS CDFETTTKVE DCRVWAYGYM NIEDHSEYKI GNSLDEFMAW VLKVQADLYF
HNLKFDGAFI INWLERNGFK WSADGLPNTY NTIISRMGQW YMIDICLGYK GKRKIHTVIY
DSLKKLPFPV KKIAKDFKLT VLKGDIDYHK ERPVGYKITP EEYAYIKNDI QIIAEALLIQ
FKQGLDRMTA GSDSLKGFKD IITTKKFKKV FPTLSLGLDK EVRYAYRGGF TWLNDRFKEK
EIGEGMVFDV NSLYPAQMYS RLLPYGEPIV FEGKYVWDED YPLHIQHIRC EFELKEGYIP
TIQIKRSRFY KGNEYLKSSG GEIADLWLSN VDLELMKEHY DLYNVEYISG LKFKATTGLF
KDFIDKWTYI KTTSEGAIKQ LAKLMLNSLY GKFASNPDVT GKVPYLKENG ALGFRLGEEE
TKDPVYTPMG VFITAWARYT TITAAQACYD RIIYCDTDSI HLTGTEIPDV IKDIVDPKKL
GYWAHESTFK RAKYLRQKTY IQDIYMKEVD GKLVEGSPDD YTDIKFSVKC AGMTDKIKKE
VTFENFKVGF SRKMKPKPVQ VPGGVVLVDD TFTIK
``` complementary or non-complementary nucleotide to a polymerase, and inhibits nucleotide incorporation.

17 Claims, 41 Drawing Sheets

Specification includes a Sequence Listing.

Related U.S. Application Data continuation of application No. 15/690,945, filed on Aug. 30, 2017, now Pat. No. 10,597,642, which is a division of application No. 14/991,230, filed on Jan. 8, 2016, now Pat. No. 9,765,310, which is a continuation of application No. 14/108,166, filed on Dec. 16, 2013, now Pat. No. 9,255,258, which is a continuation of application No. 12/790,760, filed on May 28, 2010, now Pat. No. 8,632,975.

(60) Provisional application No. 61/295,533, filed on Jan. 15, 2010, provisional application No. 61/263,320, filed on Nov. 20, 2009, provisional application No. 61/242,762, filed on Sep. 15, 2009, provisional application No. 61/184,774, filed on Jun. 5, 2009.

(51) Int. Cl.

| | | |
|---|---|---|
| *C12Q 1/6804* | (2018.01) | |
| *C12Q 1/6818* | (2018.01) | |
| *C12Q 1/6827* | (2018.01) | |
| *C12Q 1/6869* | (2018.01) | |
| *C12Q 1/6872* | (2018.01) | |

(52) U.S. Cl.
CPC ......... *C12Q 1/6818* (2013.01); *C12Q 1/6827* (2013.01); *C12Q 1/6869* (2013.01); *C12Q 1/6872* (2013.01); *C12Y 207/07007* (2013.01); *G01N 2500/00* (2013.01)

(56) References Cited

U.S. PATENT DOCUMENTS

| | | | |
|---|---|---|---|
| 5,576,204 A | 11/1996 | Blanco et al. | |
| 5,707,804 A | 1/1998 | Mathies et al. | |
| 5,798,210 A | 8/1998 | Canard et al. | |
| 6,309,836 B1 | 10/2001 | Kwiatkowski | |
| 6,482,590 B1 | 11/2002 | Ullman et al. | |
| 6,833,246 B2 | 12/2004 | Balasubramanian | |
| 6,883,246 B1 | 4/2005 | Latham | |
| 6,982,146 B1 | 1/2006 | Schneider et al. | |
| 7,041,812 B2 | 5/2006 | Kumar et al. | |
| 7,052,839 B2 | 5/2006 | Nelson et al. | |
| 7,125,671 B2 | 10/2006 | Sood et al. | |
| 7,169,560 B2 | 1/2007 | Lapidus et al. | |
| 7,223,541 B2 | 5/2007 | Fuller et al. | |
| 7,264,934 B2 | 9/2007 | Fuller | |
| 7,270,951 B1 | 9/2007 | Stemple et al. | |
| 7,279,563 B2 | 10/2007 | Kwiatkowski | |
| 7,329,492 B2 | 2/2008 | Hardin et al. | |
| 7,361,466 B2 | 4/2008 | Korlach et al. | |
| 7,393,640 B2 | 7/2008 | Kumar et al. | |
| 7,405,281 B2 | 7/2008 | Xu et al. | |
| 7,416,844 B2 | 8/2008 | Korlach et al. | |
| 7,427,673 B2 | 9/2008 | Balasubramanian et al. | |
| 7,476,504 B2 | 1/2009 | Turner | |
| 7,482,120 B2 | 1/2009 | Buzby et al. | |
| 7,485,424 B2 | 2/2009 | Korlach et al. | |
| 7,541,444 B2 | 6/2009 | Milton et al. | |
| 8,133,672 B2* | 3/2012 | Bjornson | C12Q 1/6869 |
| | | | 536/23.1 |
| 8,257,954 B2 | 9/2012 | Clark et al. | |
| 8,399,196 B2 | 3/2013 | Hoser | |
| 2005/0100932 A1 | 5/2005 | Lapidus et al. | |
| 2006/0003383 A1 | 1/2006 | Graham | |
| 2006/0051807 A1* | 3/2006 | Fuller | C12Q 1/6869 |
| | | | 435/6.1 |
| 2007/0072196 A1 | 3/2007 | Xu et al. | |
| 2007/0148645 A1* | 6/2007 | Hoser | B82Y 10/00 |
| | | | 435/6.12 |
| 2007/0196846 A1 | 8/2007 | Hanzel et al. | |
| 2008/0009007 A1 | 1/2008 | Lyle et al. | |
| 2008/0050780 A1 | 2/2008 | Lee et al. | |
| 2008/0091005 A1 | 4/2008 | Wang et al. | |
| 2008/0103053 A1 | 5/2008 | Siddiqi et al. | |
| 2008/0108082 A1 | 5/2008 | Rank et al. | |
| 2008/0132692 A1 | 6/2008 | Wu et al. | |
| 2008/0138804 A1 | 6/2008 | Buzby | |
| 2008/0227970 A1 | 9/2008 | Siddiqi et al. | |
| 2008/0269476 A1 | 10/2008 | Siddiqi | |
| 2008/0286837 A1 | 11/2008 | Siddiqi | |
| 2008/0287305 A1 | 11/2008 | Fuller et al. | |
| 2008/0293071 A1 | 11/2008 | Gelfand et al. | |
| 2009/0061437 A1 | 3/2009 | Efcavitch et al. | |
| 2009/0081686 A1 | 3/2009 | Wu et al. | |
| 2009/0087850 A1 | 4/2009 | Eid et al. | |
| 2009/0176233 A1 | 7/2009 | Clark et al. | |
| 2009/0286245 A1 | 11/2009 | Bjornson et al. | |
| 2010/0047802 A1 | 2/2010 | Bjorson et al. | |
| 2010/0075328 A1 | 3/2010 | Bjornson et al. | |
| 2010/0075332 A1 | 3/2010 | Patel et al. | |
| 2010/0112645 A1* | 5/2010 | Clark | C12Q 1/6869 |
| | | | 435/174 |
| 2010/0311144 A1 | 12/2010 | Peris et al. | |
| 2010/0330570 A1 | 12/2010 | Vander et al. | |
| 2011/0014612 A1 | 1/2011 | Hendricks et al. | |
| 2011/0189659 A1 | 8/2011 | Clark et al. | |
| 2012/0034602 A1 | 2/2012 | Emig et al. | |
| 2012/0046176 A1 | 2/2012 | Su et al. | |
| 2015/0132756 A1 | 5/2015 | Peter et al. | |

FOREIGN PATENT DOCUMENTS

| | | |
|---|---|---|
| WO | WO-0070073 A1 | 11/2000 |
| WO | WO-2005080605 A2 | 9/2005 |
| WO | WO-2005123957 A2 | 12/2005 |
| WO | WO-2007048033 A1 | 4/2007 |
| WO | WO-2009091847 A2 | 7/2009 |
| WO | WO-2010141390 A2 | 12/2010 |

OTHER PUBLICATIONS

Arzumanov, Andrey A. et al., "γ-Phosphate-substituted 2'-Deoxynucleoside 5'-Triphosphates as Substrates for DNA Polymerases", J. Biol. Chem., vol. 271(40), 1996, pp. 24389-24394.

Bai, Xiaopeng et al., "Design and synthesis of a photocleavable biotinylated nucleotide for DNA analysis by mass spectrometry", Nucleic Acids Research, vol. 32, No. 2, 2004, 535-541.

Bakhtina, Marina et al., "Contribution of the Reverse Rate of the Conformational Step to Polymerase B Fidelity", Biochem. vol. 48 2009, 3197-3208.

Barone, A. D. et al., "Novel Nucleoside Triphosphate Analogs for the Enzymatic Labeling of Nucleic Acids", Nucleosides, Nucleotides & Nucleic Acids, 20(4-7), 2001, 1141-1145.

Beaucage S.L., et al., "Advances in the Synthesis of Oligonucleotides by the Phosphoramidite Approach," Tetrahedron Report, 1992, vol. 48, No. 12, pp. 2223-2311.

Bebenek, Anna et al., "Dissecting the Fidelity of Bacteriophage RB69 DNA Polymerase: Site-Specific Modulation of Fidelity by Polymerase Accessory Proteins" Genetics Society of America, 2002, 1003-1018.

Beese, Lorena et al., "Structural basis for the 3'-5' exonuclease activity of *Escherichia coli* DNA polymerase 1: a two metal ion mechanism", The EMBO Journal, vol. 10 No. 1, 1991, 25-33.

Bentley D.R., et al., "Accurate Whole Human Genome Sequencing Using Reversible Terminator Chemistry," Nature, Nov. 6, 2008, vol. 456, No. 6, pp. 53-59.

Berg, et al., "DNA Polymerases Require a Template and a Primer", Biochemistry, 5th edition, New York: W H Freeman, 2002, 1-4.

(56) References Cited

OTHER PUBLICATIONS

Berman, Andrea J. et al., "Structures of phi29 DNA polymerase complexed with substrate: the mechanism of translocation in B-family polymerases", The EMBO Journal, vol. 26, 2007, 3494-3505.
Braslavsky, Ido et al., "Sequence information can be obtained from single DNA molecules", Proc. Natl. Acad. Sci. vol. 100(7) 2003, pp. 3960-3964.
Burgers, Peter et al., "Eukaryotic DNA Polymerases: Proposal for a Revised Nomenclature", The Journal of Biological Chemistry, vol. 276, No. 47, 2001, 43487-43490.
Castro, Christian et al., "Nucleic acid polymerases use a general acid for nucleotidyl transfer", Nature Structural & Molecular Biology, vol. 16 No. 2, 2009, 212-218.
Castro, Christian et al., "Two proton transfers in the transition state for nucleotidyl transfer catalyzed by RNA- and DNA-dependent RNA and DNA polymerases", PNAS, vol. 104, No. 11, 2007, 4267-4272.
Dos Remedios, C. G. et al., "Fluorescence Resonance Energy Transfer Spectroscopy is a Reliable 'Ruler' for Measuring Structural Changes in Proteins. Dispelling the Problem with the Unknown Orientation Factor", J Struct Biol, 115(2), 1995, 175-85.
Dunaway- Mariano, De Bra et al., " Preparation and Properties of Chromium( III) Adenosine 5'- Triphosphate, Chromium(III) Adenosine 5'-Diphosphate, and Related Chromium(III) Complexes", Biochemistry, 19, 1980, 1496-1505.
Dunaway-Mariano, De Bra et al., "Investigations of Substrate Specificity and Reaction Mechanism of Several Kinases Using Chromium(III) Adenosine 5'-Triphosphate and Chromium(III) Adenosine 5'-Diphosphate", Biochemistry. 19, 1980, 1506-1515.
File history of U.S. Appl. No. 14/108,166, filed Dec. 16, 2013.
Forster, T., "Intermolecular energy migration and fluorescence", Annalen der Physik, vol. 437(1-2), 1948, 55-75.
Gangurde, Rajiv et al., "Participation of Active-Site Carboxylates of *Escherichia coli* DNA Polymerase I (Klenow Fragment) in the Formation of a Prepolymerase Ternary Complex", Biochemistry, 41, 2002, 14552-14559.
Guo, Jia et al., "Four-color DNA sequencing with 3'-O-modified nucleotide reversible terminators and chemically cleavable fluorescent dideoxynucleotides", PNAS, vol. 105, No. 27, Jul. 8, 2008, 9145-9150.
Johnson, K. , "Rapid kinetic analysis of mechanochemical adenosinetriphosphatases", Methods Enzvmol. vol. 134, 1986, pp. 677-705.
Joyce, Catherine et al., "Fingers-Closing and Other Rapid Conformational Changes in DNA Polymerase I (Klenow Fragment) and Their role in Nucleotide Selectivity", Biochemistry, 47, 2008, 6103-6116.
Ju, et al., "Four-color DNA sequencing by synthesis using cleavable fluorescent nucleotide reversible terminators," Proceedings of the National Academy of Sciences of USA, vol. 103, No. 52, pp. 19635-19640 (2006).
Kaushik, Neerja et al., "Biochemical Analysis of Catalytically Crucial Aspartate Mutants of Human Immunodeficiency Virus Type 1 Reverse Transcriptase", Biochemistry, 35, 1996, 11536-11546.
Kumar, Amarendra et al., "Inhibition of T7 RNA Polymerase: Transcription Initiation and Transition from Initiation to Elongation Are Inhibited by T7 Lysozyme via a Ternary Complex with RNA Polymerase and Promoter DNA", Biochemistry. vol. 36, No. 45, 1997, pp. 13954-13962.
Kumar, Shiv et al., "Terminal Phosphate Labeled Nucleotides: Synthesis, Applications, and Linker Effect on Incorporation by DNA Polymerases", Nucleosides, Nucleotides and Nucleic Acids vol. 24 Nos. 5-7 2005, 401-408.
Laitala, Ville et al., "Homogeneous Assay Based on Anti-Stokes' Shift Time-Resolved Fluorescence Resonance Energy-Transfer Measurement", Analytical Chem vol. 77. 2005, 1483-1487.
Lee, Harold et al., "The Reopening Rate of the Fingers Domain Is a Determinant of Base Selectivity for RB69 DNA Polymerase", Biochemistry, 48, 2009, 2087-2098.

Marshall, P. N. , "Rules for the visible absorption spectra of halogenated Fluorescein dyes", Histochemical Journal vol. 7, 1975, pp. 299-303.
Meijer, Wilfried et al., "Phi29 Family of Phages", Microbiology and Molecular Biology Reviews, vol. 65, No. 2, 2001, 261-287.
Merriam-Webster, definition of "complex," attached, accessed May 26, 2015, available at http://www.merriam-webster.com/dictionary/complex.
Patel, et al., "Insights into DNA Polymerization Mechanisms from Structure and Function Analysis of HIV-1 Reverse Transcriptase", Biochemistry. vol. 34, No. 16, Apr. 1995, 5351-5363.
PCT/US2010/036755, International Search Report and Written Opinion mailed Jun. 23, 2011,10 pgs.
Pelletier H., et al., "Structures of Ternary Complexes of Rat DNA Polymerase Beta, a DNA Template-Primer, and ddCTP," Science, Jun. 24, 1994, vol. 264, pp. 1891-1903.
Piston, David W. et al., "Fluorescent protein FRET: the good, the bad and the ugly", Trends Biochem. Sci., vol. 32, No. 9, 2007, 407-414.
Rienitz, Axel et al., "On the fidelity of DNA polymerase alpha: the influence of alpha-thio dNTPs, Mn2+ and mismatch repair", Nucleic Acids Research, vol. 13, No. 15, 1985, 5685-5695.
Roberts, K., "Replication," accessed on May 26, 2015 at http://academic.pgcc.edu/.about.kroberts/Lecture/Chapter%207/replication.html.
Roettger, Michelle P. et al., "Mismatched and Matched dNTP Incorporation by DNA Polymerase# Proceed via Analogous Kinetic Pathways", Biochemistry, vol. 47, No. 37, 2008, 9718-9727.
Rothwell, et al., "Structure and Mechanism of DNAPolymerases", Advances in Protein Chemistry, vol. 71, 2005, pp. 401-440.
Ruparel, Hameer, "Design and synthesis of a 3'-O-allyl photocleavable fluorescent nucleotide as a reversible terminator for DNA sequencing by synthesis", PNAS, vol. 102, No. 17, pp. 5932-5937 (Apr. 26, 2005).
Sawaya, Michael et al., "Crystal Structures of Human DNA Polymerase B Complexed with Gapped and Nicked DNA: Evidence for an Induced Fit Mechanism", Biochemistry, 36, 1997, 11205-11215.
Scaringe, Stephen et al., "Novel RNA Synthesis Method Using 5'-0-Silyl-2'-0-orthoester ProtectinQ Groups", J. Am. Chem. Soc., 120, 1998, 11820-11821.
Selvin P.R., "Fluorescence Resonance Energy Transfer Methods in Enzymology," 1995, vol. 246, pp. 300-334.
Seo, Tae Seok et al., "Four-color DNA sequencing by synthesis on a chip using photocleavable fluorescent nucleotides", PNAS, vol. 102, No. 17, 2005, 5926-5931.
Shimkus, M et al., "A chemically cleavable biotinylated nucleotide: Usefulness in the recovery of protein-DNA complexes from avidin affinity columns", PNAS, vol. 82, 1985, pp. 2593-2597.
Socratic, "How does DNA Polymerase Work ", accessed May 26, 2015, available at http://socratic.orQ/questions/how-does-dna-polymerase-work, 2 paQes.
Sood, Anup et al., "Terminal Phosphate-Labeled Nucleotides with Improved Substrate Properties for Homogeneous Nucleic Acid Assays", J. Am. Chem. Soc .. vol. 127, No. 8, 2005, 2394-2395.
Steitz, Thomas , "A mechanism for all polymerases", Nature, vol. 391, 1998, 231-232.
Steitz, Thomas et al., "A general two-metal-ion mechanism for catalytic RNA", Proc. Natl. Acad. Sci. USA, vol. 90, 1993, 6498-6502.
Stryer, "Fluorescence Energy Transfer as a Spectroscopic Ruler", Annual Review of Biochemistry. vol. 47, Jul. 1978, 819-846.
Tsai, Yu-Chih et al., "A New Paradigm for DNA Polymerase Specificity", Biochemistry, vol. 45, No. 32, 2006, 9675-9687.
Turcatti, Gerardo et al., "A new class of cleavable fluorescent nucleotides: synthesis and optimization as reversible terminators for DNA sequencing by synthesis", Nucleic Acids Research, vol. 36, No. 4, e25, 2008, 1-13.
Wang, Mina et al., "Effect of A and B Metal Ion Site Occupancy on Conformational Changes in an RB69 DNA Polymerase Ternary Complex", Biochemistry, 48, 2009, 2075-2086.
Wu, J et al., "3'-O-modified nucleotides as reversible terminators for pyrosequencing", PNAS, vol. 104 (42), 2007, pp. 16462-16467.

(56) References Cited

OTHER PUBLICATIONS

Wu, J et al., "Termination of DNA synthesis by N6-alkylated, not 3'-O-alkylated, photocleavable 2'—deoxyadenosine triphosphates", Nuc Acids Research, vol. 35(19), 2007, pp. 6339-6349.

Wu, P. et al., "Resonance Energy Transfer: Methods and Applications", Anal. Biochem., vol. 218(1), 1994, pp. 1-13.

Yang et al. (Critical Role of Magnesium Ions in DNA Polymerase .beta.'s Closing and Active Site Assembly, J Am Chem Soc. Jul. 14, 2004; 126(27):8441-53).

Zhang, H. et al., "Fluorescence of 2-aminopurine reveals rapid conformational changes in the RB69 DNA polymerase-primer/template complexes upon binding and incorporation of matched deoxynucleoside triphosphates", Nucleic Acids Research, vol. 35, No. 18, 2007, 6052-6062.

Zhong, Xuejun et al., "DNA Polymerase .beta.. 5. Dissecting the Functional Roles of the Two Metal Ions with Cr(III)dTTP", J. Am. Chem. Soc., 120, 1998, 235-236.

* cited by examiner

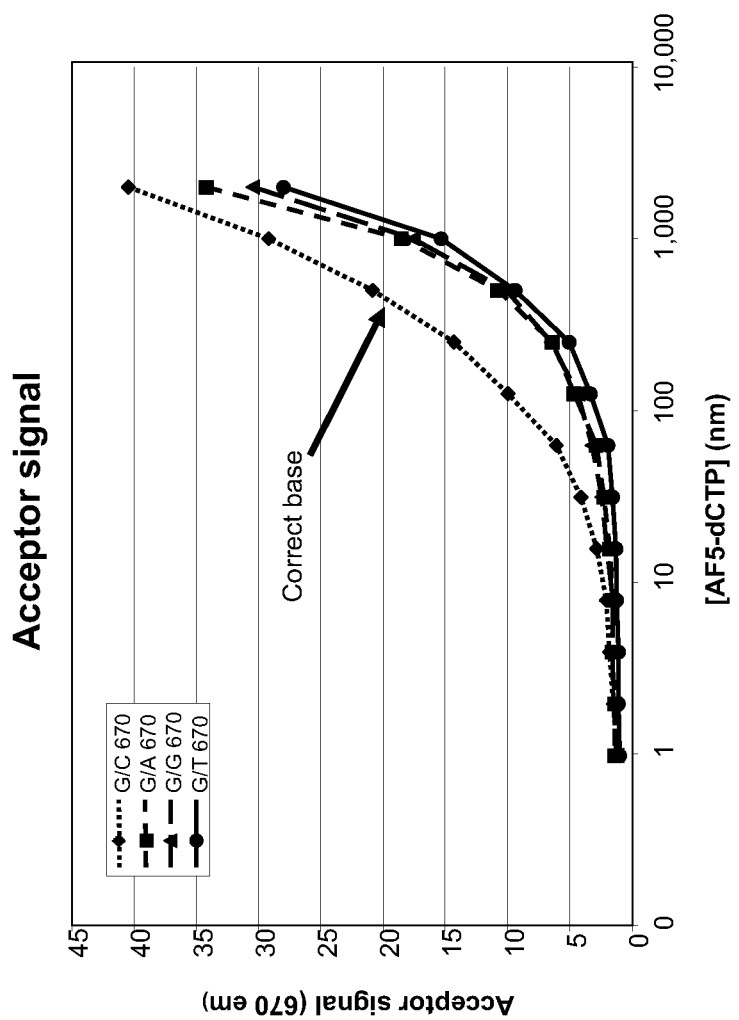

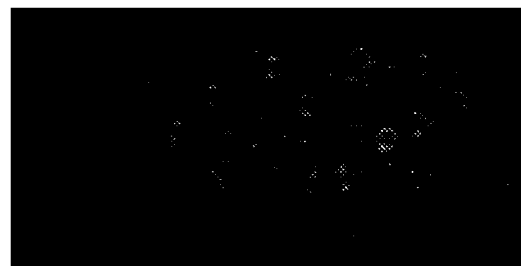
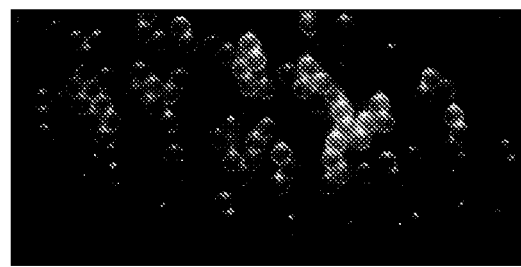
FIG. 3B
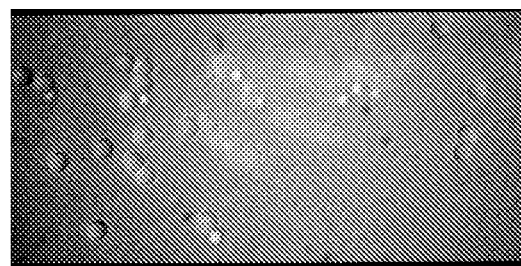
FIG. 3A

```
MKHMPRKMYS CDFETTTKVE DCRVWAYGYM NIEDHSEYKI GNSLDEFMAW VLKVQADLYF
HNLKFDGAFI INWLERNGFK WSADGLPNTY NTIISRMGQW YMIDICLGYK GKRKIHTVIY
DSLKKLPFPV KKIAKDFKLT VLKGDIDYHK ERPVGYKITP EEYAYIKNDI QIIAEALLIQ
FKQGLDRMTA GSDSLKGFKD IITTKKFKKV FPTLSLGLDK EVRYAYRGGF TWLNDRFKEK
EIGEGMVFDV NSLYPAQMYS RLLPYGEPIV FEGKYVWDED YPLHIQHIRC EFELKEGYIP
TIQIKRSRFY KGNEYLKSSG GEIADLWLSN VDLELMKEHY DLYNVEYISG LKFKATTGLF
KDFIDKWTYI KTTSEGAIKQ LAKLMLNSLY GKFASNPDVT GKVPYLKENG ALGFRLGEEE
TKDPVYTPMG VFITAWARYT TITAAQACYD RIIYCDTDSI HLTGTEIPDV IKDIVDPKKL
GYWAHESTFK RAKYLRQKTY IQDIYMKEVD GKLVEGSPDD YTDIKFSVKC AGMTDKIKKE
VTFENFKVGF SRKMKPKPVQ VPGGVVLVDD TFTIK
```

FIG. 4

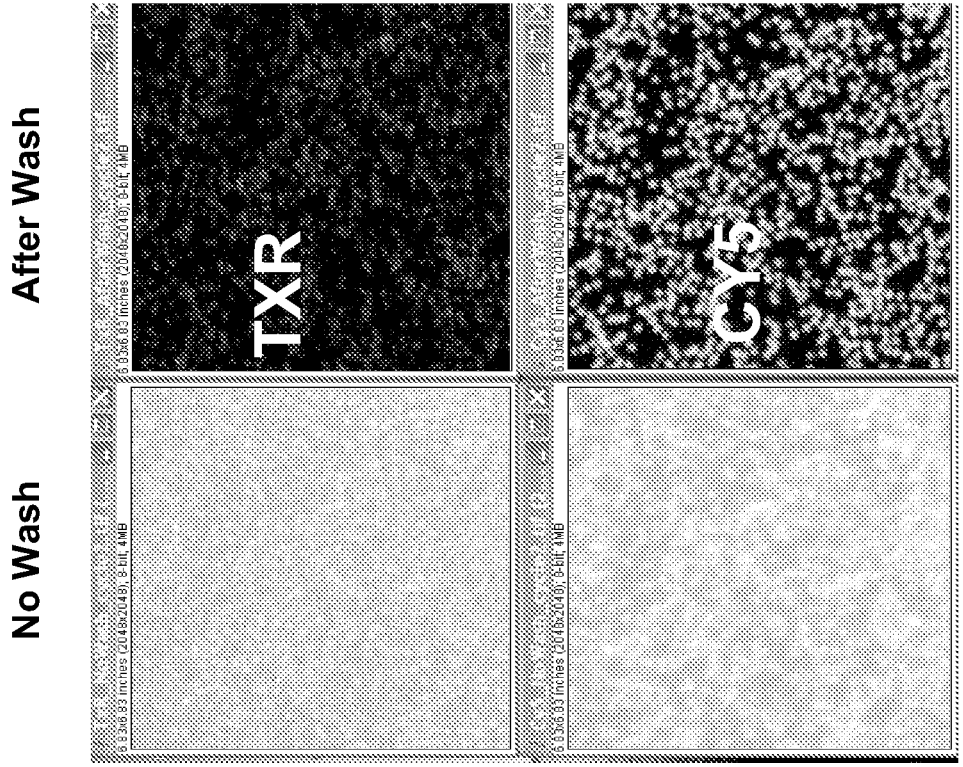
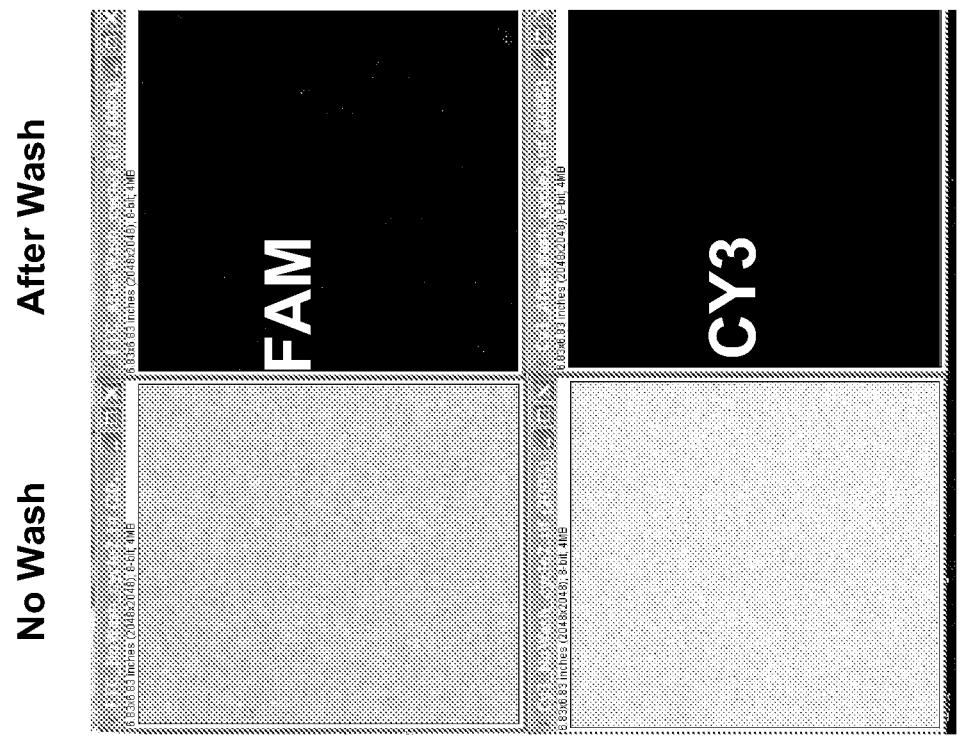
FIG. 14B

MKEFYLTVEQIGDSIFERYIDSNGRERTREVEYKPSLFAHCPESQATKYFDIYGKPCTRK

LFANMRDASQWIKRMEDIGLEALGMDDFKLAYLSDTYNYEIKYDHTKIRVANFDIEVTSP

DGFPEPSQAKHPIDAITHYDSIDDRFYVFDLLNSPYGNVEEWSIEIAAKLQEQGGDEVPS

EIIDKIIYMPFDNEKELLMEYLNFWQQKTPVILTGWNVESFDIPYVYNRIKNIFGESTAK

RLSPHRKTRVKVIENMYGSREIITLFGISVLDYIDLYKKFSFTNQPSYSLDYISEFELNV

GKLKYDGPISKLRESNHQRYISYNIIDVYRVLQIDAKRQFINLSLDMGYYAKIQIQSVFS

PIKTWDAIIFNSLKEQNKVIPQGRSHPVQPYPGAFVKEPIPNRYKYVMSFDLTSLYPSII

RQVNISPETIAGTFKVAPLHDYINAVAERPSDVYSCSPNGMMYYKDRDGVVPTEITKVFN

QRKEHKGYMLAAQRNGEIIKEALHNPNLSVDEPLDVDYRFDFSDEIKEKIKKLSAKSLNE

MLFRAQRTEVAGMTAQINRKLLINSLYGALGNVWFRYYDLRNATAITTFGQMALQWIERK

VNEYLNEVCGTEGEAFVLYGDTDSIYVSADKIIDKVGESKFRDTNHWVDFLDKFARERME

PAIDRGFREMCEYMNNKQHLMFMDREAIAGPPLGSKGIGGFWTGKKRYALNVWDMEGTRY

AEPKLKIMGLETQKSSTPKAVQKALKECIRRMLQEGEESLQEYFKEFEKEFRQLNYISIA

SVSSANNIAKYDVGGFPGPKCPFHIRGILTYNRAIKGNIDAPQVVEGEKVYVLPLREGNP

FGDKCIAWPSGTEITDLIKDDVLHWMDYTVLLEKTFIKPLEGFTSAAKLDYEKKASLFDM

FDF

FIG. 18

```
  1 MPRKMFSCDFETTTKLDDCRVWAYGYMEIGNLDNYKIGNSLDEFMQWVMEIQADLYFHNL
 61 KFDGAFIVNWLEHHGFKWSNEGLPNTYNTIISKMGQWYMIDICFGYKGKRKLHTVIYDSL
121 KKLPFPVKKIAKDFQLPLLKGDIDYHAERPVGHEITPEEYEYIKNAIEIIARALDIQFKQ
181 GLDRMTAGSDSLKGFKDILSTKKFNKVFPKLSLPMDKEIRRAYRGGFTWLNDKYKEKEIG
241 EGMVFDVNSLYPSQMYSRPLPYGAPIVFQGKYEKDEQYPLYIQRIRFEFELKEGYIPTIQ
301 IKKNPFFKGNEYLKNSGAEPVELYLTNVDLELIQEHYEMYNVEYIDGFKFREKTGLFKEF
361 IDKWTYVKTHEKGAKKQLAKLMLNSLYGKFASNPDVTGKVPYLKEDGSLGFRVGDEEYKD
421 PVYTPMGVFITAWARFTTITAAQACYDRIIYCDTDSIHLTGTEVPEIIKDIVDPKKLGYW
481 AHESTFKRAKYLRQKTYIQDIYAKEVDGKLIECSPDEATTTKFSVKCAGMTDTIKKKVTF
541 DNFRVGFSSTGKPKPVQVNGGVVLVDSVFTIK
```

FIG. 19

```
ATGAAAGAATTTTACTTAACGGTTGAACAGATTGGTGATTCAATTTTTGAACGTTACATC
 M  K  E  F  Y  L  T  V  E  Q  I  G  D  S  I  F  E  R  Y  I

GATTCTAATGGCCGTGAACGTACTCGTGAAGTAGAATATAAACCATCACTGTTTGCTCAT
 D  S  N  G  R  E  R  T  R  E  V  E  Y  K  P  S  L  F  A  H

TGTCCAGAAAGTCAGGCTACGAAATATTTCGATATCTACGGTAAACCGTGTACTCGTAAG
 C  P  E  S  Q  A  T  K  Y  F  D  I  Y  G  K  P  C  T  R  K

TTGTTCGCTAATATGCGTGATGCCTCCCAATGGATTAAACGCATGGAAGATATCGGACTT
 L  F  A  N  M  R  D  A  S  Q  W  I  K  R  M  E  D  I  G  L

GAAGCACTTGGCATGGACGATTTCAAATTGGCGTATTTGTCTGACACTTATAACTATGAA
 E  A  L  G  M  D  D  F  K  L  A  Y  L  S  D  T  Y  N  Y  E

ATCAAATACGACCATACAAAAATTCGTGTGGCTAACTTCGACATCGAAGTAACATCTCCG
 I  K  Y  D  H  T  K  I  R  V  A  N  F  D  I  E  V  T  S  P

GATGGGTTCCCTGAGCCGTCACAAGCAAAACATCCGATTGATGCTATCACCCATTATGAC
 D  G  F  P  E  P  S  Q  A  K  H  P  I  D  A  I  T  H  Y  D

TCAATTGACGACAGGTTCTACGTATTTGATCTATTGAATTCTCCATATGGTAATGTAGAA
 S  I  D  D  R  F  Y  V  F  D  L  L  N  S  P  Y  G  N  V  E

GAATGGTCTATTGAAATCGCTGCTAAGCTTCAAGAACAAGGTGGTGATGAAGTTCCATCT
 E  W  S  I  E  I  A  A  K  L  Q  E  Q  G  G  D  E  V  P  S

GAAATTATTGATAAAATCATTTATATGCCGTTCGATAACGAAAAGAATTGTTGATGGAA
 E  I  I  D  K  I  I  Y  M  P  F  D  N  E  K  E  L  L  M  E

TATCTCAACTTCTGGCAACAGAAAACTCCTGTCATTTTGACTGGATGGAACGTTGAGTCA
 Y  L  N  F  W  Q  Q  K  T  P  V  I  L  T  G  W  N  V  E  S

TTTGATATTCCGTACGTGTATAACCGAATCAAGAATATTTTTGGCGAATCAACTGCGAAA
 F  D  I  P  Y  V  Y  N  R  I  K  N  I  F  G  E  S  T  A  K

CGTTTATCACCACATCGTAAAACTCGTGTTAAAGTTATCGAAAACATGTATGGTTCTCGT
 R  L  S  P  H  R  K  T  R  V  K  V  I  E  N  M  Y  G  S  R

GAAATCATTACATTGTTCGGTATCTCTGTTCTTGATTACATTGACCTTTACAAAAAATTC
 E  I  I  T  L  F  G  I  S  V  L  D  Y  I  D  L  Y  K  K  F

TCTTTTACCAATCAACCGTCGTATTCTCTGGATTACATTTCAGAATTTGAATTGAACGTT
 S  F  T  N  Q  P  S  Y  S  L  D  Y  I  S  E  F  E  L  N  V
```

FIG. 20A

```
GGTAAACTGAAATATGACGGCCCTATTTCTAAGCTTCGTGAAAGCAATCACCAACGATAT
G  K  L  K  Y  D  G  P  I  S  K  L  R  E  S  N  H  Q  R  Y

ATTTCTTATAACATTATCGACGTGTATCGTGTATTGCAAATTGATGCTAAGCGTCAGTTC
I  S  Y  N  I  I  D  V  Y  R  V  L  Q  I  D  A  K  R  Q  F

ATCAACTTGAGTTTGGACATGGGTTATTATGCTAAGATACAGATTCAATCTGTGTTTAGC
I  N  L  S  L  D  M  G  Y  Y  A  K  I  Q  I  Q  S  V  F  S

CCAATTAAAACATGGGATGCTATTATTTTTAATAGCCTTAAAGAGCAGAACAAGGTGATT
P  I  K  T  W  D  A  I  I  F  N  S  L  K  E  Q  N  K  V  I

CCACAAGGTCGTTCTCACCCGGTTCAACCTTATCCGGCGCTTTTGTTAAGGAACCTATT
P  Q  G  R  S  H  P  V  Q  P  Y  P  G  A  F  V  K  E  P  I

CCAAATCGATACAAATATGTAATGAGTTTCGACCTTACATCTCTATATCCAAGTATTATT
P  N  R  Y  K  Y  V  M  S  F  D  L  T  S  L  Y  P  S  I  I

CGCCAAGTGAATATTAGCCCAGAAACAATAGCAGGAACGTTTAAAGTAGCTCCATTGCAT
R  Q  V  N  I  S  P  E  T  I  A  G  T  F  K  V  A  P  L  H

GATTATATTAACGCTGTTGCTGAACGTCCTTCTGATGTGTACAGTTGTTCTCCTAACGGC
D  Y  I  N  A  V  A  E  R  P  S  D  V  Y  S  C  S  P  N  G

ATGATGTATTATAAAGACCGTGATGGTGTAGTTCCAACTGAAATCACTAAGGTCTTTAAT
M  M  Y  Y  K  D  R  D  G  V  V  P  T  E  I  T  K  V  F  N

CAACGTAAAGAACATAAAGGTTACATGCTTGCAGCTCAACGTAATGGTGAAATAATTAAA
Q  R  K  E  H  K  G  Y  M  L  A  A  Q  R  N  G  E  I  I  K

GAGGCATTGCATAATCCTAATCTTTCTGTTGACGAACCATTAGATGTTGATTATCGTTTC
E  A  L  H  N  P  N  L  S  V  D  E  P  L  D  V  D  Y  R  F

GACTTCAGCGATGAGATTAAAGAAAAGATTAAAAAGTTGTCTGCTAAATCTCTTAATGAA
D  F  S  D  E  I  K  E  K  I  K  K  L  S  A  K  S  L  N  E

ATGTTGTTTAGAGCTCAACGTACTGAAGTTGCAGGTATGACTGCACAAATTAACCGTAAA
M  L  F  R  A  Q  R  T  E  V  A  G  M  T  A  Q  I  N  R  K

TTGCTTATCAACTCACTTTATGGTGCACTTGGCAACGTTTGGTTCCGTTATTATGATTTG
L  L  I  N  S  L  Y  G  A  L  G  N  V  W  F  R  Y  Y  D  L

CGTAATGCTACTGCAATCACAACATTCGGGCAAATGGCTTTACAGTGGATTGAACGTAAA
R  N  A  T  A  I  T  T  F  G  Q  M  A  L  Q  W  I  E  R  K
```

FIG. 20B

```
GTTAATGAATATCTGAATGAAGTTTGTGGTACAGAAGGTGAAGCTTTCGTTCTTTATGGT
 V  N  E  Y  L  N  E  V  C  G  T  E  G  E  A  F  V  L  Y  G

GATACAGACTCTATTTACGTATCTGCTGATAAAATTATCGATAAGGTTGGTGAATCTAAA
 D  T  D  S  I  Y  V  S  A  D  K  I  I  D  K  V  G  E  S  K

TTCCGTGATACCAACCATTGGGTAGACTTCTTAGATAAGTTTGCACGTGAACGTATGGAA
 F  R  D  T  N  H  W  V  D  F  L  D  K  F  A  R  E  R  M  E

CCAGCTATTGATAGAGGTTTCCGTGAAATGTGTGAATACATGAACAATAAACAACACTTA
 P  A  I  D  R  G  F  R  E  M  C  E  Y  M  N  N  K  Q  H  L

ATGTTCATGGACCGAGAAGCTATCGCTGGGCCTCCGCTTGGTTCTAAAGGTATTGGCGGA
 M  F  M  D  R  E  A  I  A  G  P  P  L  G  S  K  G  I  G  G

TTTTGGACTGGTAAGAAACGTTATGCATTAAACGTGTGGGATATGGAAGGTACTCGTTAC
 F  W  T  G  K  K  R  Y  A  L  N  V  W  D  M  E  G  T  R  Y

GCTGAGCCTAAACTCAAAATCATGGGTCTAGAGACTCAGAAATCTTCGACTCCTAAAGCA
 A  E  P  K  L  K  I  M  G  L  E  T  Q  K  S  S  T  P  K  A

GTACAGAAAGCTCTTAAAGAATGTATTCGTCGTATGCTTCAAGAAGGTGAAGAATCATTA
 V  Q  K  A  L  K  E  C  I  R  R  M  L  Q  E  G  E  E  S  L

CAAGAATATTTTAAAGAGTTTGAAAAGAATTCCGTCAATTGAATTATATTAGCATCGCG
 Q  E  Y  F  K  E  F  E  K  E  F  R  Q  L  N  Y  I  S  I  A

TCGGTATCTTCTGCGAATAACATTGCTAAATATGACGTAGGTGGATTCCCTGGTCCCAAA
 S  V  S  S  A  N  N  I  A  K  Y  D  V  G  G  F  P  G  P  K

TGCCCGTTCCATATTCGTGGAATTCTGACATATAACCGAGCTATCAAAGGTAATATTGAT
 C  P  F  H  I  R  G  I  L  T  Y  N  R  A  I  K  G  N  I  D

GCACCACAAGTTGTAGAAGGTGAAAAAGTATATGTTCTGCCTTTACGTGAAGGAAACCCA
 A  P  Q  V  V  E  G  E  K  V  Y  V  L  P  L  R  E  G  N  P

TTCGGTGATAAATGTATCGCATGGCCTTCTGGTACTGAAATCACAGATTTAATTAAAGAC
 F  G  D  K  C  I  A  W  P  S  G  T  E  I  T  D  L  I  K  D

GACGTACTTCATTGGATGGACTACACTGTTCTCCTTGAGAAGACATTTATTAAACCACTT
 D  V  L  H  W  M  D  Y  T  V  L  L  E  K  T  F  I  K  P  L

GAAGGATTCACATCAGCAGCGAAACTCGATTACGAGAAGAAAGCATCTCTGTTCGATATG
 E  G  F  T  S  A  A  K  L  D  Y  E  K  K  A  S  L  F  D  M

TTCGATTTT
 F  D  F
```

FIG. 20C

```
ATGAAAGAATTTTACTTAACGGTTGAACAGATTGGTGATTCAATTTTTGAACGTTACATC
 M   K   E   F   Y   L   T   V   E   Q   I   G   D   S   I   F   E   R   Y   I

GATTCTAATGGCCGTGAACGTACTCGTGAAGTAGAATATAAACCATCACTGTTTGCTCAT
 D   S   N   G   R   E   R   T   R   E   V   E   Y   K   P   S   L   F   A   H

TGTCCAGAAAGTCAGGCTACGAAATATTTCGATATCTACGGTAAACCGTGTACTCGTAAG
 C   P   E   S   Q   A   T   K   Y   F   D   I   Y   G   K   P   C   T   R   K

TTGTTCGCTAATATGCGTGATGCCTCCCAATGGATTAAACGCATGGAAGATATCGGACTT
 L   F   A   N   M   R   D   A   S   Q   W   I   K   R   M   E   D   I   G   L

GAAGCACTTGGCATGGACGATTTCAAATTGGCGTATTTGTCTGACACTTATAACTATGAA
 E   A   L   G   M   D   D   F   K   L   A   Y   L   S   D   T   Y   N   Y   E

ATCAAATACGACCATACAAAAATTCGTGTGGCTAACTTCGACATCGAAGTAACATCTCCG
 I   K   Y   D   H   T   K   I   R   V   A   N   F   D   I   E   V   T   S   P

GATGGGTTCCCTGAGCCGTCACAAGCAAAACATCCGATTGATGCTATCACCCATTATGAC
 D   G   F   P   E   P   S   Q   A   K   H   P   I   D   A   I   T   H   Y   D

TCAATTGACGACAGGTTCTACGTATTTGATCTATTGAATTCTCCATATGGTAATGTAGAA
 S   I   D   D   R   F   Y   V   F   D   L   L   N   S   P   Y   G   N   V   E

GAATGGTCTATTGAAATCGCTGCTAAGCTTCAAGAACAAGGTGGTGATGAAGTTCCATCT
 E   W   S   I   E   I   A   A   K   L   Q   E   Q   G   G   D   E   V   P   S

GAAATTATTGATAAAATCATTTATATGCCGTTCGATAACGAAAAGAATTGTTGATGGAA
 E   I   I   D   K   I   I   Y   M   P   F   D   N   E   K   E   L   L   M   E

TATCTCAACTTCTGGCAACAGAAAACTCCTGTCATTTTGACTGGATGGAACGTTGAGTCA
 Y   L   N   F   W   Q   Q   K   T   P   V   I   L   T   G   W   N   V   E   S

TTTGCTATTCCGTACGTGTATAACCGAATCAAGAATATTTTTGGCGAATCAACTGCGAAA
 F   A   I   P   Y   V   Y   N   R   I   K   N   I   F   G   E   S   T   A   K

CGTTTATCACCACATCGTAAAACTCGTGTTAAAGTTATCGAAAACATGTATGGTTCTCGT
 R   L   S   P   H   R   K   T   R   V   K   V   I   E   N   M   Y   G   S   R

GAAATCATTACATTGTTCGGTATCTCTGTTCTTGATTACATTGACCTTTACAAAAAATTC
 E   I   I   T   L   F   G   I   S   V   L   D   Y   I   D   L   Y   K   K   F

TCTTTTACCAATCAACCGTCGTATTCTCTGGATTACATTTCAGAATTTGAATTGAACGTT
 S   F   T   N   Q   P   S   Y   S   L   D   Y   I   S   E   F   E   L   N   V
```

FIG. 21A

```
GGTAAACTGAAATATGACGGCCCTATTTCTAAGCTTCGTGAAAGCAATCACCAACGATAT
 G  K  L  K  Y  D  G  P  I  S  K  L  R  E  S  N  H  Q  R  Y

ATTTCTTATAACATTATCGCTGTGTATCGTGTATTGCAAATTGATGCTAAGCGTCAGTTC
 I  S  Y  N  I  I  A  V  Y  R  V  L  Q  I  D  A  K  R  Q  F

ATCAACTTGAGTTTGGACATGGGTTATTATGCTAAGATACAGATTCAATCTGTGTTTAGC
 I  N  L  S  L  D  M  G  Y  Y  A  K  I  Q  I  Q  S  V  F  S

CCAATTAAAACATGGGATGCTATTATTTTTAATAGCCTTAAAGAGCAGAACAAGGTGATT
 P  I  K  T  W  D  A  I  I  F  N  S  L  K  E  Q  N  K  V  I

CCACAAGGTCGTTCTCACCCGGTTCAACCTTATCCCGGCGCTTTTGTTAAGGAACCTATT
 P  Q  G  R  S  H  P  V  Q  P  Y  P  G  A  F  V  K  E  P  I

CCAAATCGATACAAATATGTAATGAGTTTCGACCTTACATCTTCAGCTGTAAGTATTATT
 P  N  R  Y  K  Y  V  M  S  F  D  L  T  S  S  A  V  S  I  I

CGCCAAGTGAATATTAGCCCAGAAACAATAGCAGGAACGTTTAAAGTAGCTCCATTGCAT
 R  Q  V  N  I  S  P  E  T  I  A  G  T  F  K  V  A  P  L  H

GATTATATTAACGCTGTTGCTGAACGTCCTTCTGATGTGTACAGTTGTTCTCCTAACGGC
 D  Y  I  N  A  V  A  E  R  P  S  D  V  Y  S  C  S  P  N  G

ATGATGTATTATAAAGACCGTGATGGTGTAGTTCCAACTGAAATCACTAAGGTCTTTAAT
 M  M  Y  Y  K  D  R  D  G  V  V  P  T  E  I  T  K  V  F  N

CAACGTAAAGAACATAAAGGTTACATGCTTGCAGCTCAACGTAATGGTGAAATAATTAAA
 Q  R  K  E  H  K  G  Y  M  L  A  A  Q  R  N  G  E  I  I  K

GAGGCATTGCATAATCCTAATCTTTCTGTTGACGAACCATTAGATGTTGATTATCGTTTC
 E  A  L  H  N  P  N  L  S  V  D  E  P  L  D  V  D  Y  R  F

GACTTCAGCGATGAGATTAAAGAAAAGATTAAAAAGTTGTCTGCTAAATCTCTTAATGAA
 D  F  S  D  E  I  K  E  K  I  K  K  L  S  A  K  S  L  N  E

ATGTTGTTTAGAGCTCAACGTACTGAAGTTGCAGGTATGACTGCACAAATTAACCGTAAA
 M  L  F  R  A  Q  R  T  E  V  A  G  M  T  A  Q  I  N  R  K

TTGCTTATCAACTCACTTTATGGTGCACTTGGCAACGTTTGGTTCCGTTATTATGATTTG
 L  L  I  N  S  L  Y  G  A  L  G  N  V  W  F  R  Y  Y  D  L

CGTAATGCTACTGCAATCACAACATTCGGGCAAATGGCTTTACAGTGGATTGAACGTAAA
 R  N  A  T  A  I  T  T  F  G  Q  M  A  L  Q  W  I  E  R  K
```

FIG. 21B

```
GTTAATGAATATCTGAATGAAGTTTGTGGTACAGAAGGTGAAGCTTTCGTTCTTTATGGT
 V  N  E  Y  L  N  E  V  C  G  T  E  G  E  A  F  V  L  Y  G

GATACAGACTCTATTTACGTATCTGCTGATAAAATTATCGATAAGGTTGGTGAATCTAAA
 D  T  D  S  I  Y  V  S  A  D  K  I  I  D  K  V  G  E  S  K

TTCCGTGATACCAACCATTGGGTAGACTTCTTAGATAAGTTTGCACGTGAACGTATGGAA
 F  R  D  T  N  H  W  V  D  F  L  D  K  F  A  R  E  R  M  E

CCAGCTATTGATAGAGGTTTCCGTGAAATGTGTGAATACATGAACAATAAACAACACTTA
 P  A  I  D  R  G  F  R  E  M  C  E  Y  M  N  N  K  Q  H  L

ATGTTCATGGACCGAGAAGCTATCGCTGGGCCTCCGCTTGGTTCTAAAGGTATTGGCGGA
 M  F  M  D  R  E  A  I  A  G  P  P  L  G  S  K  G  I  G  G

TTTTGGACTGGTAAGAAACGTTATGCATTAAACGTGTGGGATATGGAAGGTACTCGTTAC
 F  W  T  G  K  K  R  Y  A  L  N  V  W  D  M  E  G  T  R  Y

GCTGAGCCTAAACTCAAAATCATGGGTCTAGAGACTCAGAAATCTTCGACTCCTAAAGCA
 A  E  P  K  L  K  I  M  G  L  E  T  Q  K  S  S  T  P  K  A

GTACAGAAAGCTCTTAAAGAATGTATTCGTCGTATGCTTCAAGAAGGTGAAGAATCATTA
 V  Q  K  A  L  K  E  C  I  R  R  M  L  Q  E  G  E  E  S  L

CAAGAATATTTTAAAGAGTTTGAAAAGAATTCCGTCAATTGAATTATATTAGCATCGCG
 Q  E  Y  F  K  E  F  E  K  E  F  R  Q  L  N  Y  I  S  I  A

TCGGTATCTTCTGCGAATAACATTGCTAAATATGACGTAGGTGGATTCCCTGGTCCCAAA
 S  V  S  S  A  N  N  I  A  K  Y  D  V  G  G  F  P  G  P  K

TGCCCGTTCCATATTCGTGGAATTCTGACATATAACCGAGCTATCAAAGGTAATATTGAT
 C  P  F  H  I  R  G  I  L  T  Y  N  R  A  I  K  G  N  I  D

GCACCACAAGTTGTAGAAGGTGAAAAAGTATATGTTCTGCCTTTACGTGAAGGAAACCCA
 A  P  Q  V  V  E  G  E  K  V  Y  V  L  P  L  R  E  G  N  P

TTCGGTGATAAATGTATCGCATGGCCTTCTGGTACTGAAATCACAGATTTAATTAAAGAC
 F  G  D  K  C  I  A  W  P  S  G  T  E  I  T  D  L  I  K  D

GACGTACTTCATTGGATGGACTACACTGTTCTCCTTGAGAAGACATTTATTAAACCACTT
 D  V  L  H  W  M  D  Y  T  V  L  L  E  K  T  F  I  K  P  L

GAAGGATTCACATCAGCAGCGAAACTCGATTACGAGAAGAAAGCATCTCTGTTCGATATG
 E  G  F  T  S  A  A  K  L  D  Y  E  K  K  A  S  L  F  D  M

TTCGATTTT
 F  D  F
```

FIG. 21C

NUCLEOTIDE TRANSIENT BINDING FOR SEQUENCING METHODS

This application is a continuation application of U.S. application Ser. No. 16/825,788, filed Mar. 20, 2020, which is a continuation of U.S. application Ser. No. 15/690,945, filed Aug. 30, 2017, now U.S. Pat. No. 10,597,642; which is a divisional application of U.S. application Ser. No. 14/991,230, filed Jan. 8, 2016, now U.S. Pat. No. 9,765,310; which is a continuation application of U.S. application Ser. No. 14/108,166, filed Dec. 16, 2013, now U.S. Pat. No. 9,255,258; which is a continuation application of U.S. application Ser. No. 12/790,760, filed May 28, 2010, now U.S. Pat. No. 8,632,975; which claims the benefit of priority under 35 U.S.C. § 119 to U.S. Provisional Application Nos.: 61/184,774, filed on Jun. 5, 2009; 61/242,762, filed on Sep. 15, 2009; 61/263,320, filed on Nov. 20, 2009; and 61/295,533, filed on Jan. 15, 2010. The contents of each foregoing patent applications are incorporated by reference in their entirety.

Throughout this application various publications are referenced. The disclosures of these publications in their entireties are hereby incorporated by reference into this application in order to more fully describe the state of the art to which this invention pertains.

This application contains a Sequence Listing which has been submitted via EFS-Web and is hereby incorporated by reference in its entirety. The ASCII copy was created on Jul. 9, 2010, and is named LT00034.txt, and is 68,256 bytes in size. The XML copy was created on Nov. 8, 2022, and is named TP103243USCON4.xml, and is 99,375 bytes in size.

FIELD

Provided herein are polymerase-dependent, nucleotide identification methods using any reaction condition under which a complementary nucleotide is transiently-bound to a polymerase in a template-dependent manner. The frequency and duration of the transiently-bound nucleotide differs for complementary compared to non-complementary nucleotides, and this difference can be used to identify the template nucleotide. The sequence of the template molecule can be deduced from obtaining the sequence of transiently-bound labeled nucleotides in successive transient-binding reactions.

BACKGROUND

Nucleic acid sequence information is an important starting point for medical and academic research endeavors. The sequence information facilitates medical studies of active disease, genetic disease predispositions, and assists in rational design of drugs that target specific diseases. Sequence information is also the basis for genomic and evolutionary studies, and many genetic engineering applications. Reliable sequence information is also critical for paternity tests, criminal investigations, and forensic studies.

Nucleic acid sequence information was typically obtained using chain termination and size separation procedures, such as those described by Sanger, et al., (1977 Proc. Nat. Acad. Sci. USA 74:5463-5467). Prior to gel separation, the nucleic acid template molecules of interest are cloned, amplified, and isolated. Then the sequencing reactions are conducted in four separate reaction vessels, one for each nucleotide: A, G, C and T. These sequencing methods are adequate for read lengths of 500-1,000 nucleotides. However, they require template molecule amplification steps which are known to be error-prone which can jeopardize acquiring reliable sequence information. Furthermore, and these methods suffer from sequence-dependent artifacts including band compression of repetitive sequences and homo-polymeric regions during gel separation.

The technological advances in chemistry, automated sequencing machines, fluorescently-labeled nucleotides, and detection systems, have improved the read lengths, and permit massively parallel sequencing runs for high throughput methods which do not require gel separation.

Other recently developed techniques include single molecule sequencing methods which typically employ optical detection and resolution of signals from fluorescently-labeled nucleotides during polymerase-catalyzed nucleotide incorporation onto the extending nucleic acid strand. But these procedures suffer from inaccurate reads of regions containing highly repetitive sequences and homo-polymeric regions. Furthermore, read errors can be introduced which are caused by the incorporation of non-detectable nucleotides (e.g., unlabeled or attached to a non-fluorescent dye molecule).

The compositions, systems, and methods provided herein overcome many problems associated with current nucleotide incorporation procedures. The methods provided herein rely on nucleotide transient-binding to the polymerase, instead of nucleotide incorporation. For example, in one step, a labeled nucleotide transiently-binds the polymerase in a template-dependent manner, but does not incorporate. The transiently-bound nucleotide emits a signal which can be used to identify the nucleotide. The methods provided herein can provide accurate sequence information of repetitive and homo-polymeric regions. The methods provided herein are readily adaptable for use in existing single molecule and bulk sequencing platforms making it feasible to deliver sequence information as part of a healthcare or forensic program.

SUMMARY

Provided herein are methods for identifying a nucleotide by polymerase-dependent transient-binding of the complementary nucleotide. The methods can be practiced for determining the sequence of a nucleic acid molecule or for SNP analysis. The methods involve detecting the presence of a transiently-bound nucleotide.

In one embodiment, the disclosed relates to methods for identifying a nucleotide bound to a polymerase, comprising the steps of: (a) contacting at least one type of a labeled nucleotide to an immobilized complex having a polymerase bound to a template nucleic acid molecule which is bound to a polymerization initiation site, under suitable conditions to transiently-bind the at least one type of labeled nucleotide to the polymerase in a nucleic acid template-dependent manner and to inhibit nucleotide polymerization by the polymerase; (b) exciting the labeled nucleotide with an excitation source; (c) detecting a signal, or a change in a signal, from the transiently-bound labeled nucleotide; and (d) identifying the nucleotide transiently-bound to the polymerase.

The suitable conditions in step (a) comprise any combination of: (i) reducing the levels or omission of a metal cation that permits nucleotide incorporation and/or addition of a cation that inhibits nucleotide incorporation; (ii) using a polymerase which selectively binds the nucleotide in a template-dependent manner and exhibits reduced nucleotide incorporation activity; (iii) using at least one type of labeled nucleotide which is a labeled non-incorporatable nucleotide; and/or (iv) using a polymerization initiation site which is a non-extendible polymerization initiation site.

The method can further comprise the steps of: (c) removing the transiently-bound nucleotide; and (f) contacting the complex with at least one type of nucleotide under suitable conditions for the polymerase to polymerize the nucleotide.

The suitable conditions in step (f) comprise: (i) including a metal cation that permits nucleotide incorporation and/or reducing the levels or omission of a cation that inhibits nucleotide incorporation; (ii) using a polymerase which selectively binds the nucleotide in a template-dependent manner and polymerizes the bound nucleotide; (iii) using at least one type of incorporatable nucleotide; and/or (iv) using a polymerization initiation site having an extendible polymerization initiation site.

In another embodiment, the disclosed relates to methods for identifying a nucleotide bound to a polymerase, comprising the steps of: (a) contacting at least one type of a labeled nucleotide to an immobilized complex having a first polymerase bound to a template nucleic acid molecule which is bound to a polymerization initiation site, under suitable conditions to transiently-bind the at least one type of labeled nucleotide to the polymerase in a nucleic acid template-dependent manner and to inhibit nucleotide polymerization by the polymerase; (b) exciting the labeled nucleotide with an excitation source; (c) detecting a signal, or a change in a signal, from the transiently-bound labeled nucleotide; and (d) identifying the nucleotide transiently-bound to the polymerase.

The suitable conditions in step (a) comprise: (i) reducing the levels or omission of a metal cation that permits nucleotide incorporation and/or addition of a cation that inhibits nucleotide incorporation; (ii) using a polymerase which selectively binds the nucleotide in a template-dependent manner and exhibits reduced nucleotide incorporation activity; (iii) using at least one type of labeled nucleotide which is a labeled non-incorporatable nucleotide; and/or (iv) using a polymerization initiation site which is a non-extendible polymerization initiation site.

The polymerization initiation site can be a 3' terminal end of a nucleic acid primer molecule or a 3' terminal end of a self-priming template nucleic acid molecule.

The method can further comprise the steps of: (c) removing the first polymerase and the transiently-bound nucleotide so that the template nucleic acid molecule, nucleic acid primer molecule or self-priming template nucleic acid molecule remains immobilized to the surface; (f) binding the remaining template nucleic acid molecule with a second polymerase; and (g) contacting the second polymerase with at least one type of nucleotide under suitable conditions for the second polymerase to polymerize the nucleotide.

The suitable conditions in step (g) comprise: (i) including a metal cation that permits nucleotide incorporation and/or reducing the levels or omission of a cation that inhibits nucleotide incorporation; (ii) using a polymerase which selectively binds the nucleotide in a template-dependent manner and polymerizes the bound nucleotide; (iii) using at least one type of incorporatable nucleotide; and/or (iv) using a polymerization initiation site having an extendible polymerization initiation site.

DESCRIPTION OF THE DRAWINGS

FIG. 2A shows data from a FRET-based nucleotide transient-binding assay (Example 2).

FIG. 3A shows data from a bead-immobilized, nucleotide transient-binding assay (Example 3).

FIG. 3B shows data from a bead-immobilized, nucleotide transient-binding assay (Example 3).

FIG. 4 shows the amino acid sequence of phi29 polymerase (SEQ ID NO:1).

FIG. 14B shows transient binding reactions using the P2-1 primer, Klenow fragment, and labeled nucleotides, in the presence of calcium (Example 11).

FIG. 18 shows the amino acid sequence of RB69 (exo-) polymerase (SEQ ID NO:2).

FIG. 19 shows the amino acid sequence of B103 (exo-) polymerase (SEQ ID NO:3).

FIGS. 20A-C show aligned nucleotide and amino acid sequence of native RB69 polymerase, where the underlined and bolded regions represent the various mutated positions (SEQ ID NO:4).

FIGS. 21A-C show the amino acid sequence of 3PDX, an RB69 mutant polymerase (SEQ ID NO:5).

DETAILED DESCRIPTION

Figure 1:
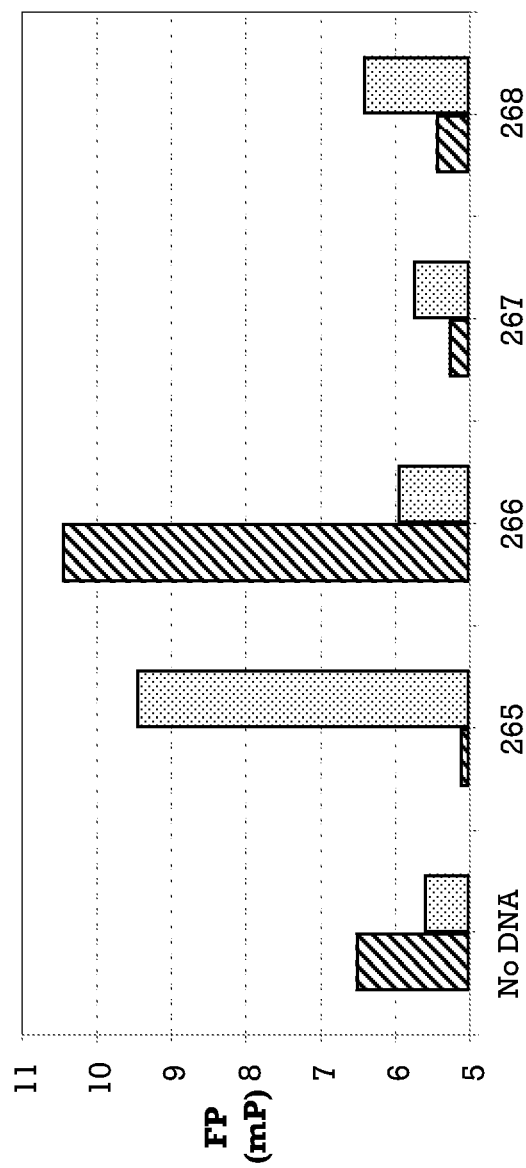
FIG. 1 shows data from a fluorescent polarization assay (Example 1).

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein which is contrary to or otherwise inconsistent with any definition set forth in the patents, patent applications, published applications, and other publications that are herein incorporated by reference, the definition and/or description set forth herein prevails over the definition that is incorporated by reference.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, *Molecular Cloning: A Laboratory Manual*, Third Edition; Ausubel, F. M., et al., eds., 2002, *Short Protocols In Molecular Biology*, Fifth Edition.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, unrecited additives, components, integers, elements or method steps.

As used herein, the terms "a," "an," and "the" and similar referents used herein are to be construed to cover both the singular and the plural unless their usage in context indicates otherwise. Accordingly, the use of the word "a" or "an" when used in the claims or specification, including when used in conjunction with the term "comprising", may mean "one," but it is also consistent with the meaning of "one or more." "at least one," and "one or more than one."

As used herein, the terms "link", "linked", "linkage", "operably linked", and variants thereof comprise any type of fusion, bond, adherence or association between any combination of compounds or molecules that is of sufficient stability to withstand use in the particular biological application of interest. The biological applications of interest include, but are not limited to: nucleotide transient-binding; nucleotide incorporation; de-blocking; washing; removing; flowing; detecting; and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a protein and an energy transfer donor moiety; between a nucleotide and an energy transfer acceptor moiety; between a nucleic acid molecule and a solid surface; and the like. Some examples of linkages can be found, for example, in Hermanson, G., "Bioconjugate Techniques", Second Edition (2008); Aslam, M., Dent, A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

Other objects, features and advantages of the disclosed methods, systems and compositions will become apparent from the following detailed description. It should be understood, however, that the detailed description and the specific examples, while indicating specific embodiments, are given by way of illustration only, since various changes and modifications within the spirit and scope of the inventions provided herein will become apparent to those skilled in the art from this detailed description.

Provided herein are compositions and systems for use in polymerase-dependent, template-dependent nucleotide transient-binding methods. The methods are useful for deducing the sequence of a template nucleic acid molecule and for single nucleotide polymorphism (SNP) analyses. The methods rely on the fact that the frequency and/or duration of nucleotide transient-binding to a polymerase for a complementary nucleotide is different (e.g., longer) compared to that of a non-complementary nucleotide, when the polymerase is bound to a template molecule. The methods can employ nucleotides operably linked to at least one reporter moiety that emits a signal.

The polymerase can be complexed with a template nucleic acid molecule which is bound to a polymerization initiation site. A transient-binding event occurs when the polymerase, as part of the complex, binds the nucleotide but does not incorporate the nucleotide onto the polymerization initiation site (i.e., no nucleotide polymerization).

The methods are conducted under any reaction condition which permits the polymerase to selectively bind a complementary nucleotide, but incorporation of the complementary nucleotide is perturbed, impeded, or inhibited. Such reaction conditions include utilizing: (1) any reaction conditions and reagents, such as temperature, pH, ionic strength, multivalent cations, and/or time; (2) any polymerase which selectively binds a complementary nucleotide but exhibits reduced nucleotide incorporation activity; (3) non-incorporatable nucleotides; and/or (4) a non-extendible polymerization initiation site.

The polymerase acts as a molecular sensor for discriminating between transient-binding of complementary and non-complementary nucleotides. The temporal order of the signals from the transiently-bound complementary nucleotides, in successive transient-binding reactions, can be used to determine the sequence of the template molecule.

The transient-binding methods overcome certain problems that plague other sequencing methods. Traditional sequencing methods require nucleotide incorporation as part of the base-calling step. However, incorporation of non-reporting nucleotides is not detected, leading to inaccurate sequencing information. This is often caused by non-fluorescing labeled nucleotides contained in preparations of fluorophore-labeled nucleotides. The non-fluorescing labeled nucleotides can be due to photo-bleached fluorophores, damaged fluorophores, or non-labeled nucleotides. In the nucleotide transient-binding methods provided herein, both reporting and non-reporting complementary nucleotides can transiently bind the polymerase. But only the signals from the reporting nucleotides are detected and identified. Thus, the non-reporting nucleotides, which transiently bind the polymerase, do not interfere with accurate base-calling. Additionally, nucleotide mis-incorporation is another source of inaccurate sequencing information using traditional sequencing methods which use nucleotide incorporation for the base-calling step. In the methods provided herein, incorporation of a nucleotide is not part of the base-calling step.

The transient-binding methods can be performed on any type of polymerase-dependent platform, including: single molecule, arrays of single molecules, populations of immobilized template molecules (i.e., multiple copies of the same template molecule immobilized on a solid surface or bead, etc), direct excitation/detection, FRET-based excitation/detection, fluorescence polarization, non-immobilized polymerase/template complex, or any combination thereof.

Nucleotide Binding and Incorporation Events

Provided herein are methods for detecting a signal, or a change in a signal, emitted by a labeled nucleotide which is transiently-bound to a polymerase and the template nucleotide. The detected signal can be used to identify the transiently-bound nucleotide and deduce the identity of the bound nucleotide. One skilled in the art will appreciate that the events of nucleotide binding and incorporation can provide information that can be applied to the nucleotide transient-binding methods provided herein. Nucleotide binding and incorporation events include DNA- and RNA-dependent events.

By way of a non-limiting example of nucleotide binding and polymerization, the steps or events of DNA polymerization are well known and generally comprise: (1) complementary base-pairing a template DNA molecule with a DNA primer molecule having a terminal 3' OH (the terminal 3' OH provides the polymerization initiation site for DNA polymerase); (2) binding the base-paired template/primer duplex with a DNA-dependent polymerase to form a complex (e.g., open complex); (3) a candidate nucleotide binds with the DNA polymerase which interrogates the candidate nucleotide for complementarity with the template nucleotide on the template DNA molecule; (4) the DNA polymerase may undergo a conformational change (e.g., to a closed complex if the candidate nucleotide is complementary); (5) the polymerase catalyzes nucleotide polymerization.

In one embodiment, the polymerase catalyzes nucleotide incorporation by forming a bond between the candidate nucleotide and the nucleotide at the terminal end of the polymerization initiation site. The polymerase can catalyze the terminal 3' OH of the primer exerting a nucleophilic attack on the bond between the a and B phosphates of the candidate nucleotide to mediate a nucleotidyl transferase reaction resulting in phosphodiester bond formation between the terminal 3' end of the primer and the candidate nucleotide (i.e., nucleotide incorporation in a template-dependent manner), and concomitant cleavage to form a cleavage product. The polymerase can liberate the cleavage product. In some embodiments, where the polymerase incorporates a nucleotide having phosphate groups, the cleavage product includes one or more phosphate groups. In other embodiments, where the polymerase incorporates a nucleotide having substituted phosphate groups, the cleavage product may include one or more substituted phosphate groups.

The length of time, frequency, or duration, of the transient-binding of the complementary candidate nucleotide can differ from that of the non-complementary candidate nucleotide. This time difference can be used to distinguish between the two types of nucleotides, and deduce the sequence of the template molecule (or identify the transiently-bound nucleotide) by identifying a series of complementary nucleotides in successive transient-binding reactions. The candidate nucleotide may or may not be complementary to the template nucleotide on the template molecule. The candidate nucleotide can bind the polymerase and then dissociate from the polymerase. If the nucleotide dissociates from the polymerase (e.g., it is not incorporated), it can be liberated and typically carries intact polyphosphate groups.

Nucleotide incorporation also includes RNA polymerization which does not require a primer molecule to initiate nucleotide polymerization. Nucleotide incorporation events involving RNA polymerization are well known in the art.

Methods for Nucleotide Transient-Binding

Provided herein are methods for transiently binding a nucleotide to a polymerase which are conducted under any reaction condition which permits the polymerase to selectively bind a complementary nucleotide, but incorporation of the complementary nucleotide is perturbed, impeded, or inhibited. Such reaction conditions include utilizing: (1) any reaction conditions and reagents, such as temperature, pH, ionic strength, multivalent cations, and/or time; (2) any polymerase which selectively binds a complementary nucleotide but exhibits reduced nucleotide incorporation activity; (3) non-incorporatable nucleotides; and/or (4) a non-extendible polymerization initiation site. Any combination of these reaction conditions can be practiced in any order in the transient-binding methods provided herein. Each of these four conditions is described in more detail below.

1) Reaction Conditions and Reagents

Provided herein are methods which are conducted under any reaction condition which permits the polymerase to selectively bind a complementary nucleotide, in a template-dependent manner, but incorporation of the complementary nucleotide is perturbed, impeded, or inhibited.

a) Temperature, pH, Ionic Strength

In one aspect, the methods include any reaction conditions and reagents, such as temperature, pH, and/or ionic strength. For example, the transient-binding reactions can be conducted at a pH range which inhibits polymerase-dependent nucleotide incorporation, such as a pH range of about 4-12, or about 4-10, or about 4-8, or about 4-7.5, or about 4-7, or about 4-6, or about 6-7.5. In another example, the reaction can be conducted at reduced temperatures (e.g., between about 4-25° C.), or elevated temperatures (e.g., between about 25-80° C.). In another example, the reaction can be conducted with increased ionic strength.

b) Time

Other reaction conditions include reducing the time that a nucleotide is contacted with the polymerase to a time that is statistically insufficient to incorporate more than 1 or 2 successive nucleotides (Lapidus, U.S. Pat. No. 7,169,560). The reduced contact time can be achieved by introducing the nucleotide to the incorporation reaction in rapid flow or wash steps.

c) Metal Cations-Reducing Concentrations of Catalytic Metal Ions

Without wishing to be bound to any theory, a two-metal ion mechanism has been postulated for the phosphoryl transfer reaction of DNA polymerases. The postulate suggests that the catalytic metal ion site (site A) coordinates with the alpha phosphate group of a nucleotide bound to the polymerase, and the B site metal group coordinates with the leaving phosphate groups (Beese and Steitz 1991 EMBO Journal 10:25-33; Steitz and Steitz 1993 Proc. Natl. Acad. Sci. USA 90:6498-6502; Steitz 1998 Nature 391:231-232). Catalytic metal ions can include magnesium, manganese, cobalt, strontium, or barium.

Accordingly, the reaction conditions can include a reduction, omission, or chelation of any metal ion which permits nucleotide incorporation. The reduction, omission, or chelation of divalent cations, such as magnesium, manganese, cobalt, strontium, or barium, may inhibit nucleotide incorporation. Chelation includes any procedure which renders the divalent cation unavailable for the nucleotide incorporation reaction, including using EDTA and/or EGTA.

The selection of the metal cation for which the concentration will be reduced, omitted or chelated in the reaction conditions, may depend upon the polymerase and nucleotides to be used in the transient-binding reaction. It is known that certain polymerases use magnesium for catalyzing phosphoryl transfer of an incoming triphosphate nucleotide, such as rat polymerase-beta (H Pelletier 1994 Science 264:1981-1903), human polymerase-beta (MR Sawaya 1997 Biochemistry 36:11205-11212), RB69 polymerase (M Wang 2009 Biochemistry 48:2075-2086; HR Lee 2009 48:2087-2098), Klenow (CM Joyce 2008 Biochemistry 47:6103-6116), and HIV reverse transcriptase (N Kaushik 1996 Biochemistry 35:11536-11546; HP Patel 1995 Biochemistry 34:5351-5363). Additionally, it is known that certain polymerases exhibit a preference for unlabeled nucleotides in the presence of magnesium.

It has also been shown that certain DNA polymerases (e.g., phi29) use manganese for incorporating nucleotide polyphosphates having four or more phosphate groups (Kumar, U.S. Pat. No. 7,393,640). Other DNA polymerases, including FY7 polymerase, may use manganese for catalysis (Fuller, U.S. Pat. No. 7,264,934; and Fuller, WO/2007/048033). Still other polymerases may use magnesium or manganese (Fuller, U.S. published patent application No. 2008/0287305), or magnesium and manganese.

Thus, the use of certain combinations of polymerases and nucleotides may guide the selection of the metal cation(s) that permit/support nucleotide incorporation, and it's concentration to be reduced, omitted, or chelated, in order to inhibit nucleotide incorporation. For example, the transient-binding methods can be conducted using manganese, Phi29 or RB69 polymerase, and dye-labeled nucleotides (e.g., nucleotides having 3-7 phosphates linked at the terminal phosphate group to a fluorophore via an intervening linker moiety).

In one embodiment, the magnesium can be any magnesium compound including $MgCl_2$. In another embodiment, the manganese can be a manganese compound including $MnCl_2$. In one embodiment, the amount of manganese or magnesium compounds which permits nucleotide incorporation can be about 0.01-10 mM, or about 0.01-5 mM, or about 0.01-3 mM, or about 0.01-2 mM, or about 0.01-1 mM. In another embodiment, the amount of manganese or magnesium compounds which permits nucleotide incorporation can be about 0.01-5 mM, or about 0.05-5 mM, or about 0.1-5 mM, or about 0.2-5 mM, or about 0.3-5 mM, or about 0.4-5 mM, or about 0.5-5 mM, or about 1-5 mM, or about 2-5 mM, or about 3-5 mM, or about 4-5 mM, or about 2-10 mM.

d) Cations which Inhibit Nucleotide Incorporation

In still another example, the reaction conditions can include at least one type of multivalent cation which permits transient-binding of the nucleotide to the polymerase but inhibits incorporation of the bound nucleotide. The transiently-bound nucleotide can be a complementary or non-complementary nucleotide. The reaction conditions can include a period IV cation including: calcium, scandium, titanium, vanadium, chromium, iron, cobalt, nickel, copper, zinc, gallium, germanium, arsenic, and selenium. The reaction conditions can include other multivalent cations, including rhodium or strontium. The period IV cation compound can be ZnCl2, CuCl2, CoCl2, FeSO4, or NiCl2. It has been previously shown that substituting calcium for magnesium and/or manganese permits nucleotide binding to wild-type or mutant polymerase (e.g., Klenow), but inhibits nucleotide incorporation (Gangurde 2002 Biochemistry 41:14552-14559). The transient-binding reaction conditions can include calcium at about 0.1-50 mM, or about 0.1-40 mM, or about 0.1-30 mM, or about 0.1-20 mM, or about 0.1-10 mM, or about 0.1-5 mM. The reaction condition can include calcium at about 1-20 mM, or about 2-20 mM, or about 3-20 mM, or about 4-20 mM, or about 5-20 mM, or about 6-20 mM, or about 7-20 mM, or about 8-20 mM, or about 9-20 mM, or about 10-20 mM. In another embodiment, the transient-binding reaction conditions can include any calcium compound, including $CaCl_2$) or a nucleotide which is complexed or bound with calcium.

e) Cations Which Permit Incorporation

The transient-binding reaction can be followed by a separate reaction/step which permits nucleotide incorporation, which can include the presence of any cation which permits nucleotide incorporation (e.g., manganese and/or magnesium). Accordingly, the methods provided herein include a nucleotide transient-binding step, and a nucleotide incorporation step. The methods can include a nucleotide transient-binding step, a detection step, and a nucleotide incorporation step. The reaction conditions can include a nucleotide transient-binding step, a detection step, a washing step, and a nucleotide incorporation step.

For example, during the nucleotide transient-binding step, the reaction conditions can include a reduced concentration, omission, or chelation, of any metal cation which permit nucleotide incorporation (e.g., magnesium, manganese, cobalt, strontium, or barium), and includes at least one multivalent cation which permits transient-binding but inhibits nucleotide incorporation (e.g., any period IV cation, including calcium, scandium, titanium, vanadium, chromium, iron, cobalt, nickel, copper, zinc, gallium, germanium, arsenic, and selenium; and includes rhodium and strontium).

In another example, the nucleotide transient-binding step can include calcium to permit nucleotide binding but inhibit incorporation, followed by a nucleotide incorporation step which includes a manganese compound (Clark, U.S. published patent application No. 2009/0176233), a magnesium compound, and/or a combination of manganese and magnesium.

In another example, a chemical quench assay can be conducted with calcium during the pulse step and magnesium during the chase step (Lee 2009 Biochemistry 48:2087-2098). In a related example, a FRET/quench assay can be conducted in the presence of calcium or magnesium (Joyce 2008 Biochemistry 47:6103-6116) for testing Klenow fragment (cysteine 744 mutant) labeled with IAEDNAS donor dye bound to primer/template labeled with DABCYL acceptor/quench dye.

In another example, the transient-binding reaction includes a concentration of any metal cation which permits nucleotide incorporation, and a concentration of any multivalent cation which permits transient-binding but inhibits nucleotide incorporation. In one embodiment, the A and B metal binding sites on the polymerase are both occupied by the multivalent cation, or one of the sites is occupied by the multivalent cation.

f) Cations Which Promote Ternary Complex Formation and/or Stability

In yet another example, the reaction conditions can include at least one type of exchange-inert cation which is complexed with a nucleotide, to permit transient-binding of the nucleotide to the polymerase and inducing ternary complex formation (or stabilizing the ternary complex), but inhibiting incorporation of the bound nucleotide. The transiently-bound nucleotide can be a complementary or non-complementary nucleotide.

During nucleotide polymerization events, the polymerase can be in an open conformation prior to binding a nucleotide. Upon binding the complementary nucleotide, the polymerase can change to a closed conformation (also known as the ternary complex). The ternary complex can include the polymerase (in a closed conformation) which is bound to the template nucleic acid molecule which is base-paired with the polymerization initiation site, and the nucleotide. The polymerase, in a closed conformation, can catalyze incorporation of the bound nucleotide. It is known that some cation-nucleotide complexes (e.g., chromium-nucleotides) promote the formation and/or stability of the ternary complex.

The transient binding reactions can include at least one type of cation which promotes the formation and/or the stability of the ternary complex. These reactions can be conducted in the presence or absence of cations that are required for catalysis (e.g., $Mg^{2+}$ and/or $Mn^{2+}$). For example, Cr(III)•nucleotide complexes have been previously used as Mn(II)•nucleotide analogs when conducting exchange-inert reactions with polymerases (Zhong, et al., 1998 Journal am Chem Soc 120:235-236). Zhong complexed DNA polymerase ß from rat brain with DNA template/primer duplexes containing the 2-aminopurine nucleotide analog opposite of the incoming nucleotide insertion site, and reacted the polymerase-DNA binary complex with a Cr(III)•nucleotide complex in the absence of a catalytic metal cation (e.g., $Mg^{2+}$). The Cr(III)•nucleotide complex induced the polymerase to form a ternary conformation without catalysis, as indicated by the change of the 2-aminopurine fluorescence.

In one embodiment, the transient binding reactions can be conducted with a polymerase bound to a nucleic acid template molecule which is base-paired with a polymerization initiation site and a Cr(III)•nucleotide complex (e.g., a complementary nucleotide) without $Mg^{2+}$ or $Mn^{2+}$. The Cr(III)•nucleotide complex can induce the formation of a ternary complex. The presence of the bound Cr(III)•nucleotide complex, and/or the identity of the base in the Cr(III)•nucleotide complex, can be detected if the Cr(III)•nucleotide complex is labeled with a fluorescent reporter moiety. A catalytic cation can be added (e.g., $Mg^{2+}$ or $Mn^{2+}$) to induce cleavage and incorporation of the chromium-complexed nucleotide.

The Cr(III)•nucleotide complex can be a chromium monodentate, bidentate, or tridentate complex. The Cr(III)•nucleotide complex can be an a-monodentate, or ß-γ-bidentate nucleotide. The Cr(III)•nucleotide complex can be prepared using any well known methods, including mixing together nucleotides (e.g., dATP, dGTP, dCTP, dTTP, or dUTP) with chromium (e.g., $CrCl_3$) at an elevated temperature (e.g., approximately 80° C. (see Dunaway-Mariano and Cleland 1980 Biochemistry 19:1496-1505; Dunaway-Mariano and Cleland 1980 Biochemistry 19:1506-1515). The various diastereomers of the β-γ-bidentate can be separated using reverse-phase HPLC techniques (Gruys and Schuster 1982 Analytical Biochemistry 125:66-73). Characterization of the various diastereomers can be done using phosphorus NMR or mass spectrometry.

2) Polymerases

Provided herein are nucleotide transient-binding methods which can be conducted using wild type or modified polymerases which permit nucleotide binding but inhibit nucleotide incorporation, where the nucleotide can be a native or analog molecule. The modified polymerases can be mutant polymerases, or can be polymerases which are bound to a cofactor to inhibit nucleotide incorporation. The selection of the polymerase for use in the transient-binding methods can be based on the combination of the polymerase and nucleotides, and the reaction conditions, to be used for the transient-binding step. For example, certain polymerases in combination with nucleotides which comprise 3-10 phosphates groups, can be selected for performing the transient-binding methods. In another example, certain polymerases in combination with nucleotides which are operably linked to a reporter moiety at the base or the terminal phosphate group, can be selected for performing the transient-binding methods.

In one embodiment, mutant polymerases may be prepared that retain the ability to bind nucleotides but exhibit reduced nucleotide incorporation activity. The modified polymerases can be selected based on nucleotide binding, nucleotide polymerization, and/or nucleotide dissociation kinetics.

Some modified polymerases that exhibit nucleotide binding and a reduced rate of nucleotide incorporation have been described (Rank, U.S. published patent application No. 2008/0108082; Hanzel, U.S. published patent application No. 2007/0196846). It is known in the art, that in polymerases from different classes (including DNA-dependent polymerases), an active-site lysine interacts with the phosphate groups of a nucleoside triphosphate molecule bound to the active site. The lysine residue has been shown to protonate the pyrophosphate leaving-group upon nucleotidyl transfer. Mutant polymerases having this lysine substituted with leucine or arginine exhibit greatly reduced nucleotide incorporation rates (Castro, et al., 2009 Nature Structural and Molecular Biology 16:212-218). One skilled in the art can use amino acid alignment and/or comparison of crystal structures of polymerases as a guide to determine which lysine residue to replace with alternative amino acids. The sequences of Phi29 (FIG. 4), RB69 (FIG. 18), mutant RB69 (FIG. 20), B103 (FIG. 19), and Klenow fragment can be used as the basis for selecting the amino acid residues to be modified (for mutant RB69 polymerases, see Peris, U.S. Ser. No. 61/263,320, filed on Nov. 20, 2009) (for B103 polymerases, see Hendricks, U.S. Ser. Nos: 61/242,771, filed on Sep. 15, 2009; 61/293,618, filed on Jan. 8, 2010; and Ser. No. 12/748,359, filed on Mar. 26, 2010). In one embodiment, a modified phi29 polymerase can include lysine at position 379 and/or 383 substituted with leucine or arginine.

The polymerases, nucleotides, and reaction conditions, can be screened for their suitability for use in the transient-binding methods, using well known screening techniques. For example, the reaction kinetics for nucleotide binding, incorporation, and/or dissociation rates, can be determined using rapid kinetics techniques (e.g., stopped-flow or quench flow techniques). Using stopped-flow or quench flow techniques, the transient-binding time of a nucleotide can be estimated by calculating the $1/k_{pol}$ value. Stopped-flow techniques that analyze absorption and/or fluorescence spectroscopy properties of the nucleotide binding, incorporation, or dissociation rates to a polymerase are well known in the art (Kumar and Patel 1997 Biochemistry 36:13954-13962; Tsai and Johnson 2006 Biochemistry 45:9675-9687; Hanzel, U.S. published patent application No. 2007/0196846). Other methods include quench flow (Johnson 1986 Methods Enzymology 134:677-705), time-gated fluorescence decay time measurements (Korlach, U.S. Pat. No. 7,485,424), plate-based assays (Clark, U.S. published patent application No. 2009/0176233), and X-ray crystal structure analysis (Berman 2007 EMBO Journal 26:3494). Nucleotide incorporation by a polymerase can also be analyzed by gel separation of the primer extension products. In one embodiment, stopped-flow techniques can be used to screen and select combinations of nucleotides (and/or nucleotide analogs) with polymerases having a $t_{pol}$ value (e.g., $1/K_{pol}$) which is less than a $t_{-1}$ (e.g., $1/k_{-1}$) value. Stopped-flow techniques for measuring $t_{pol}$ (MP Roettger 2008 Biochemistry 47:9718-9727; M Bakhtina 2009 Biochemistry 48:3197-320) and $t_{-1}$ (M Bakhtina 2009 Biochemistry 48:3197-3208) are known in the art.

For example, some phi29 polymerases mutants and RB69 (FIG. 15) exhibit $t_{pol}$ values that are less than $t_{-1}$ values, when reacted with nucleotide tetraphosphate or hexaphosphate molecules.

In another embodiment, polymerases can be modified by binding it to a chemical compound or an antibody, in order to inhibit nucleotide incorporation.

3) Non-Incorporatable Nucleotides

In another aspect, the nucleotide transient-binding methods can be conducted using nucleotide analogs which can bind transiently to the polymerase in a template-dependent manner, but are not incorporatable (or are substantially non-incorporatable) in a polymerase-dependent reaction. The non-incorporatable nucleotides can bind reversibly to the polymerase. The non-incorporatable nucleotide analogs may or may not have a structure similar to that of a native nucleotide which may include base, sugar, and phosphate moieties.

The non-incorporatable nucleotides can bind the polymerase/template complex in a template-dependent manner, or can act as a universal mimetic and bind the polymerase/template complex in a non-template-dependent manner. The non-incorporatable nucleotides can be a nucleotide mimetic of incorporatable nucleotides, such as adenosine, guanosine, cytidine, thymidine or uridine nucleotides. The non-incorporatable nucleotide includes any compound having a nucleotide structure, or a portion thereof, which can bind a polymerase.

For example, the non-incorporatable nucleotides can have the general structure:

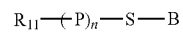

Where B can be a base moiety, such as a hetero cyclic base which includes substituted or unsubstituted nitrogen-containing heteroaromatic ring. Where S can be a sugar moiety, such as a ribosyl, riboxyl, or glucosyl group. Where n can be 1-10, or more. Where P can be one or more substituted or unsubstituted phosphate or phosphonate groups. Where $R_{11}$, if included, can be a reporter moiety (e.g., a fluorescent dye). In one embodiment, the non-incorporatable nucleotide having multiple phosphate or phosphonate groups, the linkage between the phosphate or phosphonate groups can be non-hydrolyzable by the polymerase. The non-hydrolyzable linkages include, but are not limited to, amino, alkyl, methyl, and thio groups. Non-incorporatable nucleotide tetraphosphate analogs having alpha-thio or alpha boreno substitutions having been described (Rank, U.S. published patent application No. 2008/0108082; and Gelfand, U.S. published patent application No. 2008/0293071).

The phosphate or phosphonate portion of the non-incorporatable nucleotide can have the general structure:

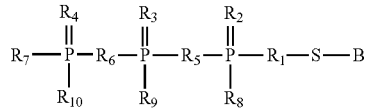

Where B can be a base moiety and S can be a sugar moiety. Where any one of the $R_1$-$R_7$ groups can render the nucleotide non-hydrolyzable by a polymerase. Where the sugar C5 position can be $CH_2$, $CH_2O$, $CH=$, $CHR$, or $CH_2$. Where the $R_1$ group can be O, S, $CH=$, $CH(CN)$, or NH. Where the $R_2$, $R_3$, and $R_4$, groups can independently be O, $BH_3$, or SH. Where the $R_5$ and $R_6$ groups can independently be an amino, alkyl, methyl, thio group, or CHF, $CF_2$, CHBr, $CCl_2$, O—O, or —C≡C—. Where the $R_7$ group can be oxygen, or one or more additional phosphate or phosphonate groups, or can be a reporter moiety. Where $R_8$ can be SH, $BH_3$, $CH_3$, $NH_2$, or a phenyl group or phenyl ring. Where $R_9$ can be SH. Where $R_{10}$ can be $CH_3$, $N_3CH_2CH_2$, $NH_2$, ANS, $N_3$, MeO, SH, Ph, F. PhNH, PhO, or RS (where Ph can be a phenyl group or phenyl ring, and F can be a fluorine atom or group). The substituted groups can be in the S or R configuration.

The non-incorporatable nucleotides can be alpha-phosphate modified nucleotides, alpha-beta nucleotide analogs, beta-phosphate modified nucleotides, beta-gamma nucleotide analogs, gamma-phosphate modified nucleotides, caged nucleotides, or di-nucleotide analogs.

Many examples of non-incorporatable nucleotides are known (Rienitz 1985 Nucleic Acids Research 13:5685-5695), including commercially-available ones from Jena Bioscience (Jena, Germany).

4) Non-Extendible Polymerization Initiation Site

In yet another aspect, the nucleotide transient-binding methods can be conducted using a non-extendible polymerization initiation site. The extendible polymerization initiation site can include a terminal 3' —OH group which serves as a substrate for the polymerase to form a phosphodiester bond between the terminal 3' —OH group and an incoming nucleotide. The extendible polymerization initiation site can be the terminal 3'-OH group on a primer molecule, or an internal 3' —OH group in a nick or gap within a nucleic acid molecule. The non-extendible polymerization initiation site can be a terminal group which does not serve as a substrate for polymerase-dependent nucleotide incorporation. For example, the non-extendible polymerization initiation site can be a terminal nucleotide which lacks a terminal 3' —OH group, or includes a sugar-linked 2' or 3' blocking group, or can include a base-linked moiety which inhibits extension by a given polymerase, or can include a sugar- or base-linked moiety which is bulky or is negatively charged.

In one embodiment, the nucleotide transient-binding methods can be performed by binding the polymerase to a template molecule which is base-paired with a polymerization initiation site having a non-extendible end. The polymerase binds and interrogates a candidate nucleotide, but the candidate nucleotide is not incorporated. A signal from the transiently-bound candidate nucleotide is detected, and its identity is deduced. The non-extendible end can include a dideoxynucleotide or a terminator nucleotide.

Strand extension can be performed if the non-extendible end of the polymerization initiation site is modified or removed to provide an extendible end (e.g., de-blocking). When a terminator nucleotide is incorporated at the extendible end, it can provide a new non-extendible end. The polymerase binds and interrogates another candidate labeled nucleotide, and a signal is detected from the transiently-bound nucleotide. And the steps can be repeated.

The reaction conditions can include using a polymerase (e.g., mutant polymerase), reducing the temperature and/or pH, omitting manganese and/or magnesium, and/or adding calcium, or any combination thereof.

Nucleotide Transient-Binding Reactions and Methods

Provided herein are methods for: detecting the length of the transient-binding time for complementary and non-complementary nucleotides; detecting the presence of a transiently-bound nucleotide (complementary and non-complementary); determining the identity of the complementary nucleotides; detecting the presence of a transiently-bound nucleotide (complementary and non-complementary) in successive nucleotide binding reactions; determining the identity of a transiently-bound nucleotide in successive nucleotide binding reactions; and/or determining the identity of the transiently-bound nucleotide.

The methods can be practiced using any suitable reaction condition comprising reagents and components which mediate polymerase-dependent reactions, including: forming the complex (template molecule/initiation site/polymerase); transient-binding a labeled nucleotide to a polymerase in a template-dependent manner; and detecting the signal (or change in a signal) from the transiently-bound labeled nucleotide. The methods can include a separate step for incorporating a nucleotide. The methods can be practiced using one or more different types of polymerases. For example, the methods can be practiced using one type of polymerase for the transient-binding step, and the same or different type of polymerase for the nucleotide incorporation step. The methods can be practiced using one or more different types of nucleotides. The methods can be practiced using separate, step-wise reactions: contacting, binding, detecting, incorporating, and/or removing.

The suitable conditions include well known parameters for permitting polymerase-dependent incorporation of terminator nucleotides and inhibiting the incorporation of the next nucleotide, including parameters such as: time, temperature, pH, buffers, reagents, salts, co-factors, nucleotides, template DNA, primer DNA, enzymes such as nucleic acid-dependent polymerase, amounts and/or ratios of the components in the reactions, and the like. The reagents or buffers can include a source of ions, such as KCl, K-acetate, $NH_4$-acetate, K-glutamate, $NH_4Cl$, or ammonium sulfate. The reagents or buffers can include a source of divalent ions, such as $Mg^{2+}$ or $Mn^{2+}$, $MgCl_2$, $MnCl_2$, or Mg-acetate. The buffer can include Tris, Tricine, HEPES, MOPS, ACES, MES, or inorganic buffers such as phosphate or acetate-based buffers which can provide a pH range of about 4 to about 12. The buffer can include chelating agents such as EDTA and EGTA, and the like. In one embodiment, the buffer composition can include dithiothreitol (DTT), glycerol, spermidine, and/or BSA (bovine serum albumin) (Buzby, U.S. published patent application No. 2008/0138804).

The solid surfaces, nanoparticles and biomolecules (e.g., terminator nucleotides, labeled nucleotides, non-incorporatable nucleotides, polymerases, template molecules, primers, oligonucleotides, inhibitor moieties, or reporter moieties) can be used presently for any procedure described herein, or can be stored or preserved for later use by employing suitable storage procedures.

Detecting the Presence of a Transiently-Bound Nucleotide

The presence of a transiently-bound nucleotide can be detected according to the methods provided herein. In one aspect, methods for detecting the presence of a transiently-bound nucleotide comprise the steps of: (a) contacting at least one type of a labeled nucleotide to a complex which comprises a polymerase bound to a template nucleic acid molecule which is base-paired to a polymerization initiation site, under conditions suitable to transiently-bind the labeled nucleotide to the polymerase in a template-dependent manner but inhibits incorporation of the nucleotide; (b) exciting the labeled nucleotide or the polymerase with an excitation source; and (c) detecting a signal, or a change in a signal, emitted by the transiently-bound labeled nucleotide in step (a), thereby detecting the presence of the transiently-bound nucleotide.

a) Metals and pH

In one embodiment, the suitable conditions include labeled nucleotide that may be contacted with the complex in the presence of a combination of: (1) reduced levels or omission of any metal cations that permits nucleotide incorporation (e.g., manganese and/or magnesium); and/or (2) in the presence of any multivalent cations that inhibit nucleotide incorporation (e.g., calcium). The multivalent (e.g., calcium) cation can be added during any stage of the transient binding step. For example, the multivalent cation can be added before, during, or after the step of: contacting the polymerase with the template nucleic acid molecule and polymerization initiation site; contacting the polymerase with the labeled nucleotide; or detecting a signal (or change in the signal) emitted by the transiently bound nucleotide. In another embodiment, the suitable conditions include a pH range of about 6-7.5.

b) Polymerases

In one embodiment, the suitable polymerase can be a wild-type or modified polymerase that, under certain reaction conditions, can bind nucleotides but exhibits reduced nucleotide incorporation activity. In another embodiment, a suitable polymerase can be selected that can bind the labeled nucleotide. In another embodiment, a suitable polymerase can be selected that can bind the template nucleic acid molecule which is base-paired to the polymerization initiation site. In another embodiment, the polymerization initiation site can include a terminal 3'OH extendible end or a terminal 3' non-extendible end. In another embodiment, a suitable polymerase can be selected that can bind an incorporatable or a non-incorporatable nucleotide. In still another embodiment, the polymerase can be operably linked to a reporter moiety (e.g., energy transfer donor moiety). In another embodiment, the polymerase in step (a) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment.

c) Non-Extendible Ends

In one embodiment, the polymerization initiation site can be a terminal 3' non-extendible end which can include a terminator nucleotide. In another embodiment, the terminator nucleotide can be adenosine, guanosine, cytidine, thymidine or uridine terminator nucleotides, or any other type of terminator nucleotide. In another embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, heat, chemical or light cleavage reaction. In another embodiment, the complex can be contacted with one or more than one type of terminator nucleotide (e.g., A, G, C, and/or T/U, or others). In another embodiment, the terminator nucleotide can be labeled or un-labeled.

d) Labeled Nucleotides

In one embodiment, the labeled nucleotide can include 3-10 or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

e) FRET Detection

In one embodiment, the polymerase can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In still another embodiment, the signal emitted by the transiently-bound nucleotide can be a FRET signal.

f) Immobilized Complex

In another embodiment, the complex can be immobilized to a solid surface. For example, the polymerase, or template or primer molecule can be immobilized to a solid surface.

g) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

h) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

i) Washing Steps

In one embodiment, washing steps can be included after any of the steps, for example, to remove the labeled nucleotides. In the wash step, magnesium, manganese, or calcium can be omitted or included Identifying a Nucleotide Bound to a Polymerase:

The identity of a transiently-bound nucleotide can be determined according to the methods provided herein. In one aspect, methods for identifying a nucleotide bound to a polymerase, comprises the steps of: (a) contacting at least one type of a labeled nucleotide to an immobilized complex having a first polymerase bound to a template nucleic acid molecule which is bound to a polymerization initiation site, under suitable conditions to transiently-bind the at least one type of labeled nucleotide to the active site of the polymerase in a nucleic acid template-dependent manner and to inhibit nucleotide polymerization by the polymerase; (b) exciting the labeled nucleotide with an excitation source; (c) detecting a signal, or a change in a signal, from the transiently-bound labeled nucleotide; and (d) identifying the nucleotide transiently-bound to the polymerase.

In one embodiment, the methods for identifying a nucleotide bound to a polymerase, further comprises the steps of: (e1) removing the transiently-bound nucleotide; and (f1) contacting the complex with at least one type of nucleotide under suitable conditions for the polymerase to polymerize the nucleotide. In this embodiment, the same polymerase in step (a) is contacted in step (f).

In another embodiment, the methods for identifying a nucleotide bound to a polymerase, further comprises the steps of: (e2) removing the first polymerase and the transiently-bound nucleotide so that the template nucleic acid molecule, nucleic acid primer molecule or self-priming template nucleic acid molecule remains immobilized to the surface; (f2) binding the remaining template nucleic acid molecule with a second polymerase; and (g2) contacting the second polymerase with at least one type of nucleotide under suitable conditions for the second polymerase to polymerize the nucleotide. In this embodiment, the polymerase in step (a) is different from the polymerase in step (f).

Nucleotide Transient-Binding Reactions I:

In one embodiment, a method for identifying a nucleotide bound to a polymerase, comprises the steps of: (a1) contacting at least one type of a labeled nucleotide to an immobilized complex having a polymerase bound to a template nucleic acid molecule which is bound to a polymerization initiation site, under suitable conditions to transiently-bind the at least one type of labeled nucleotide to the polymerase in a nucleic acid template-dependent manner and to inhibit nucleotide polymerization by the polymerase; (b1) exciting the first labeled nucleotide with an excitation source; (c1) detecting a signal, or a change in a signal, from the transiently-bound labeled nucleotide; and (d1) identifying the nucleotide transiently-bound to the polymerase; (e1) removing the transiently-bound nucleotide; (f1) contacting the complex with at least one type of nucleotide under suitable conditions for the polymerase to polymerize the nucleotide; and (g1) repeating steps (a1)-(e1)

Nucleotide Transient-Binding Reactions II:

In one embodiment, a method for identifying a nucleotide bound to a polymerase, comprises the steps of: (a2) contacting at least one type of a labeled nucleotide to an immobilized complex having a polymerase bound to a template nucleic acid molecule which is base-paired to a nucleic acid primer molecule or the immobilized complex having a polymerase bound to a self-priming template nucleic acid molecule, under suitable conditions to transiently-bind the at least one type of labeled nucleotide to the polymerase in a nucleic acid template-dependent manner and to inhibit nucleotide polymerization by the polymerase; (b2) exciting the first labeled nucleotide with an excitation source; (c2) detecting a signal, or a change in a signal, from the transiently-bound labeled nucleotide; and (d2) identifying the nucleotide transiently-bound to the polymerase; (e2) removing the polymerase and the transiently-bound nucleotide so that the template nucleic acid molecule, primer nucleic acid molecule or self-priming template nucleic acid molecule remains immobilized to the surface; (f2) binding the remaining template nucleic acid molecule with a second polymerase; (g2) contacting the second polymerase with at least one type of nucleotide under suitable conditions for the second polymerase to polymerize the nucleotide; and (h2) repeating steps (a2)-(f2).

a) Suitable Conditions for Nucleotide Transient Binding:

In one embodiment, the suitable conditions to transiently bind the nucleotide to the polymerase in step (a1) or (a2) comprise: (i) reducing the levels or omission of a metal cation that permits nucleotide incorporation and/or addition of a cation that inhibits nucleotide incorporation; (ii) using a polymerase which selectively binds the nucleotide in a template-dependent manner and exhibits reduced nucleotide incorporation activity; (iii) using at least one type of labeled nucleotide which can be a labeled non-incorporatable nucleotide; and/or (iv) using a polymerization initiation site which can be a non-extendible polymerization initiation site. Any combination of these suitable conditions can be practiced to identify the nucleotide bound to the polymerase.

b) Suitable Conditions for Nucleotide Incorporation:

In another embodiment, the suitable conditions for polymerizing the nucleotide in step (f1) or (g2) comprise: (i) including a metal cation that permits nucleotide incorporation and/or reducing the levels or omission of a cation that inhibits nucleotide incorporation; (ii) using a polymerase which selectively binds the nucleotide in a template-dependent manner and polymerizes the bound nucleotide; (iii) using at least one type of incorporatable nucleotide; and/or (iv) using a polymerization initiation site having an extendible polymerization initiation site.

c) Polymerization Initiation Site:

In one embodiment, the polymerization initiation site can be the 3' terminal end of a nucleic acid primer molecule or of self-priming template nucleic acid molecule. In another embodiment, the polymerization initiation site can be base-paired to the template nucleic acid molecule. In another embodiment, the polymerization initiation site can be an extendible terminal 3'OH group or a non-extendible terminal group. In another embodiment, the polymerization initiation site can be a terminal 3'OH group of the nucleic acid primer molecule or a terminal 3'OH group of a self-priming template nucleic acid molecule.

d) Template Molecules:

In one embodiment, the template nucleic acid molecule can be a DNA molecule, RNA molecule, or DNA/RNA hybrid molecule.

e) Immobilized Template Molecules:

In one embodiment, the template nucleic acid molecule, the nucleic acid primer molecule, or self-priming template nucleic acid molecule can be immobilized to a surface.

f) Cation:

In one embodiment, the cation that inhibits nucleotide incorporation can be calcium, scandium, titanium, vanadium, chromium, iron, cobalt, nickel, copper, zinc, gallium, germanium, arsenic, selenium, rhodium, or strontium.

g) Polymerases:

In one embodiment, the first polymerase binds the labeled nucleotide in a nucleic acid template-dependent manner and exhibits reduced nucleotide polymerization activity. In another embodiment, the first polymerase can be a DNA-dependent polymerase, RNA-dependent polymerase, or a reverse transcriptase. In one embodiment, the suitable polymerase can be a wild-type or modified polymerase that, under certain reaction conditions, can bind nucleotides but exhibits reduced nucleotide incorporation activity. In another embodiment, a suitable polymerase can be selected that can bind the labeled nucleotide. In another embodiment, a suitable polymerase can be selected that can bind the template nucleic acid molecule which can be base-paired to the polymerization initiation site. In another embodiment, the polymerization initiation site can include a terminal 3'OH extendible end or a terminal 3' non-extendible end. In another embodiment, a suitable polymerase can be selected that can bind an incorporatable or a non-incorporatable nucleotide. In still another embodiment, the polymerase can be operably linked to a reporter moiety (e.g., energy transfer donor moiety). In another embodiment, the polymerase in step (a) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment. In another embodiment, the first polymerase can be any 9°N polymerase or derivative thereof, including THERMINATOR, THERMINATOR II, or THERMINATOR-GAMMA polymerase (New England Biolabs, catalog #s M0261L, M0266L, and M0334L, respectively).

In another embodiment, the second polymerase can be the same type or a different type as the first polymerase.

h) Labeled Nucleotides:

In one embodiment, the labeled nucleotide can include 3-10 or more phosphate groups. In another embodiment, the labeled nucleotide can be adenosine, guanosine, cytidine, thymidine or uridine, or any other type of labeled nucleotide. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, the labeled nucleotide can be a non-incorporatable nucleotide.

In one embodiment, the non-incorporatable nucleotide can bind to the polymerase and template nucleic acid molecule which can be base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

i) Non-Incorporatable Nucleotides:

In one embodiment, the labeled nucleotide in step (a) can be a labeled non-incorporatable nucleotide. In another embodiment, the labeled non-incorporatable nucleotide can be an adenosine, guanosine, cytidine, thymidine, or uridine nucleotide.

j) The Labels:

In one embodiment, the label (on the incorporatable or non-incorporatable nucleotides) can be an energy transfer acceptor reporter moiety. In another embodiment, the label can be a fluorescent dye. In another embodiment, the adenosine, guanosine, cytidine, thymidine, or uridine nucleotides can be operably linked to different types of labels. In another embodiment, the complex can be contacted with at least two types of labeled nucleotides in step (a). In another embodiment, the at least two types of nucleotides can have different types of labels.

k) Energy Transfer Moieties:

In one embodiment, the polymerase can be operably linked to an energy transfer donor reporter moiety. In another embodiment, the energy transfer donor reporter moiety can be an inorganic nanoparticle or a fluorophore. In another embodiment, the polymerase can be operably linked to an energy transfer donor reporter moiety and the transiently-bound nucleotide can be operably linked to an energy transfer acceptor reporter moiety. In another embodiment, the transiently-bound labeled nucleotide can emit a FRET signal. In another embodiment, the signal from the transiently-bound labeled nucleotide can be optically detectable.

l) FRET Signals

In one embodiment, the polymerase can be operably linked to an energy transfer donor (e.g., fluorescent dye or nanoparticle). In another embodiment, the labeled nucleotide can have an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In still another embodiment, the signal emitted by the transiently-bound nucleotide can be a FRET signal.

m) Chain Terminating Nucleotides:

In one embodiment, the non-extendible terminal group can be an inhibitor moiety which inhibits incorporation of a subsequent in-coming nucleotide. In another embodiment, the inhibitor moiety can be removable via an enzymatic, heat, chemical, or light cleavage reaction.

n) Excitation Source and Signals:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which can be operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal.

The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

o) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

p) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

q) Washing Steps

In yet another embodiment, washing steps can be included after any of the steps, for example, to remove the non-incorporated nucleotides and/or the labeled nucleotides. In the wash step, magnesium, manganese, or calcium can be omitted or included.

Determining the Identity of a Transiently-Bound Nucleotide

The identity of a transiently-bound nucleotide can be determined according to the methods provided herein. In one aspect, methods for determining the identity of a transiently-bound nucleotide comprises the steps of: (a) contacting at least one type of a labeled nucleotide to a complex which comprises a polymerase bound to a template nucleic acid molecule which is base-paired to a polymerization initiation site, under conditions suitable to transiently-bind the labeled nucleotide to the polymerase in a template-dependent manner but inhibits incorporation of the nucleotide; (b) exciting the labeled nucleotide or the polymerase with an excitation source; (c) detecting a signal, or a change in a signal, emitted by the transiently-bound labeled nucleotide in step (a); and (d) identifying the nucleotide transiently-bound to the polymerase.

a) Metals and pH

In one embodiment, the suitable conditions include labeled nucleotide that may be contacted with the complex in the presence of a combination of: (1) reduced levels or omission of any metal cations that permits nucleotide incorporation (e.g., manganese and/or magnesium); and/or (2) in the presence of any multivalent cations that inhibit nucleotide incorporation (e.g., calcium). The multivalent (e.g., calcium) cation can be added during any stage of the transient binding step. For example, the multivalent cation can be added before, during, or after the step of: contacting the polymerase with the template nucleic acid molecule and polymerization initiation site; contacting the polymerase with the labeled nucleotide; or detecting a signal (or change in the signal) emitted by the transiently bound nucleotide. In another embodiment, the suitable conditions include a pH range of about 6-7.5.

b) Polymerases

In one embodiment, the suitable polymerase can be a wild-type or modified polymerase that, under certain reaction conditions, can bind nucleotides but exhibits reduced nucleotide incorporation activity. In another embodiment, a suitable polymerase can be selected that can bind the labeled nucleotide. In another embodiment, a suitable polymerase can be selected that can bind the template nucleic acid molecule which is base-paired to the polymerization initiation site. In another embodiment, the polymerization initiation site can include a terminal 3'OH extendible end or a terminal 3' non-extendible end. In another embodiment, a suitable polymerase can be selected that can bind an incorporatable or a non-incorporatable nucleotide. In still another embodiment, the polymerase can be operably linked to a reporter moiety (e.g., energy transfer donor moiety). In another embodiment, the polymerase in step (a) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment.

c) Non-Extendible Ends

In one embodiment, the polymerization initiation site can be a terminal 3' non-extendible end which can include a terminator nucleotide. In another embodiment, the terminator nucleotide can be adenosine, guanosine, cytidine, thymidine or uridine terminator nucleotides, or any other type of terminator nucleotide. In one embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, heat, chemical or light cleavage reaction. In another embodiment, the complex can be contacted with one or more than one type of terminator nucleotide (e.g., A, G, C, and/or T/U, or others). In another embodiment, the terminator nucleotide can be labeled or un-labeled.

d) Labeled Nucleotides

In one embodiment, the labeled nucleotide can include 3-10 or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

e) FRET Detection

In one embodiment, the polymerase can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In still another embodiment, the signal emitted by the transiently-bound nucleotide can be a FRET signal.

f) Immobilized Complex

In one embodiment, the complex can be immobilized to a solid surface. For example, the polymerase, or template or primer molecule can be immobilized to a solid surface.

g) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

h) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

i) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

j) Washing Steps

In yet another embodiment, washing steps can be included after any of the steps, for example, to remove the non-incorporated nucleotides and/or the labeled nucleotides. In the wash step, magnesium, manganese, or calcium can be omitted or included.

SNP and Other Types of Analyses

The methods for determining the identity of a transiently-bound nucleotide can be used for a single nucleotide polymorphism (SNP) analysis or sequencing methods. For example, the methods provided herein can be practiced using a template molecule which is base-paired with a primer molecule. The primer molecule can anneal to a region that abuts the SNP site. In one aspect, the method for detecting a single nucleotide polymorphism in a template nucleic acid molecule, comprises the steps of: (a) contacting at least one type of a labeled nucleotide with a complex which comprises a polymerase bound to a template nucleic acid molecule which is base-paired to a primer molecule, under conditions suitable to transiently-bind the nucleotide to the polymerase in a template-dependent manner, where the primer molecule hybridizes to a region on the template molecule that abuts the single nucleotide polymorphism site; (b) exciting the labeled nucleotide or the polymerase with an excitation source; (c) detecting a signal, or a change in a signal, emitted by the transiently-bound labeled nucleotide in step (a); and (d) identifying the nucleotide transiently-bound to the polymerase.

a) Primer

In one embodiment, the sequence of the primer molecule can be complementary, or partially complementary, to the sequence of the template molecule. In another embodiment, the primer molecule can have a terminal 3' non-extendible end. In another embodiment, the 3' non-extendible end can include a terminator nucleotide.

b) Metals and pH

In one embodiment, the suitable conditions include labeled nucleotide that may be contacted with the complex in the presence of a combination of: (1) reduced levels or omission of any metal cations that permits nucleotide incorporation (e.g., manganese and/or magnesium); and/or (2) in the presence of any multivalent cations that inhibit nucleotide incorporation (e.g., calcium). The multivalent cation can be added during any stage of the transient binding step. For example, the multivalent cation can be added before, during, or after the step of: contacting the polymerase with the template nucleic acid molecule and polymerization initiation site; contacting the polymerase with the labeled nucleotide; or detecting a signal (or change in the signal) emitted by the transiently bound nucleotide. In another embodiment, the suitable conditions include a pH range of about 6-7.5.

c) Polymerases

In one embodiment, the suitable polymerase can be a wild-type or modified polymerase that, under certain reaction conditions, can bind nucleotides but exhibits reduced nucleotide incorporation activity. In another embodiment, a suitable polymerase can be selected that can bind the labeled nucleotide. In another embodiment, a suitable polymerase can be selected that can bind the template nucleic acid molecule which is base-paired to the polymerization initiation site. In another embodiment, the polymerization initiation site can include a terminal 3'OH extendible end or a terminal 3' non-extendible end. In another embodiment, a suitable polymerase can be selected that can bind an incorporatable or a non-incorporatable nucleotide. In still another embodiment, the polymerase can be operably linked to a reporter moiety (e.g., energy transfer donor moiety). In another embodiment, the polymerase in step (a) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment.

d) Non-Extendible Ends

In one embodiment, the polymerization initiation site can be a terminal 3' non-extendible end which can include a terminator nucleotide. In another embodiment, the terminator nucleotide can be adenosine, guanosine, cytidine, thymidine or uridine terminator nucleotides, or any other type of terminator nucleotide. In one embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, heat, chemical or light cleavage reaction. In another embodiment, the complex can be contacted with one or more than one type of terminator nucleotide (e.g., A, G, C, and/or T/U, or others). In another embodiment, the terminator nucleotide can be labeled or un-labeled.

e) Labeled Nucleotides

In one embodiment, the labeled nucleotide can include 3-10 or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

In another embodiment, if steps (a)-(d) of the method are practiced using one type of labeled nucleotide, then steps (a)-(d) can be repeated (e.g., multiple rounds of steps (a)-(d)) by contacting the complex with one type of labeled nucleotide which differs from the labeled nucleotide used in a previous round of steps (a)-(d). The frequency, duration, or intensity of the signals emitted from the two different transiently-bound labeled nucleotides, which were used in the various rounds, can be compared to determine which type of labeled nucleotide is complementary to the template molecule, thereby identifying the SNP.

In yet another embodiment, if steps (a)-(d) of the method are practiced using more than one type of labeled nucleotide in step (a), the frequency, duration, or intensity of the signal emitted from the transiently-bound complementary labeled nucleotide is expected to be different compared to that from the non-complementary labeled nucleotides. This difference can be used to identify the SNP.

f) FRET Detection

In one embodiment, the polymerase can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In still another embodiment, the signal emitted by the transiently-bound nucleotide can be a FRET signal.

g) Immobilized Complex

In one embodiment, the complex can be immobilized to a solid surface. For example, the polymerase, or template or primer molecule can be immobilized to a solid surface.

h) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

i) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

j) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

k) Washing Steps

In one embodiment, washing steps can be included after any of the steps. In the wash step, magnesium, manganese, or calcium can be omitted or included.

Successive Transient-Binding Reactions

The identity and order of the nucleotides in a template nucleic acid molecule can be determined by detecting the presence of transiently-bound nucleotides in successive binding reactions, according to the methods provided herein. In one aspect, detecting the presence of transiently-bound nucleotides in successive nucleotide binding reactions comprises the steps of: (a) contacting at least one type of a first labeled nucleotide to a complex which comprises a polymerase bound to a template nucleic acid molecule which is base-paired to a polymerization initiation site, under conditions suitable to transiently-bind the first labeled nucleotide to the polymerase in a template-dependent manner but inhibits incorporation of the first labeled nucleotide; (b) exciting the first labeled nucleotide or the polymerase with an excitation source; (c) detecting a signal, or a change in a signal, emitted by the transiently-bound first labeled nucleotide in step (a), thereby detecting the presence of the transiently-bound first labeled nucleotide; (d) contacting at least one type of a second nucleotide with the complex of step (a) under conditions suitable to incorporate the one type of second nucleotide in a template-dependent manner; (e) contacting at least one type of a third labeled nucleotide to the complex in step (c) under conditions suitable to transiently-bind the third labeled nucleotide to a polymerase in a template-dependent manner but inhibits incorporation of the third labeled nucleotide so as to transiently bind the third labeled nucleotides to the polymerase in a template-dependent manner; (f) exciting the third labeled nucleotide or the polymerase with an excitation source; and (g) detecting a signal, or a change in a signal, emitted by the transiently-bound third labeled nucleotide in step (e), thereby detecting the presence of the transiently-bound successive nucleotide.

In one embodiment, steps (d)-(g) can be repeated. In another embodiment, the method further comprises the step of: identifying the nucleotide transiently-bound to the polymerase in steps (a) or (e).

In one aspect, the nucleotide transient-binding steps, polymerase translocation steps, and nucleotide transient-binding steps, can be conducted alternately, and can be repeated.

a) Metals and pH

In one embodiment, the suitable conditions for the transient binding in steps (a) and/or (e) include contacting the labeled nucleotide with the complex in the presence of a combination of: (1) reduced levels or omission of any metal cations that permits nucleotide incorporation (e.g., manganese and/or magnesium); and/or (2) in the presence of any multivalent cations that inhibit nucleotide incorporation (e.g., calcium). The multivalent cation (e.g., calcium) can be added during any stage of the transient binding steps (a) and/or (e). For example, the multivalent cation can be added before, during, or after the step of: contacting the polymerase with the template nucleic acid molecule and polymerization initiation site; contacting the polymerase with the labeled nucleotide; or detecting a signal (or change in the signal) emitted by the transiently bound nucleotide.

In one embodiment, the suitable conditions for the nucleotide incorporation in step (d) include contacting the nucleotide with the complex in the presence of a combination of: (1) a level of any metal cation that permits nucleotide incorporation (e.g., manganese and/or magnesium); and/or (2) reduced levels or omission of any multivalent cation that inhibits nucleotide incorporation (e.g., calcium). The metal cation that permits nucleotide incorporation can be added during any stage of the nucleotide incorporation step (d). For example, the metal cation can be added before, during, or after the step of: contacting the polymerase with the one type of nucleotide. In another embodiment, the suitable conditions include a pH range of about 6-7.5.

b) Polymerases

In one embodiment, the suitable polymerase can be a wild-type or modified polymerase that, under certain reaction conditions, can bind nucleotides but exhibits reduced nucleotide incorporation activity. In another embodiment, a suitable polymerase can be selected that can bind the labeled nucleotide. In another embodiment, a suitable polymerase can be selected that can bind the template nucleic acid molecule which is base-paired to the polymerization initiation site. In another embodiment, the polymerization initiation site can include a terminal 3'OH extendible end or a terminal 3' non-extendible end. In another embodiment, a suitable polymerase can be selected that can bind an incorporatable or a non-incorporatable nucleotide. In still another embodiment, the polymerase can be operably linked to a reporter moiety (e.g., energy transfer donor moiety). In another embodiment, the polymerase in step (a) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment. In another embodiment, the polymerases in steps (a), (d) and/or (e) can be the same type or different types of polymerases. Washing steps can be included after any step. In another embodiment, the polymerase can be removed, washed away, or inactivated after any of steps (a)-(g). In another embodiment, the polymerase in any of steps (a), (d), and/or (e) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment.

c) Non-Extendible Ends

In one embodiment, the polymerization initiation site in step (a) can be a terminal 3' non-extendible end which can include a terminator nucleotide. In another embodiment, the one type of nucleotide in step (d) can be a terminator nucleotide. Incorporation of the terminator nucleotide in step (d) can produce a polymerization initiation site having a non-extendible end. In one embodiment, the terminator nucleotide can be adenosine, guanosine, cytidine, thymidine or uridine terminator nucleotides, or any other type of terminator nucleotide. In one embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, heat, chemical or light cleavage reaction (e.g., de-blocking). In another embodiment, the inhibitor moiety can be removed after any of steps (d)-(g). In another embodiment, the complex can be contacted with one or more than one type of terminator nucleotide (e.g., A, G, C, and/or T/U, or others). In another embodiment, the terminator nucleotide can be labeled or un-labeled. In one embodiment, step (d) can be conducted with a labeled terminator nucleotide which can confirm the identity of the signal detected by the transiently-bound nucleotide in step (c).

d) Labeled Nucleotides

In one embodiment, the labeled nucleotide can include 3-10 or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, steps (a) and/or (e) can be practiced by contacting the polymerase with one type of labeled nucleotide, and if a signal (or a change in the signal) is not detected from a transiently-bound nucleotide, repeating the contacting step with the other types of labeled nucleotides until a signal (or change in the signal) is detected from a transiently-bound nucleotide. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

e) FRET Detection

In one embodiment, the polymerase can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In another embodiment, the reporter moiety which is operably linked to the polymerase in steps (a) and (e) can be the same or different. In still another embodiment, the signal emitted by the transiently-bound nucleotide can be a FRET signal.

f) Immobilized Complex

In one embodiment, the complex can be immobilized to a solid surface. For example, the polymerase, or template or primer molecule can be immobilized to a solid surface.

g) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

h) Detection:

In one embodiment, the detecting the signal or change in the signal can be performed using confocal laser scanning microscopy. Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

i) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

j) Washing Steps

In one embodiment, washing steps can be included after any of the steps, for example, to remove the non-incorporated nucleotides and/or the labeled nucleotides. In the wash step, magnesium, manganese, or calcium can be omitted or included.

Successive Transient-Binding Reactions with Multiple Polymerases

The identity and order of the nucleotides in a template nucleic acid molecule can be determined by detecting the presence of transiently-bound nucleotides in successive binding reactions using multiple polymerases, according to the methods provided herein. The methods can be practiced by replacing the polymerases in the various steps. The new polymerases, which replace the old ones, can be the same type or different types of polymerases. The old polymerases, which may be photo-damaged or may not be suitable for conducting the next step, can be replaced with new or more suitable polymerases.

In one aspect, detecting the presence of transiently-bound nucleotides in successive nucleotide binding reactions comprises the steps of: (a) contacting at least one type of a first labeled nucleotide to a complex which comprises a first polymerase bound to a template nucleic acid molecule which is base-paired to a polymerization initiation site, under conditions suitable to transiently-bind the first labeled nucleotide to the polymerase in a template-dependent manner but inhibits incorporation of the first labeled nucleotide; (b) exciting the first labeled nucleotide with an excitation source; (c) detecting a signal, or a change in a signal, emitted by the transiently-bound first labeled nucleotide in step (a), thereby detecting the presence of the transiently-bound first labeled nucleotide; (d) contacting a second polymerase with the template nucleic acid molecule which is base-paired to a polymerization initiation site so as to replace the first polymerase with the second polymerase; (c) contacting at least one type of a second nucleotide with the second polymerase of step (c) under conditions suitable to incorporate the second nucleotide in a template-dependent manner; (f) contacting a third polymerase with the template nucleic acid molecule which is base-paired to a polymerization initiation site so as to replace the second polymerase with the third polymerase; (g) contacting at least one type of a third labeled nucleotide with the third polymerase of step (c) under conditions suitable to transiently-bind the third labeled nucleotide to the polymerase in a template-dependent manner; (h) exciting the third labeled nucleotide with an excitation source; and (i) detecting a signal, or a change in a signal, emitted by the transiently-bound third labeled nucleotide in step (d), thereby detecting the presence of the transiently-bound successive nucleotide. In one embodiment, steps (d)-(i) can be repeated.

a) Metals and pH

In one embodiment, the suitable conditions for the transient binding in steps (a) and/or (g) include contacting the labeled nucleotide with the complex in the presence of a combination of: (1) reduced levels or omission of any metal cations that permits nucleotide incorporation (e.g., manganese and/or magnesium); and/or (2) in the presence of any multivalent cations that inhibit nucleotide incorporation (e.g., calcium). The multivalent cation (e.g., calcium) can be added during any stage of the transient binding steps (a) and/or (g). For example, the multivalent cation can be added before, during, or after the step of: contacting the polymerase with the template nucleic acid molecule and polymerization initiation site; contacting the polymerase with the labeled nucleotide; or detecting a signal (or change in the signal) emitted by the transiently bound nucleotide.

In one embodiment, the suitable conditions for the nucleotide incorporation in step (e) include contacting the nucleotide with the complex in the presence of a combination of: (1) a level of any metal cations that permits nucleotide incorporation (e.g., manganese and/or magnesium); and/or (2) reduced level or omission of any multivalent cation that inhibits nucleotide incorporation (e.g., calcium). The metal cation that permits nucleotide incorporation can be added during any stage of the nucleotide incorporation step (e). For example, the metal cation can be added before, during, or after the step of: contacting the polymerase with the one type of nucleotide. In another embodiment, the suitable conditions include a pH range of about 6-7.5.

b) Polymerases

In one embodiment, the first and third polymerases can be a wild-type or modified polymerase that, under certain reaction conditions, can bind nucleotides but exhibits reduced nucleotide incorporation activity. In another embodiment, the first and third polymerases can be selected that can bind the labeled nucleotide. In another embodiment, the first and third polymerases can be selected that can bind an incorporatable nucleotide or a non-incorporatable nucleotide. In another embodiment, the first and third polymerases can be selected that can bind the template nucleic acid molecule which is base-paired to the polymerization initiation site. In one embodiment, the second polymerase can be a wild-type or modified polymerase that, under certain reaction conditions, can bind and incorporate a complementary nucleotide. In another embodiment, the second polymerase can be selected that can bind the nucleotide. In another embodiment, the second polymerase can be selected that can bind the template nucleic acid molecule which is base-paired to the polymerization initiation site. In another embodiment, the polymerization initiation site in step (a) or (f) can include a terminal 3'OH extendible end or a terminal 3' non-extendible end. In still another embodiment, the first, second, and/or third polymerase(s) can be operably linked to a reporter moiety (e.g., an energy transfer donor moiety). In another embodiment, the first, second, and/or third polymerases can be the same type or different types of polymerases. Washing steps can be included after any step. In another embodiment, any of the polymerases can be removed, washed away, or inactivated after any of steps (a)-(i). In another embodiment, the polymerase in any of steps (a), (d), and/or (f) can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment.

c) Non-Extendible Ends

In one embodiment, the polymerization initiation site in step (a) or (g) can be a terminal 3' non-extendible end which can include a terminator nucleotide. In another embodiment, the one type of nucleotide in step (e) can be a terminator nucleotide. In one embodiment, the terminator nucleotide can be adenosine, guanosine, cytidine, thymidine or uridine terminator nucleotides, or any other type of terminator nucleotide. In one embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, inhibitor moiety can be removed after any of steps (e)-(i). In another embodiment, the complex in step (a) can be contacted with one or more than one type of terminator nucleotide (e.g., A, G, C, and/or T/U, or others). In another embodiment, the terminator nucleotide can be labeled or un-labeled. In one embodiment, step (e) can be conducted with a labeled terminator nucleotide which can confirm the identity of the signal detected by the transiently-bound nucleotide in step (c).

d) Labeled Nucleotides

In one embodiment, the labeled nucleotide can include 3-10 or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, steps (a) and/or (f) can be practiced by contacting the first and/or third polymerase with one type of labeled nucleotide, and if a signal (or a change in the signal) is not detected from a transiently-bound nucleotide, repeating the contacting step with the other types of labeled nucleotides until a signal (or change in the signal) is detected from a transiently-bound nucleotide. In another embodiment, the labeled nucleotide can be an incorporatable or a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

e) FRET Detection

In one embodiment, the polymerase can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In another embodiment, the reporter moiety which is operably linked to the first, second, third, or fourth polymerase can be the same or different. In still another embodiment, the signal emitted by the transiently-bound nucleotide can be a FRET signal.

f) Immobilized Complex

In one embodiment, the complex can be immobilized to a solid surface. For example, the polymerase, or template or primer molecule can be immobilized to a solid surface.

g) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

h) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

i) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

j) Washing Steps

In one embodiment, washing steps can be included after any of the steps, for example, to remove the non-incorporated nucleotides and/or the labeled nucleotides. In the wash step, magnesium, manganese, or calcium can be omitted or included.

For the methods provided herein, the skilled artisan will appreciate how to repeat the contacting, detecting, removing, and/or washing steps in order to detect the presence of a transiently-bound nucleotide and/or determine the identity of the transiently-bound nucleotide. The skilled artisan will also appreciate how to repeat the contacting, detecting, removing, and/or washing steps, in order to transiently bind the labeled nucleotides in a template-dependent manner, in successive reactions.

Arrays of Single Template Molecules or Amplified Template Molecule Arrays

The transient-binding reactions provided herein can be conducted on multiple complexes, where each complex comprises a polymerase bound to a template nucleic acid molecule which is base-paired with a polymerization initiation site. Each complex can be immobilized at a different location on a solid surface, or each complex can reside in separate reaction vessels (with or without immobilization) (e.g., array of single molecules). Alternatively, multiple complexes can be immobilized to a single location, area, or region, on a solid surface (e.g., array of amplified template molecules). For example, multiple complexes can be immobilized on a bead. Any component of the complex (e.g., polymerase, template molecule, and/or polymerization initiation site) can be immobilized to a solid surface. The template nucleic acid molecules in each complex can include the same or different template sequences. The complexes at each location on the solid surface can have different polymerases.

The methods for transient binding can be conducted in parallel, on the multiple complexes, simultaneously or essentially simultaneously. For example: the labeled nucleotides can be contacted with the multiple complexes; the non-incorporatable nucleotides can be contacted with the multiple complexes; the terminator nucleotides can be contacted with the multiple complexes; the signals from the multiple complexes can be detected; and inhibitor moieties can be removed from the multiple complexes. In this manner, the methods provided herein can be conducted synchronously, or essentially synchronously, on multiple complexes. The signals from the multiple reaction sites can be optically resolvable.

Multiple Reactions on the Same Template Molecule

In one embodiment, the transient-binding reactions provided herein can be conducted at multiple sites along the same template nucleic acid molecule. For example, multiple polymerases can be bound to different sites on the same template molecule, where the template molecule is base-paired with a polymerization initiation site (e.g., nick or gap) or a terminal protein (e.g., TP from Phi29 phage). In this manner, the methods provided herein can be conducted synchronously, or essentially synchronously, on multiple sites on the same template molecule. The signals from the multiple reaction sites can be optically resolvable.

An Embodiment: Using Non-Incorporatable Nucleotides

In one aspect, methods for detecting the presence of a transiently-bound nucleotide in successive nucleotide binding reactions comprises the steps of: (a) contacting at least one type of a first labeled nucleotide with a complex which comprises a first polymerase bound to a template nucleic acid molecule which is base-paired to a primer, under conditions suitable to transiently-bind the first labeled nucleotide to the polymerase in a template-dependent manner but inhibits incorporation of the first labeled nucleotide, where the suitable conditions comprise the first labeled nucleotide is a first labeled non-incorporatable nucleotide, and where the primer is immobilized to a solid surface; (b) exciting the first labeled non-incorporatable nucleotide with an excitation source; (c) detecting a signal, or a change in a signal, emitted by the transiently-bound first labeled non-incorporatable nucleotide in step (a), thereby detecting the presence of the transiently-bound first labeled non-incorporatable nucleotide; (d) removing the transiently-bound first labeled non-incorporatable nucleotide in step (b); (e) removing, washing away, or inactivating the first polymerase from the template molecule; (f) contacting a second polymerase with the template molecule which is base-paired with the immobilized primer molecule in step (d); (g) contacting the second polymerase with at least one type of a second nucleotide under conditions suitable to incorporate the one type of second nucleotide onto the primer in a template-dependent manner; (h) removing, washing away, or inactivating the second polymerase from the template molecule; (i) contacting a third polymerase with the template molecule which is base-paired with the immobilized primer molecule in step (g); (j) contacting the third polymerase with at least one type a third labeled nucleotide, under conditions suitable to transiently-bind the third labeled nucleotide to the polymerase in a template-dependent manner but inhibits incorporation of the third labeled nucleotide, where the suitable conditions comprise the third labeled nucleotide is a second labeled non-incorporatable nucleotide; (k) exciting the second labeled non-incorporatable nucleotide with an excitation source; (l) detecting a signal, or a change in a signal, emitted by the transiently-bound second labeled non-incorporatable nucleotide in step (i), thereby detecting the presence of the transiently-bound second labeled non-incorporatable nucleotide; (m) removing the transiently-bound second labeled non-incorporatable nucleotide in step (j); (n) removing, washing away, or inactivating the third polymerase from the template molecule; (o) contacting a fourth polymerase with the template molecule which is base-paired with the immobilized primer molecule in step (l); (p) contacting the fourth polymerase with at least one type of a fourth nucleotide under conditions suitable to incorporate the one type of nucleotide onto the primer in a template-dependent manner; and (q) removing, washing away, or inactivating the fourth polymerase from the template molecule.

In one embodiment, steps (i)-(q) can be repeated. In another embodiment, the first, second, third, and/or fourth polymerases are not removed or replaced.

a) Calcium

In one embodiment, the conditions suitable to transiently-bind the labeled nucleotide in any of steps (a) and/or (j) include a calcium compound, or the calcium compound can be omitted. In another embodiment, the calcium compound can be $CaCl_2$). In another embodiment, the amount of calcium compound can be about 4-15 mM, or about 4-10 mM, or about 1-5 mM. In another embodiment, the calcium compound can be washed away or chelated during any of steps (a)-(q).

b) Manganese and Magnesium

In one embodiment, the conditions suitable to incorporate the one type of nucleotide in any of steps (g) and/or (p) include a manganese and/or magnesium compound. In one embodiment, the manganese compound can be $MnCl_2$. In another embodiment, the magnesium compound can be $MgCl_2$. In another embodiment, the amount of manganese or magnesium compound can be about 1-5 mM, or about 2-5 mM. In another embodiment, the manganese or magnesium compound can be washed away or chelated during any of steps (a)-(q).

c) pH Conditions

In another embodiment, any of the steps (a)-(q) can be conducted at a pH range of about 6-7.5.

d) Polymerases

In one embodiment, the first and/or third polymerases can be a wild-type or modified polymerase that, under certain reaction conditions, can bind nucleotides but exhibits reduced nucleotide incorporation activity. In another embodiment, the first and/or third polymerases can be selected that can bind the labeled nucleotide. In another embodiment, the first and/or third polymerases can be selected that can bind a non-incorporatable nucleotide. In another embodiment, the second and/or fourth polymerases can be selected that can bind a terminator nucleotide. In another embodiment, the second and/or fourth polymerases can bind a terminator nucleotide in any of steps (g) and/or (p). In another embodiment, the second and/or fourth polymerases can be selected that can bind and incorporate a terminator nucleotide. In still another embodiment, the first, second, third and/or fourth polymerase(s) can be operably linked to a reporter moiety. In another embodiment, the first, second, third and/or fourth polymerases can be the same type or different types of polymerases. In another embodiment, the first and/or third polymerases can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment. Washing steps can be included after any step.

e) Non-Extendible Ends

In one embodiment, the polymerization initiation site in step (a) or (g) can be a terminal 3' non-extendible end which can include a terminator nucleotide. In one embodiment, the terminator nucleotide can be adenosine, guanosine, cytidine, thymidine or uridine terminator nucleotides, or any other type of terminator nucleotide. In one embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, inhibitor moiety can be removed prior to any of steps (h)-(j) or after any of steps (p)-(q). In another embodiment, the complex can be contacted with one or more than one type of terminator nucleotide (e.g., A, G, C, and/or T/U, or others). In another embodiment, the terminator nucleotide can be labeled or un-labeled.

f) Labeled Nucleotides

In one embodiment, the labeled nucleotide can include 3-10, or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U. or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, steps (a) and/or (j) can be practiced by contacting the first and/or third polymerases with one type of labeled nucleotide, and if a signal (or a change in the signal) is not detected from a transiently-bound nucleotide, repeating the contacting step with the other types of labeled nucleotides until a signal (or change in the signal) is detected from a transiently-bound nucleotide. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

g) FRET Detection

In one embodiment, any of the polymerases can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In another embodiment, the reporter moiety which is operably linked to the first, second, third, or fourth polymerase can be the same or different. In still another embodiment, the signal emitted by the transiently-bound nucleotide can be a FRET signal.

h) Immobilized Complex

In one embodiment, the complex can be immobilized to a solid surface. For example, the polymerase, or template or primer molecule can be immobilized to a solid surface.

i) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

j) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

k) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

l) Washing Steps

In one embodiment, washing steps can be included after any of the steps, for example, to remove the non-incorporated nucleotides and/or the labeled nucleotides and/or polymerases. In any washing step, magnesium, manganese, or calcium can be omitted or included. In another embodiment, any of the steps involving removing, washing away, or inactivating the polymerase, (e.g., steps (e), (h), (n), and/or (q)) can be omitted. In another embodiment, the first polymerase can be used for steps (a)-(q).

An Embodiment: Using Terminator Nucleotides

In one aspect, methods for detecting the presence of a transiently-bound nucleotide in successive nucleotide binding reactions comprises the steps of: (a) contacting at least one type of a first terminator nucleotide with a complex which comprises a first polymerase bound to a template nucleic acid molecule which is base-paired to a primer, under conditions suitable to incorporate the first terminator nucleotide onto the primer in a template-dependent manner, where the first terminator nucleotide comprises an inhibitor moiety which permits polymerase-catalyzed incorporation of the first terminator nucleotide but inhibits incorporation of a subsequent in-coming nucleotide, where the inhibitor moiety on the first terminator nucleotide is removable with a cleavage reaction, and where the primer is immobilized to a solid surface; (b) removing, washing away, or inactivating the first polymerase from the template molecule; (c) removing the inhibitor moiety from the incorporated first terminator nucleotide in step (a); (d) contacting a second polymerase with the template molecule which is base-paired with the immobilized primer molecule in step (b); (e) contacting the second polymerase with at least one type of a first labeled nucleotide under conditions suitable to transiently bind the first labeled nucleotide to the second polymerase in a template-dependent manner; (f) exciting the first labeled nucleotide with an excitation source; (g) detecting a signal, or a change in a signal, emitted by the transiently-bound first labeled nucleotide in step (e), thereby detecting the presence of the transiently-bound first labeled nucleotide; (h) removing the transiently-bound first labeled nucleotide in step (f); (i) removing, washing away, or inactivating the second polymerase from the template molecule; (j) contacting a third polymerase with the template molecule which is base-paired with the immobilized primer molecule in step (h); (k) contacting the third polymerase with at least one type of a second terminator nucleotide under conditions suitable to incorporate the second terminator nucleotide onto the primer in a template-dependent manner, where the second terminator nucleotide comprises an inhibitor moiety which permits polymerase-catalyzed incorporation of the second terminator nucleotide but inhibits incorporation of a subsequent in-coming nucleotide, where the inhibitor moiety on the second terminator nucleotide is removable with a cleavage reaction; (l) removing, washing away, or inactivating the third polymerase from the template molecule; (m) removing the inhibitor moiety from the incorporated second terminator nucleotide in step (j); (n) contacting a fourth polymerase with the template molecule which is base-paired with the immobilized primer molecule in step (k); (o) contacting the fourth polymerase with at least one type of a second labeled nucleotide under conditions suitable to transiently bind the second labeled nucleotide to the fourth polymerase in a template-dependent manner; (p) exciting the second labeled nucleotide with an excitation source; (q) detecting a signal, or a change in a signal, emitted by the transiently-bound second labeled nucleotide in step (n), thereby detecting the presence of the transiently-bound second labeled nucleotide; (r) removing the transiently-bound second labeled nucleotide in step (o); and (s) removing, washing away, or inactivating the fourth polymerase from the template molecule.

In one embodiment, steps (j)-(s) can be repeated. In another embodiment, the first, second, third, and/or fourth polymerases are not removed or replaced. In another embodiment, the inhibitor moiety in any of steps (c) and/or (m) can instead be removed during or after any of steps (d) and/or (n).

a) Manganese and Magnesium

In one embodiment, suitable conditions for incorporating the terminator nucleotide in any of steps (a) and (k) can include a manganese or magnesium compound, or the manganese or magnesium compound can be omitted. In another embodiment, the manganese compound can be $MnCl_2$. In another embodiment, the magnesium compound can be $MgCl_2$. In another embodiment, the amount of manganese or magnesium compound can be about 1-5 mM, or about 2-5 mM. In another embodiment, the manganese or magnesium compound can be washed away or chelated after any of steps (b)-(d) and/or (l)-(n).

b) Calcium

In one embodiment, the suitable conditions for transiently binding the labeled nucleotide in any of steps (e) and/or (o) include a calcium compound, or the calcium compound can be omitted. In another embodiment, the calcium compound can be $CaCl_2$). In another embodiment, the amount of calcium compound can be about 4-15 mM, or about 4-10 mM, or about 2-5 mM. In another embodiment, the calcium compound can be washed away or chelated during any of steps (a)-(d) or (h)-(n).

c) pH Conditions

In another embodiment, any of the steps (a)-(s) can be conducted at a pH range of about 6-7.5.

d) Polymerases

In one embodiment, the second and/or fourth polymerases can be a wild-type or modified polymerase that, under certain reaction conditions, can bind nucleotides but exhibits reduced nucleotide incorporation activity. In yet another embodiment, the second and/or fourth polymerases can be selected that can bind the labeled nucleotide. In another embodiment, the second and/or fourth polymerases can be selected that can bind a non-incorporatable nucleotide. In another embodiment, the first and/or third polymerases can be selected that can bind a terminator nucleotide. In another embodiment, the first and/or third polymerases can be selected that can bind and incorporate a terminator nucleotide. In still another embodiment, the first, second, third and/or fourth polymerase(s) can be operably linked to a reporter moiety. In another embodiment, the first, second, third and/or fourth polymerases can be the same type or different types of polymerases. In another embodiment, the second and/or fourth polymerases can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment. In another embodiment, the first and/or third polymerase can be a THERMINATOR (New England Biolabs, Ipswich, MA) or a Phi29 polymerase.

e) Non-Extendible Ends

In one embodiment, the terminator nucleotide can be adenosine, guanosine, cytidine, thymidine or uridine terminator nucleotides, or any other type of terminator nucleotide. In another embodiment, the terminator nucleotide comprises an inhibitor moiety which permits incorporation of the terminator nucleotide but inhibits incorporation of a subsequent in-coming nucleotide. In another embodiment, the inhibitor moiety can be removed via an enzymatic, heat, chemical or light cleavage reaction (e.g., de-blocking). In another embodiment, the inhibitor moiety can be removed at any of steps (b)-(d) or (l)-(n). In another embodiment, the complex can be contacted with one or more than one type of terminator nucleotide (e.g., A, G, C, and/or T/U, or others). In another embodiment, the terminator nucleotide can be labeled or un-labeled. In one embodiment, step (k) can be conducted with a labeled terminator nucleotide which can confirm the identity of the signal detected by the transiently-bound nucleotide in step (g).

f) Labeled Nucleotides

In one embodiment, the labeled nucleotide can include 3-10, or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, steps (e) and/or (o) can be practiced by contacting the second and/or fourth polymerases with one type of labeled nucleotide, and if a signal (or a change in the signal) is not detected from a transiently-bound nucleotide, repeating the contacting step with the other types of labeled nucleotides until a signal (or change in the signal) is detected from a transiently-bound nucleotide. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

g) FRET Detection

In one embodiment, any of the polymerase can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In another embodiment, the reporter moiety which is operably linked to the first, second, third, or fourth polymerase can be the same or different. In still another embodiment, the signal emitted by the transiently-bound nucleotide can be a FRET signal.

h) Immobilized Complex

In another embodiment, the complex can be immobilized to a solid surface. For example, the polymerase, or template or primer molecule can be immobilized to a solid surface.

i) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

j) Detection:

In one embodiment, the detecting the signal or change in the signal can be performed using confocal laser scanning microscopy. Total Internal Reflection (TIR). Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

k) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

l) Washing Steps

In one embodiment, washing steps can be included after any of the steps (a)-(s), for example, to remove the non-incorporated nucleotides and/or the labeled nucleotides and/ or polymerases. In any washing step, magnesium, manganese, or calcium can be omitted or included.

An Embodiment: Using Suitable Polymerases

In one aspect, methods for detecting the presence of a transiently-bound nucleotide in successive nucleotide binding reactions comprises the steps of: (a) contacting at least one type of a first labeled nucleotide with a complex which comprises a first polymerase bound to a template nucleic acid molecule which is base-paired to a primer, under conditions suitable to transiently-bind the first labeled nucleotide to the polymerase in a template-dependent manner but inhibits incorporation of the first labeled nucleotide, where the primer or template nucleic acid molecule is immobilized to a solid surface; (b) exciting the first labeled nucleotide with an excitation source; (c) detecting a signal, or a change in a signal, emitted by the transiently-bound first labeled nucleotide in step (a), thereby detecting the presence of the transiently-bound first labeled nucleotide; (d) removing the transiently-bound first labeled nucleotide in step (b); (e) removing, washing away, or inactivating the first polymerase from the template molecule; (f) contacting a second polymerase with the template molecule which is base-paired with the immobilized primer molecule in step (d); (g) contacting the second polymerase with at least one type of a second nucleotide under conditions suitable to incorporate the one type of second nucleotide onto the primer in a template-dependent manner; (h) removing, washing away, or inactivating the second polymerase from the template molecule; (i) contacting a third polymerase with the template molecule which is base-paired with the immobilized primer molecule in step (g); (j) contacting the third polymerase with at least one type a third labeled nucleotide, under conditions suitable to transiently-bind the third labeled nucleotide to the polymerase in a template-dependent manner but inhibits incorporation of the third labeled nucleotide; (k) exciting the third labeled nucleotide with an excitation source; (l) detecting a signal, or a change in a signal, emitted by the transiently-bound third labeled nucleotide in step (i), thereby detecting the presence of the transiently-bound third labeled nucleotide; (m) removing the transiently-bound third labeled nucleotide in step (j); (n) removing, washing away, or inactivating the third polymerase from the template molecule; (o) contacting a fourth polymerase with the template molecule which is base-paired with the immobilized primer molecule in step (l); (p) contacting the fourth polymerase with at least one type of a fourth nucleotide under conditions suitable to incorporate the one type of fourth nucleotide onto the primer in a template-dependent manner; and (q) removing, washing away, or inactivating the fourth polymerase from the template molecule.

In one embodiment, steps (i)-(q) can be repeated. In another embodiment, the first, second, third, and/or fourth polymerases are not removed or replaced.

a) Calcium

In one embodiment, the conditions suitable to transiently-bind the labeled nucleotide in any of steps (a) and/or (j) include a calcium compound, or the calcium compound can be omitted. In another embodiment, the calcium compound can be $CaCl_2$). In another embodiment, the amount of calcium compound can be about 4-15 mM, or about 4-10 mM, or about 1-5 mM. In another embodiment, the calcium compound can be washed away or chelated during any of steps (c)-(i) and/or (m)-(q).

b) Manganese and Magnesium

In one embodiment, the conditions suitable to incorporate the one type of nucleotide in any of steps (g) and/or (p) include a manganese and/or magnesium compound. In one embodiment, the manganese compound can be $MnCl_2$. In another embodiment, the magnesium compound can be $MgCl_2$. In another embodiment, the amount of manganese or magnesium compound can be about 1-5 mM, or about 2-5 mM. In another embodiment, the manganese or magnesium compound can be washed away or chelated during any of steps (a)-(q).

c) pH Conditions

In another embodiment, any of the steps (a)-(q) can be conducted at a pH range of about 6-7.5.

d) Polymerases

In one embodiment, the conditions suitable to transiently-bind the labeled nucleotide in step (a) include a first polymerase which can be a wild-type or modified polymerase that, under certain reaction conditions, can bind nucleotides but exhibits reduced nucleotide incorporation activity. In one embodiment, the conditions suitable to transiently-bind the labeled nucleotide in step (j) include a third polymerase which can be a wild-type or modified polymerase that, under certain reaction conditions, can bind nucleotides but exhibits reduced nucleotide incorporation activity. In another embodiment, the first and/or third polymerases can bind a non-incorporatable nucleotide. In another embodiment, the first and/or third polymerases can be selected that can bind the labeled nucleotide.

In one embodiment, the conditions suitable to incorporate the at least one type of nucleotide in step (g) includes a second polymerase which can be a wild-type of modified polymerase that, under certain reaction conditions, can incorporate the at least one type of nucleotide. In another embodiment, the conditions suitable to incorporate the at least one type of nucleotide in step (p) includes a fourth polymerase which can be a wild-type of modified polymerase that, under certain reaction conditions, can incorporate the at least one type of nucleotide. In another embodiment, the second and/or fourth polymerases can incorporate a terminator nucleotide.

In still another embodiment, the first, second, third and/or fourth polymerase(s) can be operably linked to a reporter moiety. In another embodiment, the first, second, third and/or fourth polymerases can be the same type or different types of polymerases. In another embodiment, the first and/or third polymerases can be an RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment. Washing steps can be included after any step. In another embodiment, the second and/or fourth polymerases can be a THERMINATOR polymerase (New England Biolabs, Ipswich, MA), RB69 (exo-) (FIG. 18, 20 or 21; SEQ ID NO:2, 4 or 5, respectively), a Phi29 (exo-) (FIG. 4, SEQ ID NO:1), or B103 (exo-) polymerase (FIG. 19, SEQ ID NO:3), or a Klenow fragment.

c) Non-Extendible Ends

In one embodiment, the at least one type of nucleotide which is incorporated in step (g) and/or (p) can be a terminator nucleotide, which can produce a primer having a non-extendible end. In one embodiment, the terminator nucleotide can be adenosine, guanosine, cytidine, thymidine or uridine terminator nucleotides, or any other type of terminator nucleotide. In one embodiment, the terminator nucleotide comprises an inhibitor moiety which permits incorporation of the terminator nucleotide but inhibits incorporation of a subsequent nucleotide. In another embodiment, the inhibitor moiety can be removed via an enzymatic, heat, chemical or light cleavage reaction (e.g., de-blocking). In another embodiment, the inhibitor moiety can be removed prior to any of steps (h)-(j) or after any of steps (p)-(q). In another embodiment, the complex can be contacted with one or more than one type of terminator nucleotide (e.g., A, G, C, and/or T/U, or others). In another embodiment, the terminator nucleotide can be labeled or un-labeled.

f) Labeled Nucleotides

In one embodiment, the labeled nucleotide can include 3-10, or more phosphate groups. In another embodiment, the labeled nucleotide can be adenosine, guanosine, cytidine, thymidine or uridine, or any other type of labeled nucleotide. In one embodiment, the label can be an energy transfer acceptor reporter moiety. In another embodiment, the label can be a fluorescent dye. In another embodiment, the polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, steps (a) and/or (i) can be practiced by contacting the first and/or third polymerases with one type of labeled nucleotide, and if a signal (or a change in the signal) is not detected from a transiently-bound nucleotide, repeating the contacting step with the other types of labeled nucleotides until a signal (or change in the signal) is detected from a transiently-bound nucleotide. In another embodiment, the labeled nucleotide can be a non-incorporatable nucleotide. In one embodiment, the non-incorporatable nucleotide can bind to the polymerase and template nucleic acid molecule which is base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

g) FRET Detection

In one embodiment, any of the polymerases can be operably linked to an energy transfer donor (e.g., fluorescent dye or nanoparticle). In another embodiment, the labeled nucleotide comprises an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In another embodiment, the reporter moiety which is operably linked to the first, second, third, or fourth polymerase can be the same or different. In still another embodiment, the signal emitted by the transiently-bound nucleotide can be a FRET signal.

h) Immobilized Complex

In one embodiment, the complex can be immobilized to a solid surface. For example, the polymerase, or template or primer molecule can be immobilized to a solid surface.

i) The Excitation Source and Signal:

In one embodiment, the excitation source can be electromagnetic radiation. The excitation source can be a laser. The signal, or the change in the signal, can be optically detectable. In one embodiment, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

j) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

k) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

l) Washing Steps

In one embodiment, washing steps can be included after any of the steps, for example, to remove the non-incorporated nucleotides and/or the labeled nucleotides and/or polymerases. In any washing step, magnesium, manganese, or calcium can be omitted or included. In another embodiment, any of the steps involving removing, washing away, or inactivating the polymerase, (e.g., steps (e), (h), (n), and/or (q)) can be omitted. In another embodiment, the first polymerase can be used for any of steps (a)-(q).

Compositions and Systems

Provided herein are systems, comprising various compositions useful for practicing the nucleotide transient-binding methods. The compositions include: labeled nucleotides, non-incorporatable nucleotides, terminator nucleotides, different polymerases suitable for transient binding of the nucleotide or for incorporating nucleotides, template molecules (i.e., template molecules), polymerization initiation sites, nanoparticles, reporter moieties, and solid surfaces. The system provided herein comprises a polymerase which is complexed with a template nucleic acid molecule which is bound to a polymerization initiation site, and a nucleotide which is transiently bound to the active site of the polymerase in a template-dependent manner. In the system, the transiently-bound nucleotide is inhibited from incorporation onto the polymerization initiation site by suitable conditions which include: (i) reducing the levels or omission of a metal cation that permits nucleotide incorporation and/or addition of a cation that inhibits nucleotide incorporation; (ii) using a polymerase which selectively binds the nucleotide in a template-dependent manner and exhibits reduced nucleotide incorporation activity; (iii) using at least one type of labeled nucleotide which is a labeled non-incorporatable nucleotide; and/or (iv) using a polymerization initiation site which is a non-extendible polymerization initiation site.

Nucleotides

Provided herein are nucleotides which are transiently-bound by a polymerase. In one aspect, nucleotides are compounds that can bind selectively to, or can be polymerized by, a polymerase. Typically, but not necessarily, the polymerase selectively binds the nucleotide and catalyzes polymerization of the nucleotide onto a nucleic acid strand (e.g., nucleotide incorporation). Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the present disclosure can include compounds lacking any one, some or all of such moieties.

The nucleotides can be operably linked to a reporter moiety (e.g., labeled nucleotides) or can be un-labeled nucleotides. The nucleotides also include non-incorporatable nucleotides, and terminator nucleotides (e.g., chain terminating nucleotides and reversible terminator nucleotides). The nucleotides can be nucleotide polyphosphate molecules. Examples of nucleotide polyphosphate molecules and nucleoside polyphosphate molecules include ribonucleotides, deoxyribonucleotides, ribonucleotide polyphosphate molecules, deoxyribonucleotide polyphosphate molecules, peptide nucleotides, nucleoside polyphosphate molecules, metallonucleosides, phosphonate nucleosides, and modified phosphate-sugar backbone nucleotides, and any analogs or variants of the foregoing.

Phosphate Groups

The nucleotides typically comprise a chain of phosphorus atoms comprising three, four, five, six, seven, eight, nine, ten or more phosphorus atoms. In some embodiments, the phosphorus chain can be attached to any carbon of a sugar ring, such as the 2, 3, or 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. Some examples of nucleotide analogs are described in Xu, U.S. Pat. No. 7,405,281. The phosphate groups include analogs, such as phosphoramidate, phosphorothioate, phosphorodithioate, and O-methylphosphoroamidite groups. At least one of the phosphate groups can be substituted with a fluoro and/or chloro group. The phosphate groups can be linked to the sugar moiety by an ester or phosphoramide linkage.

Base Moieties

The nucleotides typically comprise a hetero cyclic base which includes substituted or unsubstituted nitrogen-containing parent heteroaromatic ring which is commonly found in nucleic acids, including naturally-occurring, substituted, modified, or engineered variants, or analogs of the same. The base is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7 mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, 04-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Florida.

Sugar Moieties

The nucleotides typically comprise a suitable sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284: 2118-2124; and U.S. Pat. No. 5,558,991). The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars.

Labeled Nucleotides

Provided herein are labeled nucleotides which can bind in a template-dependent manner, to a nucleic acid-dependent polymerase. In practicing the methods provided herein, the incorporation of the labeled nucleotides can be inhibited by any reaction condition which permits transient binding of a nucleotide (e.g., complementary or non-complementary) to a polymerase, and inhibits nucleotide incorporation, including: (1) reaction conditions and reagents (e.g., temperature, pH, ionic strength, divalent cations, and/or time); (2) modified polymerases; (3) modifications of the nucleotide which inhibit incorporation; and/or (4) non-extendible polymerization initiation site.

The labeled nucleotide can bind the polymerase, which is bound to a base-paired template nucleic acid molecule and polymerization initiation site. The polymerase can interrogate the labeled nucleotide for complementarity with the template nucleotide on the template molecule. The transient-binding time of the complementary labeled nucleotide can be longer compared to the transient-binding time of the non-complementary labeled nucleotide.

The labeled nucleotides comprise a nucleotide operably linked to at least one reporter moiety at any position of the base or sugar, or any of the phosphate groups (alpha, beta, gamma, any phosphate group distal to the sugar moiety, or a terminal phosphate group).

The labeled nucleotide can be a non-incorporatable nucleotide or a terminator nucleotide which is operably linked to at least one reporter moiety. The reporter moiety can be a fluorescent dye, energy transfer dye, or any other type of reporter moiety. The labeled nucleotide can be operably linked to different types of reporter moieties. The same type or different types of reporter moieties can be operably linked to different types of nucleotides, for example, to permit base distinction and/or identification. A linear or branched linker can be used to attach the nucleotide to the reporter moiety. An intervening linker can connect different reporter moieties to each other and/or to the nucleotide in any combination of linking arrangements. The labeled nucleotide can be incorporated by a naturally occurring, modified, or engineered nucleic acid-dependent polymerase. The labeled nucleotide can be resistant to degradation by 3'-5' exonuclease activity of the polymerase. Sec for example, U.S. Ser. No. 61/164,091, Ronald Graham, filed Mar. 27, 2009. See for example U.S. Pat. Nos. 7,041,812, 7,052,839, 7,125,671, and 7,223,541; U.S. Pub. Nos. 2007/072196 and 2008/0091005; Sood et al., 2005, J. Am. Chem. Soc. 127:2394-2395; Arzumanov et al., 1996, J. Biol. Chem. 271:24389-24394; and Kumar et al., 2005, Nucleosides, Nucleotides & Nucleic Acids, 24(5):401-408.

Linking schemes for attaching reporter moieties to the nucleobase are known (European Patent Application 87310256.0; International Application PCT/US90/05565; Marshall 1975 Histochemical Journal 7:299-303; Barone et al., 2001 Nucleosides, Nucleotides, and Nucleic Acids, 20:1141-1145). Other useful linking schemes include attaching reporter moieties to oligonucleotides synthesized using phosphoramidate to incorporate amino-modified dT (Mathies, U.S. Pat. No. 5,707,804). In one embodiment, the reporter moiety (e.g., fluorophore) can be linked to the base of the nucleotide via a hexylacrylamide linker. In another embodiment, the reporter moiety (e.g., fluorophore) can be linked to the C5 position of the base (e.g., cytosine or uracil) via a hexylacrylamide linker (Molecular Probes, A32763 and A32771), or can be linked to the C5 position of the base (e.g., uracil) via a propargylamino linker (Jena Bioscience, NU-. In yet another embodiment, the reporter moiety (fluorophore) can be linked to the N7 position of the base (e.g., guanosine) via a propargylamino linker (Jena Bioscience, NU-1619-CY5).

Reporter Moieties

Provided herein are one or more reporter moieties which are operably linked to the labeled nucleotides, terminator nucleotides, non-incorporatable nucleotides, nanoparticles, polymerases, template nucleic acid molecules, primer molecules, surfaces, and/or oligonucleotides.

The reporter moiety generates, or causes to generate, a detectable signal. Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. The reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other.

The reporter moieties may be selected so that each absorbs excitation radiation and/or emits fluorescence at a wavelength distinguishable from the other reporter moieties to permit monitoring the presence of different reporter moieties in the same reaction. Two or more different reporter moieties can be selected having spectrally distinct emission profiles, or having minimal overlapping spectral emission profiles.

In one aspect, the signals from the different reporter moieties do not significantly overlap or interfere, by quenching, colorimetric interference, or spectral interference.

The chromophore moiety may be 5-bromo-4-chloro-3-indolyl phosphate, 3-indoxyl phosphate, p-nitrophenyl phosphate, and derivatives thereof, or β-lactamase or peroxidase based chemistry.

The chemiluminescent moiety may be a phosphatase-activated 1,2-dioxetane compound. The 1,2-dioxetane compound includes disodium 2-chloro-5-(4-methoxyspiro[1,2-dioxetane-3,2'-(5-chloro-)tricyclo[3,3,1-1$^{3,7}$]-decan]-1-yl)-1-phenyl phosphate (e.g., CDP-STAR), chloroadamant-2'-ylidenemethoxyphenoxy phosphorylated dioxetane (e.g., CSPD), and 3-(2'-spiroadamantane)-4-methoxy-4-(3"-phosphoryloxy)phenyl-1,2-dioxetane (e.g., AMPPD).

The fluorescent moiety includes: rhodols; resorufins; coumarins; xanthenes; acridines; fluoresceins; rhodamines;

erythrins; cyanins; phthalaldehydes; naphthylamines; fluorescamines; benzoxadiazoles; stilbenes; pyrenes; indoles; borapolyazaindacenes; quinazolinones; cosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green (M. Kamiya, et al., 2005 Angew. Chem. Int. Ed. 44:5439-5441); and CF dyes including CF 647 and CF555 (Biotium).

Quencher dyes may include: ATTO 540Q. ATTO 580Q, and ATTO 612Q (Atto-Tec); QSY dyes including QSY 7, QSY 9, QSY 21, and QSY 35 (Molecular Probes); and EPOCH ECLIPSE QUENCHER (phosphoramidate) (Glen Research). The fluorescent moiety can be a 7-hydroxycoumarin-hemicyanine hybrid molecule which is a far-red emitting dye (Richard 2008 Org. Lett. 10:4175-4178).

The fluorescent moiety may be a fluorescence-emitting metal such as a lanthanide complex, including those of Europium and Terbium.

A number of examples of fluorescent moieties are found in PCT publication WO/2008/030115, and in Haugland, Molecular Probes Handbook, (Eugene, Oregon) 6th Edition; The Synthegen catalog (Houston, Tex.), Lakowicz, Principles of Fluorescence Spectroscopy, 2nd Ed., Plenum Press New York (1999).

Energy Transfer Moieties

Provided herein are reporter moieties which can be energy transfer moieties, such as energy transfer pairs (e.g., donors and acceptors), which are operably linked to the labeled nucleotides, terminator nucleotides, non-incorporatable nucleotides, nanoparticles, polymerases, template nucleic acid molecules, primer molecules, surfaces, and/or oligonucleotides.

In one aspect, the energy transfer moiety can be an energy transfer donor, such as a nanoparticle or an energy transfer dye. In another aspect, the energy transfer moiety can be an energy transfer acceptor, such as an energy acceptor dye.

In one aspect, the energy transfer pair can be operably linked to the same molecule. In another aspect, the donor and acceptor can be operably linked to different molecules in any combination. For example, the donor can be linked to the polymerase, template molecule, or primer molecule, and the acceptor can be linked to the nucleotide (e.g., non-incorporatable nucleotide or terminator nucleotide), the template molecule, or the primer molecule.

The energy transfer donor is capable of absorbing electromagnetic energy (e.g., light) at a first wavelength and emitting excitation energy in response. The energy acceptor is capable of absorbing excitation energy emitted by the donor and fluorescing at a second wavelength in response.

The donor and acceptor moieties can interact with each other physically or optically in a manner which produces a detectable signal when the two moieties are in proximity with each other. A proximity event includes two different moieties (e.g., energy transfer donor and acceptor) approaching each other, or associating with each other, or binding each other.

The donor and acceptor moieties can transfer energy in various modes, including: fluorescence resonance energy transfer (FRET) (L. Suryer 1978 Ann. Rev. Biochem. 47: 819-846: Schneider, U.S. Pat. No. 6,982,146; Hardin, U.S. Pat. No. 7,329,492; Hanzel, U.S. published patent application No. 2007/0196846), scintillation proximity assays (SPA) (Hart and Greenwald 1979 Molecular Immunology 16:265-267; U.S. Pat. No. 4,658,649), luminescence resonance energy transfer (LRET) (G. Mathis 1995 Clin. Chem. 41:1391-1397), direct quenching (Tyagi et al, 1998 Nature Biotechnology 16:49-53), chemiluminescence energy transfer (CRET) (Campbell and Patel 1983 Biochem. Journal 216:185-194), bioluminescence resonance energy transfer (BRET) (Y. Xu, et al., 1999 Proc. Natl. Acad. Sci. 96:151-156), and excimer formation (J. R. Lakowicz 1999 "Principles of Fluorescence Spectroscopy", Kluwer Academic/Plenum Press, New York).

FRET

In one aspect, the energy transfer pair can be FRET donor and acceptor moieties. FRET is a distance-dependent radiationless transmission of excitation energy from a donor moiety to an acceptor moiety. For example, a donor moiety, in an excited state, transfers its energy to a proximal acceptor moiety by non-radiative dipole-dipole interaction (Forster 1948 "Intermolecular Energy Migration and Fluorescence", Ann. Phys., 2:55-75; and Lakowicz 1999 Principles of Fluorescence Spectroscopy, 2nd ed. Plenum, New York. 367-394) or energy transfer not strictly following the Forster's theory, such as nonoverlapping energy transfer occurring when nonoverlapping acceptors are utilized (Anal. Chem. 2005, 77: 1483-1487). Typically, the efficiency of FRET energy transmission is dependent on the inverse sixth-power of the separation distance between the donor and acceptor, which is approximately 10-100 Angstroms. FRET is useful for investigating changes in proximity between and/or within biological molecules. FRET efficiency may depend on donor-acceptor distance r as $1/r^6$ or $1/r^4$. The distance where FRET efficiency is 50% is termed $R_O$, also know as the Forster distance. $R_O$ is unique for each donor-acceptor combination and may be about 5 to 10 nm. The efficiency of FRET energy transfer can sometimes be dependent on energy transfer from a point to a plane which varies by the fourth power of distance separation (E. Jares-Erijman, et al., 2003 Nat. Biotechnol. 21:1387).

In biological applications, FRET can provide an on-off type signal indicating when the donor and acceptor moieties are within proximity of each other. Additional factors affecting FRET efficiency include the quantum yield of the donor, the extinction coefficient of the acceptor, and the degree of spectral overlap between the donor and acceptor. Procedures are well known for maximizing the FRET signal and detection by selecting high yielding donors and high absorbing acceptors with the greatest possible spectral overlap between the two (D. W. Piston and G. J. Kremers 2007 Trends Biochem. Sci. 32:407). The change in fluorescence from a donor (e.g., reduced fluorescence signal) during a FRET event, can be an indication of proximity between a donor and acceptor moiety.

The production of signals from FRET donors and acceptors can be sensitive to the distance between donor and acceptor moieties, the orientation of the donor and acceptor moieties, and/or a change in the environment of one of the moieties (Deuschle et al. 2005 Protein Science 14: 2304-2314; Smith et al. 2005 Protein Science 14:64-73). For example, a nucleotide (e.g., non-incorporatable or terminator nucleotide) linked with a FRET moiety (e.g., acceptor) may produce a detectable signal when it approaches, associates with, or binds a polymerase linked to a FRET moiety (e.g., donor). In another example, a FRET donor and acceptor linked to one protein can emit a FRET signal upon conformational change of the protein. Some FRET donor/acceptor pairs exhibit changes in absorbance or emission in response to changes in their environment, such as changes in pH, ionic strength, ionic type (NO). $Ca^{+2}$, $Mg^{+2}$, $Zn^{+2}$, $Na^+$, $Cl^-$, $K^+$), oxygen saturation, and solvation polarity.

The FRET donor and/or acceptor may be a fluorophore, luminophore, chemiluminophore, bioluminophore, or quencher (P. Selvin 1995 Methods Enzymol 246:300-334; CG dos Remedios 1995 J. Struct. Biol. 115:175-185; P. Wu and L. Brand 1994 Anal Biochem 218:1-13). Accordingly, the FRET donor and acceptors may undergo fluorescence or other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized (Laitala and Hemmila 2005 Anal. Chem. 77: 1483-1487).

Quenchers

The energy transfer moiety can be a FRET quencher. Typically, quenchers have an absorption spectrum with large extinction coefficients, however the quantum yield for quenchers is reduced, such that the quencher emits little to no light upon excitation. Quenching can be used to reduce the background fluorescence, thereby enhancing the signal-to-noise ratio. In one aspect, energy transferred from the donor may be absorbed by the quencher which emits moderated (e.g., reduced) fluorescence. In another aspect, the acceptor can be a non-fluorescent chromophore which absorbs the energy transferred from the donor and emits heat (e.g., the energy acceptor is a dark quencher).

For an example, a quencher can be used as an energy acceptor with a nanoparticle donor in a FRET system (I. L. Medintz, et al., 2003 Nat. Mater. 2:630). One exemplary method involves the use of quenchers in conjunction with reporters comprising fluorescent reporter moieties. In this strategy, certain nucleotides in the reaction mixture are labeled with a reporter comprising a fluorescent label, while the remaining nucleotides are labeled with one or more quenchers. Alternatively, each of the nucleotides in the reaction mixture is labeled with one or more quenchers. Discrimination of the nucleotide bases is based on the wavelength and/or intensity of light emitted from the FRET acceptor, as well as the intensity of light emitted from the FRET donor. If no signal is detected from the FRET acceptor, a corresponding reduction in light emission from the FRET donor indicates transient-binding of the nucleotide labeled with a quencher. The degree of intensity reduction may be used to distinguish between different quenchers.

Examples of fluorescent donors and non-fluorescent acceptor (e.g., quencher) combinations have been developed for detection of proteolysis (Matayoshi 1990 Science 247: 954-958) and nucleic acid hybridization (L. Morrison, in: "Nonisotopic DNA Probe Techniques", ed., L. Kricka, Academic Press, San Diego, 1992, pp. 311-352; S. Tyagi 1998 Nat. Biotechnol. 16:49-53; S. Tyagi 1996 Nat. Biotechnol. 14:947-8). FRET donors, acceptors and quenchers can be moieties that absorb electromagnetic energy (e.g., light) at about 300-900 nm, or about 350-800 nm, or about 390-800 nm.

Energy transfer donor and acceptor moieties can be made from materials which typically fall into four general categories (see the review in: K. E. Sapford, et al . . . 2006 Angew. Chem. Int. Ed. 45:4562-4588), including: (1) organic fluorescent dyes, dark quenchers and polymers (e.g., dendrimers); (2) inorganic material such as metals, metal chelates and semiconductors nanoparticles: (3) biomolecules such as proteins and amino acids (e.g., green fluorescent protein and derivatives thereof); and (4) enzymatically catalyzed bioluminescent molecules. The material for making the energy transfer donor and acceptor moieties can be selected from the same or different categories.

The FRET donor and acceptor moieties which are organic fluorescent dyes, quenchers or polymers include traditional dyes that emit in the UV, visible, or near-infrared region. The UV emitting dyes include coumarin-, pyrene-, and naphthalene-related compounds. The visible and near-infrared dyes include xanthene-, fluorescein-, rhodol-, rhodamine-, and cyanine-related compounds. The fluorescent dyes also includes DDAO ((7-hydroxy-9H-(1,3-dichloro-9,9-dimethylacridin-2-one)), resorufin, ALEXA FLUOR and BODIPY dyes (both Molecular Probes), HILYTE Fluors (AnaSpec). ATTO dyes (Atto-Tec), DY dyes (Dyomics GmbH). TAMRA (Perkin Elmer), tetramethylrhodamine (TMR), TEXAS RED, DYLIGHT (Thermo Fisher Scientific), FAM (AnaSpec), JOE and ROX (both Applied Biosystems), and Tokyo Green.

Additional fluorescent dyes which can be used as quenchers includes: DNP, DABSYL, QSY (Molecular Probes), ATTO (Atto-Tec). BHQ (Biosearch Technologies). QXL (AnaSpec). BBQ (Berry and Associates) and CY5Q/7Q (Amersham Biosciences).

The FRET donor and acceptor moieties which comprise inorganic materials include gold (e.g., quencher), silver, copper, silicon, semiconductor nanoparticles, and fluorescence-emitting metal such as a lanthanide complex, including those of Europium and Terbium.

Suitable FRET donor/acceptor pairs include: FAM as the donor and JOE, TAMRA, and ROX as the acceptor dyes. Other suitable pairs include: CYA as the donor and R6G, TAMRA, and ROX as the donor dyes.

In one embodiment, a nucleotide can be operably linked to a suitable reporter moiety. This labeled nucleotide can bind transiently to the polymerase. The reporter moiety can be excited and the signal emitted by the reporter moiety can be detected. In another embodiment, a polymerase can be operably linked to a suitable nanoparticle and a nucleotide can be operably linked to a suitable reporter moiety. The labeled nucleotide can bind to the polymerase. The nanoparticle can be excited and the resulting energy from the excited nanoparticle can be transferred to the reporter moiety. The transferred energy can excite the reporter moiety, which can be emitted as a detectable signal.

Terminator Nucleotides

Provided herein are terminator nucleotides which can be incorporated onto the polymerization initiation site, in a template-dependent manner, by a nucleic acid-dependent polymerase, but the terminator nucleotide (which is incorporated) inhibits the incorporation of the next nucleotide. The terminator nucleotide can be incorporated by a naturally occurring, modified, or engineered nucleic acid-dependent polymerase.

The extending strand comprises the polymerization initiation site and a nucleotide which is incorporated at the terminal 3' end of the initiation site. The extending strand can have an extendible- or non-extendible 3' terminal end. The extendible end includes a terminal 3' —OH group. The non-extendible end is not extendible by a polymerase. The non-extendible end can include any moiety which inhibits incorporation of the next nucleotide. A terminator nucleotide, which is incorporated onto the polymerization initiation site, forms the new non-extendible end of the extending strand.

The terminator nucleotide comprises a nucleotide operably linked to an inhibitor moiety. The inhibitor moiety comprises any chemical compound or chemical group which permits incorporation of the terminator nucleotide by the polymerase but inhibits incorporation of the next nucleotide. Thus, the polymerase can incorporate one and only one terminator nucleotide, thereby advancing nucleotide incorporation by only one base. The inhibitor moiety can be operably linked to any portion of the nucleoside or nucleotide (e.g., any phosphate group, or base or sugar moiety). The same type or different types of inhibitor moieties can be operably linked to different types of nucleotides. The terminator nucleotide can be resistant to degradation by 3'-5' exonuclease activity of the polymerase.

On the terminator nucleotide, the inhibitor moiety can be modified so that the next nucleotide can be incorporated (e.g., reversible terminator nucleotide). Alternatively, the inhibitor moiety can be removed (de-blocking) to permit incorporation of the next nucleotide. Accordingly, on a polymerization initiation site which has a terminator nucleotide incorporated onto its 3' end, the inhibitor moiety can be modified or removed to permit incorporation of the next nucleotide.

In one embodiment, the terminator nucleotides can be non-labeled, or can be operably linked to at least one reporter moiety at any position of the base or sugar, or any of the phosphate groups (alpha, beta, gamma, or terminal phosphate group).

Many suitable terminator nucleotides having inhibitor moieties attached to the sugar 3' position, base-linked dyes, where the linkers are cleavable under the same conditions are described by Tsien (WO/1991/006678). Additionally, suitable terminator nucleotides having photocleavable linkers are described by Stemple (U.S. Pat. No. 7,270,951; Turner, U.S. Pat. No. 7,476,504).

Inhibitor Moieties

The terminator nucleotides comprise a nucleotide operably linked to at least one suitable inhibitor moiety. The inhibitor moiety comprises any chemical compound or chemical group which permits incorporation onto the polymerization initiation site, in a template-dependent manner, by a nucleic acid-dependent polymerase, but inhibits incorporation of the next nucleotide. The inhibitor moiety can modify, substitute, or protect, any portion of the nucleotide (e.g., base, sugar, or phosphate group). A suitable inhibitor moiety can be operably linked to any part of the nucleotide (or nucleoside) including the base or sugar moiety, or any phosphate group. The suitable inhibitor moiety can permit incorporation of the terminator nucleotide, in a polymerase-driven, template-dependent manner, but inhibits, stalls, or slows down incorporation of the next nucleotide by the polymerase. The suitable inhibitor moiety inhibits incorporation of the next nucleotide by physical, chemical, or charge interaction with the polymerase and/or incoming nucleotide.

The suitable inhibitor moiety can be operably linked to the 2' or 3' position of the sugar moiety. In one embodiment, the 2' or 3'-H or —OH group of the sugar moiety can be modified, substituted, or protected. For example, it is well known that DNA polymerases require a polymerization initiation site having a terminal 3' —OH group. Thus, the inhibitor moiety can be any chemical group or compound, which is not an —OH group, operably linked to the 3' C of the sugar moiety. In some embodiments, the suitable inhibitor moiety can be an —H group operably linked to the 3' C of the sugar moiety. Such embodiments include dideoxynucleosides and dideoxynucleotides. Examples of inhibitor moieties attached to the sugar 3' position are described by Balasubramanian (U.S. Pat. No. 7,427,673) and Milton (U.S. Pat. No. 7,541,444).

The suitable inhibitor moiety can be operably linked to any position of the nitrogenous base, such as a purine group, including the C2, C4, C5, N3, or C6, of cytosine, thymine, and uracil. The suitable inhibitor moiety can be operably linked to any position of the pyrimidine group, including the C2, C6, C8, N3 and N7 of adenine and guanine.

The suitable inhibitor moiety can be operably linked to any phosphate group, such as the alpha, beta, gamma, or a terminal phosphate group.

In another embodiment, the suitable inhibitor moiety can be linked to any portion of the nucleoside or nucleotide, and sterically hinder the incoming nucleotide. In yet another embodiment, the suitable inhibitor moiety can be a charged group (positive or negative) and linked to any portion of the nucleoside or nucleotide and can inhibit the polymerase from incorporating the next nucleotide. In another embodiment, the suitable inhibitor moiety can be linked to at least one of: a sterically-hindering group, fluorophore, and/or quencher, in any order and in any combination.

The suitable inhibitor moiety comprises any group including: amine, alkyl, alkenyl, alkynyl, alkyl amide, aryl, ether, ester, benzyl, propargyl, propynyl, phosphate, or analog thereof. For example, the suitable inhibitor moiety can be a 3'-O-allyl moiety (Ruparel, et al., 2005 Proc. Natl. Acad. Sci. USA 102:5932-5937).

Suitable inhibitor moieties are well known in the art, and include: fluorenylmethyloxycarbonyl (FMOC), 4-(anisyl) diphenylmethyltrityl (MMTr), dimethoxytrityl (DMTr), monomethoxytrityl, trityl (Tr), benzoyl (Bz), isobutyryl (ib), pixyl (pi), ter-butyl-dimethylsilyl (TBMS), and 1-(2-fluorophenyl)-4-methoxypiperidin 4-yl (FPMP). See also T W Greene 1981, in "Protective Groups in Organic Synthesis", publishers Wiley-Interscience; Beaucage and Iyer 1992 Tetrahedron, 48:2223-2311; Beaucage and Iyer 1993 Tetrahedron 49:10441-10488; and Scaringe et al., 1998 J. Am. Chem. Soc. 120:11820-11821.

The suitable inhibitor moiety can be a reporter moiety (e.g., fluorescent dye) operably linked to the base or sugar moiety. For example, a fluorescent dye operably linked to the base via a 2-nitrobenzyl group, where the 2-nitrobenyl group has the alpha carbon substituted with one alkyl or aryl group (Wu, et al., U.S. published patent application No. 2008/0132692). The 2-nitrobenzyl group can be photocleavable.

In another example, the suitable inhibitor moiety can be a reporter moiety (e.g., fluorescent dye, e.g., ALEXA FLUOR 549) operably linked to the 5 position of pyrimidines or the 7 position of the purines, via a cleavable disulfide linker (Turcatti, et al., 2008 Nucleic Acids Research vol. 36, No. 4, doi: 10.1093/nar/gkn021).

In yet another example, the suitable inhibitor moiety can be a rhodamine-type dyes, such as R6G, R110, ROX, or TAMRA, or dichloro-derivatives thereof, which are based-linked dyes, including the commercially-available rhodamine dye terminator nucleotides from Applied Biosystems.

The suitable inhibitor moiety can be a charged group (positive or negative) or a group capable of becoming charged (Efcavitch, U.S. published patent application No. 2009/0061437), including a carboxylic acid, carboxylated, phosphate, di-phosphate, peptide, dipeptide, sulfate, disulfate, caproic acid, or amino acid (e.g., a negatively charged amino acid such as aspartic acid, glutamic acid, histidine, lysine, or arginine).

The suitable inhibitor moiety can be a non-incorporatable nucleotide or nucleoside which is linked to the base by a tether. The tether can be linked to a fluorescent label. The tether can include a cleavable moiety, such as a disulfide group (Siddiqi, U.S. published patent application No. 2008/0103053 and 2008/0227970).

The suitable inhibitor moiety can be a hydrocaryldithiomethyl-modified compound (Kwiatkowski, U.S. Pat. No. 7,279,563.

The suitable inhibitor moiety can include an ethyl dithio linker (Siddiqi, U.S. published patent application No. 2008/0269476).

The suitable inhibitor moiety can be an alkyl chain homologue having any chain length, which can be produced by replacing 2-bromoethanol and ethylsulfide reagents with any alkyl chain homologue (Siddiqi, U.S. published patent application No. 2008/0269476).

The suitable inhibitor moiety can be any phosphate, $SO_3$, or C(O)R group, or modified groups thereof (Lee, U.S. published patent application No. 2008/0050780). In the C(O)R group, R can be an H, alkyl, benzyl, aryl, alkenyl, alkynyl group, any combination thereof.

In one embodiment, removal or modification of the inhibitor moiety which is attached to the 3' C of the sugar moiety, and restoration of a 3' —OH group, can permit incorporation of a subsequent nucleotide (e.g., reversible terminator nucleotide). In another embodiment, removal or modification of the inhibitor moiety which is attached to the sugar, base, or phosphate group, can permit incorporation of a subsequent nucleotide (e.g., reversible terminator nucleotide).

Linkers for Terminator Nucleotides

In one aspect, a suitable linker operably links the terminator nucleotide to the inhibitor moiety. The suitable linker does not interfere with the function or activity of the nucleotide, nucleoside, or inhibitor moiety. The suitable linker can be cleavable or fragmentable to permit removal of the inhibitor moiety. The suitable linker can be the inhibitor moiety. In one embodiment, the nucleotide can be attached directly to the inhibitor moiety without an intervening linker. Various linkers and linker chemistries for generating the terminator nucleotides are disclosed infra.

The terminator nucleotides can be linked to inhibitor moieties using any suitable linking scheme, including linking schemes using amine linkers (Hobbs, U.S. Pat. No. 5,151,507), or primary or secondary amines, or a rigid hydrocarbon arm (RF Service, 1998 Science 282:1020-21).

The terminator nucleotide can include more than one linker, where the linkers are the same or different. The multiple linkers can be removed, cleaved or fragmented using different temperatures, enzymatic activities, chemical agents, and/or different wavelengths of electromagnetic radiation.

Cleavable Linkers

In the terminator nucleotide, the suitable linker can be cleavable by heat, enzymatic activity, chemical agent, or electromagnetic radiation. Cleavable groups include: disulfide, amide, thioamide, ester, thioester, vicinal diol, or hemiacetal. Other cleavable bonds include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases).

In one embodiment, the cleavable linker can be a photocleavable linker, such as a 2-nitrobenzyl linker (Bai 2004 Nucl. Acid Res. 32:535-541; Seo, et al., 2005 Proc. Natl. Acad. Sci. USA 102:5926-5931; Wu, et al., 2007 Proc. Natl. Acad. Sci. USA 104:16462-16467), or others (Lyle, U.S. published patent application No. 2008/0009007). Analogs of the 2-nitrobenzyl linker, and other photocleavable linkers can be used as cleavable blocking groups, including: 2-nitrobenzyloxycarbonyl (NBOC); nitroveratryl; 1-pyrenylmethyl; 6-nitroveratryloxycarbonyl (NVOC); dimethyldimethoxy-benzyloxycarbonyl (DDZ); 5-bromo-7-nitroindolinyl; O-hydroxy-alpha-methyl-cinnamoyl; methyl-6-nitroveratryloxycarbonyl; methyl-6-nitropiperonyloxycarbonyl; 2-oxymethylene anthraquinone; dimethoxybenzyloxy carbonyl; 5-bromo-7-nitroindolinyl; O-hydroxy-alpha-methyl cinnamoyl; t-butyl oxycarbonyl (TBOC), and 2-oxymethylene anthriquinone (see: McGall, U.S. Pat. No. 5,412,087; Pirrung, U.S. Pat. No. 5,143,854; and Conrad, U.S. Pat. No. 5,773,308). The photocleavable linkers can be illuminated with an electromagnetic source at about 320-800 nm, depending on the particular linker, to achieve cleavage. For example, 1-(2-nitrophenyl)ethyl can be cleaved with light at about 300-350 nm, and 5-bromo-7-nitroindolinyl can be cleaved with light at about 420 nm. In another embodiment, the photocleavable linker can serve as the inhibitor moiety.

In another embodiment, the terminator nucleotide can include two or more cleavable linkers, each attached to a different portion of the nucleotide. For example, the terminator nucleotide can include two different photo-cleavable linkers that are cleavable with the same or different wavelengths of light.

In another embodiment, the linker can be an ethyl dithio or an alkyl chain linker (Siddiqi, U.S. published patent application Nos. 2008/0269476 and 2008/0286837). In another embodiment, the cleavable linker can be a disulfide-linker which is a chemically-cleavable linker (Shimkus 1985 Proc. Natl. Acad. Sci. USA 82:2593-2597). In yet another embodiment, the cleavable linker can be an allyl moiety which is cleavable by palladium (Pd(0)) in a deallylation reaction (Ju, et al., 2006 Proc. Natl. Acad. Sci. USA 103: 19635-19640; Wu, et al., 2007 Proc. Natl. Acad. Sci. USA 104:16462-16467), or an azidomethyl group which is cleavable with Tris(2-carboxyethyl)phosphine (TCEP) in aqueous solution (Guo, et al., 2008 Proc. Natl. Acad. Sci. USA 105:9145-9150; Bentley, et al., 2008 Nature 456:53-59, and Supplemental Materials and Methods). In still another embodiment, the linker can be cleavable with silver nitrate ($AgNO_3$). In another embodiment, an azidomethyl group can serve as an inhibitor moiety and a cleavable linker.

A procedure for synthesizing a terminator nucleotide having an unblocked 3'OH group and carrying a biotin molecule linked to the base moiety (N6-alkylated base) via a 2-nitrobenzyl linker may be adapted from the method described by Wu (Nucl. Acid. Res. 2007, 35:6339-6349).

Fragmentable Linkers

In the terminator nucleotide, the suitable fragmentable linker is capable of fragmenting in an electronic cascade self-elimination reaction (Graham, U.S. published patent application No. 2006/0003383; and Lee, U.S. published patent application No. 2008/0050780). In some embodiments, the fragmentable linker comprises a trigger moiety. The trigger moiety comprises a substrate that can be cleaved or "activated" by a specified trigger agent. Activation of the trigger moiety initiates a spontaneous rearrangement that results in the fragmentation of the linker and release of the enjoined compound. For example, the trigger moiety can initiate a ring closure mechanism or elimination reaction. Various elimination reactions, include 1,4-, 1,6- and 1,8-elimination reactions.

Any means of activating the trigger moiety may be used. Selection of a particular means of activation, and hence the trigger moiety, may depend, in part, on the particular fragmentation reaction desired. In some embodiments, activation is based upon cleavage of the trigger moiety. The trigger moiety can include a cleavage site that is cleavable by a chemical reagent or enzyme. For example, the trigger moiety can include a cleavage recognition site that is cleavable by a sulfatase (e.g., $SO_3$ and analogs thereof), esterase, phosphatase, nuclease, glycosidase, lipase, esterase, protease, or catalytic antibody.

Polymerases

Provided herein are polymerases which are enzymes that can catalyze the polymerization of nucleotide (including nucleotide analogs) onto a nucleic acid strand. Typically but not necessarily such nucleotide polymerization can occur in a template-dependent fashion. The polymerases can bind to complementary nucleotides more selectively compared to non-complementary nucleotides. The polymerase can transiently bind complementary and non-complementary nucleotides in a template-dependent manner, but the frequency or duration of the transient-binding differs between the complementary and non-complementary nucleotides.

One or more different types of polymerases can be used to practice the nucleotide transient-binding methods provided herein. The polymerases can transiently-bind a labeled nucleotide and/or a non-incorporatable nucleotide and/or a terminator nucleotide, in a template-dependent manner. Multiple cycles of transient-binding reactions can be practiced using the same type or different types of polymerases. The polymerase can bind a template nucleic acid molecule, which is base-paired with a polymerization initiation site. The polymerization initiation site may have an extendible or non-extendible terminal end. The polymerase may or may not mediate incorporation of a nucleotide onto a polymerization initiation site having an extendible end.

The polymerases are nucleic acid-dependent polymerases which are biologically active polypeptide molecules, or fragments thereof. In one embodiment, the polymerases catalyze the transfer of a nucleoside monophosphate from a nucleoside triphosphate (or analog thereof) to a polymerization initiation site having an extendible end.

In one embodiment, the polymerases are not linked to a reporter moiety, or are operably linked to a reporter moiety at the site at or near the nucleotide binding site on the polymerase to facilitate energy transfer signals to or from the transiently-bound labeled nucleotides.

In one aspect, the polymerases can be replicases, DNA-dependent polymerases, primases, RNA-dependent polymerases, RNA-dependent DNA polymerases (e.g., reverse transcriptases), strand-displacement polymerases, or thermo-stable polymerases. In another aspect, the polymerase can be any Family A or B type polymerase. Many types of Family A (*E. coli* Pol I), B (*E. coli* Pol II), C (*E. coli* Pol III), D (Euryarchaeotic Pol II), X (human Pol beta), and Y (*E. coli* UmuC/DinB and eurkaryotic RAD30/xeroderma pigmentosum variants) polymerases are described by Rothwell and Watsman (see: 2005 Advances in Protein Chemistry 71:401-440) and Bergers (see: 2001 Journal of Biological Chemistry 276:43487-43490).

In another aspect, the polymerases include intact subunits, biologically-active fragments, mutant variants, fusion variants, chimeric variants, naturally occurring polymerases, or non-naturally occurring polymerases. The mutations include amino acid substitutions, insertions, or deletions.

In yet another aspect, the polymerases can be isolated from a cell, or generated using recombinant DNA technology or chemical synthesis methods. In another aspect, the polymerases can be expressed in prokaryote, eukaryote, viral, or phage organisms. In another aspect, the polymerases can be post-translationally modified proteins or fragments thereof.

In one aspect, the polymerase can be a recombinant protein which is produced by a suitable expression vector/host cell system. The polymerases can be encoded by suitable recombinant expression vectors carrying inserted nucleotide sequences of the polymerases. The polymerase sequence can be operably linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker that confers resistance to drugs (e.g., kanamycin, ampicillin, tetracycline, chloramphenicol, or the like) or a requirement for a nutrient. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. The expression vector can enter a host cell which can replicate the vector, produce an RNA transcript of the inserted sequence, and/or produce protein encoded by the inserted sequence. The recombinant polymerase can include an affinity tag for enrichment or purification, including a poly-His, GST and/or HA sequence tag. Methods for preparing suitable recombinant expression vectors and expressing the RNA and/or protein encoded by the inserted sequences are well known in the art (Sambrook et al, *Molecular Cloning* (1989)).

The polymerases may be DNA polymerases and include without limitation bacterial DNA polymerases, eukaryotic DNA polymerases, archacal DNA polymerases, viral DNA polymerases and phage DNA polymerases. The polymerases can be commercially-available.

Suitable bacterial DNA polymerase include *E. coli* DNA polymerases I, II and III, IV and V, the Klenow fragment of *E. coli* DNA polymerase, *Clostridium stercorarium* (Cst)

DNA polymerase, *Clostridium thermocellum* (Cth) DNA polymerase and *Sulfolobus solfataricus* (Sso) DNA polymerase.

Suitable eukaryotic DNA polymerases include DNA polymerases α, β, γ, δ, ε, η, ζ, σ, λ, μ, ι, and κ, as well as the Rev1 polymerase (terminal deoxycytidyl transferase) and terminal deoxynucleotidyl transferase (TdT).

Suitable viral DNA polymerases include T4 DNA polymerase, RB69 (FIGS. 18, 20 and 21; SEQ ID NO:2, 4 and 5), phi-29 DNA polymerase (*Bacillus subtilis* phage; U.S. Pat. No. 5,198,543; see FIG. 4, SEQ ID NO:1), B103 (FIG. 19, SEQ ID NO:3), GA-1, phi-29-like DNA polymerases (Meijer 2001 Microbiology and Molecular Biology Reviews 65:261-287), T7 DNA polymerase, and T4 polymerase.

Suitable archaeal DNA polymerases include thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase (Vent™ DNA polymerase, New England Biolabs), *Pyrococcus* sp. GB-D polymerase (Deep Vent™ DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2.

In one embodiment, the suitable polymerase can any 9° N-7 DNA polymerase, or derivatives thereof, including THERMINATOR, THERMINATOR II, THERMINATOR III, or THERMINATOR GAMMA polymerase (New England Biolabs, catalog #s M0261L, M0266L, and M0334L, respectively).

Suitable RNA polymerases include T7, T3 and SP6 RNA polymerases.

Suitable reverse transcriptases include reverse transcriptases from HIV, HTLV-I, HTLV-II, FeLV, FIV, SIV, AMV, MMTV and MoMuLV, as well as the commercially available SUPERSCRIPT reverse transcriptases. (Invitrogen, Carlsbad, CA) and telomerases.

Selecting a Polymerase

The methods provided herein rely on nucleotide transient-binding to the polymerase, instead of nucleotide incorporation. Therefore, the desirable polymerases bind selectively to complementary nucleotides compared to non-complementary nucleotides. For example, polymerases having higher $K_d$ values can be selected for use in performing the nucleotide transient-binding methods provided herein.

In one embodiment, the mutant polymerases can be phi29 polymerases which exhibit reduced nucleotide incorporation rates, which comprise lysine substituted with leucine, arginine, or other amino acids (Castro, et al., 2009 Nature Structural and Molecular Biology 16:212-218).

In one embodiment, the mutant phi29 polymerases include: K383R. K371E/K383E/N387Y/D458N, K132A, K379A, Y266F/Y390F, K379A/Q380A, E375Y, E375Y/Q380A/K383R, E375Y/Q380A/K383H, E375Y/Q380A/K383L, E375Y/Q380A/V250A, E375Y/Q380A/V250C, K379A/E375Y, K379A/K383R, K379A/K383H, K379A/K383L, K379A/Q380A, K383H, K383L, Q380A, E375Y, V250A/K379A, V250A/K379A/Q380A, V250C/K379A/Q380A, K132A/K379A, D332Y, L342G, and deletion of R306 to K311 (the mutant amino acid numeration is based on the sequence shown in FIG. 4, SEQ ID NO:1).

The selection of the polymerase may also be determined by the rate of nucleotide incorporation such as about one nucleotide per 3-5 seconds, or about one nucleotide per second, or about 5 nucleotides per second, or about 10 nucleotides per second, or about 20 nucleotides per second, or about 30 nucleotides per second, or more than 40 nucleotides per second, or more than 50-100 per second, or more than 100 per second.

The polymerase can be a mutant which retains nucleotide binding activity but lacks 3'→5' or 5'→3' exonuclease activity. For example, phi29 mutant polymerases having exo-minus activity (or at least reduce exonuclease activity) can include any one or a combination of the following mutations: N62D, D12A, T15I, E14I, and D66A (see FIG. 4 for the sequence of wild-type phi29 for comparison).

The selection of the polymerase can also be determined by processivity, which may be beneficial, but not necessary, for practicing the methods provided herein.

Evolved Polymerases

The polymerase can be a modified polymerase having certain desired characteristics, such as an evolved polymerase selected from a directed or non-directed molecular evolution procedure. The evolved polymerase can exhibit modulated characteristics or functions, such as changes in: affinity, specificity, or binding rates for substrates (e.g., template molecules, polymerization initiation sites, or nucleotides); binding stability to the substrates (e.g., template molecules, polymerization initiation sites, or nucleotides); nucleotide incorporation rate; nucleotide analog permissiveness; exonuclease activity (e.g., 3'-+5' or 5'→3'); rate of extension; processivity; fidelity; stability; or sensitivity and/or requirement for temperature, chemicals (e.g., DTT), salts, metals, pH, or electromagnetic energy (e.g., excitation or emitted energy). Many examples of evolved polymerases having altered functions or activities can be found in U.S. provisional patent application No. 61/020,995, filed Jan. 14, 2008.

Methods for creating and selecting proteins and enzymes having the desired characteristics are well known in the art, and include: oligonucleotide-directed mutagenesis in which a short sequence is replaced with a mutagenized oligonucleotide; error-prone polymerase chain reaction in which low-fidelity polymerization conditions are used to introduce point mutations randomly across a sequence up to about 1 kb in length (R. C. Caldwell, et al., 1992 PCR Methods and Applications 2:28-33; H. Gramm, et al., 1992 Proc. Natl. Acad. Sci. USA 89:3576-3580); and cassette mutagenesis in which a portion of a sequence is replaced with a partially randomized sequence (A. R. Oliphant, et al., 1986 Gene 44:177-183; J. D. Hermes, et al., 1990 Proc. Natl. Acad. Sci. USA 87:696-700; A. Arkin and D. C. Youvan 1992 Proc. Natl. Acad. Sci. USA 89:7811-7815; E. R. Goldman and D. C. Youvan 1992 Bio/Technology 10:1557-1561; Delagrave et al., 1993 Protein Engineering 6: 327-331; Delagrave et al., 1993 Bio/Technology 11: 1548-155); and domain shuffling.

Methods for creating evolved antibody and antibody-like polypeptides can be adapted for creating evolved polymerases, and include applied molecular evolution formats in which an evolutionary design algorithm is applied to achieve specific mutant characteristics. Many library formats can be used for evolving polymerases including: phage libraries (J. K. Scott and G. P. Smith 1990 Science 249:386-390; S. E. Cwirla, et al. 1990 Proc. Natl. Acad. Sci. USA 87:6378-6382; J. McCafferty, et al. 1990 Nature 348:552-554) and lacI (M. G. Cull, et al., 1992 Proc. Natl. Acad. Sci. USA 89:1865-1869).

Another adaptable method for evolving polymerases employs recombination (crossing-over) to create the mutagenized polypeptides, such as recombination between two different plasmid libraries (Caren et al. 1994 Bio/Technology 12: 517-520), or homologous recombination to create a hybrid gene sequence (Calogero, et al., 1992 FEMS Microbiology Lett. 97: 41-44; Galizzi et al., WO91/01087). Another recombination method utilizes host cells with defective mismatch repair enzymes (Radman et al., WO90/07576). Other methods for evolving polymerases include random fragmentation, shuffling, and re-assembly to create mutagenized polypeptides (published application No. U.S. 2008/0261833, Stemmer). Adapting these mutagenesis procedures to generate evolved polymerases is well within the skill of the art.

In one embodiment, the polymerase can be a mutant which retains nucleotide polymerization activity but lacks 5'→3' exonuclease activity. In another embodiment, the polymerase can be an exonuclease minus mutant which is based on wild type phi29 polymerase (Blanco, U.S. Pat. Nos. 5,001,050, 5,198,543, and 5,576,204; and Hardin, et al., PCT/US2009/31027, International filing date of Jan. 14, 2009) and comprising one or more substitution mutations, including (using single-letter amino acid abbreviations): D12A, D66A, D169A, H61R, $N_{62}D$, Q380A, and/or S388G, and any combination thereof. For example, a Phi29 (exo-) polymerase (HP-1) comprises the amino acid sequence shown in FIG. 4, and also includes point mutations D12A and D66A and an N-terminal 6×His linker. In another embodiment, a Phi29 (exo-) polymerase comprises the amino acid sequence shown in FIG. 4, which includes point mutation D169A and no linker sequence.

Polymerases Linked with Reporter Moieties

The polymerase (or polymerase fusion protein) may be non-labeled or operably linked with at least one reporter moiety, such as a fluorescent dye or energy transfer moiety (e.g., donor or acceptor). In the polymerase fusion protein, the reporter moiety can be attached to the polymerase portion or to the second enzyme portion. One or more reporter moieties can be operably linked to the polymerase (or polymerase fusion protein) at the amino end or carboxyl end, or any amino acid residue between the amino or carboxy ends. The reporter moiety can be attached to the polymerase or to the polymerase fusion protein in a manner that does not interfere with the nucleotide binding activity, or with the nucleotide incorporation activity, or with the activity of the second enzyme.

The polymerase can be operably linked to at least one binding partner, such as biotin. For example, biotin can be operably linked to the N-terminal end or to a lysine residue on the polymerase. In another example, EDC crosslinking can be used to operably link biotin to a carboxyl group (e.g., aspartic or glutamic acid residues) or to the carboxy-terminal end of the polymerase.

Polymerases and Linker Moieties

The polymerase (including polymerase fusion protein) may be unlinked, or operably linked to one or more reporter moieties (e.g., energy transfer moieties) and/or to one or more biomolecules (e.g., template nucleic acid molecules, primers, and/or oligonucleotides) and/or to a surface, via a linker moiety. The linker moiety includes: a covalent or non-covalent bond; amino acid tag; chemical compound (e.g., polyethylene glycol); protein-protein binding pair (e.g., biotin-avidin); affinity coupling; capture probes; or any combination of these. The linker moiety can be separate from or part of the polymerase (e.g., recombinant His-tagged polymerase). The linker moiety does not interfere with the nucleotide binding activity, or catalytic activity of the polymerase.

In one example, the polymerase (or polymerase fusion protein) can include an amino acid analog which provides a reactive group for linking to the reporter moiety, biomolecule, or surface. For example, the amino acid analog can be produced using a cell (e.g., bacterial cell) which is genetically engineered to have a 21 amino acid genetic code which is capable of inserting the amino acid analog into the encoded polymerase (or fusion protein). The inserted amino acid analog can be used in a linking chemistry procedure to attach the polymerase (or fusion protein) to the reporter moiety, biomolecule, or the surface.

In another example, the polymerase, or polymerase fusion protein, can be attached to a surface via an anchor or tether. The anchor or tether can be flexible or rigid. The anchor or tether can orient the polymerase, or polymerase fusion protein, in a manner that does not interfere with the nucleotide binding activity or the catalytic activity of the polymerase. In one embodiment, the anchor or tether can be a poly His-tag, which is attached to the polymerase. The poly-His-tag can bind with $Ni^{2+}$, $Co^{2+}$, or $Cu^{2+}$ on the surface. Other linkers and linker chemistries for attaching polymerases to reporter moieties or solid surfaces are disclosed herein.

Nanoparticles

Provided herein are suitable nanoparticles for use in the nucleotide transient-binding methods. The suitable nanoparticles can serve as donor fluorophores in energy transfer reactions such as FRET. The suitable nanoparticles can be attached to the solid surface or to any component of the nucleotide transient-binding reactions, in any combination (e.g., polymerases, terminator nucleotides, labeled nucleotides, non-incorporatable nucleotides, template nucleic acid molecules, primer molecules, and/or oligonucleotides).

In one embodiment, a semiconductor nanoparticle can be linked to a site near the nucleotide binding site on the polymerase, to facilitate energy transfer signals to/from the transiently-bound labeled nucleotides. In another embodiment, the template molecule (and/or primer molecule), polymerase, or nanoparticle is immobilized.

In one aspect, the nanoparticle can be a core/shell nanoparticle which typically comprises a core surrounded by at least one shell. For example, the core/shell nanoparticle can be surrounded by an inner and outer shell. In another aspect, the nanoparticle is a core nanoparticle which has a core but no surrounding shell. The outmost shell is typically coated with tightly associated ligands that are not removed by ordinary solvation.

The nanoparticle includes the core, shell(s), and ligand coatings. Methods for making core nanoparticles, core/shell nanoparticles, and ligand coated nanoparticles are well known in the art.

In one aspect, the nanoparticle core and shell can be made from any suitable metal and/or non-metal atoms for forming semiconductor nanoparticles. The core and shell can be composed of different semiconductor materials.

The core can be composed of a semiconductor material (including ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AIS; and/or Group IV, including Ge, Si, Pb.

The shell can be composed of materials (including ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb. The nanoparticle may be a doped metal oxide nanoparticle.

In one aspect, the dimensions of the nanoparticle can be, in their largest dimensions, about 50-100 nm, about 40-50 nm, about 30-40 nm, about 20-30 nm, about 15-20 nm, about 10-15 nm, about 5-10 nm, or about 1-5 nm.

In one aspect, the nanoparticles can have different shapes, each of which has distinctive properties including spatial distribution of the surface charge; orientation dependence of polarization of the incident light wave; and spatial extent of the electric field. The shapes include spheres, rods, discs, triangles, nanorings, nanoshells, tetrapods, nanowires and so on.

In one aspect, the nanoparticle can be a semiconductor nanoparticle having size-dependent optical and electronic properties. For example, the nanoparticle can emit a fluorescent signal in response to excitation energy. The spectral emission of the nanoparticle can be tunable to a desired energy by selecting the particle size, size distribution, and/or composition of the semiconductor nanoparticle. For example, depending on the dimensions, the semiconductor nanoparticle can be a fluorescent nanoparticle that emits light in the UV-visible-IR spectrum. The shell material can have a bandgap greater than the bandgap of the core material. Nanoparticles are available In another aspect, the nanoparticle can be a fluorescent nanoparticle. The nanoparticles can be excited by an electromagnetic source such as a laser beam, or multi-photon excitation, or electrical excitation. The excitation wavelength can range between 190-800 nm including all values and ranges there between. The signal emitted by the nanoparticle can be between about 400-800 nm. In certain aspects, the nanoparticle can be excited by an energy source having a wavelength of about 405 nm. In other aspects, in response to excitation, the nanoparticles can emit a fluorescent signal at about 605 nm.

As with common energy transfer donors, the efficiency of energy transfer (e.g., FRET) of a nanoparticle can depend sharply upon the donor-acceptor distance R as $1/R^6$. The distance where FRET efficiency is 50% is termed $R_0$, also known as the Förster distance. $R_0$ is unique for each donor-acceptor combination and may be 5 to 10 nm. For nanoparticles that are size-tuned to emit in the visible light spectrum, the radius from the nanoparticle's energy transferring core to its surface typically ranges from 2 to 5 nm. Given typical $R_0$ distances of 5-10 nm, this means that acceptor chromophores must be within a few nanometers of the nanoparticle surface for efficient FRET between donor-acceptor pairs.

Various types of core-shell nanoparticles are commercially-available. For example, InP/ZnS, CdS, CdSe, CdSe/ZnS, and D-dots™ are available from NN-Labs. CdSe/ZnS Lumidots™ are available from Aldrich Materials Science in collaboration with Nanoco Technologies. Aggregated nanoparticles, such as TriLite™ nanoclusters containing about 8-12 individual nanoparticles are available from Crystal Plex. These nanoclusters are 40-50 nm in size and are functionalized on the surface with carboxyl groups. Various QDOTS conjugated with streptavidin that emit light in the range of about 525-800 nm, as well as several biotin-labeled QDOTS are available from Invitrogen. Also, Qdot™ ITK™ nanoparticles that have an amphiphilic polymer coating and functionalized surface chemistry (carboxyl, amino-PEG, and organic soluble groups) for custom conjugation to any desired molecule, are available from Invitrogen.

Other types of nanoparticles can be used. One example includes nanoparticles comprising a multi-shell layered core which is achieved by a sequential shell material deposition process, where one shell material is added at a time, to provide a nanoparticle having a substantially uniform shell of desired thickness that is substantially free of defects. The nanoparticles can be prepared by sequential, controlled addition of materials to build and/or applying layers of shell material to the core. The methods can include at least one coordinating solvent. Sec e.g., U.S. provisional applications No. 61/108,425, Treadway, et al., filed Oct. 24, 2008, and 61/144,613, Treadway, et al., filed Jan. 14, 2009.

In one aspect, at least one coordinating solvent can be a trialkylphosphine, a trialkylphosphine oxide, phosphonic acid, or a mixture of these. In another aspect, at least one coordinating solvent comprises trioctylphosphine (TOP), trioctylphosphine oxide (TOPO), tetradecylphosphonic acid (TDPA), or a mixture of these. In yet another aspect, the coordinating solvent comprises a primary or secondary amine, for example, decylamine, hexadecylamine, or dioctylamine.

In one aspect, the first inner shell precursor is $Cd(OAc)_2$ and the second inner shell precursor is bis(trimethylsilyl) sulfide ($TMS_2S$). In other aspects, the first and second inner shell precursors are added as a solution in trioctylphosphine (TOP). In other aspects, the first outer shell precursor is diethylzinc ($Et_2Zn$) and the second inner shell precursor is dimethyl zinc ($TMS_2S$). Sometimes, the first and second outer shell precursors are added as a solution in trioctylphosphine (TOP).

In one aspect, the nanoparticles can have ligands that coat the surface. The ligand coating can comprise any suitable compound(s) that provide surface functionality, including facilitating aqueous-dispersibility of the nanoparticles, or permitting binding and/or other interaction with a biomolecule. For example, the surface ligands can be: lipids; phospholipids; fatty acids; polynucleic acids; polyethylene glycol; primary antibodies; secondary antibodies; antibody fragments; protein or nucleic acid based aptamers; biotin; streptavidin; proteins; peptide; small organic molecules; organic or inorganic dyes; or precious or noble metal clusters. Examples of ligands include: amphiphilic polymer (AMP); dihydrolipoic acid (DHLA); tetradecylphosphonic acid (TDPA); octylphosphonic acid (OPA); dipeptides (e.g., His-Leu and Gly-His); alkyl phosphonate; phosphine crosslinker (e.g., tris(hydroxymethyl-phosphine; THP); L-carnosine; imidazole; 4-aminobenzophenone; tris(hydroxymethyl) phosphine; and PEG (e.g., PEG-1000 or amino-dPEG24-acid). See, e.g., U.S. Provisional Applications Nos. 61/086,750; 61/102,709; 61/102,683; 61/102,666.

In one aspect, the nanoparticle comprises a core comprising CdSe. In another aspect, the nanoparticle shell can comprise YZ wherein Y is Cd or Zn, and Z is S, or Se. In one embodiment, at least one inner shell layer comprises CdS, and the at least one outer shell layer comprises ZnS.

In one aspect, the nanoparticles exhibit modulated blinking properties, such as limited or no detectable blinking. The nanoparticles can have a stochastic blinking profile in a timescale that is shifted to very rapid blinking or very slow or infrequent blinking relative to a nanoparticle previously described in the art. For example, the nanoparticles may blink on and off on a timescale that is too rapid to be detected under the methods employed to study this behavior.

In one aspect the nanoparticles are photostable. The nanoparticles can exhibit a reduced or no photobleaching with long exposure to moderate to high intensity excitation source while maintaining a consistent spectral emission pattern.

In one aspect, the nanoparticles have a consistently high quantum yield. For example, the nanoparticles can have a quantum yield greater than about 40%, or greater than about 50%, or greater than about 60%, or greater than about 70%, or greater than about 80%.

In one embodiment, the nanoparticles can include a CdSe core. In another aspect the nanoparticles can include a CdS inner shell. In yet another aspect, the nanoparticles can include a ZnS outer shell.

In one embodiment, the spherical nanoparticles can be about 10 nm or smaller. In another embodiment, the rod-shaped nanoparticles can be about 12 nm or smaller, in their largest dimension. In one embodiment, the nanoparticles can include a ligand coating comprising: L-carnosine; dipeptides (e.g., His-Leu and/or Gly-His); 4-aminobenzophenone; citric acid; glycine; tris(hydroxymethyl)phosphine; and amino-dPEG24-acid.

It has been previously shown by others that nanoparticles produce fluorescent signals in a variety of aqueous solutions, including pure water, various buffer solutions, and weakly acidic buffers. Using a single-particle counting procedure, Zhang showed that acidic buffers decrease the fluorescent intensity, but the burst count was not affected (Zhang 2008 Journal of the American Chemical Society 130:3750-3751).

The suitable nanoparticles include those described in U.S. Ser. Nos: 61/086,750, having a 371(c) filing date of Aug. 6, 2008; 61/108,425 having a 371(c) filing date of Oct. 24, 2008; 61/102,631, having a 371(c) filing date of Oct. 3, 2008; 61/102,642, having a 371(c) filing date of Oct. 3, 2008; 61/102,709, having a 371 (c) filing date of Oct. 3, 2008; and 61/144,613, having a 371(c) filing date of Jan. 14, 2009.

Template Nucleic Acid Molecules

Provided herein are nucleotide transient-binding methods using template nucleic acid molecules which bind a polymerase. The template nucleic acid molecule may be double-stranded molecules. The template nucleic acid molecules can be linear or circular. The template nucleic acid molecules may be DNA, ssRNA, dsRNA or hybrid DNA-RNA molecules, DNA hairpins, DNA/RNA hybrids, or RNA hairpins. The template nucleic acid molecules may be isolated in any form including chromosomal, genomic, organellar (e.g., mitochondrial, chloroplast or ribosomal), recombinant molecules, cloned, amplified, cDNA, RNA such as precursor-RNA or mRNA, oligonucleotide, or any type of nucleic acid library. The template nucleic acid molecules may be isolated from any source including from: organisms such as prokaryotes, eukaryotes (e.g., humans, plants and animals), fungus, and viruses; cells; tissues; body fluids including blood, urine, serum, lymph, tumor, saliva, anal and vaginal secretions, amniotic samples, perspiration, and semen; environmental samples; culture samples; or synthesized nucleic acid molecules using recombinant DNA technology or chemical synthesis methods.

The template nucleic acid molecules comprise naturally-occurring nucleotides, nucleotide analogs, or any combination thereof. For example, the template molecules comprise alternate backbones, including: phosphoramidate; phosphorothioate; phosphorodithioate; O-methylphosphoroamidite linkages; and peptide nucleic acid backbones and linkages. Other nucleic acids analogs include those with bicyclic structures including locked nucleic acids; positive backbones; non-ionic backbones; and non-ribose backbones.

The template nucleic acid molecules can be modified using art-known methods, for example modified to carry a tag (e.g., His-tag), a poly tail (e.g., poly tail of A, G, C, T, or U), or can be methylated. The template nucleic acid molecules may be nicked, sheared, or treated with an enzyme such as a restriction endonuclease or a nuclease. The template nucleic acid molecules can be about 10-50 nucleotides, about 50-100 nucleotides, about 100-250 nucleotides, about 250-500 nucleotides, or about 500-1000 nucleotides in length, or longer. The template nucleic acid molecules may be linked to a reporter moiety or an energy transfer moiety (e.g., donor or acceptor) using methods well known in the art.

The template nucleic acid molecules can have a nucleotide sequence that has been previously determined or is unknown (e.g., de novo sequencing). The template molecule can be fragmented into shorter pieces and/or modified for immobilization. Selection of the fragmentation and modification technique may depend upon the desired fragment sizes and subsequent preparation steps. Any combination of fragmentation and/or modification techniques may be practiced in any order.

Nucleic Acid Sample Preparation

The nucleic acid molecules, including the template molecules, primers, and oligonucleotides, may be isolated and modified at their ends and/or the interior of the molecules using well known procedures, including: fragmentation, ligation, hybridization, enzymatic and/or chemical modification, conjugation with a reporter moiety, or linking to an energy transfer (donor or acceptor), or any combination of these procedures.

In one embodiment, genomic DNA can be prepared by: fragmented using DNase I digestion, size-selected, end-repaired using T4 DNA polymerase and T4 polynucleotide kinase, modified by adding a single 3' dA overhang using Taq polymerase, ligating an adaptor containing a single 5' dT overhang, adding a 3' poly dA tail using terminal deoxynucleotidyl transferase, and adding a cyanine 3-ddTTP to the polyA tail (Harris, et al., 2008 Science 320:106-109, and Supplemental Materials and Methods).

Nucleic Acid Molecules-Fragmentation

The nucleic acid molecules can be fragmented at random or specific sites using any fragmentation procedure. The nucleic acid molecules can be fragmented using mechanical force, including: shear forces (e.g., small orifice or a needle); nebulization (S. Surzycki 1990 in: "The International Conference on the Status and Future of Research on the Human Genome. Human Genome II", San Diego, CA, pp. 51; and S. J. Surzycki, 2000 in: "Basic Methods in Molecular Biology", New York, NY: Springer-Verlag); or sonication. For example, nucleic acid molecules can be fragmented by sonicating in a COVARIS (e.g., Models S2, E210, or AFA).

The nucleic acid molecules can be chemically fragmented using, for example: acid-catalyzed hydrolysis of the backbone and cleavage with piperidine; internucleosomal DNA fragmentation using a copper (II) complex of 1,10- phenanthroline (o-phenanthroline, OP), CuII(OP)$_2$ in the presence of ascorbic acid (Shui Ying Tsang 1996 Biochem. Journal 317:13-16).

The nucleic acid molecules can be enzymatically fragmented using type I, II or II restriction endonucleases (N. E. Murray 2000 Microbiol. Mol. Biol. Rev. 64: 412-34; A. Pingoud and A. Jeltsch 2001 Nucleic Acids Res. 29: 3705-27; D. T. Dryden, et al., 2001 Nucleic Acids Res. 29: 3728-41; and A. Meisel, et al., 1992 Nature 355: 467-9). Enzymatic cleavage of DNA may include digestion using various ribo- and deoxyribonucleases or glycosylases. The nucleic acid molecules can be digested with DNase I or II. The nucleic acid fragments can be generated by enzymatically copying an RNA template. Fragments can be generated using processive enzymatic degradation (e.g., S1 nuclease). The enzymatic reactions can be conducted in the presence or absence of salts (e.g., Mg$^{2+}$, Mn$^{2+}$, and/or Ca$^{2+}$), and the pH and temperature conditions can be varied according to the desired rate of reaction and results, as is well known in the art.

Modified Nucleic Acid Molecules

The 5' or 3' overhang ends of a nucleic acid molecule can be converted to blunt-ends using a "fill-in" procedure (e.g., dNTPS and DNA polymerase, Klenow, or Pfu or T4 polymerase) or using exonuclease procedure to digest away the protruding end.

The nucleic acid molecule ends can be ligated to one or more oligonucleotides using DNA ligase or RNA ligase. The nucleic acid molecules can be hybridized to one or more oligonucleotides. The oligonucleotides can serve as linkers, adaptors, bridges, clamps, anchors, or capture oligonucleotides.

The oligonucleotides can be ligation-ready, having overhang ends that can be ligated to the ends of the template molecules. The ligation-ready oligonucleotides can be used to circularize the template molecules.

A pair of oligonucleotides can include complementary sequences for hybridization. These paired oligonucleotides can be used as end-ligated oligonucleotides to permit circularization of the template molecule. These paired oligonucleotides can be used to hybridize to capture probes immobilized on a surface.

The oligonucleotides can include sequences which are: enzyme recognition sequences (e.g., restriction endonuclease recognition sites, DNA or RNA polymerase recognition sites); hybridization sites; or can include a detachable portion.

The oligonucleotide can be operably linked to a protein-binding molecule such as biotin or streptavidin.

The nucleic acid molecules can be methylated, for example, to confer resistance to restriction enzyme digestion (e.g., EcoRI). The nucleic acid molecule ends can be phosphorylated or dephosphorylated.

A nick can be introduced into the nucleic acid molecules using, for example DNase I. A pre-designed nick site can be introduced in dsDNA using a double stranded probe, type II restriction enzyme, ligase, and dephosphorylation (Fu Dong-Jing, 1997 Nucleic Acids Research 25:677-679).

A nick can be repaired using polymerase (e.g., DNA pol I or phi29), ligase (e.g., T4 ligase) and kinase (polynucleotide kinase).

A poly tail can be added to the 3' end of the fragment using terminal transferase (e.g., polyA, polyG, polyC, polyT, or polyU).

The nucleic acid molecule can be modified using bisulfite treatment (e.g., disodium bisulfite) to convert unmethylated cytosines to uracils, which permits detection of methylated cytosines using, for example, methylation specific procedures (e.g., PCR or bisulfite genomic sequencing).

The oligonucleotides can be 4-20 nt/bp in length, or 20-40 nt/bp in length, or 40-60 nt/bp in length, or longer.

Size Selection

The nucleic acid molecules can be size selected, or the desired nucleic acid molecules can separated from undesirable molecules, using any art-known methods, including gel electrophoresis, size exclusion chromatography (e.g., spin columns), sucrose sedimentation, or gradient centrifugation. Very large nucleic acid molecules, including whole chromosomes, can be size separated using pulsed-field gel electrophoresis (Schwartz and Cantor 1984 Cell, 37: 67-75).

Amplification

The nucleic acid molecules can be amplified using methods, including: polymerase chain reaction (PCR); ligation chain reaction, which is sometimes referred to as oligonucleotide ligase amplification (OLA); cycling probe technology (CPT); strand displacement assay (SDA); transcription mediated amplification (TMA); nucleic acid sequence based amplification (NASBA); rolling circle amplification (RCA); and invasive cleavage technology.

Enrichment

Undesired compounds can be removed or separated from the desired template nucleic acid molecules to facilitate enrichment of the desired template molecules. Enrichment methods can be achieved using well known methods, including gel electrophoresis, chromatography, or solid phase immobilization (reversible or non-reversible). For example, AMPURE beads (Agencourt) can bind DNA fragments but not bind unincorporated nucleotides, free primers, DNA polymerases, and salts, thereby facilitating enrichment of the desired DNA fragments.

Embodiments of the Template Molecule

In one embodiment, the template molecule can be a recombinant DNA molecule which is a self-priming hairpin oligonucleotide. The hairpin oligonucleotide can be operably linked at the 5' or 3'end, or internally, to at least one molecule of a binding partner (e.g., biotin). The biotin molecule can be used to immobilize the hairpin oligonucleotide to the surface (via avidin-like molecule), or for attachment to a reporter moiety. The hairpin oligonucleotide can be operably linked to at least one energy transfer moiety, such as a fluorescent dye or a nanoparticle.

Polymerization Initiation Sites

Provided herein are extendible and non-extendible polymerization initiation sites for use in the nucleotide transient-binding methods. An extendible polymerization initiation site can be a terminal 3' —OH group which serves as a substrate for the polymerase to form a phosphodiester bond between the terminal 3' —OH group and an incorporated nucleotide. The extendible polymerization initiation site can be the terminal 3' —OH group on a primer molecule, or an internal 3' —OH group in a nick or gap within a nucleic acid molecule. The extendible polymerization initiation sites can be the 3' —OH group on the terminal end of a secondary structure (e.g., the end of a hairpin-like structure) or an origin of replication. The extendible polymerization initiation site can be provided by an accessory protein (e.g., RNA polymerase or helicase/primase). The extendible polymerization initiation site can be provided by a terminal protein which can be bound (covalently or non-covalently) to the end of the template nucleic, including terminal protein (e.g., TP) found in phage (e.g., TP from phi29 phage).

The non-extendible polymerization initiation site can be a terminal group which does not serve as a substrate for polymerase-dependent nucleotide incorporation. For example, the non-extendible polymerization initiation site can lack a terminal 3' —OH group. In another example, the non-extendible polymerization initiation site can include a terminal nucleotide having an inhibitor moiety operably linked to the base, sugar, or phosphate group. The non-extendible polymerization initiation site can include a terminator nucleotide at the 3' terminal end.

The portion of the template molecule which is base paired with the primer or with the oligonucleotide molecule, or the self-primed portion of the template molecule, can form hydrogen bonding by Watson-Crick or Hoogstein binding to form a duplex nucleic acid structure. The primer, oligonucleotide, and self-priming sequence may be complementary, or partially complementary, to the nucleotide sequence of the template molecule. The complementary base pairing can be the standard A-T or C-G base pairing, or can be other forms of base-pairing interactions.

Primer Molecules

Provided herein are primer molecules for use in the nucleotide transient-binding methods. The 3' terminal end of the primer molecule can provide the polymerization initiation site, which can include an extendible or non-extendible end. The primer molecule can be hybridized with the template nucleic acid molecule. The sequence of the primer molecule can be complementary or partially complementary to the sequence of the template molecule.

The primers can be modified with a chemical moiety to protect the primer from serving as a polymerization initiation site or an enzyme recognition site. The chemical moiety can be a natural or synthetic amino acid linked through an amide bond to the primer.

The primer molecule, oligonucleotide, and self-priming portion of the template molecule, may comprise ribonucleotides, deoxyribonucleotides, ribonucleotide polyphosphate molecules, deoxyribonucleotide polyphosphate molecules, peptide nucleotides, nucleoside polyphosphate molecules, metallonucleosides, phosphonate nucleosides, and modified phosphate-sugar backbone nucleotides, and any analogs or variants of the foregoing.

The primer, oligonucleotide, or self-priming portion, may be naturally-occurring, or may be produced using enzymatic or chemical synthesis methods. The primer, oligonucleotide, or self-priming portion may be any suitable length including 5, 10, 15, 20, 25, 30, 40, 50, 75, or 100 nucleotides or longer in length. The primer, oligonucleotide, or self-priming portion may be linked to a reporter moiety (e.g., a dye) or an energy transfer moiety (e.g., donor or acceptor) using methods well known in the art.

Embodiments of the Primer Molecule

In one embodiment, the primer molecule can be a recombinant DNA molecule. The primer can be operably linked at the 5' or 3' end, or internally, with at least one binding partner, such as biotin. The biotin can be used to immobilize the primer molecule to the surface (via an avidin-like molecule), or for attachment to a reporter moiety. The primer can be operably linked to at least one energy transfer moiety, such as a fluorescent dye or a nanoparticle. The primer molecule can hybridize to the template nucleic acid molecule. The primer molecule can be used as a capture probe to immobilize the template molecule.

Immobilized Nucleic Acid Molecules

Provided herein are nucleotide transient-binding methods using immobilized template molecule and/or primer molecule. The template nucleic acid molecules and/or primer molecules can be immobilized onto a solid surface using any art-known method. In one embodiment, a dual anchor can be used to immobilize the template and primer molecules to the solid surface. In one example, the 3' end of the template molecule and the 5' end of the primer molecule can be operably linked to a biotin molecule. Or the 5' end of the template molecule and the 3' end of the primer molecule can be operably linked to a biotin molecule. Or the primer can be operably linked to the surface and the template molecule can be hybridized to the primer molecule. The solid surface can be operably linked to avidin-liked molecules (e.g., avidin). The avidin-like molecules (e.g., streptavidin) are capable of binding up to four biotin molecules, permitting stable binding of an biotin end-labeled template-primer duplex (Buzby, U.S. Pat. No. 7,220,549). One or multiple template/primer molecules (or self-primed template molecules) can be operably linked to the surface. Template/primer duplexes immobilized to a solid surface in this manner can withstand changes in temperature and salt concentrations during the washing steps.

Solid Surfaces

Provided herein are any component of the complex (e.g., polymerase, template molecule, and/or primer molecule) which can be operably linked to a solid surface to facilitate transient-binding methods in various platforms, including: single molecule, arrays of single molecules, populations of immobilized single molecules (i.e., immobilized on a solid surface, bead, etc), direct excitation/detection, and FRET-based excitation/detection The surfaces (e.g., solid surfaces) that can be attached covalently or non-covalently with the nanoparticles and/or the biomolecules which are components of the nucleotide transient-binding reaction (e.g., polymerases, non-incorporatable nucleotide, terminator nucleotides, labeled nucleotides, template nucleic acid molecules, primers, and/or oligonucleotides) described herein. One or more template/primer duplex(es) (or self-primed template molecules) can be operably linked to the surface of a nanoparticle. The immobilized nanoparticles and/or biomolecules may be attached to the surface in a manner that they are accessible to components of the nucleotide transient-binding reaction and/or in a manner that does not interfere with nucleotide transient-binding. The immobilized nanoparticles and/or biomolecules may be attached to the surface in a manner that renders them resistant to removal or degradation during the nucleotide transient-binding reactions, including procedures that involve washing, flowing, temperature or pH changes, and reagent changes. In another aspect, the immobilized nanoparticles and/or biomolecules may be reversibly attached to the surface. In one embodiment, the nanoparticles can be operably linked to a site on the solid surface that is near the nucleotide binding site on the polymerase, to facilitate energy transfer signals to or from the transiently-bound labeled nucleotides.

The surface may be a solid surface, and includes planar surfaces, as well as concave, convex, or any combination thereof. The surface may comprise texture (e.g., etched, cavitated or bumps). The surface includes a nanoscale device, a channel, a well, bead, particle, sphere, filter, gel, or the inner walls of a capillary. The surface can be optically transparent, minimally reflective, minimally absorptive, or exhibit low fluorescence. The surface may be non-porous. The surface may be made from materials such as glass, borosilicate glass, silica, quartz, fused quartz, mica, polyacrylamide, plastic (e.g., polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond).

The immobilized nanoparticles and/or biomolecules may be arranged in a random or ordered array on a surface. The ordered array includes rectilinear and hexagonal patterns. The distance and organization of the immobilized molecules may permit distinction of the signals generated by the different immobilized molecules. The surface can be coated with an adhesive and/or resist layer which can be applied to the surface to create the patterned array and can be applied to the surface in any order. The adhesive layer can bind/link the nanoparticle or biomolecules. The resist layer does not bind/link, or exhibits decreased binding/linking, to the nanoparticle or biomolecules.

The immobilized nucleic acid molecules (e.g., template or primer molecules) may be attached to the surface at their 5' ends or 3' ends, along their length, or along their length with a 5' or 3' portion exposed. The immobilized proteins (e.g., polymerases) can be attached to the surface in a manner that orients them to mediate their activities (nucleotide binding, nucleotide incorporation, and/or phosphate cleavage and release).

The surface can be coated to facilitate attachment of nucleic acid molecules (template and/or primers). For example, a glass surface can be coated with a polyelectrolyte multilayer (PEM) via light-directed attachment (U.S. Pat. Nos. 5,599,695, 5,831,070, and 5,959,837) or via chemical attachment. The PEM chemical attachment occurs by sequential addition of polycations and polyanions (Decher, et al., 1992 Thin Solid Films 210:831-835). In one embodiment, the glass surface can be coated with a polyelectrolyte multilayer which terminated with polyanions or polycations. The polyelectrolyte multilayer can be coated with biotin and an avidin-like compound. Biotinylated molecules (nucleic acid molecules or polymerases or nanoparticles) can be attached to the PEM/biotin/avidin coated surface (Quake, U.S. Pat. Nos. 6,818,395, 6,911,345, and 7,501,245).

Nanoscale Devices

The surface can be the surface of a nanoscale device. The nanoparticles or biomolecules (e.g., terminator nucleotides, labeled nucleotides, non-incorporatable nucleotides, polymerases, template nucleic acid molecules, primer molecules, and/or oligonucleotides) can be associated with or immobilized onto the nanoscale device.

The nanoscale device can have microscopic features (e.g., at the micro meter, nano meter size level, or pico meter level) which permit manipulation or analysis of biological molecules at a nanoscale level.

The nanoscale device can include open or enclosed (i.e., sealed) structures (e.g., nanostructures) including: channels, slits, pores, pillars, loops, arrays, pumps valves. The nanostructures can have length, width, and height dimensions. The nanostructures can be linear or branched, or can have inlet and/or outlet ports. The branched nanostructures (e.g., branched channels) can form a T or Y junction, or other shape and geometries.

The nanostructure dimensions can be about 0.01 to 1000 microns, and have a width-to-depth ratio of between 0.1:1 to 100:1. In one embodiment, the width is between about 10 to 200 microns. In another embodiment, the width-to-depth ratio is about 3:1 to about 15:1.

The nanostructure dimensions can be between about 10-25 nm, or about 25-50 nm, or about 50-100 nm, or about 100-200 nm, or about 200-500 nm. The nanostructures can have a trench width equal to or less than about 150 nanometers. The nanostructures can have a trench depth equal to or less than about 200 nanometers.

The nanoscale device can comprise one or a plurality of nanostructures, typically more than 5, 10, 50, 100, 500, 1000, 10,000 or 100,000 nanostructures for binding, holding, streaming, flowing, washing, flushing, or stretching samples. The samples can include the nanoparticles, polymerase, non-incorporatable nucleotides, terminator nucleotides, labeled nucleotides, template nucleic acid molecules, primers, oligonucleotides, and/or reagents for the transient-binding reactions. The fluid that runs through the nanoscale device can be liquid, gas or slurry.

The nanoscale device can include a light source for directing light to the nucleotide transient-binding reaction, a detector (e.g., photon detector), a camera, and/or various plumbing components such as microvalves, micropumps, connecting channels, and microreservoirs for controlled flow (in and/or out) of the components of the transient-binding reactions.

Nanoscale devices and/or their component nanostructures may be fabricated from any suitable substrate including: silicon, carbon, glass, polymer (e.g., poly-dimethylsiloxane), metals, boron nitrides, aluminum, chromium, gold, synthetic vesicles, silicone, or any combination thereof.

The nanoscale devices and and/or nanostructures may be fabricated using any suitable method, including: lithography; photolithography; diffraction gradient lithography (DGL); nanoimprint lithography (NIL); interference lithography; self-assembled copolymer pattern transfer; spin coating; electron beam lithography; focused ion beam milling; plasma-enhanced chemical vapor deposition; electron beam evaporation; sputter deposition; bulk or surface micromachining; replication techniques such as embossing, printing, casting and injection molding; etching including nuclear track or chemical etching, reactive ion-etching, wet-etching; sacrificial layer etching; wafer bonding; channel sealing; and combinations thereof.

The nanoscale device can be used to react, confine, elongate, mix, sort, separate, flow, deliver, flush, wash, or enrich the nanoparticles or biomolecules or reagents, or the intermediates or products, of the transient-binding reactions. For example, the nanoscale device can be used to deliver and/or remove any component of the transient-binding reaction (e.g., non-incorporatable nucleotides, terminator nucleotides, labeled nucleotides, nanoparticles, polymerases, template nucleic acid molecules, primer molecules, oligonucleotides, and/or reagents).

In another example, the template nucleic acid molecule (e.g., nucleic acid molecules, or chromosomal or genomic DNA) can be elongated using pulsed field electrophoresis, or in a nanofluidic device via flow stretching (with or without tethering) or confinement elongation. Elongated nucleic acid molecules can be used to: measure the contour length of a nucleic acid molecule, locate landmark restriction sites along the length of the molecule, or detect sequencing reactions along the molecule. In one aspect, the nanostructure can be one or more nanochannels, which are capable of transporting a macromolecule (e.g., nucleic acid molecule) across its entire length in elongated form. In another aspect, the nanostructure can detect an elongated macromolecule, or detect sequencing of a single nucleic acid molecule.

The nanochannels can be enclosed by being surmounted with a sealing material using suitable methods. See, for example, U.S. Publication No. 2004/0197843. The nanoscale device can comprise a sample reservoir capable of releasing a fluid, and a waste reservoir capable of receiving a fluid, wherein both reservoirs are in fluid communication with the nanofluidic area. The nanoscale device may comprise a microfluidic area located adjacent to the nanofluidic area, and a gradient interface between the microfluidic and nanofluidic area that reduces the local entropic barrier to nanochannel entry. See, for example, U.S. Pat. No. 7,217,562.

The nanoscale device comprising a nanochannel array can be used to isolate individual nucleic acid molecules prior to conducting the transient-binding reactions, wherein the sample population of nucleic acid molecules is elongated and displayed in a spatially addressable format. Isolation of the nucleic acid molecules, which will undergo the transient-binding reactions, may be achieved using any suitable nanoscale device that comprises nanostructures or nanofluidic constrictions of a size suited to achieve isolation and separation of the test nucleic acid molecule from other sample components in a manner that will support the transient-binding reactions on the test molecule in situ. For example, a nucleic acid molecule, such as a chromosome, is isolated from a sample mixture using a nanofluidic device that is capable of receiving a sample comprising mixed population of nucleic acid molecules and elongating and displaying them in an ordered format without the need for prior treatment or chemical attachment to a support.

The nanoscale device supports analysis of intact chromosomes without the need for fragmentation or immobilization. The nanoscale device comprises at least one nanostructure, typically a nanochannel, which is designed to admit only a single polymeric molecule and elongate it as it flows through the nanostructure. Suitable nanoscale devices have been described, for example, in U.S. Pat. No. 6,635,163 (nanofluidic entropic trapping and sieving devices). Suitable nanoscale devices comprise microfluidic and nanofluidic areas separated by a gradient interface that reduces the local entropic barrier to nanochannel entry thereby reducing clogging of the device at the microfluidic-nanofluidic interface. See, for example, Cao, U.S. Pat. No. 7,217,562 and U.S. published patent application No. 2007/0020772.

The nanoscale device can include an array of nanochannels. Introduction of a sample comprising a mixed population of nucleic acid molecules into the nanoscale device results in the isolation and elongation of a single nucleic acid molecule within each nanostructure, so that an entire population of nucleic acid molecules is displayed in an elongated and spatially addressable format. After the nucleic acid molecules enter and flow through their respective nanochannel, they are contacted with one or more components of a transient-binding reaction, and the progress of the reaction is monitored using suitable detection methods. The ordered and spatially addressable arrangement of the population allows signals to be detected and monitored along the length of each nucleic acid molecule. Separate transient-binding reactions occur within each nanochannel. The spatially addressable nature of the arrayed population permits discrimination of signals generated by separate priming events, and permitting simultaneous detection and analysis of multiple priming events at multiple points in the array. The emission data can be gathered and analyzed to determine the time-sequence of transient-binding events for each individual nucleic acid (DNA) in the nanochannel array. Nanoscale devices can permit the simultaneous observation of macromolecules in multiple channels, thereby increasing the amount of sequence information obtainable from a single experiment and decreasing the cost of sequencing of an entire genome. See, for example, U.S. Pub. No. 2004/0197843, also U.S. Ser. Nos. 61/077,090, filed on Jun. 30, 2008, and 61/089,497, filed on Aug. 15, 2008, and 61/090,346, filed on Aug. 20, 2008.

In one embodiment, the nanoscale device includes: a flow cell which holds multiple immobilized template nucleic acid molecules base-paired with primer molecules and bound to polymerases; reservoirs for holding reagents for conducting a transient-binding reaction (e.g., polymerases, nanoparticles, non-incorporatable nucleotides, terminator nucleotides, labeled nucleotides, template molecules, primer molecules, cleavage reagents, wash buffers, and/or oxygen scavengers); inlet ports in fluid communication with the reservoirs and flow cell for delivering the various reagents; outlet ports in fluid communication with the flow cell for receiving the reagents for removal from the transient-binding reaction; photon detectors for detecting a signal emitted by the nanoparticles or reporter moieties; and cameras for determining the location of the signal. The surface of the flow cell can be coated with PEM/biotin/avidin (U.S. Pat. Nos. Quake, U.S. Pat. Nos. 6,818,395, 6,911,345, and 7,501,245). The base-paired template/primer duplex can be immobilized to the surface of the flow cell via biotin/avidin interaction (Buzby, U.S. Pat. No. 7,220,549). The reagents for conducting a nucleotide transient-binding reaction (e.g., nanoparticles, polymerases, non-incorporatable nucleotides, terminator nucleotides, labeled nucleotides, nanoparticles, template molecules, primers, cleavage/removal reagents, wash buffers, and oxygen scavengers) can be pulled through the inlet or outlet ports via capillary action, or by vacuum (Lawson, U.S. published patent application No. 2008/0219890; and Harris, et al., 2008 Science 320:106-109, and Supplemental Materials and Methods from the supporting online material), or moved via a pressure-driven fluidics system. In another embodiment, the reagents can be pulled through the inlet or outlet ports using a passive vacuum source (Ulmer, U.S. Pat. No. 7,276,720).

In yet another embodiment, the flow cell can be a two-sided multi-channel flow cell comprising multiple independently-addressable sample channels and removable loading blocks for sample loading (Lawson, U.S. published patent application No. 2008/0219888).

Linkers, Linking Chemistry, and Binding Partner Pairs

The term "linker" refers to a chemical moiety which attaches one compound to another compound. A suitable linker, and linker chemistry, can be used to attach the nanoparticles, reporter moieties, surfaces, and/or biomolecules (e.g., labeled nucleotides, non-incorporatable nucleotides, terminator nucleotides, polymerases, template nucleic acid molecules, primers, and oligonucleotides) to each other in any combination. See, for example, GT Hermanson 2008, in: "Bioconjugate Techniques", second edition, Academic Press.

The nanoparticles, reporter moieties, surfaces, and biomolecules, can be attached to each other, in any combination and in any order, via linking chemistry without an intervening linker moiety.

The suitable linker does not interfere with the function or activity of the nanoparticles, reporter moieties, surfaces, or biomolecules.

The suitable linker can mediate covalent or non-covalent attachment. Examples of non-covalent attachment includes: ionic, hydrogen bonding, dipole-dipole interactions, van der Waals interactions, ionic interactions, and hydrophobic interactions. In particular, examples of non-covalent attachment includes: nucleic acid hybridization, protein aptamer-template binding, electrostatic interaction, hydrophobic interaction, non-specific adsorption, and solvent evaporation.

The suitable linker can be rigid or flexible. The rigid linker can be used to improve a FRET signal by optimizing the orientation of the energy transfer dye. Examples of rigid linkers include benzyl linkers, proline or poly-proline linkers (S. Flemer, et al., 2008 Journal Org. Chem. 73:7593-7602), bis-azide linkers (M. P. L. Werts, et al., 2003 Macromolecules 36:7004-7013), and rigid linkers synthesized by modifying the so-called "click" chemistry scheme that is described by Megiatto and Schuster (2008 Journal of the Am. Chem. Soc. 130:12872-12873).

The suitable linker can optimize proximity, length, distance, orientation, or charge. For example, the linker can be a cationic poly-arginine spacer linker or an imidazolium spacer molecule.

The suitable linker can be a cleavable, self-cleavable, or fragmentable linker. The self-cleaving linker can be a trimethyl lock or a quinone methide linker. The suitable linker can be cleaved or fragmented via light (e.g., photo-cleavable linkers), a chemical reaction, enzymatic activity, heat, acid, or base. The photo-cleavable linkers include nitrobenzyl derivatives, phenacyl groups, and benzoin esters. Many cleavable groups are known in the art. See for example, J. W. Walker, et al., 1997 Bioorg. Med. Chem. Lett. 7:1243-1248; R. S. Givens, et al., 1997 Journal of the American Chemical Society 119:8369-8370; R. S. Givens, et al., 1997 Journal of the American Chemical Society 119:2453-2463; Jung et al., 1983 Biochem. Biophys. Acta, 761: 152-162; Joshi et al., 1990 J. Biol. Chem., 265: 14518-14525; Zarling et al., 1980 J. Immunol., 124: 913-920; Bouizar et al., 1986 Eur. J. Biochem., 155: 141-147; Park et al., 1986 J. Biol. Chem., 261: 205-210; Browning et al., 1989 J. Immunol., 143: 1859-1867; and Korlach, U.S. Pat. No. 7,033,764. The fragmentable linkers, include non-lamellar "detergent-like" micelles or lamellar vesicle-like micelles such as small unilamellar vesicles or liposomes ("SUVs"), small multilamellar vesicles or liposomes (SMVs"), large unilamellar vesicles or liposomes ("LUVs") and/or large multilamellar vesicles or liposomes ("LMVs") (Graham, U.S. published patent application No. 2006-0003383 and 2009-0047699). Many cleavable, and bifunctional (both homo- and heterobifunctional) spacer arms with varying lengths are available commercially.

The suitable linker can be linear, non-linear, branched, bifunctional, trifunctional, homofunctional, or heterofunctional. Some linkers have pendant side chains or pendant functional groups, or both. Examples of pendant moieties include hydrophilicity modifiers, for example solubilizing groups such as sulfo ($-SO_3H-$ or $-SO^{3-}$). The trifunctional linker can be linked to multiple reporter moieties (the same or different reporter moieties) for dendritic amplification of the signal emitted by the reporter moieties (Graham, U.S. published patent application Nos. 2006/0003383 and 2007/0009980).

The suitable linker comprises about 1-100 plural valent atoms. In some embodiments, the linker moiety comprises about 1-40 plural valent atoms, or more, selected from the group consisting of C, N, O, S and P.

The suitable linker can include any combination of single, double, triple or aromatic carbon-carbon bonds, carbon-nitrogen bonds, nitrogen-nitrogen bonds, carbon-oxygen bonds or carbon-sulfur bonds. Exemplary linking members include a moiety that includes-C(O)NH—, —C(O)O—, —NH—, —S—, —O—, and the like. The linkers can include a combination of moieties selected from amine, alkyl, alkylene, aryl, —C(O)NH—, —C(O)O—, —NH—, —S—, —O—, —C(O)—, —S(O)$_n$—, where n is 0, 1, 2, 3, 4, 5, or 6-membered monocyclic rings and optional pendant functional groups, for example sulfo, hydroxy and carboxy.

The suitable linker can be resistant to heat, salts, acids, bases, light, chemicals, or shearing forces or flow.

The suitable linker can include a short or long spacer, a hydrophilic spacer, or an extended spacer.

The suitable linker can be capable of energy transfer, such as those disclosed by Ju in U.S. published patent application No. 2006/0057565.

The suitable linker can include multiple amino acid residues, such as a poly-arginine linker.

Capture Probes

Capture probes can be used to attach the nanoparticles, reporter moieties, surfaces, terminator nucleotides, labeled nucleotides, non-incorporatable nucleotides, polymerases, template nucleic acid molecules, primers, and/or oligonucleotides, to each other in any combination. The capture probes include nucleic acid probes which form complexes with single or double stranded nucleic acid molecules. The capture probes include oligonucleotide clamps (Gryaznov, U.S. Pat. No. 5,473,060). The parameters for selecting the length and sequence of the capture probes are well known (Wetmur 1991 Critical Reviews in Biochemistry and Molecular Biology, 26: 227-259; Britten and Davidson, Chapter 1 in: "Nucleic Acid Hybridization: A Practical Approach", Hames et al, editors, IRL Press, Oxford, 1985). The length and sequence of the capture probes may be selected for sufficiently stability during low and/or high stringency wash steps. The length of the capture probes ranges from about 6 to 50 nucleotides, or from about 10 to 24 nucleotides, or longer.

PEG Attachment

Polymers of ethylene oxide can be used to attach the nanoparticles, reporter moieties, surfaces, terminator nucleotides, labeled nucleotides, non-incorporatable nucleotides, polymerases, template nucleic acid molecules, primers, and/or oligonucleotides, to each other in any combination. Examples of polymers of ethylene oxide include: polyethylene glycol (PEG), such as short to very long PEG; branched PEG; amino-PEG-acids; PEG-amines; PEG-hydrazines; PEG-guanidines; PEG-azides; biotin-PEG; PEG-thiols; and PEG-maleinimides. In some embodiments, PEG includes: PEG-1000, PEG-2000, PEG-12-OMe, PEG-8-OH, PEG-12-COOH, and PEG-12-NH$_2$.

Binding Partner Pairs

Binding partner pairs can be used to operably link the nanoparticles, reporter moieties, surfaces, non-incorporatable nucleotides, terminator nucleotides, labeled nucleotides, polymerases, template nucleic acid molecules, primers, and/or oligonucleotides, to each other in any combination. Examples of binding partners include: biotin or desthiobiotin or photoactivatable biotin and their binding partners avidin, streptavidin, NEUTRAVIDIN, or CAPTAVIDIN; His-tags which bind with nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which binds to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin is a biotin-binding protein from chicken (Hytonen, et al., BMC Structural Biology 7:8).

Other examples of binding partner pairs include: artificial biotin binding sequences, such as an AVI-TAG (Avidity LLC). In one embodiment, the artificial biotin binding sequence comprises a biotin ligase sequence. In another embodiment, the biotin binding sequence comprises the sequence (in single-letter amino acid symbols) GLNDIFEA-QKIEWHE. The biotin can bind the lysine (K) residue within the artificial biotin binding sequence. The artificial biotin binding sequence can be used for site-specific and/or mono-biotinylation of proteins. See for example Chapmann-Smith and Cronan 1999 Trends Biochem Sci 24:359-363; M. A. Eisenberg, et al., 1982 J. Biol Chem 275:15167-15173; J. E. Cronan 1990 J Biol Chem 265:10327-10333; and P. J. Schatz 1993 Biotechnology 11:1138-1143.

In one aspect, biotin binds avidin. Many examples of biotin and its variants are known, including cis-hexahydro-2-oxo-1H-thieno[3,4]imidazole-4-pentanoic acid and any derivatives and analogs thereof, including biotin-like compounds. Such compounds include, for example, biotin-e-N-lysine, biocytin hydrazide, amino or sulfhydryl derivatives of 2-iminobiotin and biotinyl-8-aminocaproic acid-N-hydroxysuccinimide ester, sulfosuccinimideiminobiotin, biotinbromoacetylhydrazide, p-diazobenzoyl biocytin, 3-(N-malcimidopropionyl)biocytin, and the like.

In one aspect, avidin comprises the native egg-white glycoprotein avidin, as well as any derivatives, analogs and other non-native forms of avidin, which can specifically bind to biotin. In some embodiments, avidin includes deglycosylated forms of avidin, bacterial streptavidins produced by selected strains of *Streptomyces* (e.g., *Streptomyces avidinii*) truncated streptavidins, and recombinant avidin and streptavidin as well as derivatives of native, deglycosylated and recombinant avidin and of native, recombinant and truncated streptavidin, for example, N-acyl avidins, e.g., N-acetyl, N-phthalyl and N-succinyl avidin, and the commercial products EXTRAVIDIN, CAPTAVIDIN, NEURTRAVIDIN, and NEUTRALITE AVIDIN. All forms of avidin-type molecules, including both native and recombinant avidin and streptavidin as well as derivatized molecules, e.g. nonglycosylated avidins, N-acyl avidins and truncated streptavidins, are encompassed within the terms "avidin". Typically, but not necessarily, avidin exists as a tetrameric protein, wherein each of the four tetramers is capable of binding at least one biotin moiety.

Reducing Non-Specific Binding

The nanoparticles, reporter moieties, surfaces, terminator nucleotides, labeled nucleotides, non-incorporatable nucleotides, polymerases, template nucleic acid molecules, primers, and/or oligonucleotides, can be modified to reduce non-specific binding to each other. For example, the solid surfaces or nanoparticles can be reacted with sugar molecules (e.g., mono or disaccharides as described by Jogikalmath in U.S. published patent application No. 2008/0213910), silane (Menchen, U.S. published patent application No. 2008-0176761) and/or PEG, to reduce non-specific binding with dyes and/or nucleotides. Silane includes: N-(3-aminopropyl)3-mercapto-benzamide; 3-aminopropyl-trimethoxysilane; 3-mercaptopropyl-trimethoxysilane; 3-(trimethoxysilyl)propyl-maleimide; and 3-(trimethoxysilyl)propyl-hydrazide.

Well Known Linking Chemistries

Many linking chemistry schemes are well known in the art for generating reactive groups for linking together the nanoparticles, reporter moieties, surfaces, non-incorporatable nucleotides, terminator nucleotides, labeled nucleotides, polymerases, template nucleic acid molecules, primers, and/or oligonucleotides, in any combination and in any order. Typically, the reactive groups include: amine, aldehyde, hydroxyl, sulfate, carboxylate groups, and others.

For example, reacting activated esters, acyl azides, acyl halides, acyl nitriles, or carboxylic acids with amines or anilines to form carboxamide bonds. Reacting acrylamides, alkyl halides, alkyl sulfonates, aziridines, haloacetamides, or maleimides with thiols to form thioether bonds. Reacting acyl halides, acyl nitriles, anhydrides, or carboxylic acids with alcohols or phenols to form an ester bond. Reacting an aldehyde with an amine or aniline to form an imine bond. Reacting an aldehyde or ketone with a hydrazine to form a hydrazone bond. Reacting an aldehyde or ketone with a hydroxylamine to form an oxime bond. Reacting an alkyl halide with an amine or aniline to form an alkyl amine bond. Reacting alkyl halides, alkyl sulfonates, diazoalkanes, or epoxides with carboxylic acids to form an ester bond. Reacting an alkyl halides or alkyl sulfonates with an alcohol or phenol to form an ether bond. Reacting an anhydride with an amine or aniline to form a carboxamide or imide bond. Reacting an aryl halide with a thiol to form a thiophenol bond. Reacting an aryl halide with an amine to form an aryl amine bond. Reacting a boronate with a glycol to form a boronate ester bond. Reacting a carboxylic acid with a hydrazine to form a hydrazide bond. Reacting a carbodiimide with a carboxylic acid to form an N-acylurea or anhydride bond. Reacting an epoxide with a thiol to form a thioether bond. Reacting a haloplatinate with an amino or heterocyclic group to form a platinum complex. Reacting a halotriazine with an amine or aniline to form an aminotriazine bond. Reacting a halotriazines with an alcohol or phenol to form a triazinyl ether bond. Reacting an imido ester with an amine or aniline to form an amidine bond. Reacting an isocyanate with an amine or aniline to form a urea. Reacting an isocyanate with an alcohol or phenol to form a urethane bond. Reacting an isothiocyanate with an amine or aniline to form a thiourea bond. Reacting a phosphoramidate with an alcohol to form a phosphite ester bond. Reacting a silyl halide with an alcohol to form a silyl ether bond. Reacting a sulfonate ester with an amine or aniline to form an alkyl amine bond. Reacting a sulfonyl halide with an amine or aniline to form a sulfonamide bond.

The linking chemistry scheme can include "click" chemistry schemes (Gheorghe, et al., 2008 Organic Letters 10:4171-4174).

The suitable linking scheme can include reacting the components to be linked in a suitable solvent in which both are soluble. Water-insoluble substances can be chemically modified in an aprotic solvent such as dimethylformamide, dimethylsulfoxide, acetone, ethyl acetate, toluene, or chloroform. Similar modification of water-soluble materials can be accomplished using reactive compounds to make them more readily soluble in organic solvents.

Modifying the Nanoparticle to Bind Molecules

A.) Dispersibility of Nanoparticles

The nanoparticles can be reacted with compounds that alter the dispersibility properties of the nanoparticles, or form reactive groups for covalent or non-covalent interactions with the surfaces, terminator nucleotides, labeled nucleotides, non-incorporatable nucleotides, polymerases, template nucleic acid molecules, primers, oligonucleotides, inhibitor moieties, or reporter moieties.

In one aspect, the nanoparticles can be modified to permit dispersibility in a solvent. For example, the nanoparticles can be dispersible in aqueous solvents, including: water, and aqueous solutions and buffers. Nanoparticles that are not dispersible in aqueous solvents typically have hydrophobic ligands which are intimately associated with the outer shell.

The ligands, sometimes referred to as a cap, can be trioctylphosphine (TOP), trioctylphosphine oxide (TOPO), oleic acid, or tetradecylphosphonic acid (TDPA). The aqueous-dispersible nanoparticles can be modified to have hydrophilic ligands via a cap exchange procedure. The cap exchange procedure can involve substituting the exposed groups on the nanoparticle (e.g., hydrophobic caps) with heterofunctional ligands. The nanoparticle surface can be modified to have hydrophilic ligands by encapsulating the nanoparticle in a coating of heterofunctional ligands. The heterofunctional ligands can include a thiol anchor moiety and a hydrophilic moiety (e.g., hydroxyl or carboxyl). Examples of heterofunctional ligands include thiol and phosphine mono and multidentate ligands, such as: mercaptocarbonic acids; alkythiol terminated molecules, thioalkylated molecules, and dihydrolipoic acid derivatives. Another example involves forming a polymerized silica shell on the nanoparticle surface. The silica shell can be functionalized with polar groups using, for example, mercaptopropyl silanols or amine box dendrimers. In yet another example, the native functional groups on the nanoparticle surface are preserved. The nanoparticles are reacted with amphiphilic diblock or triblock copolymers, or phospholipids, which have hydrophobic groups that interdigitate with the native functional groups on the nanoparticle shell. The amphiphilic copolymers and have hydrophilic groups that permit aqueous dispersal. The interdigitating compounds include: phosphatidylethanol amine, phosphatidycholine micelles, modified acrylic acid polymers, poly (maleic anhydride)-alt-1-tetradecene, amphiphilic triblock copolymer (Gao 2004 Nature Biotechnology 22:969-976), and amphiphilic saccharides. Another procedure for preserving the nanoparticle native functional groups involves reacting the nanoparticle with oligomeric phosphines that carry hydrophilic functional groups and/or carry a protein-protein binding partner (e.g., avidin or derivative thereof). Proteins can also be nonspecifically adsorbed on to the nanoparticle surface.

B.) Linking Nanoparticles

The nanoparticles can be operably linked to the surfaces, terminator nucleotides, labeled nucleotides, non-incorporatable nucleotides, polymerases (proteins), template nucleic acid molecules, primers, oligonucleotides, inhibitor moieties, or reporter moieties, using well known linking schemes. In general, these linking schemes include: (1) a condensation reaction between the amines on the proteins and the carboxy groups on the nanoparticle using, for example, 1-ethyl-3-(3-dimethylaminopropyl) carbodiimide (EDC); (2) directly binding thiolated proteins to the nanoparticles using dative thiol-bonding between the cysteine residues on the protein and the sulfur atoms on the nanoparticle surface; (3) metal-affinity coordination between the histidine residues in the proteins and the Zn atoms on the nanoparticle surface; or (4) adsorption or non-covalent self-assembly of protein on to the nanoparticle surface.

The nanoparticles can have ligand coatings, such as carboxyl groups (e.g., as carboxyl-derived amphiphilic compounds) which can be reacted with the amines, hydrazines, or hydroxylamines on the solid surface or on proteins (e.g., polymerases) in a condensation reaction (e.g., using EDC).

The nanoparticle ligands can be amino-derivatized ligands that permit crosslinking with amine reactive groups such as isothiocyanates, succinimidyl esters and other active esters.

The solid surfaces and proteins (e.g., polymerases) can be attached directly to the nanoparticle. Surfaces or proteins having a poly-His sequence (e.g., tag) can be attached directly to a nanoparticle via metal-affinity coordination between the nanoparticle Zn atoms (e.g., on the shell) and histidine residues. The histidine residues also have varying affinities for other metals including $Ni^{2+}$, $Co^{2+}$, $Cu^{2+}$, $Mn^{2+}$, $Fe^{2+}$ and $Fe^{3+}$. Surfaces and proteins can also be attached directly to the nanoparticle via dative thiol bonding between S atoms in the nanoparticle and cysteine residues on the surface or in the protein.

The proteins can adsorb (e.g., non-covalently) on to the nanoparticle, or nanoparticles can absorb non-covalently onto a surface. For example, positively charged proteins can adsorb on to the negatively charged a nanoparticle, or a negatively charge nanoparticle can adsorb on to a positively charged surface.

The nanoparticle ligand coating can be PEG or biotin, which can be linked to a protein (e.g., streptavidin) via amine linking chemistry. For example, the PEG coating can be reacted with a cross-linker (e.g., bis(sulfosuccinimidyl) suberate; (BS3)) for amine linking with streptavidin.

The nanoparticle can be reacted with a compound which can bind to some or all of the binding sites on the nanoparticle shell in order to mask the binding sites. The compounds include horseradish peroxidase (HRP), glutathione S-transferase (GST), uracil-DNA glycosylase (UDG), uracil glycosylase inhibitor (UGI), or bovine serum albumin (BSA). For example, a non-masked nanoparticle may be capable of binding many protein molecules. In another example a partially masked nanoparticle, which is coated with HRP, GST, UDG, UGI, and/or BSA, may be capable of binding fewer protein molecules. In one embodiment, one nanoparticle can bind about 1-5, or about 5-10, or about 10-20, or about 20-50, or more polymerases (or fusion proteins thereof). In one embodiment, one nanoparticle can bind one polymerase.

In one embodiment, the nanoparticle can be reacted to carry an iodoacetal functional group which can bind to a protein (e.g., polymerase) carrying a phosphorothioate functional group on a recombinantly introduced serine residue.

Attaching Nucleic Acid Molecules to the Surface

The nucleic acid molecules can be operably linked to the surface. The template nucleic acid molecules, primers, and/or oligonucleotides can be modified at their 5' or 3' end, or internally, to carry a reactive group which can bind to a reactive group on the surface. Typically, the surface is treated or untreated to provide reactive groups such as silanol, carboxyl, amino, epoxide, and methacryl groups. The nucleic acid molecules can be treated or untreated to provide reactive groups including: amino, hydroxyl, thiol, and disulfide. The nucleic acid molecules can include non-natural nucleotides having reactive group which will attach to a surface reactive group. For example, the non-natural nucleotides include peptide nucleic acids, locked nucleic acids, oligonucleotide N3'→P5' phosphoramidates, and oligo-2'-O-alkylribonucleotides.

In one aspect, nucleic acid molecules modified with one or more amino groups at the 5' or 3' end, or internally, can be attached to modified surfaces. The amino group at the 5' end of the nucleic acid molecule includes: a simple amino group; a short or long tethering arm having one or more terminal amino groups; or amino-modified thymidine or cytosine. The tethering arms can be linear or branched, have various lengths, charged or uncharged, hydrophobic, flexible, cleavable, or have one or multiple terminal amino groups. The tethering arm can include 1-40 plural valent atoms, or more. The amino group at the 3' end of the nucleic acid molecule is typically initially protected by a fluorenyl-methylcarbamoyl (Fmoc) group. To expose the amino group, the protecting group can be removed and acylated with an appropriate succinimidyl ester, such as an N-hydroxy succinimidyl ester (NHS ester).

In another aspect, the nucleic acid molecules can carry internal amino groups for binding to the solid surface. For example, 2' amino modified nucleic acid molecules can be produce by methoxyoxalamido (MOX) or succinyl (SUC) chemistry to produce nucleotide analogs having amino linkers attached at the 2' C of the sugar moiety.

In another aspect, the surface can be modified to bind the amino modified nucleic acid molecules. For example, 5' amino-modified nucleic acid molecules can be attached to surfaces modified with silane, such as epoxy silane derivatives (J. B. Lamture, et al., 1994 Nucleic Acids Res. 22:2121-2125; W. G. Beattie et al., 1995 Mol. Biotechnol. 4:213-225) or isothiocyanate (Z. Guo, et al., 1994 Nucleic Acids Res. 22:5456-5465). Acylating reagents can be used to modify the surface for attaching the amino-modified nucleic acid molecules. The acylating reagents include: isothiocyanates, succinimidyl ester, and sulfonyl chloride. The amino-modified nucleic acid molecules can attach to surface amino groups which have been converted to amino reactive phenylisothiocyanate groups by treating the surface with p-phenylene 1,4 diisothiocyanate (PDC). In other methods, the surface amino groups can be reacted with homobifunctional crosslinking agents, such as disuccinimidylcaronate (DCS), disuccinimidyloxalate (DSO), phenylenediisothiocyanate (PDITC) or dimethylsuberimidate (DMS) for attachment to the amino-modified nucleic acid molecules. In another example, metal and metal oxide surfaces can be modified with an alkoxysilane, such as 3-aminopropyltricthoxysilane (APTES) or glycidoxypropyltrimethoxysilane (GOPMS).

In another aspect, succinylated nucleic acid molecules can be attached to aminophenyl- or aminopropyl-modified surfaces (B. Joos et al., 1997 Anal. Biochem. 247: 96-101).

In yet another aspect, a thiol group can be placed at the 5' or 3' end of the nucleic acid molecules. The thiol group can form reversible or irreversible disulfide bonds with the surface. The thiol attached to the 5' or 3' end of the nucleic acid molecule can be a phosphoramidate. The phosphoramidate can be attached to the 5' end using S-trityl-6-mercaptohexyl derivatives.

In another aspect, the thiol-modified nucleic acid molecules can be attached to a surface using heterobifunctional reagents (e.g. cross linkers). For example, the surface can be treated with an alkylating agent such as iodoacetamide or maleimide for linking with thiol modified nucleic acid molecules. In another example, silane-treated surfaces (e.g., glass) can be attached with thiol-modified nucleic acid molecules using succinimidyl 4-(malemidophenyl)butyrate (SMPB).

In another aspect, the nucleic acid molecule can be modified to carry disulfide groups can be attached to thiol-modified surfaces (Y. H. Rogers et al., 1999 Anal. Biochem. 266:23-30).

Still other aspects include methods that employ modifying reagents such as: carbodiimides (e.g., dicyclohexylcarbodiimide, DCC), carbonyldiimidazoles (e.g., carbonyldiimidazole, $CDI_Z$), and potassium periodate. The nucleic acid molecules can have protective photoprotective caps (Fodor, U.S. Pat. No. 5,510,270) capped with a photoremovable protective group. DMT-protected nucleic acid molecules can be immobilized to the surface via a carboxyl bond to the 3' hydroxyl of the nucleoside moiety (Pease, U.S. Pat. No. 5,599,695; Pease et al., 1994 Proc. Natl. Acad. Sci. USA 91:5022-5026). The nucleic acid molecules can be functionalized at their 5' ends with activated 1-O-mimethoxytrityl hexyl disulfide 1'-[(2-cyanoethyl)-N,N-diisopropyl)] phosphoramidate (Rogers et al., 1999 Anal. Biochem. 266:23). Exemplary methods of attaching nucleic acid molecules to suitable substrates are disclosed, for example, in U.S. Pat. Nos. 6,221,592, 6,294,136; and Schwartz, U.S. published patent application Nos. 2006/275806 and 2007/0161028). Linking agents, can be symmetrical bifunctional reagents, such as bis-succinimide (e.g., bis-N-hydroxy succinimide) and maleimide (bis-N-hydroxy maleimide) esters, or toluene diisocyanate can be used. Heterobifunctional cross-linkers include: m-maleimido benzoyl-N-hydroxy succinimidyl ester (MBS); succinimidyl-4-(p-maleimido phenyl)-Butyrate (SMPB); and succinimidyl-4-(N-Maleimidomethyl) Cyclohexane-1-Carboxylate (SMCC) (L. A. Chrisey et al., 1996 Nucleic Acids Res. 24:3031-3039). In one example, a glass surface can be layered with a gold (e.g., about 2 nm layer) which is reacted with mercaptohexanoic acid. The mercaptohexanoic acid can be placed in a patterned array. The mercaptohexanoic acid can be reacted with PEG. The PEG can be reacted to bind nucleic acid molecules such as the template nucleic acid molecules.

Attaching Proteins to the Solid Surface

The surface can be modified to operably link the protein molecules (e.g., polymerases) via covalent or non-covalent linkage. The protein molecules may be attached to the surface via covalent cross-linking bridges, including disulfide, glycol, azo, sulfone, ester, or amide bridges. Some exemplary methods for attaching proteins to a surface are disclosed in U.S. Pat. Nos. 7,056,661, 6,982,146, 7,270,951, 6,960,437, 6,255,083, 7,229,799 and published application U.S. No. 2005/0042633.

The protein molecules can be modified at their amino- or carboxyl-terminal ends, or internally, to carry a reactive group that can bind to a reactive group on the surface.

The protein molecules can be attached to the modified surfaces using standard chemistries including: amination, carboxylation or hydroxylation. The attachment agents can be cyanogen bromide, succinimide, aldehydes, tosyl chloride, photo-crosslinkable agents, epoxides, carbodiimides or glutaraldehyde (See "Protein immobilization: Fundamentals and Applications, Richard F. Taylor, ed. (M. Dekker, New York, 1991)). The surface can be treated or untreated to provide reactive groups such as silanol, carboxyl, amino, epoxide, and methacryl groups. The protein molecules can be treated or untreated to provide reactive groups including: amino, hydroxyl, thiol, and disulfide. The surface can be coated with an electron-sensitive compound such as polymethyl methacrylate-like material (PMMA).

The protein molecules can be attached to a surface that is untreated or modified via physical or chemical interaction. See Nakanishi for a review of protein immobilization methods (K. Nakanishi, 2008 Current Proteomics 5:161-175).

The protein molecules can be adsorbed onto a surface. The adsorption can occur via ion exchange, charge-charge interaction, or hydrogen bond interactions. The adsorption can occur on to untreated surfaces, including polystyrene, polyvinylidene fluoride (PVDF), glass coated with poly-lysine (H. Ge 2000 Nucl. Acids Res. 28: e3; B. B. Haab, et al., 2001Genome Biol. 2: $R_4$-13; Zhu and Snyder 2003Curr. Opin. Chem. Biol. 7: 55-63), or onto surfaces having hydrophobic properties (Y. Sanghak, et al., 2006 Curr. Appl. Phys. 6: 267-70).

The protein molecules can be attached to the surface using a hydrogel (P. Arenkov, et al., 2000 Anal. Biochem. 278: 123-31; S. Kiyonaka, et al., 2004 Nat. Mater. 3: 58-64).

The protein molecules can be linked to an affinity His-tag (e.g., 6×His-tag) which interacts with $Ni^{2+}$, $Co^{2+}$, or $Cu^{2+}$ surfaces (T. Nakaji-Hirabayashi, et al., 2007 Biomaterials 28: 3517-29; R. Vallina-García, et al., 2007 Biosens. Bioelectron. 23: 210-7; T. Cha, et al., 2004 Proteomics 4: 1965-76; T. Cha, et al., 2005 Proteomics 5: 416-9). For example, the proteins can be a fusion protein which includes the His-tag sequence. The glass surface can be functionalized with a chelate group by treating with nitrotriacetic acid (NTA) or imidoacetic acid (IDA) and reacted with $Ni^{2+}$ or $Cu^{2+}$, respectively.

The protein molecules can be attached to the surface via chemisorption between a thiol (e.g., SH group of cysteines) on the protein and a gold surface (S. V. Rao, et al., 1998 Mikrochim. Acta 128: 127-43).

The protein molecules can be attached to the surface via a Schiff's base linkage reaction. For example, a glass surface can be silanized with silane, polysilane, trimethoxysilane, or aminosilane. The silanized glass surface can interact with amino groups (e.g., lysine) on the protein (MacBeath and Schreiber 2000 Science 289: 1760-1763; H. Zhu, et al., 2000 Nat. Genet. 26: 283-289). Metal and metal oxide surfaces can be modified with an alkoxysilane, such as 3-aminopropyltriethoxysilane (APTES) or glycidoxypropyltrimethoxysilane (GOPMS).

The protein molecules can be immobilized via protein coil-coil interaction between a heterodimeric Leu zipper pair (J. R. Moll, et al., 2001 Protein Sci. 10: 649-55; K. Zhang, et al., 2005 J. Am. Chem. Soc. 127: 10136-7). For example, the surface can be functionalized to bind one of the zipper proteins, and the proteins can be operably linked with the other zipper protein. The proteins can be fusion proteins which include a zipper protein sequence. The glass surface can be coated with a bifunctional silane coupling reagent comprising aldehyde (e.g., octyltrichlorosilane (OTC)) and functionalized with a hydrophobic elastin mimetic domain (ELF) as a hydrophobic surface anchor which serves to bind a leucine zipper sequence. The anchored zipper sequence can interact with a partner leucine zipper sequence linked to the proteins.

The protein molecules can be immobilized via an acyl transfer reaction. For example, transglutaminase (TGase) can catalyze an acyl transfer reaction between a primary amino group and a carboxyamide group (J. Tominaga, et al., 2004 Enz. Microb. Technol. 35: 613-618). In one embodiment, carboxyamide groups from a casein-coated surface can react with the primary amine groups (e.g., lysine as a peptide tag or part of the protein) on the protein molecules. In another embodiment, the amine groups on the surface can react with carboxyamide groups (e.g., glutamine-tag or glutamine groups on the protein molecules).

The protein molecules can be immobilized via interaction between an affinity peptide sequence (e.g., motif) and its cognate peptide binding partner. For example, the affinity motif could bind a protein kinase. In one embodiment, the affinity motif comprises the "minimal" motif, R—X—X—S*/T* (SEQ ID NO:6) (T. R. Soderling 1996 Biochim. Biophys. Acta 1297: 131-138), including peptide motifs RRATSNVFA (SEQ ID NO:7), RKASGPPV (SEQ ID NO:8), or LRRASLG (SEQ ID NO:9), which bind a calmodulin-dependent protein kinase.

Oriented poly-His tagged protein molecules can be immobilized on to a glass surface modified with PEG and reacted with a chelate group such as iminodiacetic acid (IDA) or nitrolotriacetic acid (NTA), and metal ions such as $Ni^{2+}$ or $Cu^{2+}$ (T. Cha, et al., 2004 Proteomics 4:1965-1976).

EDAC chemistry can be use to link a carboxylated silica surface to an avidin. The avidin can bind to a biotinylated protein (e.g., polymerase). The avidin-silica surface can bind one or more biotinylated protein molecules, or bind more than one type of biotinylated protein, In one aspect, a peptide linker can be used to attach the protein molecules to the nanoparticle or to the solid surface. The peptide linkers can be part of a fusion protein comprising the amino acid sequences of the protein molecule. The fusion protein can include the peptide linker positioned at the N- or C-terminal end or in the interior of the fusion protein. In another embodiment, the peptide linkers can be a separate linker which is attached to the protein and the solid surface or nanoparticle.

For example, the peptide linker can be a flexible linker comprising the amino acid sequence GGGGSGGGGSAAAGSAA (SEQ ID NO:10) (K. Alfthan 1995 Protein Engineering 8:725-731). In another example, the peptide linker can be a rigid linker comprising the amino acid sequence GAAAKGAAAKGSAA (SEQ ID NO:11) (Marqusee and Baldwin 1987 Proc. Natl. Acad. Sci. USA 84:8898-8902; R. Arai 2001 Protein Engineering 14:529-532). In another example, the peptide linker can be a poly-lysine linker, comprising between about 4-15 lysine residues (e.g., 12 lysine residues). BS3 coupling (bis(sulfosuccinimidyl)suburate) can be used to attach the poly-lysine linkers to PEG-amine groups on the solid surfaces or on nanoparticles. In yet another example, the peptide linker can be a poly-cysteine linker comprising between about 4-15 cysteine residues (e.g., 12 cysteine residues). SMCC coupling (succinimidyl-4-(N-maleimidomethyl)cyclohexane-1-carboxylate) can be used to attach the poly-cysteine linkers to PEG-amine groups on solid surfaces or on nanoparticles. In yet another example, the peptide linker can be a transglutaminase tag comprising the amino acid sequence PKPQQF (SEQ ID NO:12) or PKPQQFM (SEQ ID NO:13). The transglutaminase tag can provide site specific attachment of the protein to the solid surface or nanoparticle. Transglutaminase enzyme can catalyze an acyl transfer reaction between the y-carboxyamide group of an acceptor glutamine residue and a primary amine donor on the solid surface or nanoparticles. In yet another example, the peptide linker can be a protein kinases (PKA) tag comprising the amino acid sequence LRRASL (SEQ ID NO:14). The PKA tag can provide site specific attachment of the protein to the solid surface or nanoparticle. SPDP (N-succinimidyl 3-(2-pyridyldithio) propionate) and iodoacetic acid are heterobifunctional cross-linking agents that can react with amines and sulfhydryl groups to link proteins to the solid surfaces or nanoparticles.

In one embodiment, the solid surface can be modified to provide avidin (or avidin-like) binding groups. In one embodiment, the surface material is glass. In another embodiment, the glass surface is reacted with silane or its derivative. In another embodiment, the glass surface is reacted with PEG, biotin, and avidin (or avidin-like protein) to provide avidin (or avidin-like) binding sites. In yet another embodiment, the glass surface is reacted with PEG and avidin (or avidin-like protein) to provide avidin (or avidin-like) binding site. The binding sites on the glass slide can attach to the nanoparticles, proteins (e.g., or any fusion proteins thereof), template nucleic acid molecules, primers, or oligonucleotides.

In another embodiment, the polymerase (or polymerase fusion protein) is linked to the surface. In another embodiment, the solid surface can be modified for binding to a His-tagged protein. In another embodiment, the polymerase can be a biotinylated protein bound to a surface which is coated with avidin or avidin-like protein. In another embodiment, the polymerase can be a poly-His-tagged protein bound to a nickel-conjugated surface. In another embodiment, the polymerase (or polymerase fusion protein) can be linked to a nanoparticle. In another embodiment, polymerase and nanoparticle can be separately linked to the surface. The immobilized polymerase can bind the template nucleic acid molecule, which may or may not be base-paired with the polymerization initiation. The immobilized polymerase can bind the labeled nucleotide or the non-incorporatable nucleotides. The immobilized polymerase can incorporate the terminator nucleotide.

Linking Energy Transfer Moieties

Provided herein are energy transfer donor or acceptor moieties which are operably linked to the surface, nanoparticles or biomolecules (terminator nucleotides, labeled nucleotides, non-incorporatable nucleotides, polymerases, template nucleic acid molecules, primers, oligonucleotides, inhibitor moieties, or reporter moieties). The donor or acceptor moieties can be linked to any portion of the surface or biomolecules in a manner that does not interfere with the function of the biomolecule. The donor or acceptor moiety can be operably linked to the 5' or 3' end of the primer molecule, template molecule, or polymerization initiation site.

The FRET acceptor moiety may be operably linked to, or comprise part of, the nucleotide, including the sugar or base, or phosphate group. The FRET acceptor can be operably attached to a phosphate group which is cleaved and liberated upon nucleotide incorporation, or attached to a nucleotide that is not cleaved. The FRET acceptor can be operably attached to the terminal nucleotide phosphate group. The FRET acceptor can be operably linked to the polymerase, primer molecule, or template molecule.

The FRET donor can be operably attached to the polymerase, or a biologically active fragment thereof, or a fusion protein thereof. The FRET donor can be operably linked to the primer molecule, template molecule, or any portion of the nucleotide (base, sugar or phosphate group).

Many linking procedures are well known in the art, including: maleimide, iodoacetyl, or pyridyl disulfide chemistry which templates thiol groups on polypeptides; or succinimidyl esters (NHS), sulfonyl chlorides, iso(thio)cyanates, or carbonyl azide chemistry which templates primary amines in a polypeptide.

In another aspect, the acceptor and donor moieties may be a fluorescent protein (e.g., green fluorescent protein or derivatives thereof), or an enzymatically catalyzed bioluminescent molecule, which is operably linked to the surface, nanoparticles or biomolecules.

In yet another aspect, the acceptor and donor moieties may be operably linked to the surface, nanoparticles, or biomolecules, via a non-covalent interaction between binding partner pairs.

In one embodiment, the suitable FRET donor/acceptor pair includes a nanoparticle as the donor moiety and an ALEXA FLUOR dye (Molecular Probes) as the acceptor moiety. In one embodiment, the ALEXA FLUOR dye (Molecular Probes) is operably linked to the terminal phosphate group of any nucleotide, including a non-incorporatable nucleotides or terminator nucleotide. In another embodiment, the nanoparticle is operably linked to the polymerase, or a biologically active fragment thereof or a fusion protein thereof, or operably linked to the template nucleic acid molecule or primer molecule. In yet another embodiment, the nucleotide is operably linked with a second energy transfer acceptor dye which can be the same as the first acceptor dye (e.g., ALEXA FLUOR) or a different acceptor dye. In still another embodiment, the nucleotide is operably linked with a reporter moiety (e.g., a fluorophore). Thus, the nucleotide can be operably linked with an energy acceptor dye, and a second energy acceptor dye and/or a fluorophore.

Compositions and Systems

Provided herein are systems, comprising: a complex which comprises a polymerase bound to a template nucleic acid molecule which is base-paired to a polymerization initiation site; terminator nucleotides; non-incorporatable nucleotides; and labeled nucleotides. In one embodiment, the systems also include nanoparticles.

Reducing Photo-Damage

The methods disclosed herein can be practiced in the presence of compounds that reduce photo-damage. Illuminating the nucleotide transient-binding reactions with electromagnetic radiation at an excitation wavelength can induce formation of reactive oxygen species from the fluorophore or other components in the reaction. The reactive oxygen species can cause photo-damage to the fluorophores, polymerases, or any other component of the transient-binding reaction. The transient-binding reactions can include compounds that are capable of reducing photo-damage, including: protocatechuate-3,4-dioxygenase, protocatechuic acid; 6-Hydroxy-2,5,7,8-tetramethylchroman-2-carboxylic Acid (TROLOX); or cyclooctatetraene (COT).

Other compounds for reducing photo-damage include: ascorbic acid, astazanthin, bilirubin, biliverdin, bixin, captopril, canthazanthin, carotene (alpha, beta, and gamma), cysteine, beta-dimethyl cysteine, N-acetyl cysteine, diazobicyclooctane (DABCO), dithiothreitol (DTT), ergothioneine, glucose oxidase/catalase (GO/Cat), glutathione, glutathione peroxidase, hydrazine ($N_2H_4$), hydroxylamine, lycopene, lutein, polyene dialdehydes, melatonin, methionine, mercaptopropionylglycine, 2-mercaptoethane sulfonate (MESNA), pyridoxine1 and its derivatives, mercaptoethylamine (MEA), β-mercaptoethanol (BME), n-propyl gallate, p-phenylenediamene (PPD), hydroquinone, sodium azide ($NaN_3$), sodium sulfite ($Na_2SO_3$), superoxide dismutase, tocopherols, α-tocopheryl succinate and its analogs, and zeaxanthin.

Signal Detection

Provided herein is a system for optical or spectral detection of radiation (e.g., a signal or change in a signal) emitted by a reporter moiety during the transient-binding reaction. The detection system comprises: excitation illumination, optical transmission elements, detectors, and/or computers.

The detection system comprises excitation illumination which can excite the reporter moieties which produce detectable signals. The excitation illumination can be electromagnetic energy, such as radio waves, infrared, visible light, ultraviolet light, X-rays or gamma rays. The source of the electromagnetic radiation can be a laser, which possesses properties of mono-chromaticity, directionality, coherence, polarization, and/or intensity. The laser can produce a continuous output beam (e.g., continuous wave laser) or produce pulses of light (e.g., Q-switching or mode-locking). The laser can be used in a one-photon or multi-photon excitation mode. The laser can produce a focused laser beam. The wavelength of the excitation electromagnetic radiation can be between about 325-850 nm, or between about 325-752 nm, or between about 330-752 nm, or between about 405-752 nm.

The wavelength and/or power of the excitation illumination can be selected to avoid interfering with or damaging the polymerase enzymatic activities. The excitation illumination can be focused on a stationary position or moved to a different field of view (FOV). The excitation illumination can be directed at a transient-binding reaction which is: in a liquid volume (aqueous or oil); on a surface; in or on a nanodevice; in a waveguide; or in an evanescent illumination system (e.g., total internal reflection illumination). The excitation illumination can pass through a transparent or partially transparent surface which is conjugated (covalently or non-covalently) with the components of the transient-binding reaction.

The reporter moiety can be excited by the excitation illumination at a particular wavelength, and emit a signal at a longer wavelength. The reporter moiety can undergo multi-photon excitation with a longer wavelength, typically using a pulsed laser.

The detection system comprises suitable optical transmission elements that are capable of transmitting light from one location to another with the desired refractive indices and geometries. The optical transmission elements transmit the excitation illumination and/or the emitted energy in an unaltered or altered form. The optical transmission elements include: lens, optical fibers, polarization filters (e.g., dichroic filters), diffraction gratings (e.g., etched diffraction grating), arrayed waveguide gratings (AWG), optical switches, mirrors, dichroic mirrors, dichroic beam splitter, lenses (e.g., microlens and nanolens), collimators, filters, prisms, optical attenuators, wavelength filters (low-pass, band-pass, or high-pass), wave-plates, and delay lines, or any combination thereof.

The detection system comprises suitable detectors that are capable of detecting and/or distinguishing the excitation illumination and/or the emitted energy. A wide variety of detectors are available in the art, including: single or multiple channel detectors, high-efficiency photon detection systems, optical readers, charge couple devices (CCD), photodiodes (e.g. avalanche photo diodes (APD)), APD arrays, cameras, electron-multiplying charge-coupled device (EMCCD), intensified charge coupled device (ICCD), photomultiplier tubes (PMT), multi-anode PMT, complementary metal oxide semiconductor (CMOS) chip(s), and a confocal microscope equipped with any of the foregoing detectors. The location of the transient binding reaction can be aligned, with respect to the excitation illumination and/or detectors, to facilitate proper optical transmission.

Suitable detection methods can be used for detecting and/or distinguishing the excitation illumination and/or the emitted energy, including: confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, multi-foci multi-photon, or any combinations thereof. In one embodiment, a TIRF system is used to illuminate the transient-binding reaction, using terminator nucleotides, labeled nucleotides, non-incorporatable nucleotides, and nanoparticles, in a flow cell (Ulmer, U.S. Pat. No. 7,276,720).

The signals emitted from different reporter moieties can be resolved using suitable discrimination methods which are based on: fluorescence resonance energy transfer measurements; photoconversion; fluorescent lifetime measurements; polarization; fluorescent lifetime determination; correlation/anti-correlation analysis; Raman; intensity; ratiometric; time-resolved methods; anisotropy; near-field or far field microscopy; fluorescence recovery after photobleaching (FRAP); spectral wavelength discrimination; measurement and separation of fluorescence lifetimes; fluorophore identification; background suppression, parallel multi-color imaging, or any combination thereof. See, for example, J. R. Lakowitz 2006, in: "Principles of Fluorescence Spectroscopy", Third Edition. If the different terminator nucleotides are labeled with different reporter moieties, then resolving the emitted signals can be used to distinguish between the different nucleotides that are transiently-bound by the polymerase.

In one embodiment, the detection system for recording two or more colors includes: a microscope equipped with total internal reflection (TIR) illumination, two laser beams (circularly polarized), a dove prism, an image splitter, band-pass filters, and an intensified charge-coupled device (Braslavsky, et al., 2003 Proc. Natl. Acad. Sci. USA 100: 3960-3964).

In one embodiment, a system and method for detecting radiation emitted by a reporter moiety comprises: an illumination source (e.g., a laser) which produces the excitation energy (e.g., one or multi-photon excitation radiation) which is directed, via a dichroic beam splitter, through a lens, and through a transparent surface or onto a surface, where the transient-binding reaction is attached to the surface or is in a solution. The excitation illumination excites the reporter moiety resulting in emitted radiation which passes back through the dichroic beam splitter and is directed to the detector (or an array of detectors) which is capable of identifying and/or resolving the type of emission. Information about the detected emitted signals is directed to the computer where the information is registered and/or stored. The computer can process the registered and/or stored information to determine the presence of a transiently-bound nucleotide and/or identify the transiently-bound nucleotide.

In one aspect, the system and method for detecting radiation emitted by a reporter moiety includes a multifluorescence imaging system which can distinguish the signals emitted by the different reporter moieties, thereby permitting the simultaneous detection (or substantially simultaneous detection) of the different transiently-bound nucleotides. Such multifluorescent imaging can be accomplished using suitable filters, including: band pass filters, image splitting prisms, band cutoff filters, wavelength dispersion prisms, dichroic mirrors, or diffraction gratings, or any combination thereof.

In another aspect, the multifluorescence imaging system can include special filter combinations for each excitation line and/or each emission band. In one embodiment, the detection system includes tunable excitation and/or tunable emission fluorescence imaging. For tunable excitation, light from a light source can pass through a tuning section and condenser prior to irradiating the sample. For tunable emissions, emissions from the sample can be imaged onto a detector after passing through imaging optics and a tuning section. The tuning sections can be controlled to improve performance of the system.

In yet another aspect, the detection system comprises an optical train that directs signals emitted from an organized array onto different locations of an array-based detector to detect multiple optical signals from multiple locations. The optical trains typically include optical gratings and/or wedge prisms to simultaneously direct and separate signals having differing spectral characteristics from different addressable locations in an array to different locations on an array-based detector, e.g., a CCD (see also Harris, U.S. published patent application Nos. 2007/0070349; 2008/0087826; 2008/0088823; and 2008/0246949). Exemplary labeling and detection strategies, including strategies for detecting and resolving fluorescent signals are disclosed in U.S. Pat. No.

6,423,551; U.S. published patent application Nos. 2006/0176479, 2007/0109536, 2007/0111350, and 2007/0250274.

Kits

Provided herein are kits for conducting the nucleotide transient-binding reactions described herein. The kits can include, in one or more containers, the components of transient-binding reactions disclosed herein, including: the solid surfaces, terminator nucleotides, labeled nucleotides, non-incorporatable nucleotides, nanoparticles, reporter moieties, polymerases, template nucleic acid molecules (e.g., a control test template molecules), primers, and/or oligonucleotides.

In the kits, the various components of the nucleotide transient-binding reactions can be separate, or attached to each other in any combination. The kits can include positive and/or negative control samples.

Additional components can be included in the kit, such as buffers and reagents. For example, the buffers can include Tris, Tricine, HEPES, or MOPS, or chelating agents such as EDTA or EGTA. In another example, the reagents can include monovalent ions, such as KCl, K-acetate, $NH_4$-acetate, K-glutamate, $NH_4Cl$, or ammonium sulfate. In yet another example, the reagents can include divalent ions, such as $Ca^{2+}$, $Mg^{2+}$, $Mn^{2+}$, or $CaCl_2$), $MgCl_2$, $MnCl_2$, or Mg-acetate, and the like. The kits can include the components in pre-measured unit amounts. The kits can include instructions for performing the nucleotide transient-binding reactions. Where the kit is intended for diagnostic applications, the kits may further include a label indicating regulatory approval for the diagnostic procedures.

EXAMPLES

All of the compositions and methods disclosed and claimed herein can be made and executed without undue experimentation in light of the present disclosure. In some cases, the compositions and methods of this invention have been described in terms of embodiments, however these embodiments are in no way intended to limit the scope of the claims, and it will be apparent to those of skill in the art that variations may be applied to the compositions and/or methods and in the steps or in the sequence of steps of the methods described herein without departing from the concept, spirit and scope of the invention. More specifically, it will be apparent that certain components which are both chemically and physiologically related may be substituted for the components described herein while the same or similar results would be achieved. All such similar substitutes and modifications apparent to those skilled in the art are deemed to be within the spirit, scope and concept of the invention as defined by the appended claims.

Example 1

Fluorescent Polarization Assay:
Fluorescence polarization assays were conducted to characterize nucleotide transient-binding to a polymerase.
1) Oligonucleotide Template Molecules:

```
Oligo 265:
                                    (SEQ ID NO: 15)
5'-TTTTTGGGAGTGACAGGTTYTTCCTGTCACTX Oligo 266:
                                    (SEQ ID NO: 16)
5'-TTTTTAAGAGTGACAGGTTYTTCCTGTCACTX
```

-continued
```
Oligo 267:
                                    (SEQ ID NO: 17)
5'-TTTTTCCGAGTGACAGGTTYTTCCTGTCACTX Oligo 268:
                                    (SEQ ID NO: 18)
5'-TTTTTTTGAGTGACAGGTTYTTCCTGTCACTX
``` where Y=biotinTEG, and X=ddCTP

2) Transient-Binding Assay:

The transient-binding assays included: 3 µM phi29 mutant polymerase (exo-minus), 3 µM oligo template molecule (see sequence above), in a buffer (50 mM Tris HCl pH 7.5, 50 mM NaCl, 10 mM $MgCl_2$), and 200 nM of fluorescein-aha-dUTP or 200 nM fluorescein-aha-dCTP nucleotides (labeled nucleotides from Invitrogen). The fluorescein-labeled nucleotides include an amino-hexanoic acid linker (i.e., aha). The negative controls did not include the oligo template molecule.

3) Fluorescence Polarization:

100 µL aliquots of the transient-binding assays were placed in wells of a 96 well plate. The fluorescence polarization signals of the fluorophore molecules were measured in a microplate reader (Molecular Devices, model M5), excited at 490 nm, and detecting emission at 525 nm.

The g-factor used in the measurements was set to 1.0. The results are shown in FIG. 1. The fluorescein-labeled dUTP is shown as a diagnonal-striped pattern, and the fluorescein-labeled dCTP is shown as a stippled pattern. The "correct" nucleotide for binding to the oligo 265 template molecule is C, for the oligo 266 template molecule is A, for the oligo 267 template molecule is G, and for the oligo 268 template molecule is A. For the negative control assays (no DNA), and the assays that included the "incorrect" fluorescein-labeled nucleotide, the fluorescence polarization values range between approximately 50 and 70 mP (milli-polarization). For the assays that included the "correct" fluorescein-labeled nucleotide, the fluorescence polarization signals are between approximately 90 and 110 mP units. The higher mP values indicate that a larger fraction of the fluorescein-labeled dNTPs is transiently-bound by the polymerase-DNA complex. The results in FIG. 1 show that a phi29 polymerase which is bound to a template molecule, can selectively bind the correct nucleotide compared to the incorrect nucleotide, under conditions where the primer has a non-extendible 3' end. This transient-binding is detectable by fluorescence polarization.

When the same assays were performed with Klenow polymerase, no such discrimination was detected, as indicated by the relatively high fluorescence polarization values measured for correct and incorrect nucleotides.

Example 2

FRET-Based Assay:
1) Nanoparticles Conjugated with Phi29 Polymerase:

The polymerase used in this assay was a phi29 exo-minus polymerase which included a hexa-histidine tag at the N-terminal end. 300 µL, of a stock solution of His-tagged phi29 polymerase (56 µM) (in a stock solution in: 10 mM Tris (pH 7.5) buffer with 100 mM NaCl 1 mM DTT, 0.5% Tween-20, 0.1 mM EDTA and 50% v/v glycerol) was buffer exchanged into 100 mM Tris (pH 7.5) buffer with 300 mM NaCl using an NAP-5 column.

The nanoparticles are CdSe/ZnS core/shell nanoparticles with thiol ligands. Nanoparticles (160 µL. 4.9 µM in 50 mM borate buffer pH 8.0) were concentrated to approximately 30 µL by ultrafiltration (VivaSpin, at 100K MWCO0, and mixed with the buffer exchanged phi29 polymerase (440 µL, 26.9 µM in 100 mM Tris (pH 7.5) buffer with 300 mM NaCl in a 1:15 molar ratio (nanoparticle to polymerase). The resulting solution was incubated overnight at 4° C., concentrated to approximately 30 µL by ultra-filtration with a 100K MWCO VivaSpin centrifugal concentrator, further purified on SUPERDEX 200 column using 100 mM Tris (pH 7.5) buffer with 300 mM NaCl as the eluent.

2) Transient-Binding Assay:

The same buffer and oligo template molecules described above in Example 1 were used for FRET-base assays. The base-labeled nucleotides were AF5-dCTP. The AF5 fluorescent label is a Cy5 analog.

In this experiment, serial two-fold dilutions of the AF5-dCTP were prepared in the wells of a microtiter plate, starting at 2 µM. Aliquots of the nanoparticle-phi29 conjugate, plus oligo-template molecules, were added to the wells such that the final concentrations of the nanoparticle-phi29 conjugates were 10 nM and the concentrations of the template DNA molecules were 150 nM.

The fluorescence intensities of the reactions were recorded, using an excitation wavelength of 450 nm and emission wavelengths of 605 and 670 nm, for the donor (nanoparticles) and acceptor (AF5 fluorophore) moieties, respectively.

Figure 2B:
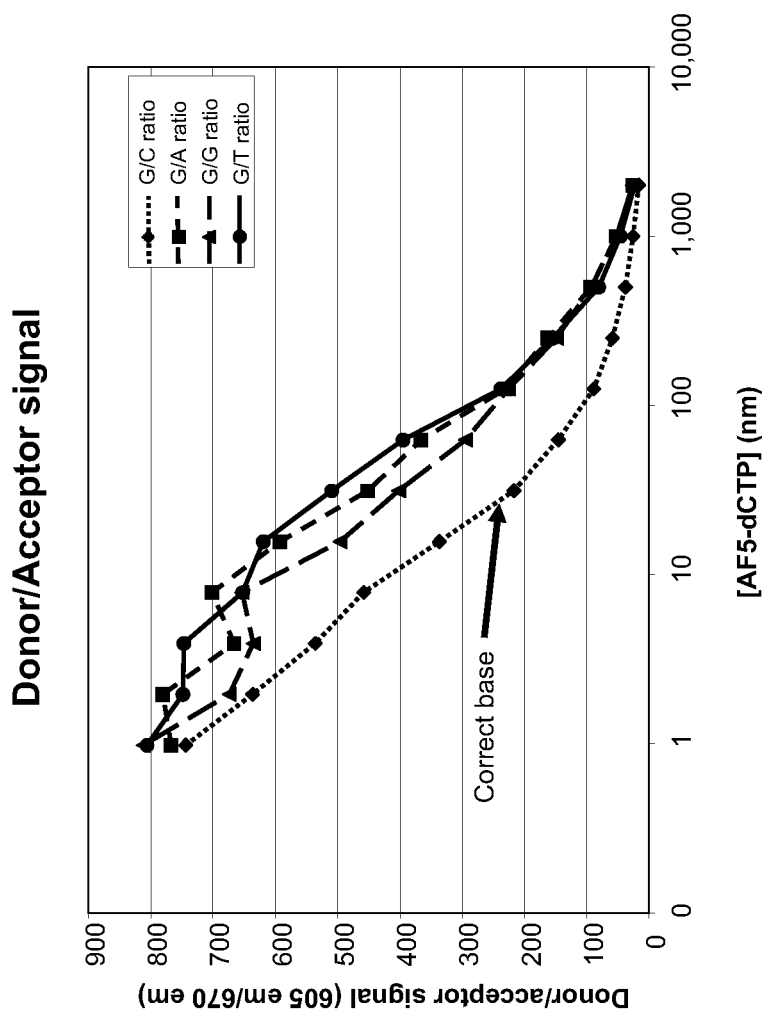
FIG. 2B shows data from a FRET-based nucleotide transient-binding assay (Example 2).

The data in FIGS. 2A and B shows that the detected fluorescent signals change with a change in the concentration of the base-labeled nucleotide. From the data in FIGS. 2A and B, the relative binding affinities of the polymerase for the nucleotide can be estimated. The results obtained in this experiment show that the binding affinity of the phi29 polymerase for AF5-dCTP is highest in the presence of a DNA template that has a "G" residue at the first position of the template strand (e.g., oligo 265 template molecule). The results show that Phi29 polymerase, which is bound to a template/primer (where the primer has a 3' non-extendible end), can selectively transiently-bind the correct nucleotide.

Example 3

Bead Immobilized Nucleotide Binding Assay:
1) Oligonucleotide Sequences:

```
188:
                                      (SEQ ID NO: 19)
5'-TTTTTGCCCCCAGGGTGACAGGTTXTTCCTGTCACCC-3'

228:
                                      (SEQ ID NO: 20)
5'-AAAAAAAAAGGGTGACAGGTT(BiotinTEG)TTCCTGTC

ACCC-3'

220:
                                      (SEQ ID NO: 21)
5'-TTTAGTCCTCCTGTCCTCCTGGGTGACAGGTT(BiotinTEG)

TTCCTGTCACCC-3'

201:
                                      (SEQ ID NO; 22)
5'-Biotin-TTTTTGGGAGTGACAGGTTTTTCCTGTCACTddC-3'

JX322:
                                      (SEQ ID NO: 23)
5'-AF647-TTTTTGCCCCCAGGGTGACAGGTTXTTCCTGTCACCC-3'
```

2) Template DNA Immobilized to Beads:

1 µL of streptavidin-coated Dynabeads (10 mg/mL, 2.8 µm diameter) (Invitrogen) were incubated with 100 µL of 20 nM DNA oligonucleotides (either JX322, 201, 220, 228 or 188) in polymerase extension buffer (50 mM pH 7.5 Tris buffer with 50 mM NaCl and 10 mM $MgCl_2$), for 10 minutes. The beads were removed from the extension buffer using a Dynal magnet. The beads were washed twice using 100 µL polymerase extension buffer 3) Detecting Fluorescently-Labeled DNA:

The fluorescently-labeled DNA, attached to the Dynabeads, was imaged under TIRF illumination in a microscope using a flow cell. The beads were suspended in DNA polymerase extension buffer (see above), with 0.4% glucose, 0.1 mg/mL glucose oxidase, 2000 units/mL catalase and 2 mM Trolox (reactive oxygen scavenger solution). The beads that stick to the surface of the coverslip were illuminated with a 633 laser (~200 µWatts) in both epi and TIR illumination modes.

4) Detecting Nucleotides Transiently-Bound to Polymerase:

A self-priming DNA oligonucleotide having a terminal dideoxynucleotide (e.g., oligo 201) was conjugated to Dynabeads in the manner described above. The DNA-conjugated beads were reacted with 20 nM Klenow polymerase in polymerase extension buffer and oxygen scavenger, and 200 nM AF5-dCTP or 200 nM Cy5-dUTP. The results are shown in FIG. 3A (epi illumination) and FIG. 3B (TIR illumination). The results show that Klenow polymerases, which are bound to amplified template molecules which are immobilized on beads, can selectively transiently-bind the correct nucleotide (when the primer includes a 3' non-extendible end).

Example 4

Analyzing Polymerase Kinetics Using Stopped-Flow Spectrometer:
1) Phi29 Polymerase: Stopped Flow Measurements of $t_{pol}$

```
Template A1 sequence:
                                      (SEQ ID NO: 24)
AF546-5'-CGTTCCACGCCCGCTCCTTTGCAAC-3'

Template T1 sequence:
                                      (SEQ ID NO: 25)
AF546-5'-CGAACCTCGCCCGCTCCTTTGCAAC-3'

Template C1 sequence:
                                      (SEQ ID NO: 26)
AF546-5'-CGTTAACCGCCCGCTCCTTTGCAAC-3'

Template G1 sequence:
                                      (SEQ ID NO; 27)
AF546-5'-CGTTAAGCGCCCGCTCCTTTGCAAC-3'

Primer sequence:
                                      (SEQ ID NO: 28)
5'-GTTGCAAAGGAGCGGGCG-3'
```

The kinetics of nucleotide incorporation by recombinant phi 29 (exo-) (HP-1) and RB69 (exo-) (see section 4 below) DNA polymerases were measured in an Applied Photophysics SX20 stopped-flow spectrometer by monitoring changes in fluorescence from ALEXA FLUOR 546-labeled primer/template duplex following the mixing of the enzyme-DNA complex with dye-labeled nucleotides in the reaction buffer containing 50 mM Tris-HCl, pH 7.5, 50 mM NaCl, 4 mM DTT, 0.2% BSA, and 2 mM $MnCl_2$ or 5 mM $CaCl_2$). The reactions included 330 nM recombinant DNA polymerase, 100 nM template/primer duplex, and 7 µM labeled nucleotides.

Figure 5A:
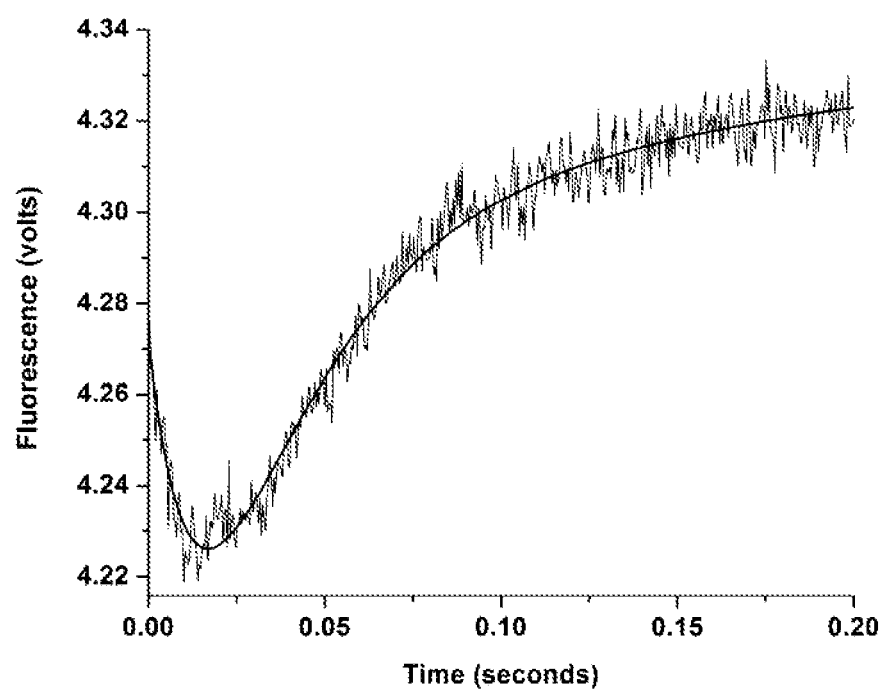
FIG. 5A shows a stopped-flow fluorescence trace ($t_{pol}$) for Phi29 (exo-) polymerase and terminal phosphate labeled dN4P nucleotides in the presence of manganese (Example 4).
Figure 5B:
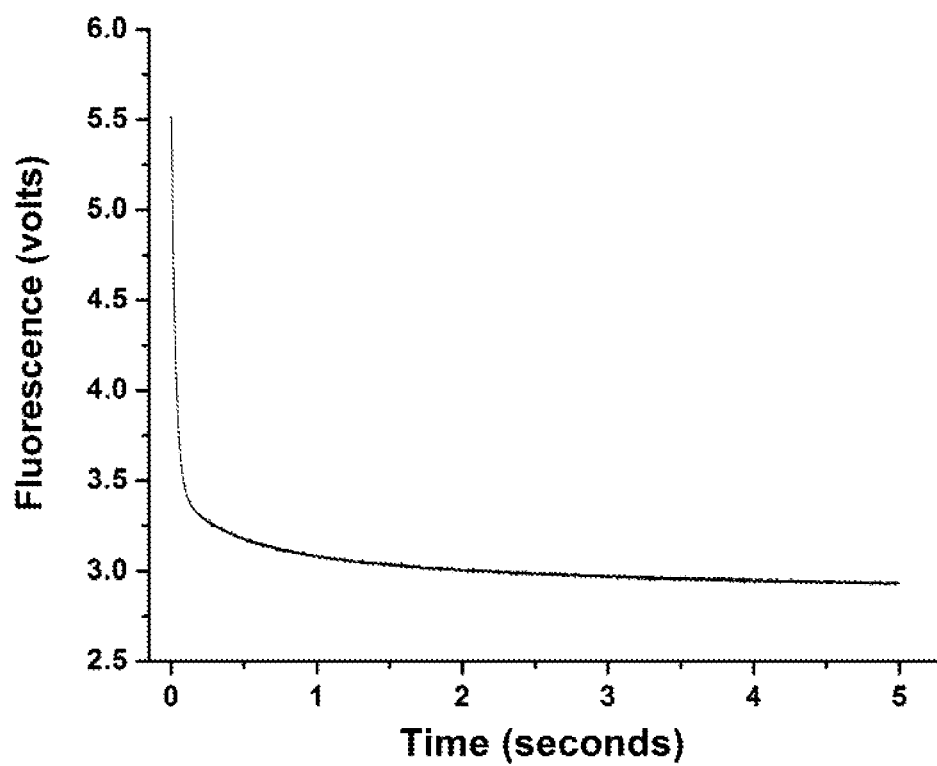
FIG. 5B shows a stopped-flow fluorescence trace ($t_{pol}$) for Phi29 (exo-) polymerase and terminal phosphate labeled dN4P nucleotides in the presence of calcium (Example 4).

The averaged (5 traces) stopped-flow fluorescence traces (>1.5 ms) were fitted with a double exponential equation (1) to extrapolate the rates of the nucleotide binding and product release, $$\text{Fluorescence} = A_1 * e^{-k1*t} + A_2 * e^{-kpol*t} + C \qquad \text{(equation 1)}$$

where $A_1$ and $A_2$ represent corresponding fluorescence amplitudes, C is an offset constant, and k1 and kpol are the observed rate constants for the fast and slow phases of the fluorescence transition, respectively. The dye-labeled nucleotides comprise terminal-phosphate-labeled nucleotides having an alkyl linker with a functional amine group attached to the dye. The stopped-flow techniques for measuring $t_{pol}$ ($1/k_{pol}$) followed the techniques described by MP Roettger (2008 Biochemistry 47:9718-9727; M. Bakhtina 2009 Biochemistry 48:3197-320). Representative stopped-flow fluorescence traces for Phi29 (exo-) polymerase and terminal phosphate labeled dN4P nucleotides in the presence of manganese are shown in FIG. 5A, or in the presence of calcium (FIG. 5B).

2) Phi 29 Polymerase: Stopped Flow Measurements of $t_{-1}$

```
Template A2 sequence:
                                            (SEQ ID NO: 29)
AF546-5'-CAGTCCAGGA GTT GGT TGG ACG GCT GCG

AGG C-3'

Template T2 sequence:
                                            (SEQ ID NO: 30)
AF546-5'-CAGTAATGGA GTT GGT TGG ACG GCT GCG

AGG C-3'

Template C2 sequence:
                                            (SEQ ID NO: 31)
AF546-5'-CAGTAACGG AGT TGG TTG GAC GGC TGC

GAG GC-3'

Template G2 sequence:
                                            (SEQ ID NO: 32)
AF546-5'-CAGTAAGGGA GTT GGT TGG ACG GCT GCG

AGG C-3'

Dideoxy-primer sequence:
                                            (SEQ ID NO: 33)
5'-GCC TCG CAG CCG TCC AAC CAA CTC ddC-3'

Primer sequence:
                                            (SEQ ID NO: 34)
5'-GCC TCG CAG CCG TCC AAC CAA CTC C-3'
```

The rate of the nucleotide dissociation ($k_{-1}$) from the ternary complex of [enzyme•DNA•nucleotide] was measured in an Applied Photophysics SX20 stopped-flow spectrometer by monitoring changes in fluorescence from ALEXAFLUOR546-labeled primer/template duplex following the mixing of the [enzyme•DNA•labeled nucleotide] ternary complex with:

(A) 50 µM cognate non-labeled deoxynucleoside triphosphate in a buffer containing 50 mM Tris-HCl (pH 7.5), 50 mM NaCl, 4 mM DTT, 0.2% BSA, and 2 mM MnCl₂, or (B) 50 µM cognate non-labeled deoxynucleoside triphosphate in a buffer containing 50 mM Tris-HCl (pH 7.5), 50 mM NaCl, 4 mM DTT, 0.2% BSA, and 5 mM CaCl₂) (for Phi29 (exo-) (HP-1) polymerase) or 10 mM CaCl₂) (for RB69 (exo-) polymerase).

The ternary complexes were prepared using: 330 nM polymerase (Phi29(exo-) or RB69), 100 nM template/primer duplex, and 7 µM terminal phosphate-labeled nucleotides.

Figure 5C:
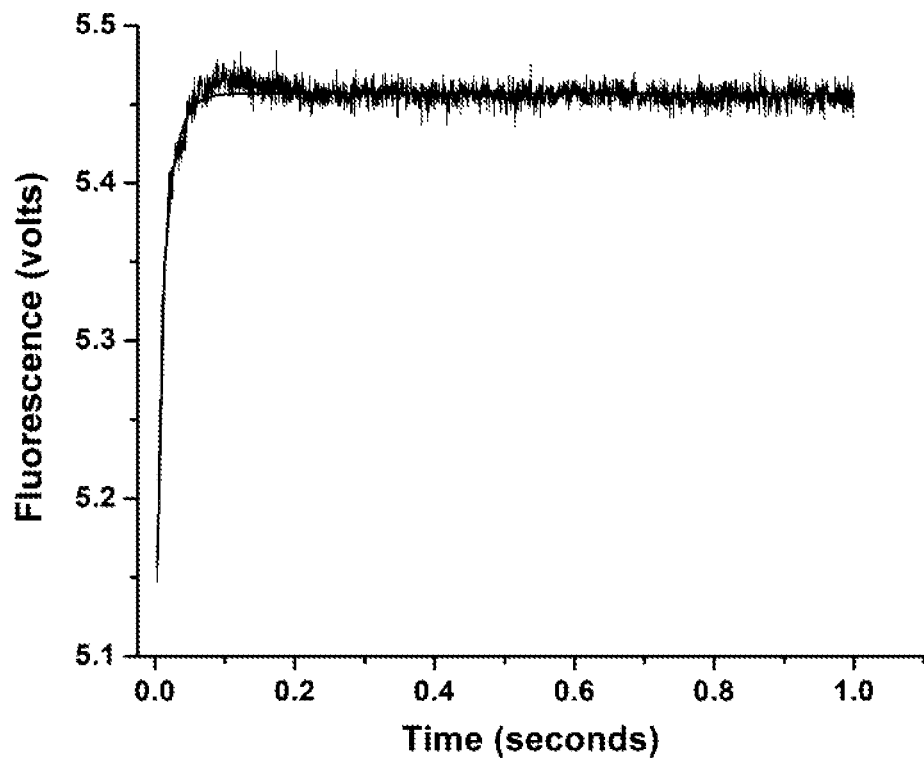
FIG. 5C shows a stopped-flow fluorescence trace ($t_{-1}$) for Phi29 (exo-) polymerase and terminal phosphate labeled dN4P nucleotides in the presence of manganese (Example 4).
Figure 5D:
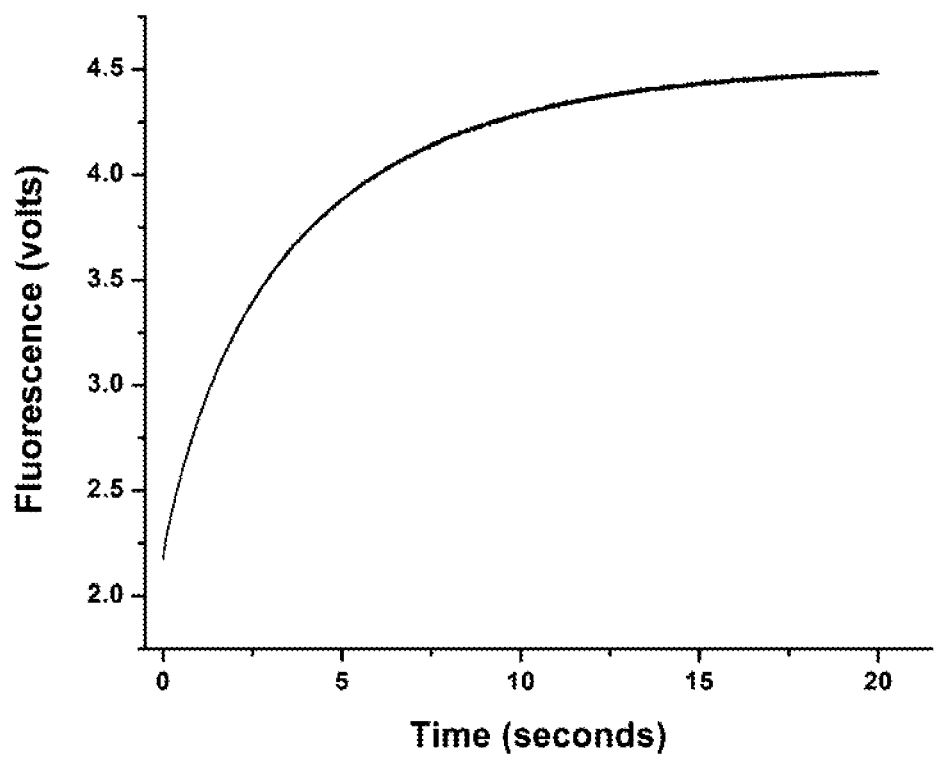
FIG. 5D shows a stopped-flow fluorescence trace ($t_{-1}$) for Phi29 (exo-) polymerase and terminal phosphate labeled dN4P nucleotides in the presence of calcium (Example 4).

The averaged stopped-flow fluorescence traces (>1.5 msec) were fitted with a single exponential equation (2) to extrapolate the rate of the nucleotide dissociation ($k_{-1}$) from the [enzyme•DNA•nucleotide] ternary complex.

$$\text{Fluorescence} = A_1 * e^{-k-1*t} + C \qquad \text{(equation 2)}$$

where $A_1$ represents the corresponding fluorescence amplitude, C is an offset constant, and $k_{-1}$ and the observed rate constants for the fluorescence transition. The stopped-flow techniques for measuring $t_{-1}$ ($1/k_{-1}$) followed the techniques described by M. Bakhtina (2009 Biochemistry 48:3197-3208). Representative stopped-flow fluorescence traces for Phi29 polymerase and terminal phosphate labeled dN4P nucleotides in the presence of manganese are shown in FIG. 5C or in the presence of calcium (FIG. 5D).

Figure 5E:
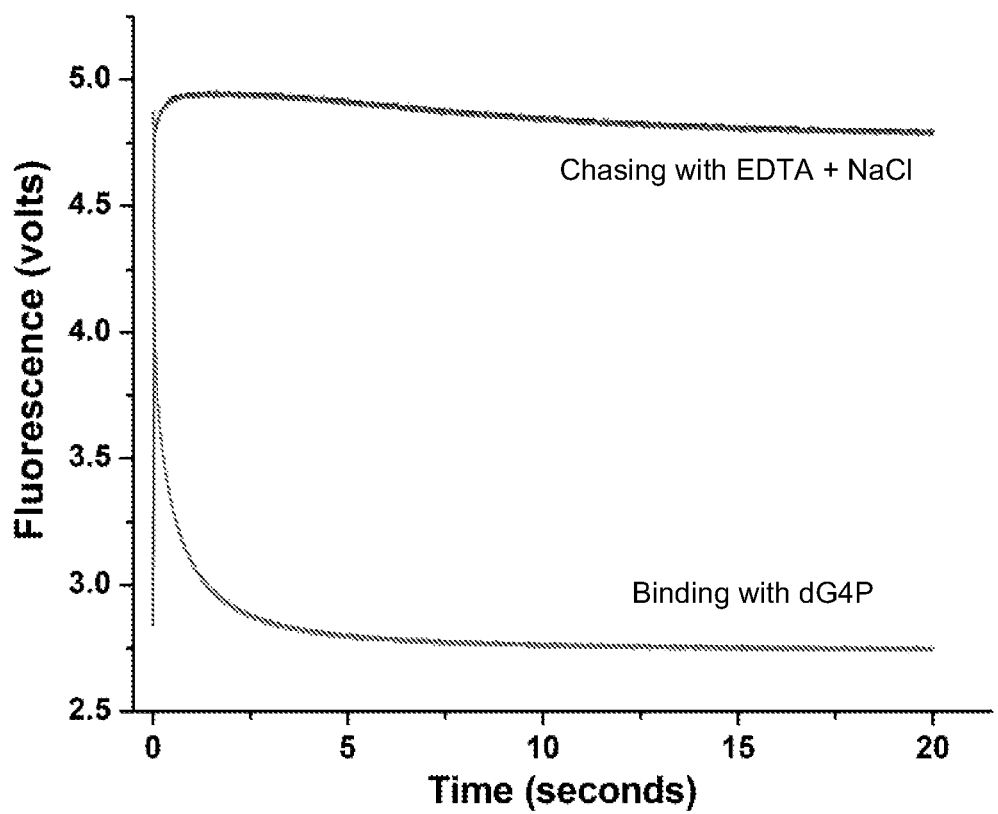
FIG. 5E shows stopped-flow fluorescence traces for Phi29 (exo-) polymerase and terminal phosphate labeled dN4P nucleotides in the presence of calcium (binding with dG4P) or manganese (chasing with EDTA+NaCl) (Example 4).

3) Phi29 Polymerase: Stopped-Flow Measurements For Characterizing Nucleotide Transient-Binding:

Stopped-flow procedures were conducted to characterize the $t_{pol}$ (using 7 µM terminal phosphate labeled dG4P-AF647 and calcium) and $t_{-1}$ rates (chased with 0.1 mM EDTA and 150 mM NaCl) of various polymerases. Representative stopped-flow fluorescence traces for Phi29 are shown in FIG. 5E. The results show that transient-binding of the nucleotide by Phi29 polymerase, in the presence of calcium, is reversible by chelating the calcium with the addition of EDTA.

Figure 5F:
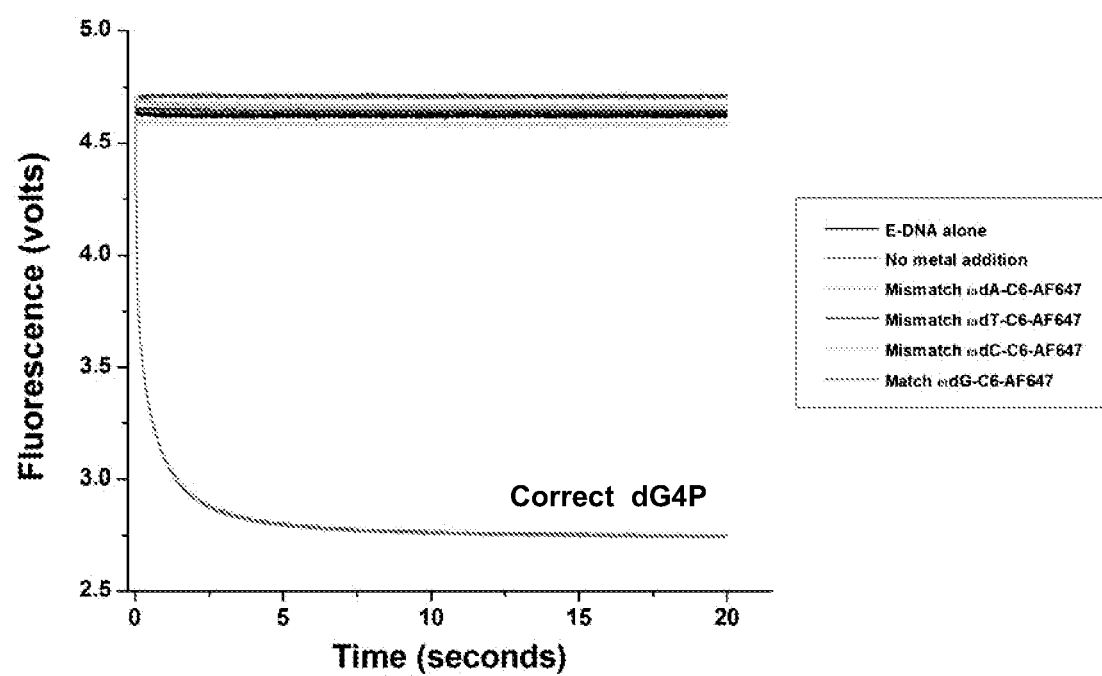
FIG. 5F shows stopped-flow fluorescence traces ($t_{pol}$) for Phi29 (exo-) polymerase, and correct and incorrect terminal phosphate labeled dN4P nucleotides, in the presence of calcium (Example 4).

Stopped flow procedures were conducted to characterize the selective binding of the correct nucleotides by various polymerases for transiently-binding in the presence of calcium. The primer/template duplexes were ALEXA FLUOR 546-labeled at the 5' end. A representative stopped-flow fluorescent trace for Phi29 (5 mM CaCl₂), FIG. 5F), reacted with one of four terminal phosphate labeled nucleotides (at 7 µM, labeled with AF647) is shown. The correct nucleotide is dG4P. The results show that Phi29 polymerase is selective in transient-binding the correct nucleotide, in the presence of calcium.

The apparent nucleotide dissociation constant ($K_d^{app}$) for the Phi29 DNA polymerase in the presence of 2 mM calcium was measured in the stopped-flow procedure. A representative stopped-flow fluorescent trace for Phi29 reacted with zero to 20 µM of the correct terminal phosphate labeled nucleotide (dG4P-AF647) is shown in FIG. 5G.

Figure 5G:
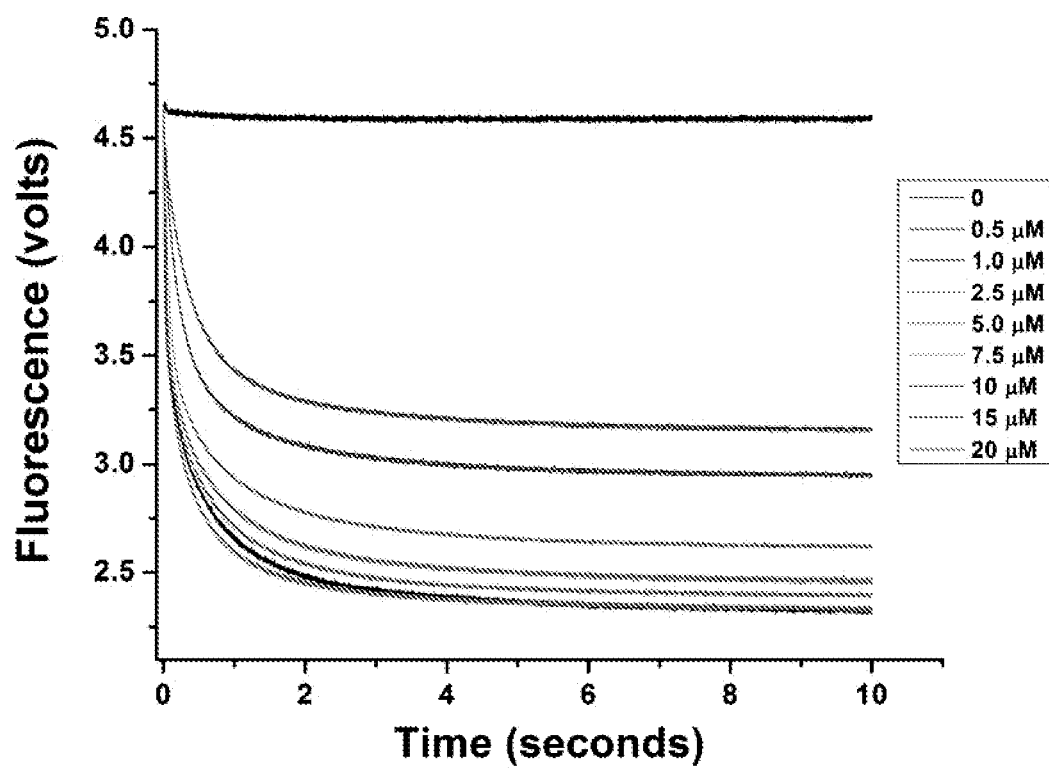
FIG. 5G shows stopped-flow fluorescence titration traces ($t_{pol}$) for Phi29 (exo-) polymerase and increasing amounts of the correct terminal phosphate labeled dN4P nucleotide in the presence of calcium (Example 4).

The averaged individual stopped-flow fluorescent trace (>1.5 msec) shown in FIG. 5G were fitted to a hyperbola equation 3 (H Zhang 2007 Nucleic Acids Research, pp. 1-11, doi:10.1093/nar/gkm587) to extrapolate the apparent nucleotide dissociation constant ($K_d^{app}$) for the Phi29 DNA polymerase.

$$\text{Fluorescence} = \frac{F_{max} \cdot [\text{nucleotide}]}{K_d^{app} + [\text{nucleotide}]} \qquad \text{(equation 3)}$$

where $F_{max}$ represents the maximum fluorescence change, [nucleotide] is the concentration of nucleotide in the reaction, and $K_d^{app}$ is the apparent nucleotide dissociation constant.

Figure 5H:
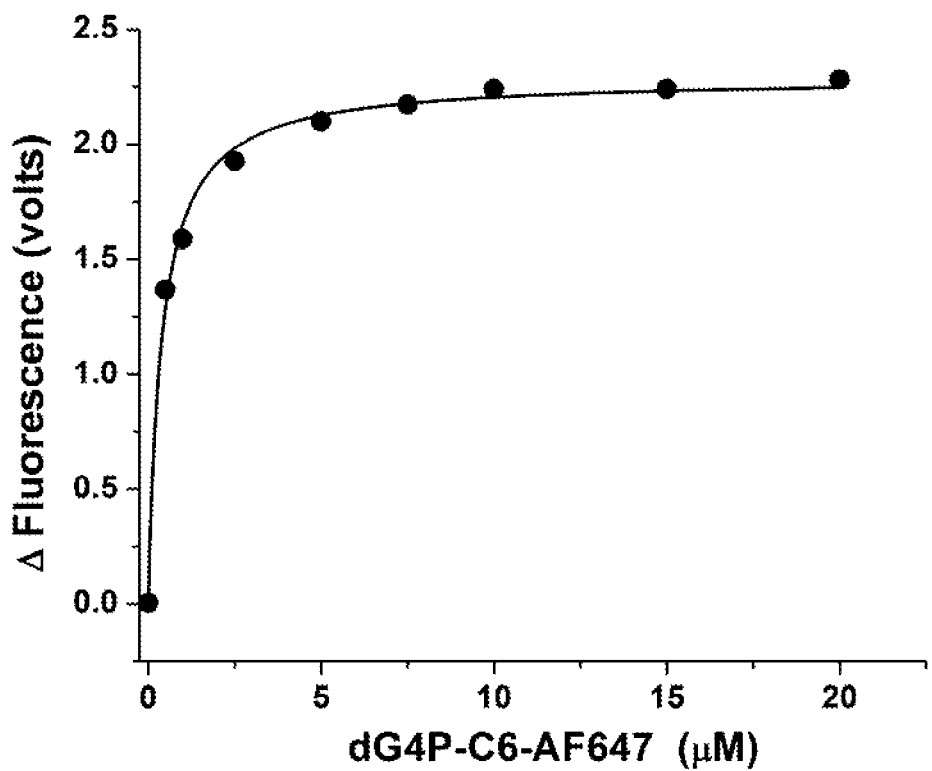
FIG. 5H shows data from FIG. 7E which is fitted to a hyperbola equation to extrapolate the apparent nucleotide dissociation constant ($k_d^{app}$) for Phi29 DNA polymerase (see Example 4).

The fitted data is shown in FIG. 5H. For Phi29 (exo-) polymerase, in the presence of 2 mM CaCl₂), the $K_d^{app}$ is about 0.38±0.03 µM.

4) RB69 Polymerase: Stopped Flow Measurements of $t_{pol}$

Figure 6A:
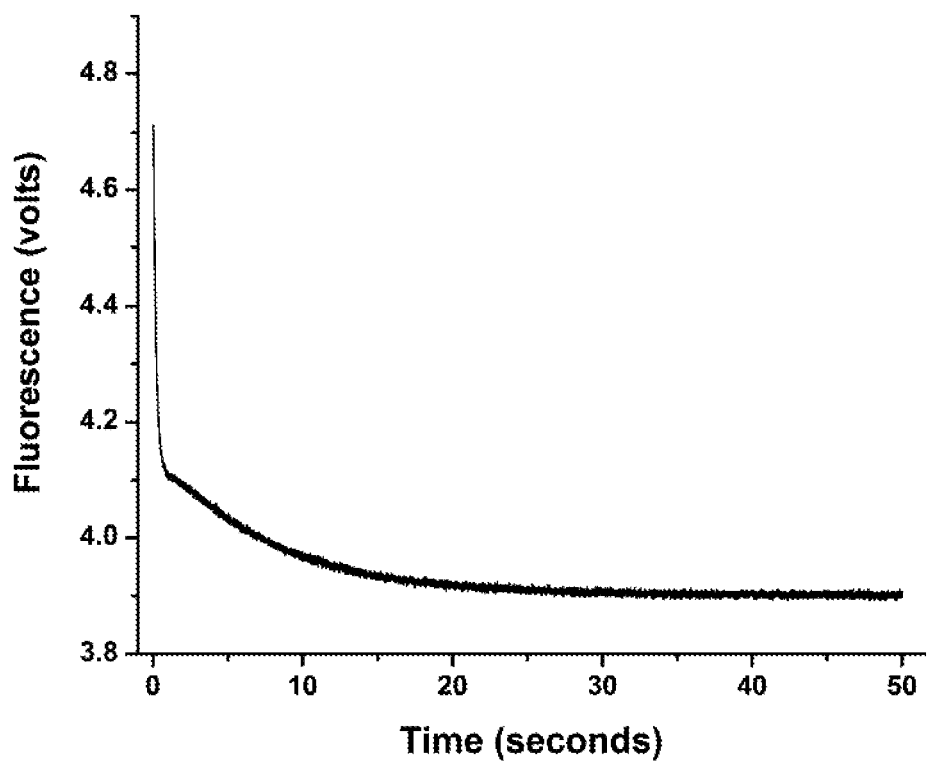
FIG. 6A shows a stopped-flow fluorescence trace ($t_{pol}$) for RB69 (exo-) polymerase and terminal phosphate labeled dN4P nucleotides in the presence of manganese (Example 4).
Figure 6B:
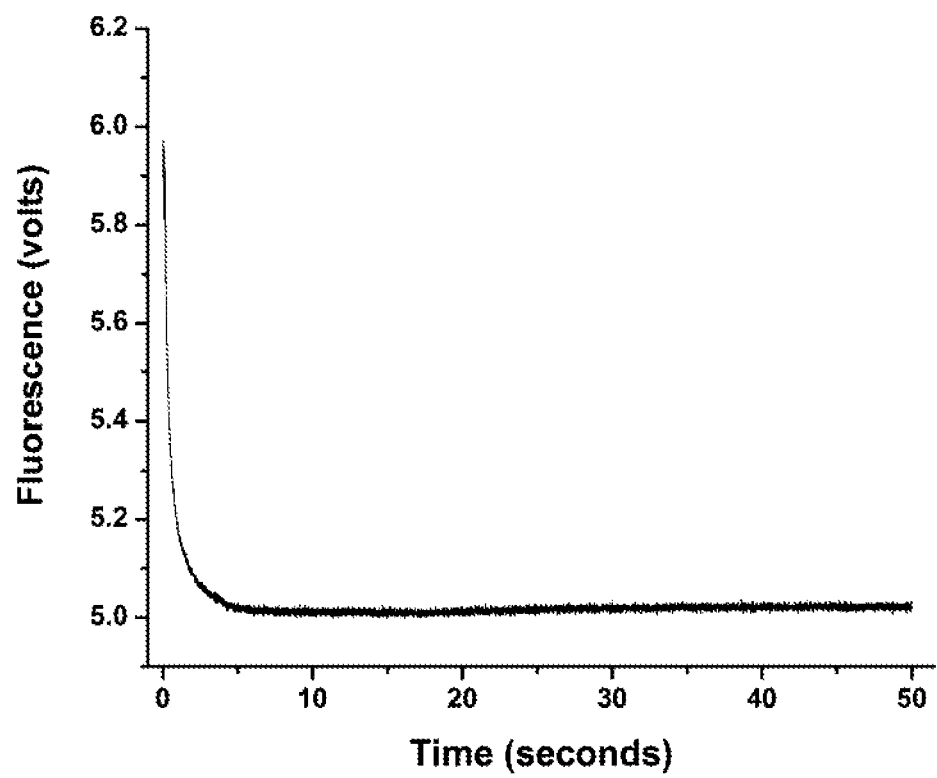
FIG. 6B shows a stopped-flow fluorescence trace ($t_{pol}$) for RB69 (exo-) polymerase and terminal phosphate labeled dN4P nucleotides in the presence of calcium (Example 4).

Stopped-flow measurements of $t_{pol}$ were conducted as described in the section above, using the A1, C1, T1 or G1 oligo-template sequences, and the same reaction conditions (see Example 4, section 1 above). Representative $t_{pol}$ stopped-flow fluorescence traces for RB69 polymerase in the presence of 2 mM manganese (FIG. 6A) or 10 mM calcium (FIG. 6B) are shown. The results show that RB69 polymerase binds the correct nucleotide but does not catalyze nucleotide incorporation in the presence of manganese (FIG. 6A).

5) RB69 Polymerase: Stopped Flow Measurements of $t_{-1}$

Figure 6C:
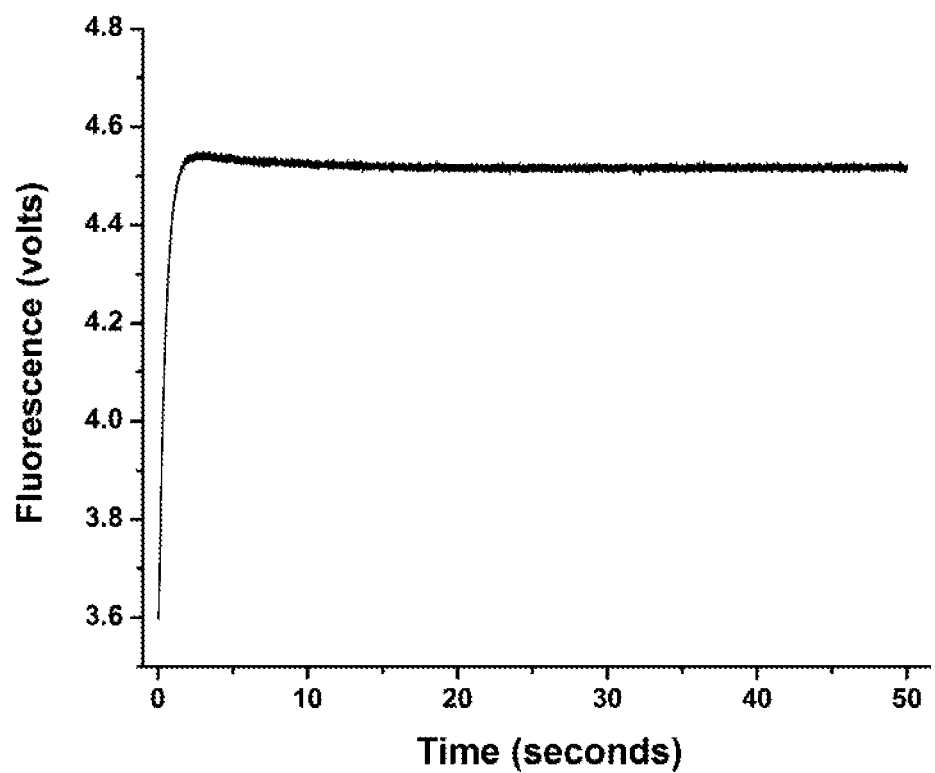
FIG. 6C shows a stopped-flow fluorescence trace ($t_{-1}$) for RB69 (exo-) polymerase and terminal phosphate labeled dN4P nucleotides in the presence of manganese (Example 4).
Figure 6D:
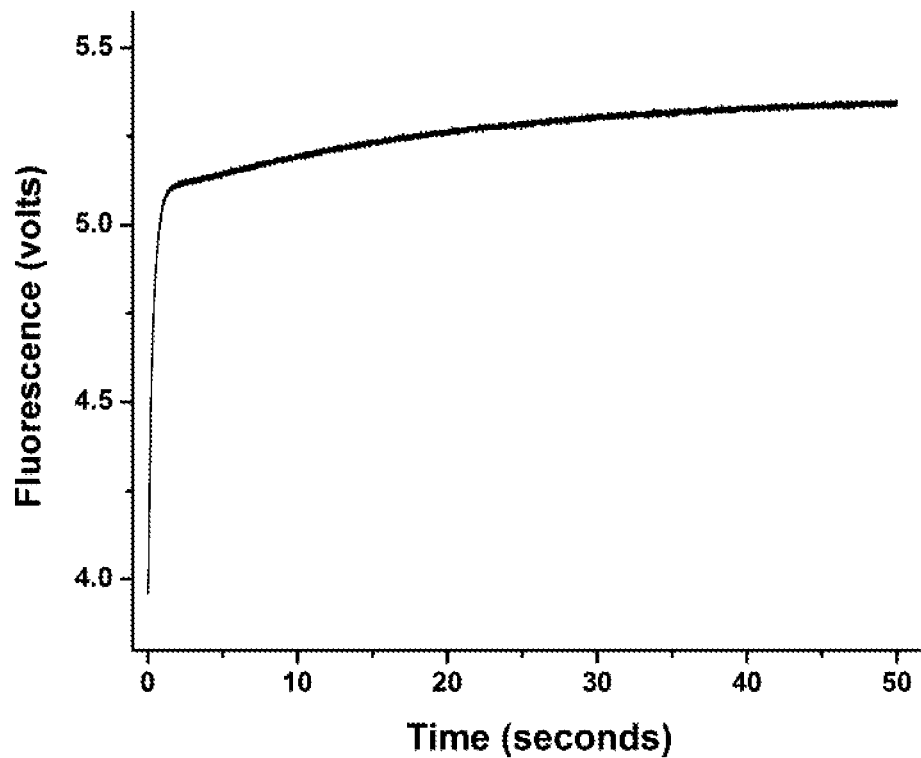
FIG. 6D shows a stopped-flow fluorescence trace ($t_{-1}$) for RB69 (exo-) polymerase and terminal phosphate labeled dN4P nucleotides in the presence of calcium (Example 4).

Stopped-flow measurements of $t_{-1}$ were conducted as described in the section above, using the A2, C2, T2, or G2 oligo-template sequences, and the same reaction conditions (see Example 4, section 2 above). Representative $t_{-1}$ stopped-flow fluorescence traces for RB69 polymerase in the presence of manganese (2 mM, FIG. 6C) or calcium (10 mM, FIG. 6D) are shown.

Figure 6E:
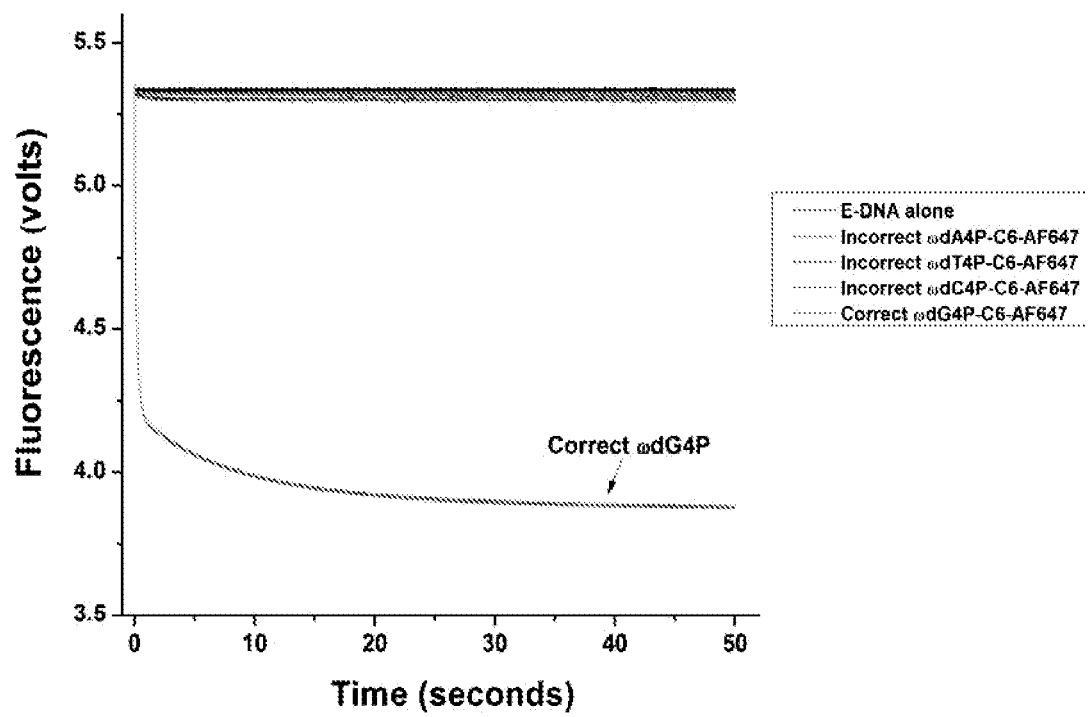
FIG. 6E shows stopped-flow fluorescence traces ($t_{pol}$) for RB69 (exo-) polymerase, and correct and incorrect terminal phosphate labeled dN4P nucleotides, in the presence of calcium (Example 4).

6) RB69 Polymerase: Stopped-Flow Measurements for Characterizing Nucleotide Transient-Binding:

Stopped flow procedures were conducted to characterize the selective binding of the correct nucleotides by RB69 polymerase for transiently-binding in the presence of calcium, as described above using the primer/template duplexes which were ALEXA FLUOR 546-labeled at the 5' end (see Example 4, section 3 above). A representative stopped-flow fluorescent trace for RB69 polymerase (10 mM CaCl$_2$, FIG. 6E), reacted with one of four terminal phosphate labeled nucleotides (at 7 μM, labeled with AF647) is shown. The correct nucleotide is dG4P. The results show that RB69 polymerase is selective in transient-binding the correct nucleotide, in the presence of calcium.

Example 5

Extension Efficiency in the Presence of Calcium:
1) Relative Polymerase Activity:

```
28-mer Template sequence:
                                    (SEQ ID NO: 35)
5'-CGTTAGTAACCGCCCGCTCCTTTGCAAC-3'

18-mer Primer sequence:
                                    (SEQ ID NO: 36)
AF546-5'-GTTGCAAAGGAGCGGGCG-3'
```

Figure 7A:
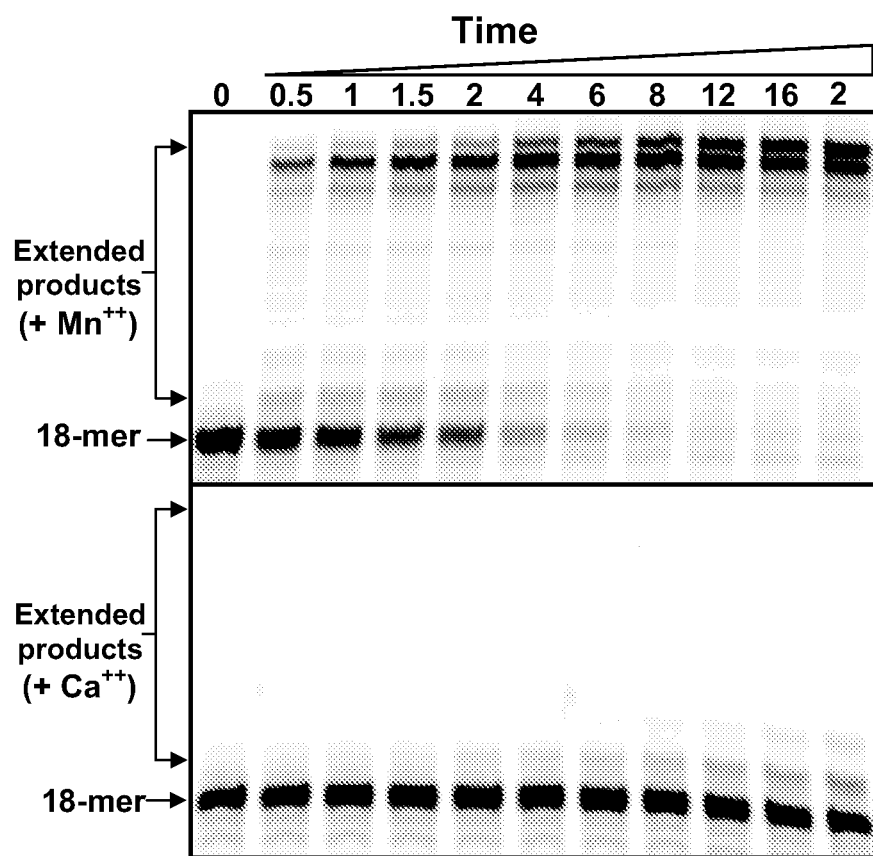
FIG. 7A shows a gel image of primer extension products for Phi29 polymerase in the presence of manganese or calcium (Example 5).
Figure 7B:
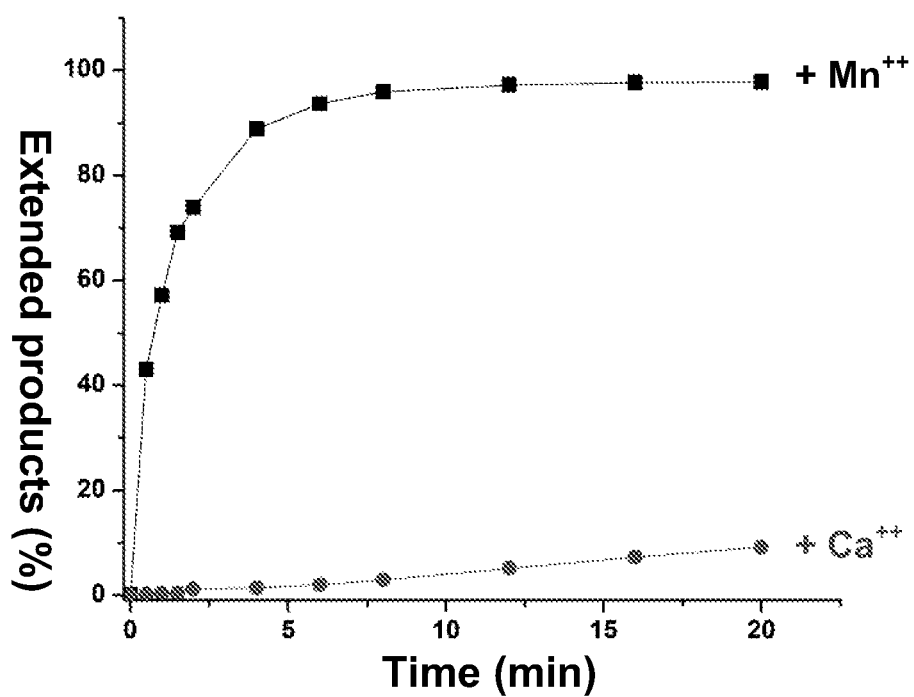
FIG. 7B shows kinetic data derived from the primer extension results shown in FIG. 7A (Example 5).

The kinetics of nucleotide incorporation by recombinant phi29 DNA (exo-) (i.e., HP-1) polymerase was analyzed in a primer-extension reaction. The reaction was initiated by adding 10 μM dNTPs to the reaction mixture (10 μL reaction) containing 300 nM phi29 DNA polymerase, 100 nM of dye-labeled duplex primer/template DNA (18-mer primer was labeled at the 5' end with ALEXAFLUOR 546, and was based-paired with a 28-mer template), 50 mM Tris-HCl (pH 7.5), 50 mM NaCl, 4 mM DTT, 0.2% BSA, and 2 mM MnCl$_2$ or CaCl$_2$). An aliquot of the reaction mixture was sampled at different time points (from 0 to 20 minutes), and the reactions were quenched by addition of 15 μL of stop solution containing 0.05% bromophenol blue, 95% de-ionized formamide, and 30 mM EDTA (pH 8.0). The reaction mixtures were heated to 95° C. for 5 minutes and the reaction products were analyzed via 20%7 M urea-polyacrylamide gel electrophoresis. The gel image was obtained by scanning using a Typhoo 8000 gel imager (GE Healthcare). The image was processed using ImageQuant software (GE Healthcare). The gel image is shown in FIG. 7A, and the kinetics data is shown in FIG. 7B.

2) Gel Analysis of Extension Products:

```
Template sequences:
1:
                                    (SEQ ID NO: 37)
3' CCATGATTCGCCGGCGTACccccccc 2:
                                    (SEQ ID NO: 38)
3' CCATGATTCGCCGGCGTACaaaaaaa 3:
                                    (SEQ ID NO: 39)
3' CCATGATTCGCCGGCGTACttttttt 4:
                                    (SEQ ID NO: 40)
3' CCATGATTCGCCGGCGTACggggggg Primer sequence:
                                    (SEQ ID NO: 41)
Fluoroscene-5' GGTACTAAGCGGCCGCATG 3'
```

The primer extension reaction included: 50 mM Tris (pH 7); 1 mM MnCl$_2$; 50 mM NaCl; 0.5% BSA; 100 nM 5' fluoroscene-labeled primer:template duplex; and 330 nM of Phi29, or RB69(exo-). The reactions were initiated by addition of 1.0 μM of either terminal-phosphate-labeled dNTP or dGTP and quenched at the time-points 10 seconds and 1 minute with 30 mM EDTA. The labeled nucleotides include an intervening linker and a fluorophore attached to the terminal phosphate group: dG6P is linked to DY634; dG4P is linked to DY634; dC4P is linked to AF660; dA4P is linked to AF660; and dT4P is linked to AF660.

Figure 8:
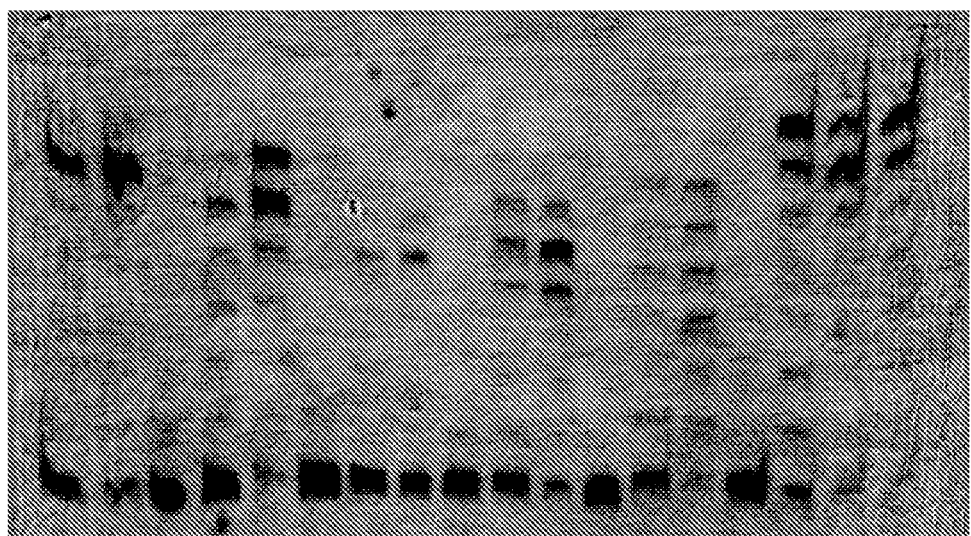
FIG. 8 shows a gel image of primer extension products for RB69 polymerase in the presence of manganese (Example 5).

The reactions were separated on a 20% denaturing acrylamide gel and imaged on the Bio-Rad Molecular Imager FX. The results were analyzed using Bio-Rad Quantity One software. The gel image (1 minute) is shown in FIG. 8. Various polymerases are shown: phi29 polymerase in lanes 1, 4, 7, 10, 13, and 16; B103 polymerase in lanes 2, 5, 8, 11, 14, and 17; RB69 polymerase in lanes 3, 6, 9, 12, 15, and 18. Various nucleotides are shown: dG6P labeled with DY634 is in lane 1-3; dG4P labeled with DY634 is in lanes 4-6; dC4P labeled with AF660 is in lanes 7-9; dA4P labeled with AF660 is in lanes 10-12; dT4P labeled with AF660 is in lanes 13-15; and unlabeled dGTP is in lanes 16-18.

Example 6

Calcium Titration:
1) Conjugating Nanoparticles and Template Molecules:

The PEG-ylated nanoparticles were functionalized with EDC (1-ethyl-3-(3-dimethylaminopropyl) carbodiimide) as follows. The nanoparticles, stored in betaine, were buffer exchanged 3-4 times in 25 mM borate buffer (pH 8.3) by ultrafiltration. The nanoparticles were purified on a NAP5 column (GE Healthcare Life Sciences, 17-0853-02) with 25 mM borate buffer (pH 8.3). The nanoparticles (150 μL of 4 μM) were mixed with 74 μL of 300 mM adipic acid hydrazide (in water to a final concentration of 50 mM hydrazide) (Sigma, A0638), and 225 μL of 500 mM MES (pH 5) (Sigma, M2933-50G). EDC (4.5 mg) was added directly to the nanoparticle/hydrazide solution, and vortexed briefly. The reaction was allowed to proceed for 1 hour at room temperature. The nanoparticles were purified on a NAP5 column with 50 mM MES (pH5.5), and concentrated to less than 50 μL using a Vivaspin 500 spin column (50 k MWCO, Sartorius Stedim). The concentrated nanoparticles were purified on a NAP-5 column with 50 μL of 50 mM MES (pH5.5).

```
Sequence: hairpin oligonucleotide:
                                      (SEQ ID NO: 42)
5'-YTTTTTTAGTCTGGGTGACAGGTTXTTCCTGTCACCC-3'
Where X = biotin TEG,
      Y = amino modifier C6 linker
```

The amine-modified hairpin oligonucleotide were activated by mixing 30 μL of 500 mM oligonucleotide with 20 μL of 1 M bicarbonate (ph ~ 7.5), and 20 μL of 20 mM SFB (succinimidyl-p-formyl benzoate, Molecular Biosciences) in DMSO, and vortexed briefly. The reaction proceeded for 1 hour at room temperature. The sample was purified on a NAP5 column (SEC 3000 MWCO) equilibrated with water.

The functionalized nanoparticles and activated oligonucleotides were conjugated by mixing 50 μL of 4.2 μM nanoparticles, 100 μL of 55 μM oligonucleotides, 50 μL of 500 mM MES (pH 5.5), and gently pipetting to mix, and quickly vortexed. The reaction proceeded for 1 hour at room temperature.

The conjugation reaction was verified by gel electrophoresis on a 0.8% agarose E-gel (Invitrogen, G5018-08). The verified conjugates nanoparticles/oligonucleotides were purified on a Superdex 200 column (VWR-95017-070) equilibrated with 1×PBS (pH 7.4). The conjugates were concentrated to about 50 μL using a spin column.

The nanoparticle/oligonucleotide conjugates (25 pM) were immobilized on biotin-embedded, PEG-coated glass slides purchased from MicroSurfaces, Inc. (Bio-01 PEG, Austin, TX) using 100 pM streptavidin.

2) Transient-Binding Reactions:

The nucleotide transient-binding reactions included the immobilized conjugates (nanoparticles/oligonucleotides) reacted with: 50 mM Tris (pH 7.5), 50 mM NaCl, 0.2% BSA, 2 mM Asp4 (asp-asp-asp-asp), 100 μg/ml glucose oxidase, 2 U/μL catalase, 0.4% glucose, 2 mM Trolox, and a range of $CaCl_2$ from 0 to 20 mM, 150 nM Phi29 polymerase (HP1), and either the correct base (200 nM of AF647-terminal phosphate labeled dA4 P) or the incorrect base (200 nM of AF647-terminal phosphate labeled dG4P). The reactions were excited at 405 nm, at 45 μW at the objective, for 33 msec exposure, and 2 minute movies were obtained.

Figure 9A:
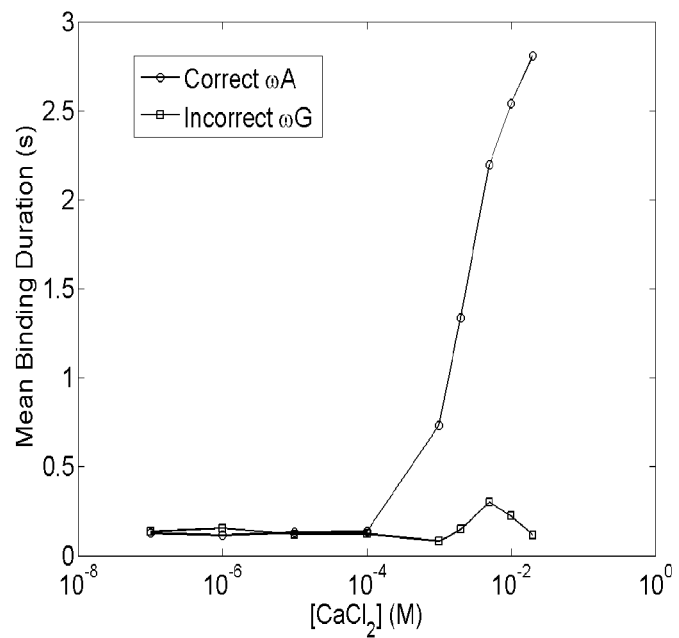
FIG. 9A shows the mean binding duration of the correct and incorrect nucleotides for Phi29 polymerase in the presence of increasing amounts of calcium (Example 6).
Figure 9B:
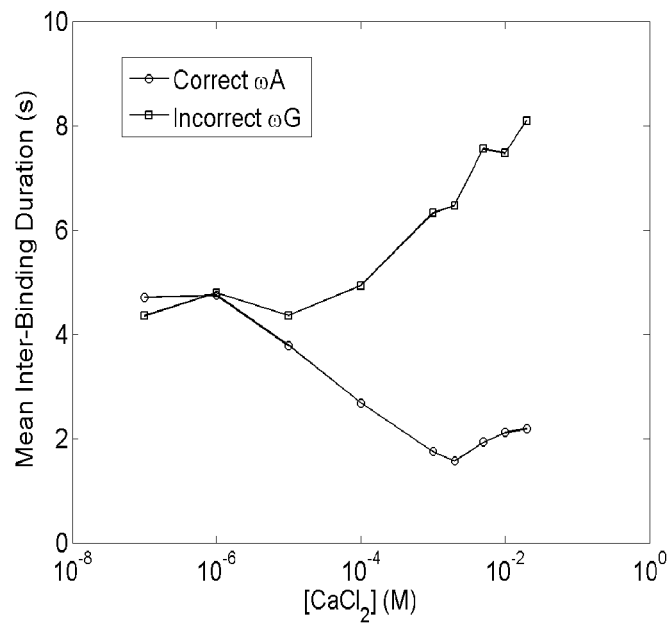
FIG. 9B shows the mean inter-binding duration of the correct and incorrect nucleotides for Phi29 polymerase in the presence of increasing amounts of calcium (Example 6).

FIG. 9A shows $1/k_{on}$ and FIG. 9B shows $1/k_{-1}$. The results show that with increasing calcium concentrations, the duration of binding of the correct nucleotide (○, open circles) increases compared to that of the incorrect nucleotide (□, open squares).

Example 7

6-Base Extension, 2-Color Sequencing, in the Presence of Calcium:

```
Template sequence:
                                      (SEQ ID NO: 43)
5'-TGACTGACTGACTGAGCATAATGCCTGCGTCATCCGCCAGC-3'-
biotin Primer sequence:
                                      (SEQ ID NO: 44)
5'-GCTGGCGGATGACGCAGGYATTATGC-3'
where "Y" is dC with C6 linker and an amine group.
``` where "Y" is dC with C6 linker and an amine group.

Base Reading Mix: 50 mM Tris HCl (pH 7.5); 50 mM NaCl; 2.5 mM $CaCl_2$); 0.2% BSA; 80 μg/mL glucose oxidase; 2000 U/mL Katalase; 1 mM Trolox; 0.5% glucose; 500 nM terminal-phosphate labeled dN4P; and 250 nM Phi29 (exo-) polymerase (D169A mutant).

Terminal Phosphate-Labeled Nucleotides: dT4P-AF647; dC4P-AF680; dA4P-AF647; dG4P-AF680.

Wash Buffer: 200 μL Stop Buffer with EDTA and high salt; 200 μL Universal Buffer with 0.04% Tween-20.

Cold Nucleotide Extension Mix: 50 mM Tris HCl (pH7.5); 50 mM NaCl; 10 mM $MgCl_2$; 0.2% BSA; 80 μg/mL glucose oxidase; 2000 U/mL Katalase; 1 mM Trolox; 0.5% glucose; 1 μM cold-dNTP; 500 nM Phi29 (exo-) polymerase.

End Point Mix: Cold Nucleotide Extension Mix, substituting the cold-dNTP with 10 μM base-labeled nucleotide (AF5-dCTP).

The primer was conjugated to commercial nanoparticles (605 ITK SAV quantum dots, Invitrogen, catalog #Q10001MP). The inner amphiphilic polymer coating of the nanoparticles was linked to the primer using a heterobifunctional cross-linking chemistry via C6 amine linker at the Y location (dC).

The primers (conjugated to the nanoparticles) were incubated with 20 fold excess of template molecules at 1 μM concentration in 50 mM Tris-HCl (pH 7.5) and 150 mM NaCl for 2 hours at room temperature.

The nanoparticle/primer/template conjugate was purified from excess template by ultra centrifugation. The conjugate was immobilized onto a low density neutravidin surface at 500 pM in universal buffer for 30 minutes. The low neutravidin surface was produced by immobilizing the neutravidin onto a commercial PEG/PEG-biotin coated glass coverslip at 250 pM for 30 seconds.

The correct nucleotide extension sequence was: TCAGTC.

The transient-binding/sequencing reaction steps included the following steps (all steps were conducted with the glass surface/chip on the microscope stage and at room temperature): (1) the transient-binding reaction was conducted using the Base Reading Mix which contained the correct nucleotide (e.g., dT4P-AF647 for the reading the first base) in the presence of calcium, for 2 minutes; (2) the wash step was conducted using a Wash Buffer; (3) the primer extension steps was conducted using the Cold Nucleotide extension mix which contained the correct nucleotide (e.g., dT4P for the first base extension) for 30 seconds; (4) the wash step was conducted using the Wash Buffer; (5) steps 1~4 were repeated to transient-bind/read and extend the second (C), third (A), fourth (G), fifth (T), and sixth (C) nucleotides in the sequence; (6) the end-point reaction was conducted using the End Point Mix which contained the correct base-labeled nucleotide (e.g., AF5-dCTP for incorporation of the sixth nucleotide) for 30 seconds.

Figure 10A:
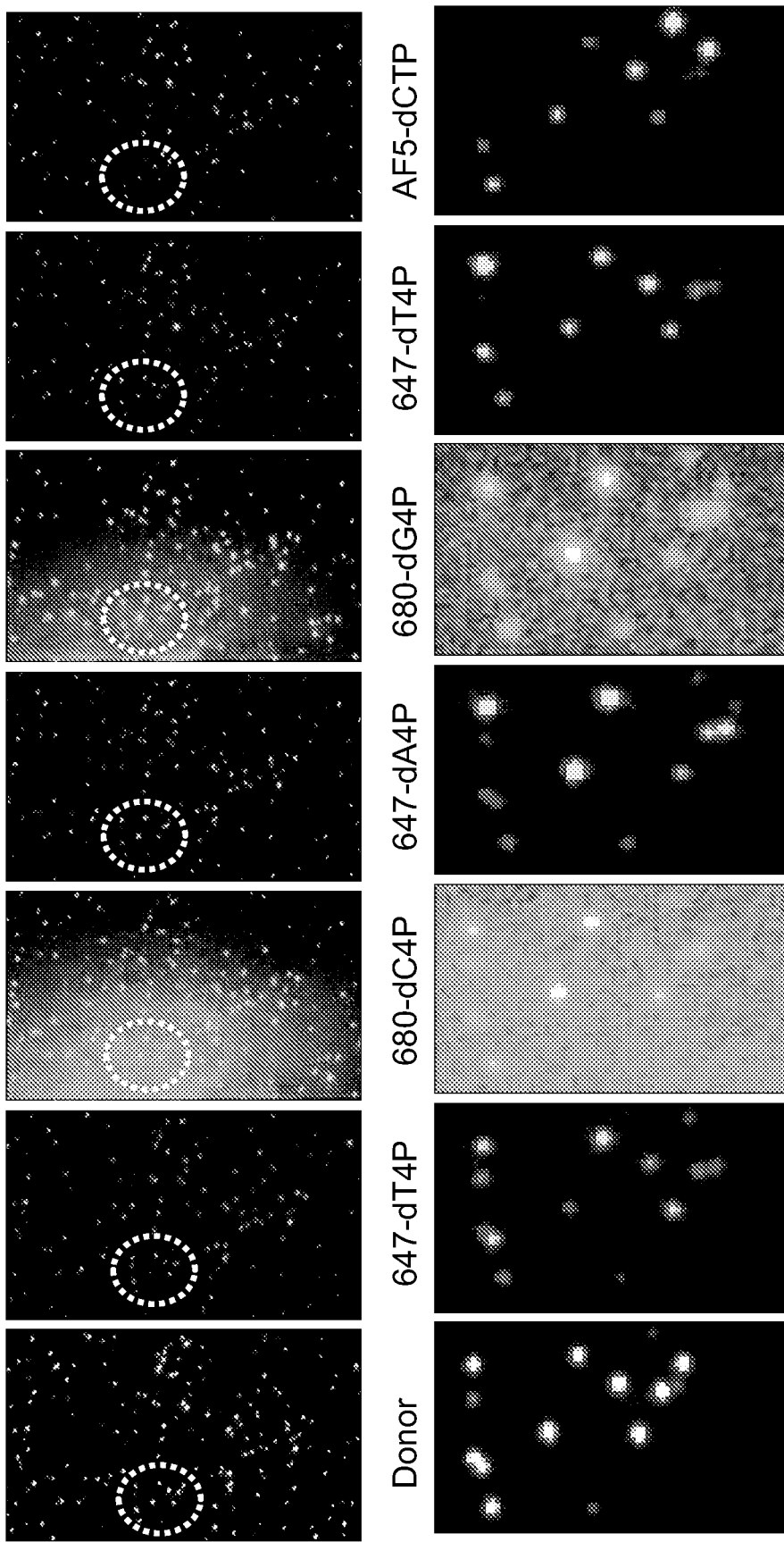
FIG. 10A shows 6-base primer extension from transient-binding reactions using Phi29-nanoparticle conjugates and labeled dN4P nucleotides in the presence of calcium (Example 7).

The images were acquired in a tri-view microscope, which images the same field of view at three different spectral windows (defined with bandpass filters) simultaneously. The tri-view microscope consists of three image channels: a donor channel for detecting signals from nanoparticles with emission maximum at 605 nm (e.g., a FRET donor) and two acceptor channels for detecting fluorescence signals from AF-647 and AF-680 dye labeled nucleotides. The donor molecule were excited at 405 nm and detected in the donor channel. The acceptor molecules were detected in their appropriate acceptor channels. The donor image was acquired at excitation power density of 2.5 W/cm² prior base-reading and extension reactions. The acceptor images were acquired at the excitation power density of 7 W/cm² during their transient binding (base-reading) steps. The images are shown in FIG. 10A, with the same field of view circled for a visual aid.

Figure 10B:
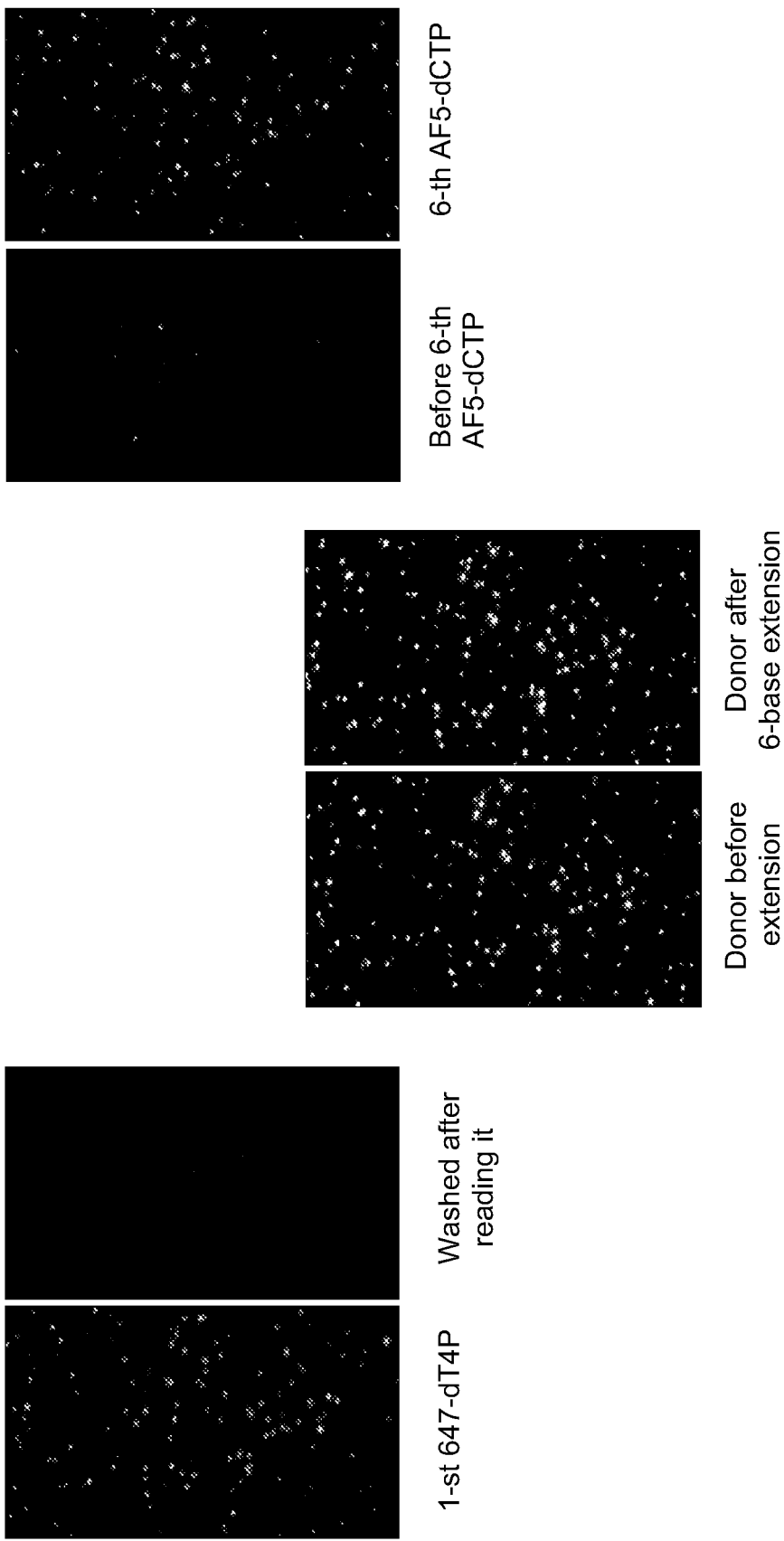
FIG. 10B shows control reactions for the 6-base primer extension reactions shown in FIG. 10A (Example 7).

Control reactions: the donor signals were imaged prior to the first transient-binding reaction and again after the sixth base extension reaction (FIG. 10B); the acceptor signals were imaged after the first transient-binding step (dT4P-AF647) and again after the washing step (FIG. 10B); and the acceptor signals were imaged prior to the end-point reaction step (AF5-dCTP) and again after the end-point reaction step (FIG. 10B).

Figure 10C:
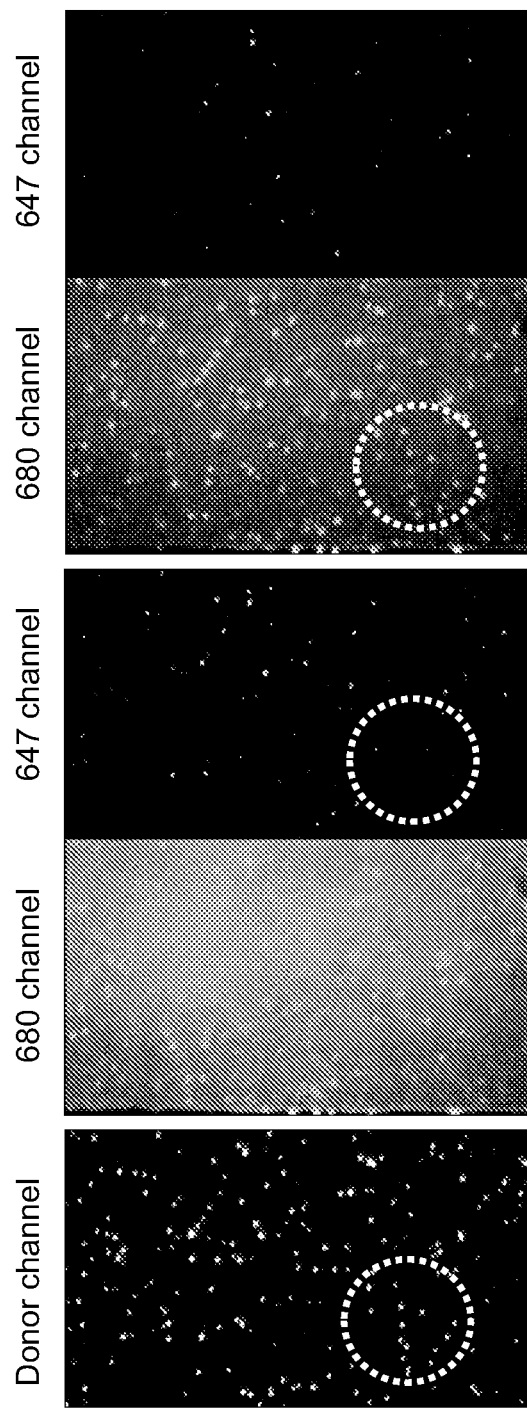
FIG. 10C shows additional control reactions for the 6-base primer extension reactions shown in Figure. 10A (Example 7).

In a separate control experiment, all 4 dye-labeled nucleotides were present during the transient-binding steps. All the reagents and protocols were the same as described above (Example 8 herein), except the Base Reading Mix contained the correct nucleotides labeled with one dye and the other three nucleotides labeled with another dye. For example, for reading the first nucleotide, dT4P-AF-647 was used and other three nucleotides (dA4P, dG4P, and dC4P) were labeled with AF-680. For reading the second nucleotide, dC4P-AF-680 was used and the other three nucleotides (dA4P, dG4P, and dT4P) were labeled with AF647. The results are shown in FIG. 10C.

Example 8

Transient-Binding with Non-Hydrolyzable Nucleotides:

```
Hairpin template sequence:
                              (SEQ ID NO: 45)
5'-TTTTTTAGTCTGGGTGACAGGTTXTTCCTGTCACCC-3'
```

Where "X" is biotin

Base Reading Mix: 50 mM Tris (pH 7.5), 50 mM NaCl, 5 mM $CaCl_2$), 0.2% BSA, 80 μg/mL glucose oxidase; 2000 U/mL Katalase; 1 mM Trolox; 0.5% glucose; 250 nM Phi29 (exo-) (D169A mutant), 500 nM non-hydrolyzable nucleotide (AF647-C6 alkyl linker-alpha-thio-dA4P nucleotide analog, labeled at the terminal phosphate with ALEXA FLUOR 647).

Cold Nucleotide Extension Mix: 50 mM Tris (pH 7.5), 50 mM NaCl, 10 mM $MgCl_2$, 0.2% BSA, 80 μg/mL glucose oxidase; 2000 U/mL Katalase; 1 mM Trolox; 0.5% glucose; 2 μM unlabeled-dNTP, 500 nM Phi29 (exo-).

Wash Buffer: 200 μL Stop Buffer with EDTA and high salt; and 200 μL universal buffer with 0.04% Tween-20.

Stop buffer: 50 mM Tris-HCl (pH 7.5); 10 mM EDTA; 100 mM NaCl; 0.2% BSA.

Universal Buffer with Tween-20: 50 mM Tris-HCl (pH 7.5); 50 mM NaCl; 0.2% BSA; 0.04% Tween-20.

Commercial nanoparticles (605 ITK SAV quantum dots, Invitrogen, catalog #Q10001MP) were immobilized onto PEG/PEG-biotin coverslip surfaces at 5 pM for 4 minutes. The surface-immobilized nanoparticles were saturated with hairpin molecules via the biotin in the loop.

All the transient-binding and extension steps as well as the protocols and the imaging conditions were identical to the ones described in Example 8 above (6-Base Extension, 2-Color Sequencing, in the Presence of Calcium). In this experiment only one non-hydrolyzable-AF647-dA4P were used in all transient-binding steps.

The correct nucleotide extension sequence was: AGA

Figure 11:
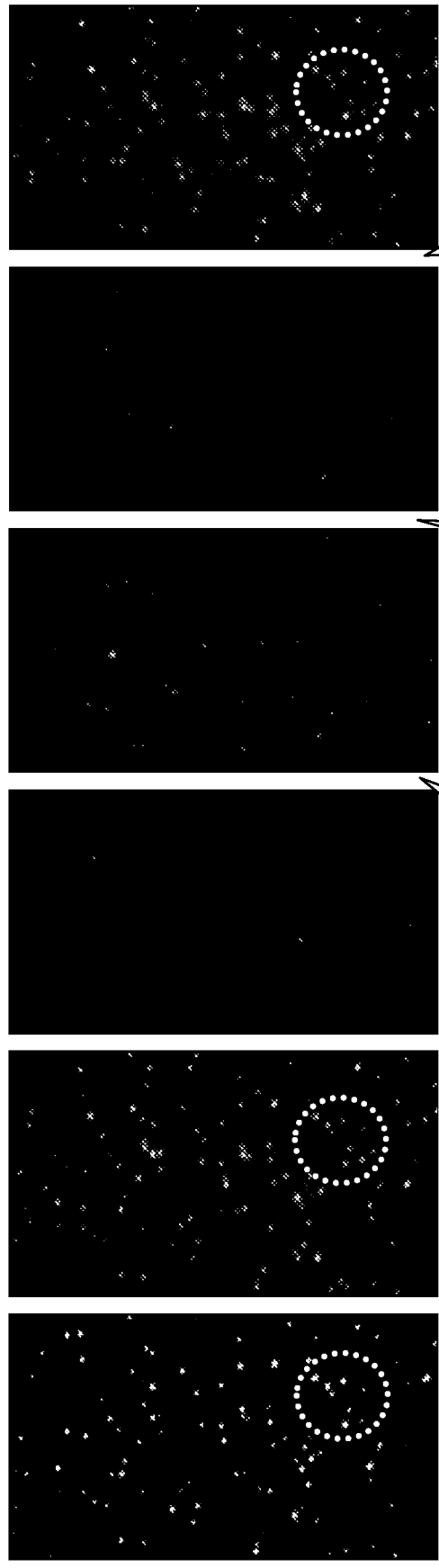
FIG. 11 shows transient binding reactions using Phi29 polymerase and non-incorporatable nucleotides in the presence of calcium (Example 8).

The transient-binding reaction steps, using labeled non-hydrolyzable nucleotides steps, were conducted at room temperature and included:

1. The transient-binding reaction was conducted using the Base Reading Mix which contained the correct nucleotide (non-hydrolyzable alpha-thio-dA4P-AF647) in the presence of calcium was conducted for 2 minutes (see FIG. 11, "Donor" image provides a point of reference since all images shown are the same field of view; "$1^{st}$ A correct" shows the first transient-binding reaction step;

2. The same field of view was imaged after washing with Wash Buffer (see FIG. 11, "After washing the $1^{st}$ A");

3. The primer was extended by one base using the Cold Nucleotide Extension Mix containing unlabeled dATP, followed by another transient-binding reaction using non-hydrolyzable dATP (described in step (1) above, the correct base is G) (see FIG. 11, "$2^{nd}$ G incorrect";

4. The reaction was washed with Wash Buffer, followed by primer extension by one base using the Cold Nucleotide Extension Mix containing unlabeled dGTP, followed by a transient-binding reaction using the Base Reading Mix containing 5 mM $MnCl_2$ (instead of $CaCl_2$)) and non-hydrolyzable alpha-thio-dA4P-AF647 (the correct nucleotide) (there is no detectable signal from the non-hydrolyzable nucleotide in the presence of manganese) (see FIG. 11, "$3^{rd}$ A correct";

5. Without washing, approximately 2 μL of 100 mM $CaCl_2$) solution was mixed into the reaction lane by pipetting (the concentration of $CaCl_2$) ions was approximated to be in the range of 5-10 mM), and transiently-bound nucleotides were detectable immediately upon addition of the calcium (see FIG. 11, "$3^{rd}$ A correct).

Example 9

Non-Extendible Terminal Ends Using Reversible Terminator Nucleotides:

```
Template sequence:
                              (SEQ ID NO: 46)
Tamra-5'-CAG TAA GGGA GTT GGT TGG ACG GCT GCG AGG C-3'-biotin Primer sequence:
                              (SEQ ID NO: 47)
5'-GCC TCG CAG CCG TCC AAC CAA CTC C-3'
```

1) Template Immobilization:

A flow cell having a biotinylated glass surface was prepared by flowing in a 10 nM streptavidin solution and incubated for 10-15 minutes. The chamber was washed with 1 mL of 50 mM Tris (pH 7.5) and 50 mM NaCl. 10 pM of the biotin-tagged template/primer duplex was flowed in, and incubated for 10-15 minutes. The chamber was washed with 1 mL of 50 mM Tris (pH 7.5) and 50 mM NaCl.

2) Transient-Binding with Non-Extendible Ends:

Transient-binding Mix: a 100 μL volume was prepared containing 50 mM Tris (pH 7.5), 50 mM NaCl, 200 nM Phi29 (exo-) (HP-1) polymerase, 0.4% glucose, 0.1 mg/mL glucose oxidase, 2000 unit/mL Katalase, 2 mM Trolox, 2 mM $CaCl_2$), and 200 nM of one terminal phosphate labeled nucleotides (e.g., AF647-dC4P, AF647-dT4P, or AF647-dA4P) (selection of the nucleotide was dependent upon the template sequence).

100 μL of the transient-binding mix was injected into the chamber, and was excited with 532 nm light having a power density of about 100 W/cm². A movie was collected at 100 ms/frame.

Reversible terminator nucleotide incorporation mix: 20 mM Tris-HCl (pH 8.8), 10 mM $(NH_4)_2SO_4$, 10 mM KCl, 2 mM MgSO$_4$, 0.1% Triton X-100, 0.1 U/μL THERMINATOR polymerase (a 9'N DNA polymerase variant from New England Biolabs, Ipswich, MA), 100 nM reversible terminator nucleotide (unlabeled, dCTP-NH$_2$, disclosed by Wu in U.S. published patent applications 2008/0132692 and 2009/0081686).

The reversible terminator nucleotide incorporation mix was injected into the chamber, and was incubated for 20 minutes at 65° C.

Figure 12:
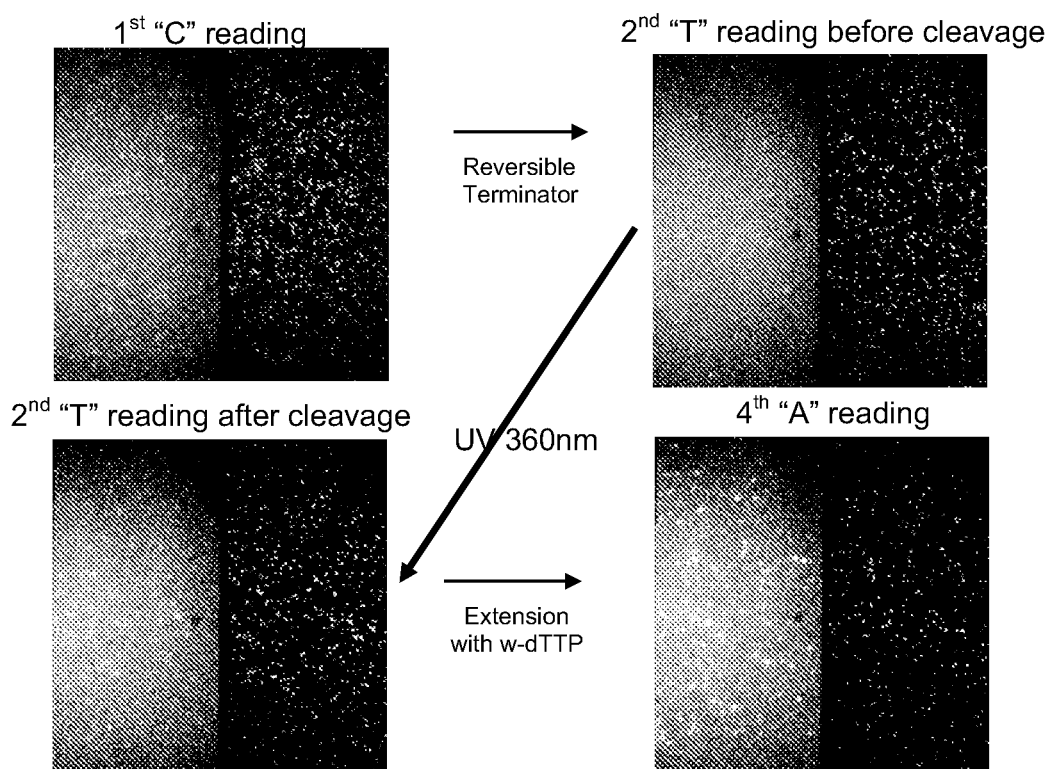
FIG. 12 shows transient binding reactions, and incorporation reactions using a heat-stable polymerase and a terminator nucleotide (Example 9).

The correct nucleotide extension sequence was: CTTA. The transient-binding steps included:
1. Transient-binding AF647-dC4P, collect movie (see FIG. 12, 1$^{st}$ "C" reading)
2. Wash away the AF647-dC4P with 10 mM Tris (pH 8)
3. Incorporate the reversible terminator dCTP
4. Wash away non-incorporated reversible terminator dCTP using 10 mM Tris (pH 8)
5. Transient-binding AF647-dT4P, collect movie (see FIG. 12, 2$^{nd}$ "T" reading before cleavage)
6. Remove the blocking group (inhibitor moiety), at 360 nm, 50 mW/cm$^2$, for 8 minutes
7. Wash with 10 mM Tris (pH 8)
8. Transient-binding AF647-dT4P, collect movie (see FIG. 12, 2$^{nd}$ "T" reading after cleavage)
9. Wash with 10 mM Tris (pH 8)
10. Incorporate two T's using AF647-dT4P (injected 100 μL of the transient-binding mix which contained 2 mM MnCl$_2$ instead of CaCl$_2$))
11. Wash with 10 mM Tris (pH 8)
12. Transient-binding AF647-dATP, collect movie (see FIG. 12, 4$^{th}$ "A" reading)

Example 10

Detecting Transiently-Bound Nucleotides Using RB69 Polymerase:

```
Template sequence:
                          (SEQ ID NO: 48)
Cy3-5'-TGCCACCGGAGTTGGT TGGACGGCTGCGAGG C-3'- biotin-TEG

Primer sequence:
                          (SEQ ID NO: 49)
5'-GCCTCGCAGCCGTCCAACCAA CTCC-3'
```

Buffer: 50 mM Tris (pH7.5), 50 mM NaCl.

The surface of a biotinylated glass flow chamber was prepared by flowing in a 10 nM streptavidin solution and incubating for 10-15 minutes. The chamber was washed with 1 mL Buffer.

The template/primer duplex was immobilized to the surface of the flow cell by flowing in 10 pM of the duplex and incubating for 10-15 minutes. The chamber was washed with 1 mL Buffer.

The correct nucleotide extension sequence was: GGTGG (SEQ ID NO:50).

The transient-binding reaction was prepared in 100 μL and contained: 50 mM Tris (pH 7.5); 50 mM NaCl; 200 nM RB69 polymerase (exo-); 200 nM terminal-phosphate labeled dG4P-AF647 (correct nucleotide); 200 nM terminal-phosphate labeled dA4P-AF680 (incorrect nucleotide); oxygen scavenging system (0.4% glucose, 0.1 mg/mL glucose oxidase, 2000 unit/mL Katalase, 1 mM Tempo); and 2 mM CaCl$_2$).

Figure 13:
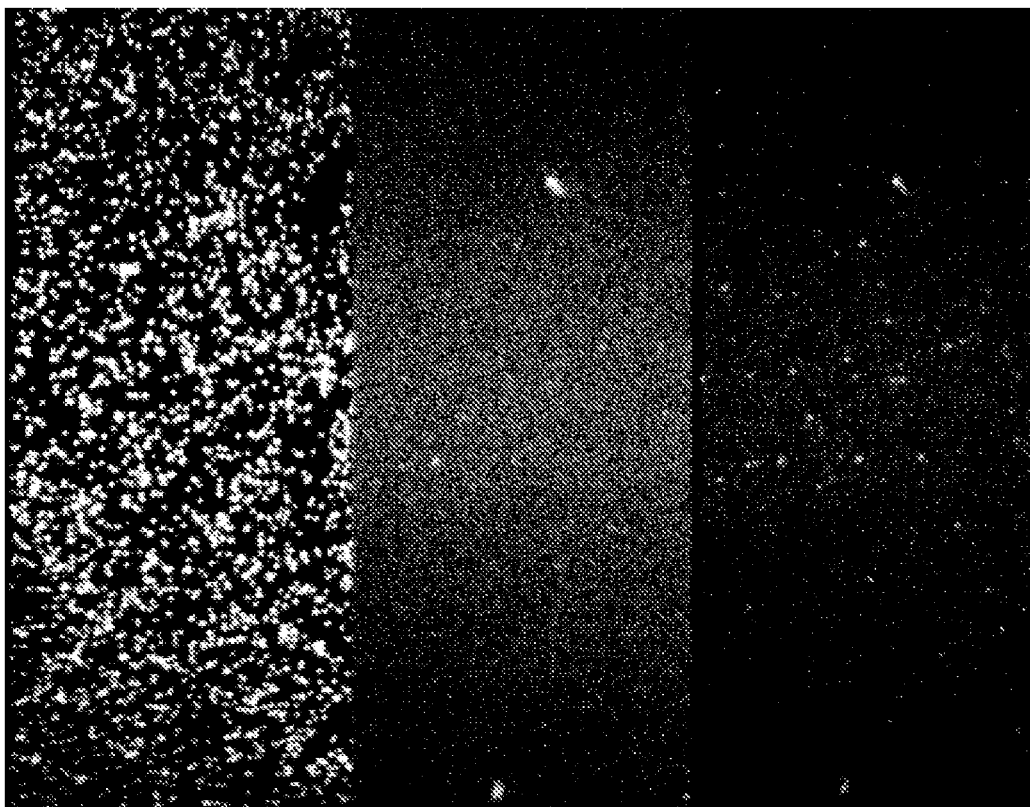
FIG. 13 shows transient binding reactions using RB69 polymerase in the presence of calcium (Example 10).

The transient-binding mix was injected into the chamber. The surface was imaged by exciting the fluorescence donor at a power density of about 100 W/cm$^2$ at 532 nm. A movie was collected at 100 ms/frame. The images are shown in FIG. 13

Example 11

Nucleotide Transient-Binding Using Klenow:

The following procedure was conducted using a SOLID sequencing instrument (SOLID 0025) (Applied Biosystems, Foster City, CA), and template/primer duplexes immobilized on SOLID S3 clonal beads, SOLID flowcells, and Klenow polymerase.

1) Immobilizing Template/Primer Duplexes:

```
Bead/template sequence:
                   (SEQ ID NO: 51 and SEQ ID NO: 52)
Bead-5'aaCCACTACGCCTCCGCTTT- - -AGAGAATGAGGAACC CGGGGCAGtt 3'

P2-Primer sequence:
                          (SEQ ID NO: 53)
3' TCTCTTACTCCTTGGGGCCCCGTCaa 5'

P2-1 Primer sequence:
                          (SEQ ID NO: 54)
3' CTCTTACTCCTTGGGGCCCCGTCaa 5' N-1
```

For the bead/template sequence, the " - - - " represents more than 1000 different sequences in the template molecules.

Seven μM of the P2 primer, in 1×SSPE (150 mM NaCl, 10 mM sodium phosphate, 1 mM EDTA), was added to a SOLID flowcell containing beads/template immobilized on a glass slide, at 25° C., then hybridized at 75° C. for 1 minute, 70° C. for 2 minutes, 65° C. for 2 minutes, 60° C. for 2 minutes, and washed with 1× Instrumentation Buffer (AB Part No. 4389784).

2) Nucleotide Transient-Binding:

The labeled nucleotides were obtained from PerkinElmer Life and Analytical Science (Boston, MA): Cy5-dUTP, Cy3-dCTP, FAM-dGTP, and Texas Red (TxR)-dATP (base-labeled nucleotides). The Klenow fragment polymerase was obtained from New England Biolabs (No. M0212L, Ipswich, MA).

The beads were washed with 3 mL of Universal Buffer (50 mM NaCl, 10 mM Tris-HCl (pH 8), 10 mM CaCl$_2$), 2 mM DTT). And 0.2 mL of Sensing Buffer Mix (200 nM each of Cy5-dUTP, Cy3-dCTP, Fam-dGTP, and Texas Red-dATP; 250 nM Klenow (exo-) in the Universal Buffer) was injected into the flowcell and incubated for 5 minutes at room temperature. Images for different dyes were taken at different exposure times (depending on the dye) sequentially in the same field of view, using arc lamp illumination and the auto-expose function on the SOLID instrument: FAM, 44 ms at gain 32, SOLID FTC Filter Cube; Cy3, 171 ms at gain 32, SOLID Cy3 Filter Cube; TxR, 132 ms at gain 32 SOLID TxR Filter Cube; Cy5, 137 ms at gain 32, SOLID Cy5 Filter Cube.

Figure 14A:
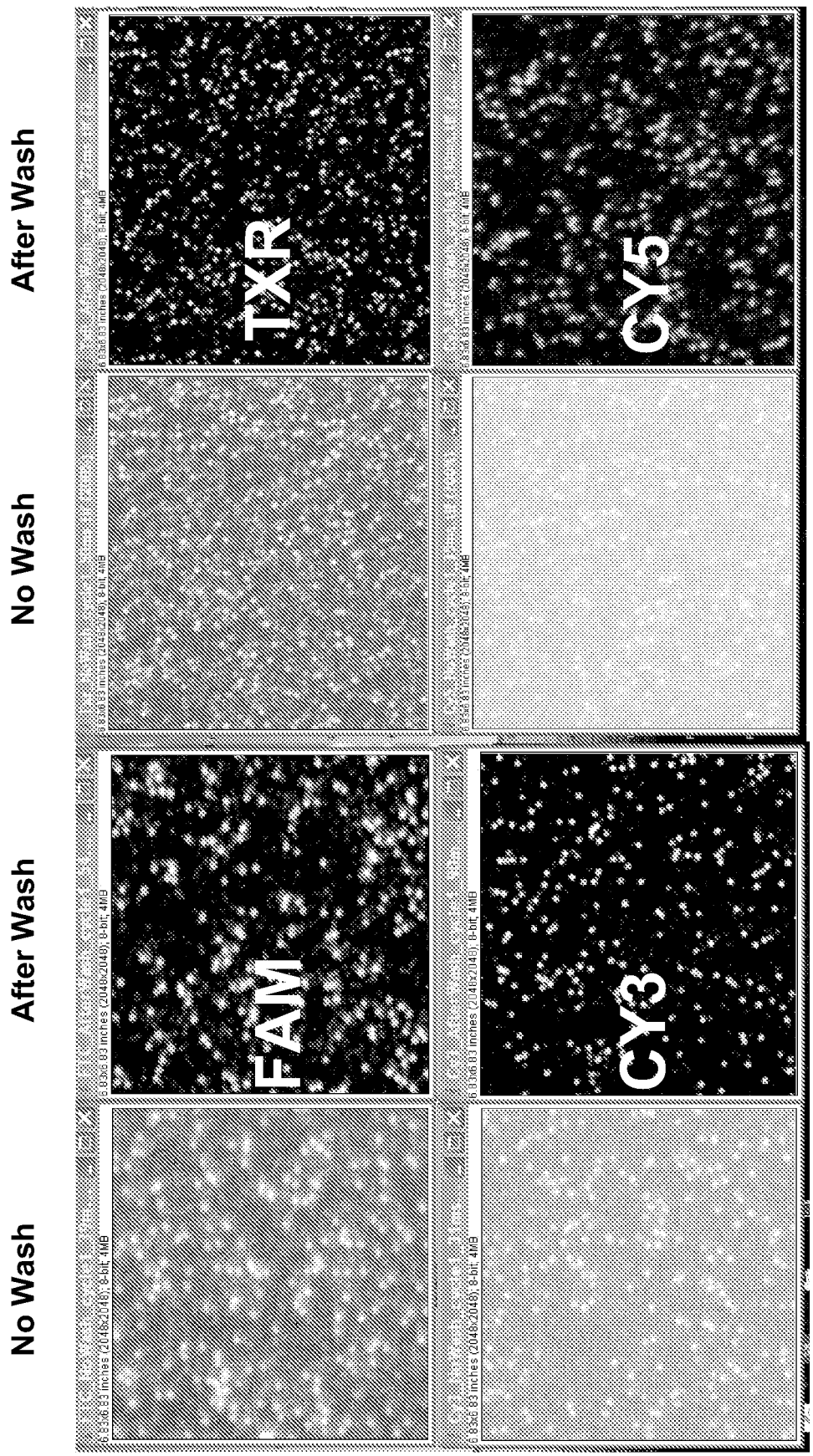
FIG. 14A shows transient binding reactions using the P2 primer, Klenow fragment, and labeled nucleotides, in the presence of calcium (Example 11).

The beads were washed with 1 mL of Universal Buffer. Images for the different dyes were taken manually (FIG. 14A). The results show that approximately 25% of the beads in each view (after wash) fluoresce. This result is expected because template nucleotide (i.e., the insert sequence in the bead/template sequence) will be A, T, C, or G.

3) Re-Hybridize with P2-1 Primer:

The P2 primer was denatured from the template sequence by washing the flow cell with SOLID Reset Buffer (AB part No. 4406519). The flow cell was incubated at 65° C. for 2 minutes, cooled to 25° C., the fluid was emptied, the flow cell was washed with 1× Instrumentation Buffer, washed with Reset Buffer, incubated at 65° C. for 2 minutes, cooled to 25° C., the fluid was emptied, and washed with 1× Instrumentation Buffer.

The P2-1 primer (0.2 mL of 10 UM in the Universal Buffer) was injected into the flowcell. The same hybridization schedule for the P2 primer was used (see above). The flowcell was washed using 3 mL Universal Buffer.

4) Nucleotide Transient-Binding:

Nucleotide transient-binding using the P2-1 primer was conducted in the same manner as described for the P2 primer. Briefly, 0.2 mL of Sensing Buffer Mix was injected into the flowcell (200 nM each of Cy5-dUTP, Cy3-dCTP, Fam-dGTP, and Texas Red-dATP; 250 nM Klenow (exo-) in the Universal Buffer) and incubated for 5 minutes at room temperature. Images for different dyes were taken at different exposure times (depending on the dye) sequentially in the same field of view.

The beads were washed with 1 mL of Universal Buffer. Images for the different dyes were taken manually for 50 ms (FIG. 14B). The results show that the Cy5-dUTP beads fluoresce to a greater degree than the other dye-labeled nucleotides. This result is expected because the template nucleotide (i.e., the insert sequence in the bead/template sequence) will be an A.

Example 12 pH Dependence of Transient-Binding:

Mutant Phi29 Polymerases: Stopped Flow Measurements of $t_{pol}$

```
Template sequence:
                                      (SEQ ID NO: 55)
AF546-5'-CGTTAACCGCCCGCTCCTTTGCAAC-3'

Primer sequence:
                                      (SEQ ID NO: 56)
5'-GTTGCAAAGGAGCGGGCG-3'
```

The effect of pH on polymerase-dependent nucleotide incorporation was tested using stopped-flow procedures. It has been previously shown that reducing pH can inhibit nucleotide incorporation (C. Castro 2007 Proc. Natl. Acad. Sci. USA 104:4267-4272; C. Castro 2009 Nature Structural and Molecular Biology 16:212-218).

The kinetics of nucleotide incorporation by a mutant recombinant phi 29 (exo-) (HP-1) DNA polymerase was measured in an Applied Photophysics SX20 stopped-flow spectrometer by monitoring changes in fluorescence from ALEXA FLUOR 546-labeled primer/template duplex following the mixing of the enzyme-DNA complex with dye-labeled nucleotides in the reaction buffer containing 50 mM of various buffers at different pH, 50 mM NaCl, 4 mM DTT, 0.2% BSA, and 2 mM $MnCl_2$. The reactions included 330 nM recombinant DNA polymerase, 100 nM template/primer duplex, and 7 µM labeled nucleotides (terminal-phosphate-labeled nucleotides having an alkyl linker with a functional amine group attached to the dye).

For each reaction, the various buffers included one of: 50 mM Tris-HCl (pH 8), 50 mM Tris-HCl (pH 7.5), 50 mM MOP (pH 7), or 50 mM ACES (pH 6.5).

As described in Example 4 above, the averaged stopped-flow fluorescence traces were fitted with a double exponential equation (1) to extrapolate the rates of the nucleotide binding and product release.

Figure 15:
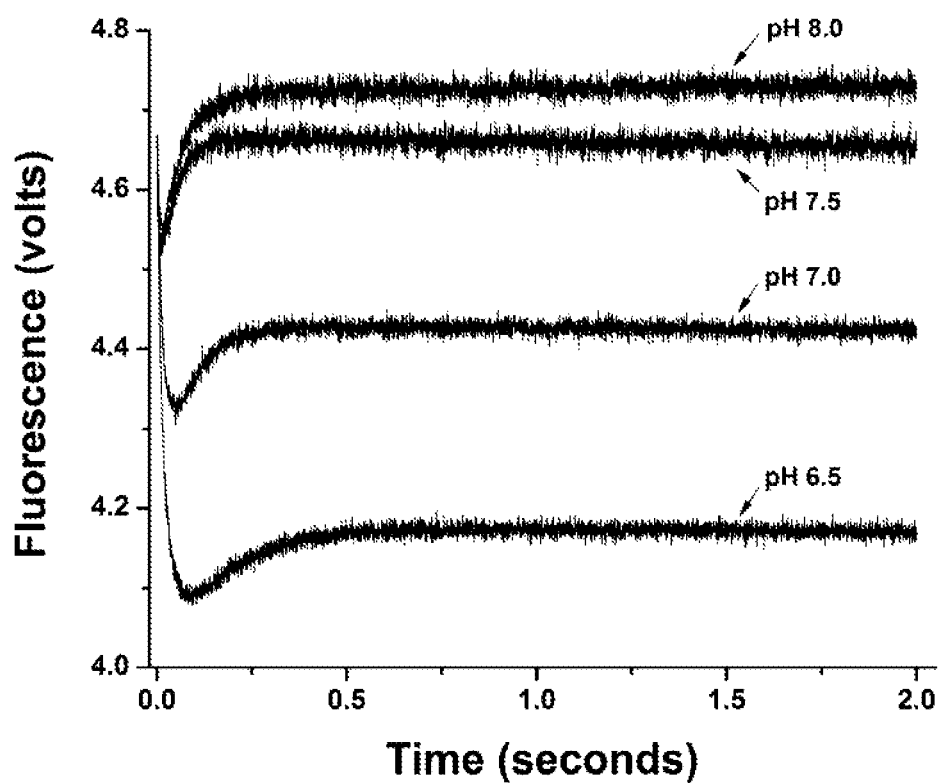
FIG. 15 shows a stopped-flow fluorescence trace ($t_{pol}$) for a mutant Phi29 polymerase and terminal phosphate labeled dN4P nucleotides in the presence of manganese, testing a range of pH conditions. (Example 12).

The stopped-flow techniques for measuring $t_{pol}$ ($1/k_{pol}$) followed the techniques described by MP Roettger (2008 Biochemistry 47:9718-9727; M. Bakhtina 2009 Biochemistry 48:3197-320). Representative stopped-flow fluorescence traces for pH 8.0, 7.5, 7.0, and 6.5 are shown in FIG. 15.

Figure 16:
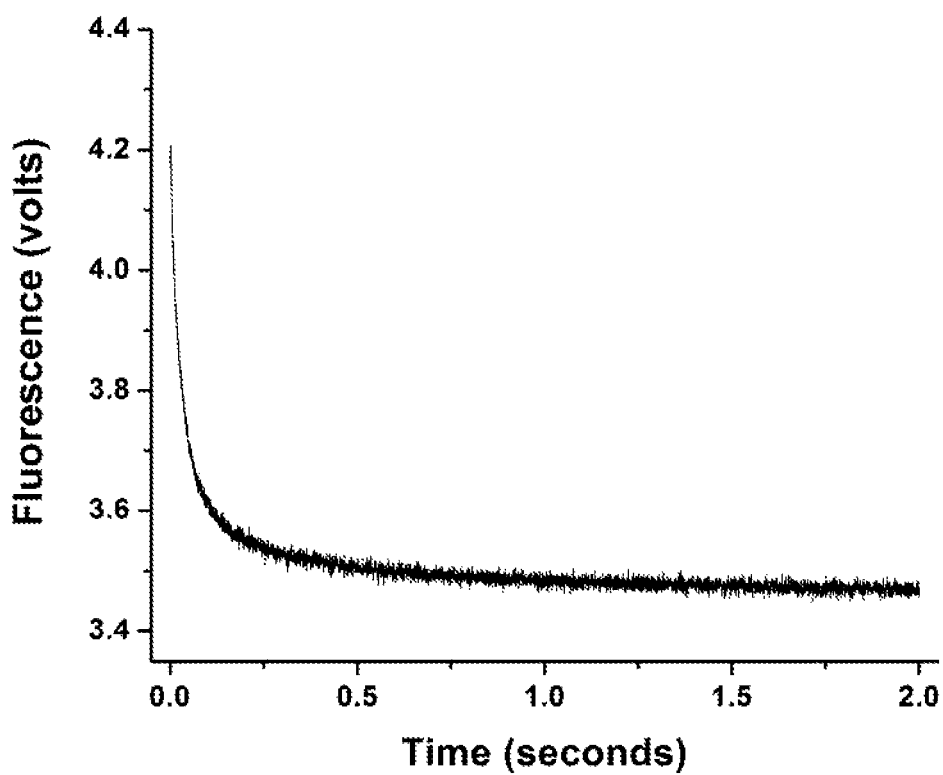
FIG. 16 shows a stopped-flow fluorescence trace ($t_{pol}$) for a different mutant Phi29 polymerase and a terminal phosphate labeled dN6P nucleotide in the presence of manganese, at pH 6. (Example 12).

A similar stopped-flow procedure was conducted, using a different mutant Phi29 polymerase and a labeled hexaphosphate nucleotide (dG6P-AF647) at pH 6 (MES buffer). A representative stopped-flow fluorescence trace for this mutant is shown in FIG. 16.

Example 13

Transient-Binding Using Non-Hydrolyzable Nucleotides

```
Template sequences:
Correct template:
                                      (SEQ ID NO: 57)
AF546-5'-CGAACCTCGCCCGCTCCTTTGCAAC-3'

Incorrect template:
                                      (SEQ ID NO: 58)
AF546-5'-CGTTAACCGCCCGCTCCTTTGCAAC-3'

Primer sequence:
                                      (SEQ ID NO: 59)
5'-GTTGCAAAGGAGCGGGCG-3'
```

Figure 17:
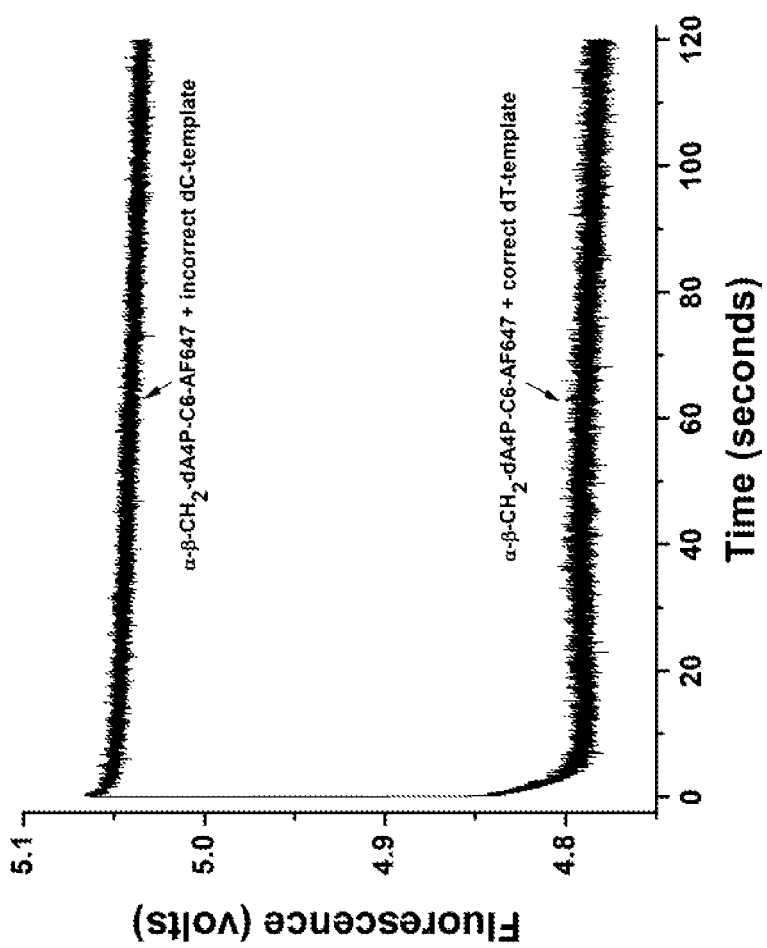
FIG. 17 shows stopped-flow fluorescence traces ($t_{pol}$) for a Phi29 (exo-) polymerase and a labeled non-hydrolyzable nucleotide in the presence of manganese, at pH 7.5 and either a correct or incorrect template. (Example 13).

The kinetics of transient-binding of non-hydrolyzable nucleotides by recombinant phi 29 (exo-) (HP-1) DNA polymerase was measured in an Applied Photophysics SX20 stopped-flow spectrometer by monitoring changes in fluorescence from ALEXA FLUOR 546-labeled primer/template duplex following the mixing of the enzyme-DNA complex with dye-labeled nucleotides in the reaction buffer containing 50 mM Tris-HCl (pH 7.5), 50 mM NaCl, 4 mM DTT. 0.2% BSA, and 2 mM $MnCl_2$. The reactions included 330 nM recombinant DNA polymerase, 100 nM template/primer duplex, and 7 µM labeled non-hydrolyzable nucleotide $\alpha$-$CH_2$-$\beta$-dA4P (labeled with ALEXA FLUOR 647; incorrect nucleotide for the dC-template, correct nucleotide for the dT-template). A representative stopped-flow fluorescence trace is shown in FIG. 17.

Example 14

Preparing Mutant RB69 Polymerase (3PDX)

The nucleotide sequence encoding the 3PDX DNA polymerase (SEQ ID NO:5) was cloned into pTTQ expression vector (Invitrogen, Carlsbad, CA). The vector was transformed into T7 express BI-21 cell line (New England Biolabs). The expressing cell line was grown in 2YT media at 37° C. (Invitrogen #22712-020). When the optical density of the growing culture reached 0.6 OD, the cells were induce with 0.5M IPTG, then shifted to 15° C. and allowed to continue to grow overnight. Cells were concentrated by differential centrifugation, stored at -80° C.

Cells were resuspended in 50 mM TRIS pH 7.5, 50 mM Glucose, 0.1 mM EDTA (pH 8.0), 0.05% Tween-20 and 1 mM DTT, and ruptured by high pressure using a Microfluidizer, ML-110PS, (Microfluidics). While stirring on ice, the salt concentration of the lysate was increased to a final concentration of 1M NaCl. Streptomycin sulfate was added to the lysate to a final concentration of 0.2% and the lysate was stirred for 20 minutes. Cell debris was removed by differential centrifugation. PEI (polyethylenime) was added to the lysate to a final concentration of 2%, while stirring on ice. The precipitated DNA was removed by differential centrifugation. The lysate was precipitated with ammonium sulfate at a final concentration of 65%. The resulting pellets were stored at −20° C. until further processing.

The expressed protein was purified using four columns. The components of the column buffers included: Buffer A: 25 mM HEPES (pH 7.5), 0.1 mM EDTA, 0.05% Tween-20 and 1 mM DTT. Buffer B: 25 mM HEPES (pH 7.5), 0.1 mM EDTA, 0.05% Tween-20, 1 mM DTT and 1M NaCl. The pellets from the ammonium sulfate precipitation were resuspended in Buffer A until the conductivity reached ~11 mS/cm. The sample was filtered with a 1 μm filter (Acrodisc 1 μM Glass fiber membrane, 37 mm; PALL) and the collected protein was purified by the following four columns: (1) EMD sulfite cation exchange column, (Merck chemicals); (2) Poros HQ20, 10×100 mm column (Life Technologies); (3) Poros PI20 (10×100 mm) column (Life Technologies); and (4) PorosHE50 (10×100 mm) column (Life Technologies). The sample was loaded on the first column, the proteins were eluted with a 20 column volume gradient from 0 to 100% Buffer B. (0 to 1 M NaCl). The fractions containing the expressed protein were identified by SDS PAGE gel (NuPAGE, 10% denaturing gel, using MES Buffer). These fractions were pooled and applied to the next column. This method was repeated for the next three columns. After the final column, the fractions containing the purified protein were identified and pooled for dialysis in 10 mM Tris pH 7.5, 0.1 mM EDTA, 100 mM NaCl and 50% glycerol. The protein was dialyzed overnight (10 MWCO).

The purified protein was concentrated four fold. The protein concentration was determined by UV280. The enzyme was assayed for exogenous DNAse contamination and polymerase activity. Protein Purity was determined by SDS PAGE gel electrophoresis.

Example 15

Transient Binding Methods Using an RB69 Mutant Polymerase (3PDX)

In this example, the nucleotide transient-binding reaction and nucleotide incorporation reactions were conducted with an RB69 mutant polymerase (3PDX), using a donor-labeled hairpin template, and acceptor-labeled nucleotides. The nucleotide incorporation reactions were conducted with unlabeled 3'-azidomethyl terminator nucleotides.

```
Hairpin template sequence:
                                      (SEQ ID NO: 60)
5'-Cy3-CAGTCTCGGGATCTTGTGCCATT(biotin-dT)

TTTGGCACAAGATCCC-3'
```

Wash Buffer: 50 mM Tris pH 7.5 (Invitrogen PN 15567-027), 50 mM NaCl, 0.2% Bovine Serum Albumin (Sigma PN A8577).

Reset Buffer: 50 mM Tris pH 7.5, 50 mM EDTA, 1 M NaCl, 0.2% BSA.

Imaging Solution: 50 mM Tris pH 7.5, 50 mM NaCl, 0.2% BSA, 1 μM 3PDX polymerase (see Example 14 above), 200 nM base-labeled nucleotides (AF647-aha-dUTP (Invitrogen, A32763), Cy5-propargylamine-dGTP (Jena Biosciences, NU-1615-CY5), AF5-propargylamine-dATP, or AF647-aha-dCTP (Invitrogen, A32771)), 0.4% glucose, 2 mM Trolox (Fluka PN 56510), 2-5 mM $CaCl_2$), 0.2 mg/mL glucose oxidase (Sigma PN G7141), 4 unit/uL Katalase (Fluka PN 02071).

1) Template Immobilization:

Flow chambers were assembled using PEG-biotin coated glass coverslips (Microsurfaces Inc., BIO 01). The flow chambers were washed with 1 mL of Wash Buffer. The flow chambers were injected with 5 nM streptavidin (in Wash Buffer) and incubated for 20 minutes. The flow chambers were rinsed with 1 mL Wash Buffer. The flow chambers were injected with 50 pM biotin-tagged DNA-Cy3 into the flow and incubated for 10 minutes. The flow chambers were washed with 1 mL Wash Buffer.

2) Nucleotide Transient-Binding Reaction:

The flow chambers were washed with 1 mL Wash Buffer. The flow chambers were injected with Imaging Solution containing one of the four dye-labeled nucleotides (e.g., dUTP), incubated for 3 minutes at room temperature, and imaged. Imaging was conducted by exciting at 532 nm at 50 W/$cm^2$. The acceptor signals were detected at 670 nm with a bandwidth of 30 nm. The 3 minute incubating step, and the imaging step, was repeated twice for a total of three incubation and three imaging steps for each type of labeled nucleotide. The flow chambers were not washed prior to injecting and imaging the other types labeled nucleotides. For the other three types of nucleotides (e.g., dATP, dGTP, dCTP), the flow chambers were injected with Imaging Solution containing dye-labeled nucleotides, and the incubating and imaging steps were repeated.

3) Nucleotide Incorporation:

The flow chambers were washed with 1 mL Reset Buffer. The flow chambers were washed with 1 mL Wash Buffer. The flow chambers were injected with 100 ul THERMINATOR Buffer (NEB, PN B9004S). The flow chambers were injected with 60 ul reversible terminator reaction mix containing four types of nucleotides having the 3' position of the sugar moiety blocked with an azidomethyl group; the reversible terminator reaction mix contained: 5 μM 3'-AM-dATP, 5 μM 3'-AM-dGTP, 2.5 μM 3'-AM-dCTP, 2.5 μM 3'-AM-dTTP, 1× THERMINATOR Buffer (NEB, PN B9004S), and 3 μM 3PDX polymerase. The flow chambers were incubated at room temperature for 45 minutes. The flow chambers were washed with 1 mL Reset Buffer. The flow chambers were washed with 1 mL Wash Buffer. The flow chambers were injected with 85 ul of 100 mM TCEP (Tris(2-carboxyethyl)phosphine) in 0.1 M Tris-HCL at pH 7.5, and allowed to incubate at room temperature for 20 minutes. The flow chambers were washed with 1 mL Reset Buffer. The nucleotide transient-binding and nucleotide incorporation reactions were repeated four times.

Example 16

Transient Binding Methods Using THERMINATOR GAMMA Polymerase

In this example, the nucleotide transient-binding reactions and nucleotide incorporation reactions were conducted with a commercially-available DNA polymerase (THERMINATOR GAMMA), using a donor-labeled hairpin template, and acceptor-labeled nucleotides. The nucleotide incorporation reactions were conducted with 3'-azidomethyl terminator nucleotides.

```
Hairpin template sequence:
                                      (SEQ ID NO: 60)
5'-Cy3-CAGTCTCGGGATCTTGTGCCATT(biotin-dT)

TTTGGCACAAGATCCC-3')
```

Wash Buffer: 50 mM Tris pH 7.5 (Invitrogen PN 15567-027), 50 mM NaCl, 0.2% Bovine Serum Albumin (Sigma PN A8577).

Reset Buffer: 50 mM Tris pH 7.5, 50 mM EDTA, 1 M NaCl, 0.2% BSA.

Imaging Solution: 50 mM Tris pH 7.5, 50 mM NaCl, 0.2% BSA, 0.2 U/uL THERMINATOR GAMMA (New England Biolabs, PN M0334S), 200 nM base-labeled nucleotides (Cy5-propargylamine-dUTP (Jena Biosciences, NU-1619-CY5), Cy5-propargylamine-dGTP (Jena Biosciences, NU-1615-CY5), AF5-propargylamine-dATP, or AF5-propargylamine-dCTP), 0.4% glucose, 2 mM Trolox (Fluka PN 56510), 2-5 mM CaCl$_2$). 0.2 mg/mL glucose oxidase (Sigma PN G7141), 4 unit/uL Katalase (Fluka PN 02071).

1) Template Immobilization:

Flow chambers were assembled using PEG-biotin coated glass coverslips (Microsurfaces Inc., BIO 01). The flow chambers were washed with 1 mL of Wash Buffer. The flow chambers were injected with 5 nM streptavidin (in Wash Buffer) and incubated for 20 minutes. The flow chambers were rinsed with 1 mL Wash Buffer. The flow chambers were injected with 50 pM biotin-tagged DNA-Cy3 into the flow and incubated for 10 minutes. The flow chambers were washed with 1 mL Wash Buffer.

2) Nucleotide Transient-Binding Reaction:

The flow chambers were washed with 1 mL Wash Buffer. The flow chambers were injected with Imaging Solution containing one of the four dye-labeled nucleotides (e.g., dUTP), incubated for 3 minutes at room temperature, and imaged. Imaging was conducted by exciting at 532 nm at 50 W/cm$^2$. The acceptor signals were detected at 670 nm with a bandwidth of 30 nm. The 3 minute incubating step, and the imaging step, was repeated twice for a total of three incubation and three imaging steps for each type of labeled nucleotide. The flow chambers were not washed prior to injecting and imaging the other types labeled nucleotides. For the other three types of nucleotides (e.g., dATP, dGTP, dCTP), the flow chambers were injected with Imaging Solution containing dye-labeled nucleotides, and the incubating and imaging steps were repeated.

3) Nucleotide Incorporation:

The flow chamber was washed with 100 ul THERMINATOR Buffer (NEB, PN B9004S). The flow chambers were injected with 60 ul reversible terminator reaction mix containing four types of nucleotides having the 3' position of the sugar moiety blocked with an azidomethyl group; the reversible terminator reaction mix contained: 5 μM 3'-AM-dATP, 5 μM 3'-AM-dGTP, 2.5 μM 3'-AM-dCTP, 2.5 μM 3'-AM-dTTP, 1× THERMINATOR Buffer (NEB, PN B9004S) and 3 μM THERMINATOR II (NEB, PN M0266S). The flow chambers were incubated at 45° C. for 45 minutes. The flow chambers were washed with 1 mL Reset Buffer. The flow chambers were washed with 1 mL Wash Buffer. The flow chambers were injected with 85 ul 100 mM TCEP (Tris(2-carboxyethyl)phosphine) in 0.1 M Tris-HCL at pH 7.5, and allowed to incubate at 35° C. for 45 minutes. The flow chambers were washed with 1 mL Reset Buffer. The nucleotide transient-binding and nucleotide incorporation reactions were repeated four times.

SEQUENCE LISTING

```
Sequence total quantity: 71
SEQ ID NO: 1            moltype = AA  length = 575
FEATURE                 Location/Qualifiers
REGION                  1..575
                        note = Phage Phi-29
source                  1..575
                        mol_type = protein
                        organism = Bacillus sp.
SEQUENCE: 1
MKHMPRKMYS CDFETTTKVE DCRVWAYGYM NIEDHSEYKI GNSLDEFMAW VLKVQADLYF   60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                            575

SEQ ID NO: 2            moltype = AA  length = 903
FEATURE                 Location/Qualifiers
REGION                  1..903
                        note = Description of Unknown: Enterobacteria phage RB69
source                  1..903
                        mol_type = protein
                        organism = unidentified
SEQUENCE: 2
MKEFYLTVEQ IGDSIFERYI DSNGRERTRE VEYKPSLFAH CPESQATKYF DIYGKPCTRK   60
LFANMRDASQ WIKRMEDIGL EALGMDDFKL AYLSDTYNYE IKYDHTKIRV ANFDIEVTSP  120
DGFPEPSQAK HPIDAITHYD SIDDRFYVFD LLNSPYGNVE EWSIEIAAKL QEQGGDEVPS  180
EIIDKIIYMP FDNEKELLME YLNFWQQKTP VILTGWNVES FDIPYVYNRI KNIFGESTAK  240
RLSPHRKTRV KVIENMYGSR EIITLFGISV LDYIDLYKKF SFTNQPSYSL DYISEFELNV  300
GKLKYDGPIS KLRESNHQRY ISYNIIDVYR VLQIDAKRQF INLSLDMGYY AKIQIQSVFS  360
PIKTWDAIIF NSLKEQNKVI PQGRSHPVQP YPGAFVKEPI PNRYKYVMSF DLTSLYPSII  420
RQVNISPETI AGTFKVAPLH DYINAVAERP SDVYSCSPNG MMYYKDRDGV VPTEITKVFN  480
QRKEHKGYML AAQRNGEIIK EALHNPNLSV DEPLDVDYRF DFSDEIKEKI KKLSAKSLNE  540
MLFRAQRTEV AGMTAQINRK LLINSLYGAL GNVWFRYYDL RNATAITTFG QMALQWIERK  600
VNEYLNEVCG TEGEAFVLYG DTDSIYVSAD KIIDKVGESK FRDTNHWVDF LDKFARERME  660
PAIDRGFREM CEYMNNKQHL MFMDREAIAG PPLGSKGIGG FWTGKKRYAL NVWDMEGTRY  720
AEPKLKIMGL ETQKSSTPKA VQKALKECIR RMLQEGEESL QEYFKEFEKE FRQLNYISIA  780
SVSSANNIAK YDVGGFPGPK CPFHIRGILT YNRAIKGNID APQVVEGEKV YVLPLREGNP  840
```

```
FGDKCIAWPS GTEITDLIKD DVLHWMDYTV LLEKTFIKPL EGFTSAAKLD YEKKASLFDM  900
FDF                                                                903

SEQ ID NO: 3              moltype = AA   length = 572
FEATURE                   Location/Qualifiers
REGION                    1..572
                          note = Phage B103
source                    1..572
                          mol_type = protein
                          organism = Bacillus sp.
SEQUENCE: 3
MPRKMFSCDF ETTTKLDDCR VWAYGYMEIG NLDNYKIGNS LDEFMQWVME IQADLYFHNL  60
KFDGAFIVNW LEHHGFKWSN EGLPNTYNTI ISKMGQWYMI DICFGYKGKR KLHTVIYDSL  120
KKLPFPVKKI AKDFQLPLLK GDIDYHAERP VGHEITPEEY EYIKNAIEII ARALDIQFKQ  180
GLDRMTAGSD SLKGFKDILS TKKFNKVFPK LSLPMDKEIR RAYRGGFTWL NDKYKEKEIG  240
EGMVFDVNSL YPSQMYSRPL PYGAPIVFQG KYEKDEQYPL YIQRIRFEFE LKEGYIPTIQ  300
IKKNPFFKGN EYLKNSGAEP VELYLTNVDL ELIQEHYEMY NVEYIDGFKF REKTGLFKEF  360
IDKWTYVKTH EKGAKKQLAK LMLNSLYGKF ASNPDVTGKV PYLKEDGSLG FRVGDEEYKD  420
PVYTPMGVFI TAWARFTTIT AAQACYDRII YCDTDSIHLT GTEVPEIIKD IVDPKKLGYW  480
AHESTFKRAK YLRQKTYIQD IYAKEVDGKL IECSPDEATT TKFSVKCAGM TDTIKKKVTF  540
DNFRVGFSST GKPKPVQVNG GVVLVDSVFT IK                                572

SEQ ID NO: 4              moltype = DNA   length = 2709
FEATURE                   Location/Qualifiers
misc_feature              1..2709
                          note = Description of Unknown: Enterobacteria phage RB69
source                    1..2709
                          mol_type = unassigned DNA
                          organism = unidentified
CDS                       1..2709
SEQUENCE: 4
atgaaagaat tttacttaac ggttgaacag attggtgatt caattttga acgttacatc    60
gattctaatg gccgtgaacg tactcgtgaa gtagaatata aaccatcact gtttgctcat   120
tgtccagaaa gtcaggctac gaaatatttc gatatctacg taaaccgtg tactcgtaag   180
ttgttcgcta atatgcgtga tgcctcccaa tggattaaac gcatgaagaa tatcggactt   240
gaagcacttg gcatggacga tttcaaattg gcgtatttgt ctgacactta taactatgaa   300
atcaaatacg accatacaaa aattcgtgtg gctaacttcg acatcgaagt aacatctccg   360
gatgggttcc ctgagccgtc acaagcaaaa catccgattg atgctatcac ccattatgac   420
tcaattgacg acaggttcta cgtatttgat ctattgaaat ctccatatgg taatgtagaa   480
gaatggtcta ttgaaatcgc tgctaagctt caagaacaag gtggtgatga agttccatct   540
gaaattattg ataaaatcat ttatatgccg ttcgataacg aaaaagaatt gttgatggaa   600
tatctcaact tctggcaaca gaaaactcct gtcattttga ctggatggaa cgttgagtca   660
tttgatattc cgtacgtgta taaccgaatc aagaatattt ttggcgaatc aactgcgaaa   720
cgttatcac cacatcgtaa aactcgtgtt aaagttatcg aaaacatgta tggttctcgt   780
gaaatcatta cattgttcgg tatctctgtt cttgattaca ttgacctta caaaaaattc   840
tcttttacca atcaaccgtc gtattctctg gattacattt cagaatttga attgaacgtt   900
ggtaaactga aatatgacgg ccctatttct aagcttcaaa aagcaatca ccaacgtat   960
atttcttata acattatcga cgtgtatcgt gtattgcaaa ttgatgctaa gcgtcagttc  1020
atcaacttga gtttggacat gggttattat gctaagatac agattcaatc tgtgtttagc  1080
ccaattaaaa catgggatgc tattattttt aatagcctta aagagcagaa caaggtgatt  1140
ccacaaggtc gttctcaccc ggttcaacct tatcccgacg cttttgttaa ggaacctatt  1200
ccaaatcgat acaaatatgt aatgagtttc gaccttacat ctctatatcc aagtattatt  1260
cgccaagtga atattagccc agaaacaata gcaggaacgt ttaaagtagc tccattgcat  1320
gattatatta acgctgttgc tgaacgtcct tctgatgtgt acagttgttc tcctaacggc  1380
atgatgtatt ataaagaccg tgatggtgta gttccaactg aaattcactaa ggtctttaat  1440
caacgtaaag aacataaagg ttacatgctt gcagctcaac gtaatgatga ataattaaa   1500
gaggcattgc ataatcctaa tctttctgtt gacgaaccat tagatgttga ttatcgtttc  1560
gacttcagcg atgagattaa agaaaagatt aaaaagttgt ctgctaaatc tcttaatgaa  1620
atgttgttta gagctcaacg tactgaagtt gcaggtatga ctgcacaaat taacgtaaga  1680
ttgcttatca actcacttta tggtgcactt ggcaacgttt ggttccgtta ttatgatttg  1740
cgtaatgcta ctgcaatcac aacattcggg caaatggctt tacagtggat tgaacgtaaa  1800
gttaatgaat atctgaatga agtttgtggt acagaaggtg aagctttcgt tctttatggt  1860
gatacagact ctatttacgt atctgctgat aaaattatcg ataaggttgg tgaatctaaa  1920
ttccgtacaa ccaaccattg ggtagacttc ttagataagt ttgcacgtga acgtatggaa  1980
ccagctattg atagaggttt ccgtgaaatg tgtgaataca tgaacaataa acaacactta  2040
atgttcatgg accgagaagc tatcgctggg cctccgcttg gttctaaagg tattggcgga  2100
ttttggactg gtaagaaacg ttatgcatta acgtgtggg atatgaagg tactcgttac  2160
gctgagccta aactcaaaat catgggtcta gagactcaga atcttcgac tcctaaagca  2220
gtacagaaag ctcttaagaa atgtattcgt cgtatgcttc aagaaggtga agaatcatta  2280
caagaatatt ttaaagagtt tgaaaaagaa ttcgtcaat tgaattatat tagcatcgcg  2340
tcggtatctt ctgcgaataa cattgctaaa tatgacgtag gtggattccc tggtcccaaa  2400
tgcccgttcc atattcgtgg aattctgaca tataaccgag ctatcaaagg taatattgat  2460
gcaccacaag ttgtagaagg tgaaaaagta tatgttctgc ctttacgtga aggaaaccca  2520
tccgtgata aatgtatcgc atggccttct gtcacaatta tcacgatttg aattaaagac  2580
gacgtacttc attggatgga ctacactgtt ctccttgaga agacatttat taaaccactt  2640
gaaggattca catcagcagc gaaactcgat tacgagaaga aagcatctct gttcgatatg  2700
ttcgatttt                                                           2709

SEQ ID NO: 5              moltype = AA   length = 903
```

-continued

```
FEATURE              Location/Qualifiers
REGION               1..903
                     note = Description of Unknown: Enterobacteria phage RB69
                      mutant
source               1..903
                     mol_type = protein
                     organism = unidentified
SEQUENCE: 5
MKEFYLTVEQ IGDSIFERYI DSNGRERTRE VEYKPSLFAH CPESQATKYF DIYGKPCTRK  60
LFANMRDASQ WIKRMEDIGL EALGMDDFKL AYLSDTYNYE IKYDHTKIRV ANFDIEVTSP 120
DGFPEPSQAK HPIDAITHYD SIDDRFYVFD LLNSPYGNVE EWSIEIAAKL QEQGGDEVPS 180
EIIDKIIYMP FDNEKELLME YLNFWQQKTP VILTGWNVES FAIPYVYNRI KNIFGESTAK 240
RLSPHRKTRV KVIENMYGSR EIITLFGISV LDYIDLYKKF SFTNQPSYSL DYISEFELNV 300
GKLKYDGPIS KLRESNHQRY ISYNIIAVYR VLQIDAKRQF INLSLDMGYY AKIQIQSVFS 360
PIKTWDAIIF NSLKEQNKVI PQGRSHPVQP YPGAFVKEPI PNRYKYVMSF DLTSSAVSII 420
RQVNISPETI AGTFKVAPLH DYINAVAERP SDVYSCSPNG MMYYKDRDGV VPTEITKVFN 480
QRKEHKGYML AAQRNGEIIK EALHNPNLSV DEPLDVDYRF DFSDEIKEKI KKLSAKSLNE 540
MLFRAQRTEV AGMTAQINRK LLINSLYGAL GNVWFRYYDL RNATAITTFG QMALQWIERK 600
VNEYLNEVCG TEGEAFVLYG DTDSIYVSAD KIIDKVGESK FRDTNHWVDF LDKFARERME 660
PAIDRGFREM CEYMNNKQHL MFMDREAIAG PPLGSKGIGG FWTGKKRYAL NVWDMEGTRY 720
AEPKLKIMGL ETQKSSTPKA VQKALKECIR RMLQEGEESL QEYFKEFEKE FRQLNYISIA 780
SVSSANNIAK YDVGGFPGPK CPFHIRGILT YNRAIKGNID APQVVEGEKV YVLPLREGNP 840
FGDKCIAWPS GTEITDLIKD DVLHWMDYTV LLEKTFIKPE EGFTSAAKLD YEKKASLFDM 900
FDF                                                              903

SEQ ID NO: 6         moltype =   length =
SEQUENCE: 6
000

SEQ ID NO: 7         moltype = AA   length = 9
FEATURE              Location/Qualifiers
REGION               1..9
                     note = Description of Artificial Sequence: Synthetic peptide
source               1..9
                     mol_type = protein
                     organism = synthetic construct
SEQUENCE: 7
RRATSNVFA                                                          9

SEQ ID NO: 8         moltype = AA   length = 8
FEATURE              Location/Qualifiers
REGION               1..8
                     note = Description of Artificial Sequence: Synthetic peptide
source               1..8
                     mol_type = protein
                     organism = synthetic construct
SEQUENCE: 8
RKASGPPV                                                           8

SEQ ID NO: 9         moltype = AA   length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 9
LRRASLG                                                            7

SEQ ID NO: 10        moltype = AA   length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 10
GGGGSGGGGS AAAGSAA                                                17

SEQ ID NO: 11        moltype = AA   length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 11
GAAAKGAAAK GSAA                                                   14
```

```
SEQ ID NO: 12              moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 12
PKPQQF                                                                            6

SEQ ID NO: 13              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 13
PKPQQFM                                                                           7

SEQ ID NO: 14              moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 14
LRRASL                                                                            6

SEQ ID NO: 15              moltype = DNA  length = 19
FEATURE                    Location/Qualifiers
misc_feature               1..19
                           note = Description of Artificial Sequence: Synthetic
                           oligonucleotide
source                     1..19
                           mol_type = other DNA
                           organism = synthetic construct
SEQUENCE: 15
tttttgggag tgacaggtt                                                             19

SEQ ID NO: 16              moltype = DNA  length = 19
FEATURE                    Location/Qualifiers
misc_feature               1..19
                           note = Description of Artificial Sequence: Synthetic
                           oligonucleotide
source                     1..19
                           mol_type = other DNA
                           organism = synthetic construct
SEQUENCE: 16
tttttaagag tgacaggtt                                                             19

SEQ ID NO: 17              moltype = DNA  length = 19
FEATURE                    Location/Qualifiers
misc_feature               1..19
                           note = Description of Artificial Sequence: Synthetic
                           oligonucleotide
source                     1..19
                           mol_type = other DNA
                           organism = synthetic construct
SEQUENCE: 17
tttttccgag tgacaggtt                                                             19

SEQ ID NO: 18              moltype = DNA  length = 19
FEATURE                    Location/Qualifiers
misc_feature               1..19
                           note = Description of Artificial Sequence: Synthetic
                           oligonucleotide
source                     1..19
                           mol_type = other DNA
                           organism = synthetic construct
SEQUENCE: 18
tttttttgag tgacaggtt                                                             19

SEQ ID NO: 19              moltype = DNA  length = 24
FEATURE                    Location/Qualifiers
misc_feature               1..24
                           note = Description of Artificial Sequence: Synthetic
                           oligonucleotide
```

```
                        source              1..24
                                            mol_type = other DNA
                                            organism = synthetic construct
SEQUENCE: 19
tttttgcccc cagggtgaca ggtt                                              24

SEQ ID NO: 20           moltype = DNA   length = 21
FEATURE                 Location/Qualifiers
misc_feature            1..21
                        note = Description of Artificial Sequence: Synthetic
                            oligonucleotide
source                  1..21
                        mol_type = other DNA
                        organism = synthetic construct
SEQUENCE: 20
aaaaaaaaag ggtgacaggt t                                                 21

SEQ ID NO: 21           moltype = DNA   length = 31
FEATURE                 Location/Qualifiers
misc_feature            1..31
                        note = Description of Artificial Sequence: Synthetic
                            oligonucleotide
source                  1..31
                        mol_type = other DNA
                        organism = synthetic construct
SEQUENCE: 21
tttagtcctc ctgtcctcct gggtgacagg t                                      31

SEQ ID NO: 22           moltype = DNA   length = 32
FEATURE                 Location/Qualifiers
misc_feature            1..32
                        note = Description of Artificial Sequence: Synthetic
                            oligonucleotide
source                  1..32
                        mol_type = other DNA
                        organism = synthetic construct
SEQUENCE: 22
tttttgggag tgacaggttt ttcctgtcac tc                                     32

SEQ ID NO: 23           moltype = DNA   length = 24
FEATURE                 Location/Qualifiers
misc_feature            1..24
                        note = Description of Artificial Sequence: Synthetic
                            oligonucleotide
source                  1..24
                        mol_type = other DNA
                        organism = synthetic construct
SEQUENCE: 23
tttttgcccc cagggtgaca ggtt                                              24

SEQ ID NO: 24           moltype = DNA   length = 25
FEATURE                 Location/Qualifiers
misc_feature            1..25
                        note = Description of Artificial Sequence: Synthetic
                            oligonucleotide
source                  1..25
                        mol_type = other DNA
                        organism = synthetic construct
SEQUENCE: 24
cgttccacgc ccgctccttt gcaac                                             25

SEQ ID NO: 25           moltype = DNA   length = 25
FEATURE                 Location/Qualifiers
misc_feature            1..25
                        note = Description of Artificial Sequence: Synthetic
                            oligonucleotide
source                  1..25
                        mol_type = other DNA
                        organism = synthetic construct
SEQUENCE: 25
cgaacctcgc ccgctccttt gcaac                                             25

SEQ ID NO: 26           moltype = DNA   length = 25
FEATURE                 Location/Qualifiers
misc_feature            1..25
                        note = Description of Artificial Sequence: Synthetic
                            oligonucleotide
source                  1..25
                        mol_type = other DNA
```

```
                            organism = synthetic construct
SEQUENCE: 26
cgttaaccgc ccgctccttt gcaac                                              25

SEQ ID NO: 27           moltype = DNA   length = 25
FEATURE                 Location/Qualifiers
misc_feature            1..25
                        note = Description of Artificial Sequence: Synthetic
                          oligonucleotide
source                  1..25
                        mol_type = other DNA
                        organism = synthetic construct
SEQUENCE: 27
cgttaagcgc ccgctccttt gcaac                                              25

SEQ ID NO: 28           moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 28
gttgcaaagg agcgggcg                                                      18

SEQ ID NO: 29           moltype = DNA   length = 32
FEATURE                 Location/Qualifiers
misc_feature            1..32
                        note = Description of Artificial Sequence: Synthetic
                          oligonucleotide
source                  1..32
                        mol_type = other DNA
                        organism = synthetic construct
SEQUENCE: 29
cagtccagga gttggttgga cggctgcgag gc                                      32

SEQ ID NO: 30           moltype = DNA   length = 32
FEATURE                 Location/Qualifiers
misc_feature            1..32
                        note = Description of Artificial Sequence: Synthetic
                          oligonucleotide
source                  1..32
                        mol_type = other DNA
                        organism = synthetic construct
SEQUENCE: 30
cagtaatgga gttggttgga cggctgcgag gc                                      32

SEQ ID NO: 31           moltype = DNA   length = 32
FEATURE                 Location/Qualifiers
misc_feature            1..32
                        note = Description of Artificial Sequence: Synthetic
                          oligonucleotide
source                  1..32
                        mol_type = other DNA
                        organism = synthetic construct
SEQUENCE: 31
cagtaacgga gttggttgga cggctgcgag gc                                      32

SEQ ID NO: 32           moltype = DNA   length = 32
FEATURE                 Location/Qualifiers
misc_feature            1..32
                        note = Description of Artificial Sequence: Synthetic
                          oligonucleotide
source                  1..32
                        mol_type = other DNA
                        organism = synthetic construct
SEQUENCE: 32
cagtaaggga gttggttgga cggctgcgag gc                                      32

SEQ ID NO: 33           moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 33
gcctcgcagc cgtccaacca actcc                                              25
```

```
SEQ ID NO: 34               moltype = DNA   length = 25
FEATURE                     Location/Qualifiers
misc_feature                1..25
                            note = Description of Artificial Sequence: Synthetic primer
source                      1..25
                            mol_type = other DNA
                            organism = synthetic construct
SEQUENCE: 34
gcctcgcagc cgtccaacca actcc                                                25

SEQ ID NO: 35               moltype = DNA   length = 28
FEATURE                     Location/Qualifiers
misc_feature                1..28
                            note = Description of Artificial Sequence: Synthetic
                             oligonucleotide
source                      1..28
                            mol_type = other DNA
                            organism = synthetic construct
SEQUENCE: 35
cgttagtaac cgcccgctcc tttgcaac                                             28

SEQ ID NO: 36               moltype = DNA   length = 18
FEATURE                     Location/Qualifiers
misc_feature                1..18
                            note = Description of Artificial Sequence: Synthetic primer
source                      1..18
                            mol_type = other DNA
                            organism = synthetic construct
SEQUENCE: 36
gttgcaaagg agcgggcg                                                        18

SEQ ID NO: 37               moltype = DNA   length = 26
FEATURE                     Location/Qualifiers
misc_feature                1..26
                            note = Description of Artificial Sequence: Synthetic
                             oligonucleotide
source                      1..26
                            mol_type = other DNA
                            organism = synthetic construct
SEQUENCE: 37
ccatgattcg ccggcgtacc cccccc                                               26

SEQ ID NO: 38               moltype = DNA   length = 26
FEATURE                     Location/Qualifiers
misc_feature                1..26
                            note = Description of Artificial Sequence: Synthetic
                             oligonucleotide
source                      1..26
                            mol_type = other DNA
                            organism = synthetic construct
SEQUENCE: 38
ccatgattcg ccggcgtaca aaaaaa                                               26

SEQ ID NO: 39               moltype = DNA   length = 26
FEATURE                     Location/Qualifiers
misc_feature                1..26
                            note = Description of Artificial Sequence: Synthetic
                             oligonucleotide
source                      1..26
                            mol_type = other DNA
                            organism = synthetic construct
SEQUENCE: 39
ccatgattcg ccggcgtact tttttt                                               26

SEQ ID NO: 40               moltype = DNA   length = 26
FEATURE                     Location/Qualifiers
misc_feature                1..26
                            note = Description of Artificial Sequence: Synthetic
                             oligonucleotide
source                      1..26
                            mol_type = other DNA
                            organism = synthetic construct
SEQUENCE: 40
ccatgattcg ccggcgtacg gggggg                                               26

SEQ ID NO: 41               moltype = DNA   length = 19
FEATURE                     Location/Qualifiers
misc_feature                1..19
                            note = Description of Artificial Sequence: Synthetic primer
```

```
source                  1..19
                        mol_type = other DNA
                        organism = synthetic construct
SEQUENCE: 41
ggtactaagc ggccgcatg                                                        19

SEQ ID NO: 42           moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 42
tttttttagtc tgggtgacag gtt                                                  23

SEQ ID NO: 43           moltype = DNA   length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 43
tgactgactg actgagcata atgcctgcgt catccgccag c                               41

SEQ ID NO: 44           moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 44
gctggcggat gacgcagg                                                         18

SEQ ID NO: 45           moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 45
tttttttagtc tgggtgacag gtt                                                  23

SEQ ID NO: 46           moltype = DNA   length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 46
cagtaaggga gttggttgga cggctgcgag gc                                         32

SEQ ID NO: 47           moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 47
gcctcgcagc cgtccaacca actcc                                                 25

SEQ ID NO: 48           moltype = DNA   length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 48
```

```
tgccaccgga gttggttgga cggctgcgag gc                                       32

SEQ ID NO: 49           moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 49
gcctcgcagc cgtccaacca actcc                                               25

SEQ ID NO: 50           moltype =    length =
SEQUENCE: 50
000

SEQ ID NO: 51           moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 51
aaccactacg cctccgcttt                                                     20

SEQ ID NO: 52           moltype = DNA  length = 25
FEATURE                 Location/Qualifiers
misc_feature            1..25
                        note = Description of Artificial Sequence: Synthetic
                        oligonucleotide
source                  1..25
                        mol_type = other DNA
                        organism = synthetic construct
SEQUENCE: 52
agagaatgag gaacccgggg cagtt                                               25

SEQ ID NO: 53           moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 53
tctcttactc cttggggccc cgtcaa                                              26

SEQ ID NO: 54           moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 54
ctcttactcc ttggggcccc gtcaa                                               25

SEQ ID NO: 55           moltype = DNA  length = 25
FEATURE                 Location/Qualifiers
misc_feature            1..25
                        note = Description of Artificial Sequence: Synthetic
                        oligonucleotide
source                  1..25
                        mol_type = other DNA
                        organism = synthetic construct
SEQUENCE: 55
cgttaaccgc ccgctccttt gcaac                                               25

SEQ ID NO: 56           moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 56
gttgcaaagg agcgggcg                                                       18
```

```
SEQ ID NO: 57            moltype = DNA   length = 25
FEATURE                  Location/Qualifiers
misc_feature             1..25
                         note = Description of Artificial Sequence: Synthetic
                         oligonucleotide
source                   1..25
                         mol_type = other DNA
                         organism = synthetic construct
SEQUENCE: 57
cgaacctcgc ccgctccttt gcaac                                               25

SEQ ID NO: 58            moltype = DNA   length = 25
FEATURE                  Location/Qualifiers
misc_feature             1..25
                         note = Description of Artificial Sequence: Synthetic
                         oligonucleotide
source                   1..25
                         mol_type = other DNA
                         organism = synthetic construct
SEQUENCE: 58
cgttaaccgc ccgctccttt gcaac                                               25

SEQ ID NO: 59            moltype = DNA   length = 18
FEATURE                  Location/Qualifiers
misc_feature             1..18
                         note = Description of Artificial Sequence: Synthetic primer
source                   1..18
                         mol_type = other DNA
                         organism = synthetic construct
SEQUENCE: 59
gttgcaaagg agcgggcg                                                       18

SEQ ID NO: 60            moltype = DNA   length = 40
FEATURE                  Location/Qualifiers
misc_feature             1..40
                         note = Description of Artificial Sequence: Synthetic
                         oligonucleotide
source                   1..40
                         mol_type = other DNA
                         organism = synthetic construct
SEQUENCE: 60
cagtctcggg atcttgtgcc atttttggc acaagatccc                                40

SEQ ID NO: 61            moltype = AA   length = 6
FEATURE                  Location/Qualifiers
REGION                   1..6
                         note = Description of Artificial Sequence: Synthetic 6xHis
                         tag
source                   1..6
                         mol_type = protein
                         organism = synthetic construct
SEQUENCE: 61
HHHHHH                                                                    6

SEQ ID NO: 62            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 62
GLNDIFEAQK IEWHE                                                          15

SEQ ID NO: 63            moltype =   length =
SEQUENCE: 63
000

SEQ ID NO: 64            moltype = AA   length = 15
FEATURE                  Location/Qualifiers
REGION                   1..15
                         note = Description of Artificial Sequence: Synthetic peptide
VARIANT                  1..15
                         note = This sequence may encompass 4-15 "Lys" residues
source                   1..15
                         mol_type = protein
                         organism = synthetic construct
SEQUENCE: 64
KKKKKKKKKK KKKKK                                                          15
```

```
SEQ ID NO: 65              moltype = AA  length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 65
KKKKKKKKKK KK                                                                  12

SEQ ID NO: 66              moltype = AA  length = 15
FEATURE                    Location/Qualifiers
REGION                     1..15
                           note = Description of Artificial Sequence: Synthetic peptide
VARIANT                    1..15
                           note = This sequence may encompass 4-15 "Cys" residues
source                     1..15
                           mol_type = protein
                           organism = synthetic construct
SEQUENCE: 66
CCCCCCCCCC CCCCC                                                               15

SEQ ID NO: 67              moltype = AA  length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 67
CCCCCCCCCC CC                                                                  12

SEQ ID NO: 68              moltype = DNA  length = 12
FEATURE                    Location/Qualifiers
misc_feature               1..12
                           note = Description of Artificial Sequence: Synthetic
                            oligonucleotide
source                     1..12
                           mol_type = other DNA
                           organism = synthetic construct
SEQUENCE: 68
ttcctgtcac tc                                                                  12

SEQ ID NO: 69              moltype = DNA  length = 12
FEATURE                    Location/Qualifiers
misc_feature               1..12
                           note = Description of Artificial Sequence: Synthetic
                            oligonucleotide
source                     1..12
                           mol_type = other DNA
                           organism = synthetic construct
SEQUENCE: 69
ttcctgtcac cc                                                                  12

SEQ ID NO: 70              moltype = DNA  length = 2709
FEATURE                    Location/Qualifiers
misc_feature               1..2709
                           note = Description of Artificial Sequence: Synthetic
                            polynucleotide
source                     1..2709
                           mol_type = other DNA
                           organism = synthetic construct
CDS                        1..2709
SEQUENCE: 70
atgaaagaat tttacttaac ggttgaacag attggtgatt caatttttga acgttacatc   60
gattctaatg gccgtgaacg tactcgtgaa gtagaatata aaccatcact gtttgctcat  120
tgtccagaaa gtcaggctac gaaatatttc gatatcgtga gtaaaccgtg tactcgtaag  180
ttgttcgcta atatgcgtga tgcctcccaa tggattaaac gcatggaaga tatcggactt  240
gaagcacttg gcatggacga tttcaaattg gcgtatttgt ctgacactta taactatgaa  300
atcaaatacg accatacaaa aattcgtgtg ctaacttcg acatcgaagt aacatctccg  360
gatgggttcc ctgagccgtc acaagcaaaa catccgattg atgctatcac ccattatgac  420
tcaattgacg acaggttcta cgtatttgat ctattgaatt ctccatatgg taatgtgaaa  480
gaatggtcta ttgaaatcgc tgctaagctt caagaacaag gtgttgatga agttccatct  540
gaaattattg ataaaatcat ttatatgccg ttcgataacg aaaaagaatt gttgatggaa  600
tatctcaact tctggcaaca gaaaactcct gtcattttga ctggatggaa cgttgagtca  660
tttgctattc cgtacgtgta taccgaatc aagaatattt ttggcgaatc aactgcgaaa  720
cgtttatcac cacatcgtaa aactcgtgtt aaagttatcg aaaacatgta tggttctcgt  780
gaaatcatta cattgttcgg tatctctgtt cttgattaca ttgaccttta caaaaaattc  840
```

```
tcttttacca atcaaccgtc gtattctctg gattacattt cagaatttga attgaacgtt    900
ggtaaactga aatatgacgg ccctatttct aagcttcgtg aaagcaatca ccaacgatat    960
atttcttata acattatcgc tgtgtatcgt gtattgcaaa ttgatgctaa gcgtcagttc   1020
atcaacttga gtttggacat gggttattat gctaagatac agattcaatc tgtgtttagc   1080
ccaattaaaa catgggatgc tattattttt aatagcctta aagagcagaa caaggtgatt   1140
ccacaaggtc gttctcaccc ggttcaacct tatcccggcg cttttgttaa ggaacctatt   1200
ccaaatcgat acaaatatgt aatgagtttc gaccttacat cttcagctgt aagtattatt   1260
cgccaagtga atattagccc agaaacaata gcaggaacgt ttaaagtagc tccattgcat   1320
gattatatta acgctgttgc tgaacgtcct tctgatgtgt acagttgttc tcctaacggc   1380
atgatgtatt ataaagaccg tgatggtgta gttccaactg aaatcactaa ggtctttaat   1440
caacgtaaag aacataaagg ttacatgctt gcagctcaac gtaatggtga aataattaaa   1500
gaggcattgc ataatcctaa tctttctgtt gacgaaccat tagatgttga ttatcgtttc   1560
gacttcagcg atgagattaa agaaaagatt aaaaagttgt ctgctaaatc tcttaatgaa   1620
atgttgttta gagctcaacg tactgaagtt gcaggtatga ctgcacaaat taaccgtaaa   1680
ttgcttatca actcacttta tggtgcactt ggcaacgttt ggttccgtta ttatgatttg   1740
cgtaatgcta ctgcaatcac aacattcggg caaatggctt tacagtggat tgaacgtaaa   1800
gttaatgaat atctgaatga agtttgtggt acagaaggtg aagctttcgt tctttatggt   1860
gatacagact ctatttacgt atctgctgat aaaattatcg ataaggttgg tgaatctaaa   1920
ttccgtgata ccaaccattg ggtagacttc ttagataagt ttgcacgtga acgtatggaa   1980
ccagctattg atagaggttt ccgtgaaatg tgtgaataca tgaacaataa acaacactta   2040
atgttcatgg accgagaagc tatcgctggg cctccgcttg gttctaaagg tattggcgga   2100
ttttggactg gtaagaaacg ttatgcatta aacgtgtggg atatggaagg tactcgttac   2160
gctgagccta aactcaaaat catgggtcta gagactcaga aatcttcgac tcctaaagca   2220
gtacagaaag ctcttaaaga atgtattcgt cgtatgcttc aagaaggtga agaatcatta   2280
caagaatatt ttaaagagtt tgaaaaagaa ttccgtcaat tgaattatat tagcatcgcg   2340
tcggtatctt ctgcgaataa cattgctaaa tatgacgtag gtggattccc tggtcccaaa   2400
tgcccgttcc atattcgtgg aattctgaca tataaccgag ctatcaaagg taatattgat   2460
gcaccacaag ttgtagaagg tgaaaaagta tatgttctgc ctttacgtga aggaaaccca   2520
ttcggtgata aatgtatcgc atggccttct ggtactgaaa tcacagattt aattaaagac   2580
gacgtacttc attggatgga ctacactgtt ctccttgaga agacatttat taaaccactt   2640
gaaggattca catcagcagc gaaactcgat tacgagaaga aagcatctct gttcgatatg   2700
ttcgatttt                                                           2709

SEQ ID NO: 71        moltype = AA   length = 4
FEATURE              Location/Qualifiers
REGION               1..4
                     note = Description of Artificial Sequence: Synthetic peptide
source               1..4
                     mol_type = protein
                     organism = synthetic construct
SEQUENCE: 71
DDDD                                                                   4
```

What is claimed:

1. A method for identifying a nucleotide bound to a polymerase, comprising:
   a) contacting at least one type of a labeled nucleotide to an immobilized complex having a first polymerase bound to a template nucleic acid molecule that is bound to a polymerization initiation site, under suitable conditions to transiently-bind the at least one type of labeled nucleotide to the polymerase in a nucleic acid template-dependent manner and to inhibit nucleotide polymerization by the polymerase;
   b) detecting the transiently-bound labeled nucleotide; and
   c) identifying the labeled nucleotide transiently-bound to the polymerase, wherein the polymerase is a modified phi29 polymerase that includes lysine at position 379 and/or 383 substituted with leucine or arginine.

2. A system comprising:
   a) a polymerase which lacks exonuclease activity complexed with a template nucleic acid molecule which is bound to a polymerization initiation site; a nucleotide including a detectable moiety which is transiently bound to the active site of the polymerase in a template-dependent manner; and a cation that inhibits nucleotide incorporation by the polymerase, present at a concentration that inhibits nucleotide incorporation by the polymerase
   b) a detection system comprising excitation illumination elements, optical transmission elements and detectors, wherein the polymerase is a modified phi29 polymerase that includes lysine at position 379 and/or 383 substituted with leucine or arginine.

3. The system of claim 2, wherein the transiently-bound nucleotide is inhibited from incorporation onto the polymerization initiation site by suitable conditions which include: (i) reducing the levels or omission of a metal cation that permits nucleotide incorporation and/or addition of a cation that inhibits nucleotide incorporation; (ii) using a polymerase which selectively binds the nucleotide in a template-dependent manner and exhibits reduced nucleotide incorporation activity; (iii) using at least one type of labeled nucleotide which is a labeled non-incorporatable nucleotide; and/or (iv) using a polymerization initiation site which is a non-extendible polymerization initiation site.

4. The system of claim 2, wherein the cation that inhibits nucleotide incorporation is calcium, scandium, titanium, vanadium, chromium, iron, cobalt, nickel, copper, zinc, gallium, germanium, arsenic, selenium, rhodium, or strontium.

5. The system of claim 2, which lacks a catalytic metal ion, including magnesium, manganese, cobalt, strontium, or barium.

6. The system of claim 2, wherein the template nucleic acid molecule, polymerase or polymerization initiation site is linked to a surface.

7. The system of claim 2, wherein the template nucleic acid molecule is a DNA, RNA, or DNA/RNA hybrid molecule.

8. The system of claim 2, wherein the nucleotide includes an optically detectable label.

9. The system of claim 2, further comprising an excitation source that emits electromagnetic radiation.

10. The system of claim 2, wherein the nucleotide comprises 3-10 phosphate groups.

11. The system of claim 2, wherein the nucleotide comprises a fluorescent label linked to the base of the nucleotide or linked to the terminal phosphate group of the nucleotide.

12. The system of claim 11, wherein the fluorescent label comprises an energy transfer acceptor reporter moiety.

13. The system of claim 2, further comprising at least two different types of nucleotides.

14. The system of claim 13, wherein each different type of nucleotide includes a different type of label.

15. The system of claim 2, wherein the polymerase comprises an energy transfer donor reporter moiety.

16. The system of claim 15, wherein the energy transfer donor reporter moiety is an inorganic nanoparticle or a fluorophore.

17. The system of claim 2, wherein the polymerase comprises a label including an energy transfer donor reporter moiety and the transiently-bound nucleotide comprises an energy transfer acceptor reporter moiety.

* * * * *